United States Patent
Bacac et al.

(10) Patent No.: US 10,766,967 B2
(45) Date of Patent: Sep. 8, 2020

(54) BISPECIFIC T CELL ACTIVATING ANTIGEN BINDING MOLECULES

(71) Applicant: Hoffmann-La Roche Inc., Little Falls, NJ (US)

(72) Inventors: Marina Bacac, Zurich (CH); Tanja Fauti, Zurich (CH); Sabine Imhof-Jung, Planegg (DE); Christian Klein, Bonstetten (CH); Stefan Klostermann, Neuried (DE); Ekkehard Moessner, Kreuzlingen (CH); Michael Molhoj, Munich (DE); Christiane Neumann, Niederweningen (CH); Joerg Thomas Regula, Munich (DE); Wolfgang Schaefer, Mannheim (DE); Pablo Umana, Wollerau (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 15/281,484

(22) Filed: Sep. 30, 2016

(65) Prior Publication Data
US 2017/0190783 A1  Jul. 6, 2017

(30) Foreign Application Priority Data

Oct. 2, 2015 (EP) ..................... 15188035

(51) Int. Cl.
*A61K 39/00* (2006.01)
*C07K 16/30* (2006.01)
*C07K 16/28* (2006.01)
*C07K 16/46* (2006.01)

(52) U.S. Cl.
CPC ...... *C07K 16/3007* (2013.01); *C07K 16/2809* (2013.01); *C07K 16/468* (2013.01); *A61K 2039/505* (2013.01); *C07K 2317/24* (2013.01); *C07K 2317/31* (2013.01); *C07K 2317/35* (2013.01); *C07K 2317/52* (2013.01); *C07K 2317/522* (2013.01); *C07K 2317/55* (2013.01); *C07K 2317/56* (2013.01); *C07K 2317/565* (2013.01); *C07K 2317/622* (2013.01); *C07K 2317/66* (2013.01); *C07K 2317/73* (2013.01); *C07K 2317/92* (2013.01); *C07K 2317/94* (2013.01); *C07K 2319/00* (2013.01)

(58) Field of Classification Search
CPC .............................. A61K 2039/505
See application file for complete search history.

(56) References Cited

U.S. PATENT DOCUMENTS

| 5,571,894 A | 11/1996 | Wels et al. |
| 5,587,458 A | 12/1996 | King et al. |
| 5,591,828 A | 1/1997 | Bosslet et al. |
| 5,731,168 A | 3/1998 | Carter et al. |
| 5,821,337 A | 10/1998 | Carter et al. |
| 5,869,046 A | 2/1999 | Presta et al. |
| 6,248,516 B1 | 6/2001 | Winter et al. |
| 6,737,056 B1 | 5/2004 | Presta |
| 6,737,086 B2 | 5/2004 | Gutierrez et al. |
| 6,809,185 B1 | 10/2004 | Schoonjans et al. |
| 7,235,641 B2 | 6/2007 | Kufer et al. |
| 7,332,581 B2 | 2/2008 | Presta |
| 7,695,936 B2 | 4/2010 | Carter et al. |
| 8,227,577 B2 | 7/2012 | Klein et al. |
| 8,236,308 B2 | 8/2012 | Kischel et al. |
| 8,242,247 B2 | 8/2012 | Klein et al. |
| 8,642,742 B2 | 2/2014 | Hofer et al. |
| 8,703,132 B2 | 4/2014 | Imhof-Jung et al. |
| 8,709,421 B2 | 4/2014 | Heiss et al. |
| 8,796,424 B2 | 8/2014 | Croasdale et al. |
| 8,846,042 B2 | 9/2014 | Zhou |
| 8,969,526 B2 | 3/2015 | Baehner et al. |
| 9,068,008 B2 | 6/2015 | Mossner et al. |
| 9,206,260 B2 | 12/2015 | Hofer et al. |
| 9,266,938 B2 | 2/2016 | Ast et al. |
| 9,266,967 B2 | 2/2016 | Klein et al. |
| 9,382,323 B2 | 7/2016 | Brinkmann et al. |
| 9,447,159 B2 | 9/2016 | Ast et al. |
| 9,526,797 B2 | 12/2016 | Gerdes et al. |
| 10,155,815 B2 | 12/2018 | Bacac et al. |
| 2002/0004587 A1 | 1/2002 | Miller et al. |
| 2005/0244333 A1 | 11/2005 | Yazaki et al. |

(Continued)

FOREIGN PATENT DOCUMENTS

| EA | 015009 B1 | 4/2011 |
| EP | 0404097 B1 | 9/1996 |

(Continued)

OTHER PUBLICATIONS

Chin et al. (Chang Gung Med J. Jan.-Feb. 2008; 31 (1): 1-15).*

(Continued)

*Primary Examiner* — Stephen L Rawlings
(74) *Attorney, Agent, or Firm* — Clark & Elbing LLP; Karen L. Elbing

(57) ABSTRACT

The present invention generally relates to novel bispecific antigen binding molecules for T cell activation and re-direction to specific target cells. In addition, the present invention relates to polynucleotides encoding such bispecific antigen binding molecules, and vectors and host cells comprising such polynucleotides. The invention further relates to methods for producing the bispecific antigen binding molecules of the invention, and to methods of using these bispecific antigen binding molecules in the treatment of disease.

50 Claims, 42 Drawing Sheets
Specification includes a Sequence Listing.

(56) References Cited

U.S. PATENT DOCUMENTS

| | | |
|---|---|---|
| 2006/0115475 A1 | 6/2006 | Carton et al. |
| 2007/0071675 A1 | 3/2007 | Wu et al. |
| 2007/0111281 A1 | 5/2007 | Sondermann et al. |
| 2007/0219133 A1 | 9/2007 | Lazar et al. |
| 2008/0241152 A1 | 10/2008 | Alitalo et al. |
| 2009/0162359 A1 | 6/2009 | Klein et al. |
| 2009/0162360 A1 | 6/2009 | Klein et al. |
| 2009/0252683 A1 | 10/2009 | Kischel et al. |
| 2010/0015133 A1 | 1/2010 | Igawa et al. |
| 2010/0150918 A1 | 6/2010 | Kufer et al. |
| 2010/0316645 A1 | 12/2010 | Imhof-Jung et al. |
| 2011/0293613 A1 | 12/2011 | Brinkmann et al. |
| 2012/0149876 A1 | 6/2012 | Von Kreudenstein et al. |
| 2012/0225071 A1 | 9/2012 | Klein et al. |
| 2012/0251531 A1 | 10/2012 | Baehner et al. |
| 2012/0276125 A1 | 11/2012 | Ast et al. |
| 2013/0022601 A1 | 1/2013 | Brinkmann et al. |
| 2013/0058936 A1 | 3/2013 | Bruenker et al. |
| 2013/0058937 A1 | 3/2013 | Auer et al. |
| 2013/0060011 A1 | 3/2013 | Bruenker et al. |
| 2013/0078249 A1 | 3/2013 | Ast et al. |
| 2013/0171095 A1 | 7/2013 | Bernett et al. |
| 2014/0088295 A1 | 3/2014 | Smith et al. |
| 2014/0112914 A1 | 4/2014 | Nezu et al. |
| 2014/0154254 A1 | 6/2014 | Kannan et al. |
| 2014/0242079 A1 | 8/2014 | Bacac et al. |
| 2014/0242080 A1 | 8/2014 | Jaeger et al. |
| 2014/0288275 A1 | 9/2014 | Moore et al. |
| 2014/0294823 A1 | 10/2014 | Moore et al. |
| 2014/0294833 A1 | 10/2014 | Desjarlais et al. |
| 2014/0302064 A1 | 10/2014 | Moore |
| 2014/0322217 A1 | 10/2014 | Moore et al. |
| 2014/0363426 A1 | 12/2014 | Moore et al. |
| 2014/0370013 A1 | 12/2014 | Desjarlais et al. |
| 2014/0377270 A1 | 12/2014 | Moore et al. |
| 2015/0166661 A1 | 6/2015 | Chen et al. |
| 2015/0274845 A1 | 10/2015 | Bruenker et al. |
| 2015/0315296 A1 | 11/2015 | Schaefer et al. |
| 2015/0368351 A1 | 12/2015 | Vu et al. |
| 2015/0376287 A1 | 12/2015 | Vu et al. |
| 2016/0075785 A1 | 3/2016 | Ast et al. |
| 2016/0130347 A1 | 5/2016 | Bruenker et al. |
| 2016/0145340 A1* | 5/2016 | Borges .................. C07K 16/28 424/136.1 |
| 2016/0145354 A1 | 5/2016 | Bacac et al. |
| 2016/0175397 A1 | 6/2016 | Umana et al. |
| 2016/0200833 A1* | 7/2016 | Amann ............. C07K 16/2815 424/134.1 |
| 2016/0208017 A1 | 7/2016 | Ast et al. |
| 2016/0208019 A1 | 7/2016 | Bacac et al. |
| 2016/0263240 A1 | 9/2016 | Ast et al. |
| 2016/0297881 A1 | 10/2016 | Vu et al. |
| 2016/0368985 A1 | 12/2016 | Hotzel et al. |
| 2017/0008971 A1 | 1/2017 | Dennis et al. |
| 2017/0096485 A1 | 4/2017 | Bacac et al. |
| 2017/0096495 A1 | 4/2017 | Bacac et al. |
| 2017/0114146 A1 | 4/2017 | Klein et al. |
| 2017/0174786 A1 | 6/2017 | Bacac et al. |
| 2017/0190783 A1 | 7/2017 | Bacac et al. |
| 2017/0209573 A1 | 7/2017 | Bacac et al. |
| 2017/0253670 A1 | 9/2017 | Klein et al. |
| 2017/0267783 A1 | 9/2017 | Nezu et al. |
| 2017/0306018 A1 | 10/2017 | Vu et al. |
| 2017/0306036 A1 | 10/2017 | Vu et al. |
| 2017/0306044 A1 | 10/2017 | Vu et al. |
| 2017/0327579 A1 | 11/2017 | Vu et al. |
| 2017/0327580 A1 | 11/2017 | Vu et al. |

FOREIGN PATENT DOCUMENTS

| | | |
|---|---|---|
| EP | 1870459 A1 | 12/2007 |
| EP | 1870459 A4 | 9/2010 |
| EP | 2261258 A1 | 12/2010 |
| EP | 2578230 A1 | 4/2013 |
| EP | 2647707 A1 | 10/2013 |
| EP | 2647707 A4 | 4/2014 |
| EP | 1870459 B1 | 6/2016 |
| JP | 2012-528092 A | 11/2012 |
| JP | 2014-534806 A | 12/2014 |
| TW | 201321413 A | 6/2013 |
| TW | 201326212 A | 7/2013 |
| WO | WO-91/01990 A1 | 2/1991 |
| WO | WO-91/03493 A1 | 3/1991 |
| WO | WO-93/01161 A1 | 1/1993 |
| WO | WO-93/16185 A2 | 8/1993 |
| WO | WO-96/01126 A1 | 1/1996 |
| WO | WO-96/27011 A1 | 9/1996 |
| WO | WO-96/40210 A1 | 12/1996 |
| WO | WO-98/50431 A2 | 11/1998 |
| WO | WO-98/50431 A3 | 1/1999 |
| WO | WO-02/09573 A2 | 2/2002 |
| WO | WO-2005/044859 A2 | 5/2005 |
| WO | WO-2005/044859 A3 | 8/2005 |
| WO | WO-2005/086875 A2 | 9/2005 |
| WO | WO2005086875 A2 * | 9/2005 |
| WO | WO-2006/082515 A2 | 8/2006 |
| WO | WO-2007/024715 A2 | 3/2007 |
| WO | WO-2007/042261 A2 | 4/2007 |
| WO | WO-2007/071422 A2 | 6/2007 |
| WO | WO-2007/071426 A1 | 6/2007 |
| WO | WO-2007/075270 A2 | 7/2007 |
| WO | WO-2007/110205 A2 | 10/2007 |
| WO | WO-2007/146968 A2 | 12/2007 |
| WO | WO-2007/147901 A1 | 12/2007 |
| WO | WO-2008/052187 A2 | 5/2008 |
| WO | WO-2007/024715 A3 | 10/2008 |
| WO | WO-2008/119566 A2 | 10/2008 |
| WO | WO-2008/119567 A2 | 10/2008 |
| WO | WO-2007/024715 A9 | 4/2009 |
| WO | WO-2009/070642 A1 | 6/2009 |
| WO | WO-2009/080251 A1 | 7/2009 |
| WO | WO-2009/080252 A1 | 7/2009 |
| WO | WO-2009/080253 A1 | 7/2009 |
| WO | WO-2009/080254 A1 | 7/2009 |
| WO | WO-2009/089004 A1 | 7/2009 |
| WO | WO-2010/115589 A1 | 10/2010 |
| WO | WO-2010/129304 A2 | 11/2010 |
| WO | WO-2010/136172 A1 | 12/2010 |
| WO | WO-2010/145792 A1 | 12/2010 |
| WO | WO-2010/145793 A1 | 12/2010 |
| WO | WO-2010/129304 A3 | 2/2011 |
| WO | WO-2011/023787 A1 | 3/2011 |
| WO | WO-2011/028952 A1 | 3/2011 |
| WO | WO-2011/090754 A1 | 7/2011 |
| WO | WO-2011/090762 A1 | 7/2011 |
| WO | WO-2011/143545 A1 | 11/2011 |
| WO | WO-2012/058768 A1 | 5/2012 |
| WO | WO-2012/058768 A8 | 6/2012 |
| WO | WO-2012/073985 A1 | 6/2012 |
| WO | WO-2012/107417 A1 | 8/2012 |
| WO | WO-2012/117002 A1 | 9/2012 |
| WO | WO-2012/130831 A1 | 10/2012 |
| WO | WO2012130831 A1 * | 10/2012 |
| WO | WO-2012/146628 A1 | 11/2012 |
| WO | WO-2012/154530 A1 | 11/2012 |
| WO | WO-2012/158818 A2 | 11/2012 |
| WO | WO-2012/162067 A2 | 11/2012 |
| WO | WO-2013/012414 A1 | 1/2013 |
| WO | WO-2013/026831 A1 | 2/2013 |
| WO | WO-2013/026832 A1 | 2/2013 |
| WO | WO-2013/026833 A1 | 2/2013 |
| WO | WO-2013/026837 A1 | 2/2013 |
| WO | WO-2013/096291 A2 | 6/2013 |
| WO | WO-2013/157953 A1 | 10/2013 |
| WO | WO-2013/157954 A1 | 10/2013 |
| WO | WO-2014/022540 A1 | 2/2014 |
| WO | WO-2014/028560 A2 | 2/2014 |
| WO | WO-2014/047231 A1 | 3/2014 |
| WO | WO2014056783 A1 * | 4/2014 |
| WO | WO-2014/028560 A3 | 5/2014 |
| WO | WO-2014/079886 A1 | 5/2014 |
| WO | WO-2014/081955 A1 | 5/2014 |
| WO | WO-2014/122143 A1 | 8/2014 |

(56) References Cited

FOREIGN PATENT DOCUMENTS

| | | |
|---|---|---|
| WO | WO-2014/122144 A1 | 8/2014 |
| WO | WO-2014/122251 A2 | 8/2014 |
| WO | WO-2014/131694 A1 | 9/2014 |
| WO | WO-2014/131711 A1 | 9/2014 |
| WO | WO-2014/131712 A1 | 9/2014 |
| WO | WO-2014/141152 A2 | 9/2014 |
| WO | WO-2014/153002 A1 | 9/2014 |
| WO | WO-2014/122251 A3 | 10/2014 |
| WO | WO-2014/167022 A1 | 10/2014 |
| WO | WO-2014/141152 A3 | 12/2014 |
| WO | WO-2014/191113 A1 | 12/2014 |
| WO | WO-2014/191113 A8 | 2/2015 |
| WO | WO-2015/101588 A1 | 7/2015 |
| WO | WO-2015/150447 A1 | 10/2015 |
| WO | WO-2016/020065 A1 | 2/2016 |
| WO | WO-2016/020332 A1 | 2/2016 |
| WO | WO-2016/036678 A1 | 3/2016 |
| WO | WO-2016/055592 A1 | 4/2016 |
| WO | WO-2016/055593 A1 | 4/2016 |
| WO | WO-2016/079081 A1 | 5/2016 |
| WO | WO-2016/079177 A1 | 5/2016 |
| WO | WO-2016/087531 A1 | 6/2016 |
| WO | WO-2016/179003 A1 | 11/2016 |
| WO | WO-2017/021450 A1 | 2/2017 |
| WO | WO-2017/097723 A2 | 6/2017 |

OTHER PUBLICATIONS

Jiang et al. (J. Biol. Chem. Feb. 11, 2005; 280 (6): 4656-4662).*
Riemer et al. (Mol. Immunol. 2005; 42: 1121-1124).*
Graves et al. (Transplantation. Apr. 27, 2011; 91 (8): 833-40).*
Rudikoff et al. (Proc. Natl. Acad. Sci. USA. 1982; 79: 1979-1983).*
Mariuzza et al. (Annu. Rev. Biophys. Biophys. Chem. 1987; 16: 139-159).*
Winkler et al. (J. Immunol. Oct. 15, 2000; 165 (8): 4505-4514).*
Gussow et al. (Methods in Enzymology. 1991; 203: 99-121).*
Giusti et al. (Proc. Natl. Acad. Sci. USA. May 1987; 84 (9): 2926-2930).*
Chien et al. (Proc. Natl. Acad. Sci. USA. Jul. 1989; 86 (14): 5532-5536).*
Caldas et al. (Mol. Immunol. May 2003; 39 (15): 941-952).*
Vajdos et al. (J. Mol. Biol. Jul. 5, 2002; 320 (2): 415-428).*
De Pascalis et al. (J. Immunol. 2002; 169 (6): 3076-3084).*
Wu et al. (J. Mol. Biol. Nov. 19, 1999; 294 (1): 151-162).*
Casset et al. (Biochem. Biophys. Res. Commun. Jul. 18, 2003; 307 (1): 198-205).*
MacCallum et al. (J. Mol. Biol. Oct. 11, 1996; 262 (5): 732-745).*
Holm et al. (Mol. Immunol. Feb. 2007; 44 (6): 1075-1084).*
Yu et al. (PLoS One. 2012; 7 (3): e33340; pp. 1-15).*
Chang et al. (Structure. Jan. 7, 2014; 22 (1): 9-21).*
Huehls et al. (Immunol. Cell. Biol. Mar. 2015; 93 (3): 290-6; pp. 1-16).*
Strop et al. (J. Mol. Biol. Jul. 13, 2012; 420 (3): 204-19).*
Merchant et al. (Nat. Biotechnol. Jul. 1998; 16 (7): 677-81).*
Moore et al. (MAbs. Nov.-Dec. 2011; 3 (6): 546-557).*
Regula et al. (Protein Eng. Des. Sel. Aug. 28, 2018; electronically published ahead of print; pp. 1-11).*
Klein et al. (MAbs. Nov.-Dec. 2012; 4 (6): 653-63).*
Atwell et al., "Stable heterodimers from remodeling the domain interface of a homodimer using a phage display library," J Mol Biol. 270(1):26-35 (1997).
Booy et al., "Monoclonal and bispecific antibodies as novel therapeutics," Arch Immunol Ther Exp (Warsz). 54(2):85-101 (2006).
Bosch et al., "MCSP/CD3-bispecific single-chain antibody construct engages CD4+ and CD8+ T cells for lysis of MCSP-expressing human uveal melanoma cells," AACR 101st Annual Meeting. Apr. 17-21, Washington, DC. 70(8 Suppl) Abstract 5621 (2010).
Carter, "Bispecific human IgG by design," J Immunol Methods. 248(1-2):7-15 (2001).
Chan et al., "Variable region domain exchange in human IgGs promotes antibody complex formation with accompanying structural changes and altered effector functions," Mol Immunol. 41(5):527-38 (2004).
Conaghan et al., "Targeted killing of colorectal cancer cell lines by a humanised IgG1 monoclonal antibody that binds to membrane-bound carcinoembryonic antigen," Br J Cancer. 98(7):1217-25 (2008).
Edelman et al., "The covalent structure of an entire gammaG immunoglobulin molecule," Proc Natl Acad Sci U S A. 63(1):78-85 (1969).
Holliger et al., "'Diabodies': small bivalent and bispecific antibody fragments," Proc Natl Acad Sci U S A. 90(14):6444-8 (1993).
Holliger et al., "Specific killing of lymphoma cells by cytotoxic T-cells mediated by a bispecific diabody," Protein Eng. 9(3):299-305 (1996).
Honeychurch et al., "Bispecific Ab therapy of B-cell lymphoma: target cell specificity of antibody derivatives appears critical in determining therapeutic outcome," Cancer Immunol Immunother. 45(3-4):171-3 (1997).
Hudson et al., "Engineered antibodies," Nat Med. 9(1):129-34 (2003).
Kipriyanov et al., "Bispecific tandem diabody for tumor therapy with improved antigen binding and pharmacokinetics," J Mol Biol. 293(1):41-56 (1999).
Klein et al., "Progress in overcoming the chain association issue in bispecific heterodimeric IgG antibodies," MAbs. 4(6):653-63 (2012).
Kontermann, "Dual targeting strategies with bispecific antibodies," MAbs. 4(2):182-97 (2012).
MacLean et al., "Anti-CD3:anti-IL-2 receptor-bispecific mAb-mediated immunomodulation. Low systemic toxicity, differential effect on lymphoid tissue, and inhibition of cell-mediated hypersensitivity," J Immunol. 155(7):3674-82 (1995).
Merchant et al., "An efficient route to human bispecific IgG," Nat Biotechnol. 16(7):677-81 (1998).
Miller et al., "Design, construction, and in vitro analyses of multivalent antibodies," J Immunol. 170(9):4854-61 (2003).
Moore et al., "A novel bispecific antibody format enables simultaneous bivalent and monovalent co-engagement of distinct target antigens," MAbs. 3(6):546-57 (2011).
Moore et al., "Application of dual affinity retargeting molecules to achieve optimal redirected T-cell killing of B-cell lymphoma," Blood. 117(17):4542-51 (2011) (11 pages).
Nagorsen et al., "Immunomodulatory therapy of cancer with T cell-engaging BiTE antibody blinatumomab," Exp Cell Res. 317(9):1255-60 (2011).
Oshimi et al., "Increased lysis of patient CD10-positive leukemic cells by T cells coated with anti-CD3 Fab' antibody cross-linked to anti-CD10 Fab' antibody," Blood. 77(5):1044-9 (1991).
Peng et al., "The CEA/CD3-bispecific antibody MEDI-565 (MT111) binds a nonlinear epitope in the full-length but not a short splice variant of CEA," PLoS One. 7(5):e36412 (2012) (14 pages).
Pessano et al., "The T3/T cell receptor complex: antigenic distinction between the two 20-kd T3 (T3-delta and T3-epsilon) subunits," EMBO J. 4(2):337-44 (1985).
Plückthun, Antibodies from *Escherichia coli. The Pharmacology of Monoclonal Antibodies.* Rosenberg & Moore, 269-315 (1994).
Ridgway et al., "'Knobs-into-holes' engineering of antibody CH3 domains for heavy chain heterodimerization," Protein Eng. 9(7):617-21 (1996).
Riedle et al., "In vivo activation and expansion of T cells by a bi-specific antibody abolishes metastasis formation of human melanoma cells in SCID mice," Int J Cancer. 75(6):908-18 (1998).
Schaefer et al., "Immunoglobulin domain crossover as a generic approach for the production of bispecific IgG antibodies," Proc Natl Acad Sci U S A. 108(27):11187-92 (2011).
Seimetz et al., "Development and approval of the trifunctional antibody catumaxomab (anti-EpCAM × anti-CD3) as a targeted cancer immunotherapy," Cancer Treat Rev. 36(6):458-67 (2010).
Stancovski et al., "Mechanistic aspects of the opposing effects of monoclonal antibodies to the ERBB2 receptor on tumor growth," Proc Natl Acad Sci U S A. 88(19):8691-5 (1991).

(56) References Cited

OTHER PUBLICATIONS

Stewart et al., "Humanisation and characterisation of PR1A3, a monoclonal antibody specific for cell-bound carcinoembryonic antigen," Cancer Immunol Immunother. 47(6):299-306 (1999).

Stubenrauch et al., "Impact of molecular processing in the hinge region of therapeutic IgG4 antibodies on disposition profiles in cynomolgus monkeys," Drug Metab Dispos. 38(1):84-91 (2010).

Sun et al., "Anti-CD20/CD3 T cell-dependent bispecific antibody for the treatment of B cell malignancies," Sci Transl Med. 7(287):287ra70 (2015) (11 pages).

Torisu-Itakura et al., "Redirected lysis of human melanoma cells by a MCSP/CD3-bispecific BiTE antibody that engages patient-derived T cells," J Immunother. 34(8):597-605 (2011).

Tutt et al., "Trispecific F(ab')3 derivatives that use cooperative signaling via the TCR/CD3 complex and CD2 to activate and redirect resting cytotoxic T cells," J Immunol. 147(1):60-9 (1991).

Wolf et al., "BiTEs: bispecific antibody constructs with unique anti-tumor activity," Drug Discov Today. 10(18):1237-44 (2005).

Wu et al., "Humanization of a murine monoclonal antibody by simultaneous optimization of framework and CDR residues," J Mol Biol. 294(1):151-62 (1999).

Zhu et al., "Identification of heavy chain residues in a humanized anti-CD3 antibody important for efficient antigen binding and T cell activation," J Immunol. 155(4):1903-10 (1995).

International Search Report and Written Opinion for International Patent Application No. PCT/EP2014/053489, dated Jun. 5, 2014 (14 pages).

International Search Report and Written Opinion for International Patent Application No. PCT/EP2014/053490, dated Jun. 10, 2014 (16 pages).

International Search Report and Written Opinion for International Patent Application No. PCT/EP2016/073171, dated Dec. 20, 2016 (13 pages).

Neumaier et al., "Cloning of the genes for T84.66, an antibody that has a high specificity and affinity for carcinoembryonic antigen, and expression of chimeric human/mouse T84.66 genes in myeloma and Chinese hamster ovary cells," Cancer Res. 50(7):2128-34 (1990) (8 pages).

Yazaki et al., "Humanization of the anti-CEA T84.66 antibody based on crystal structure data," Protein Eng Des Sel. 17(5):481-9 (2004).

International Preliminary Report on Patentability for International Patent Application No. PCT/EP2014/053490, dated Sep. 1, 2015 (11 pages).

Almagro et al., "Humanization of antibodies," Front Biosci. 13:1619-33 (2008).

Bacac et al., "A Novel Carcinoembryonic Antigen T-Cell Bispecific Antibody (CEA TCB) for the Treatment of Solid Tumors," Clin Cancer Res. 22(13):3286-97 (2016) (12 pages).

\* cited by examiner

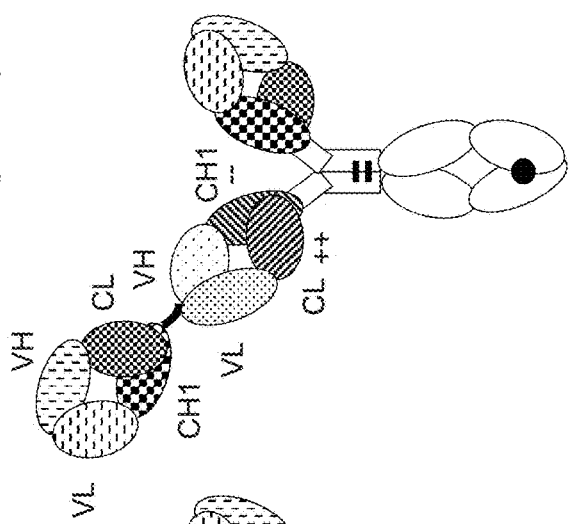
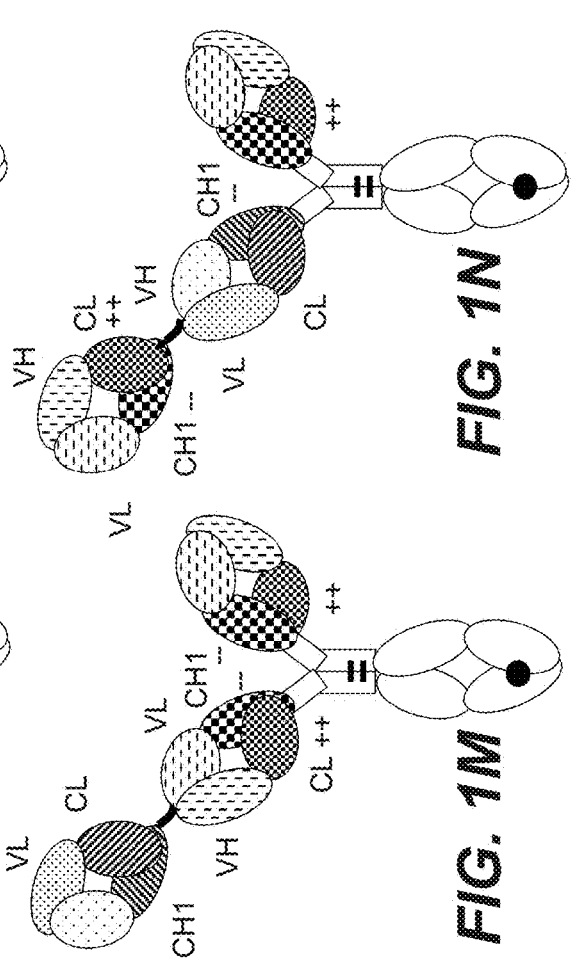
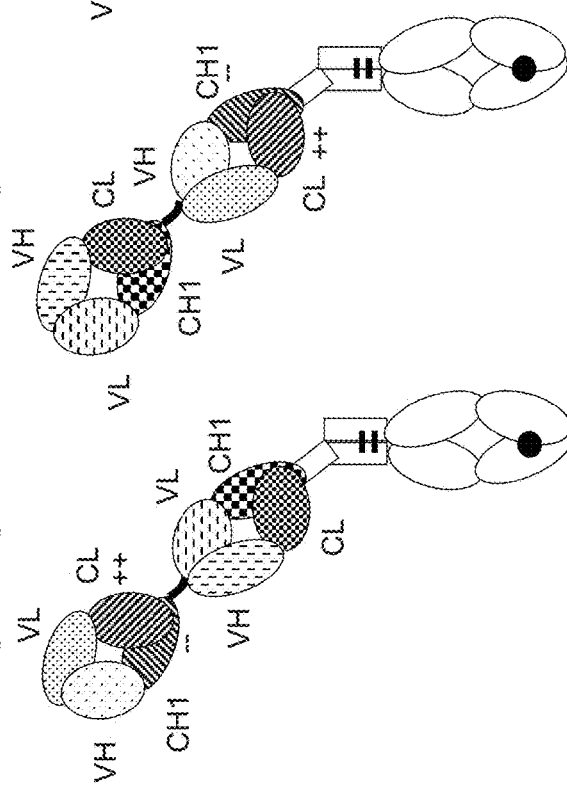
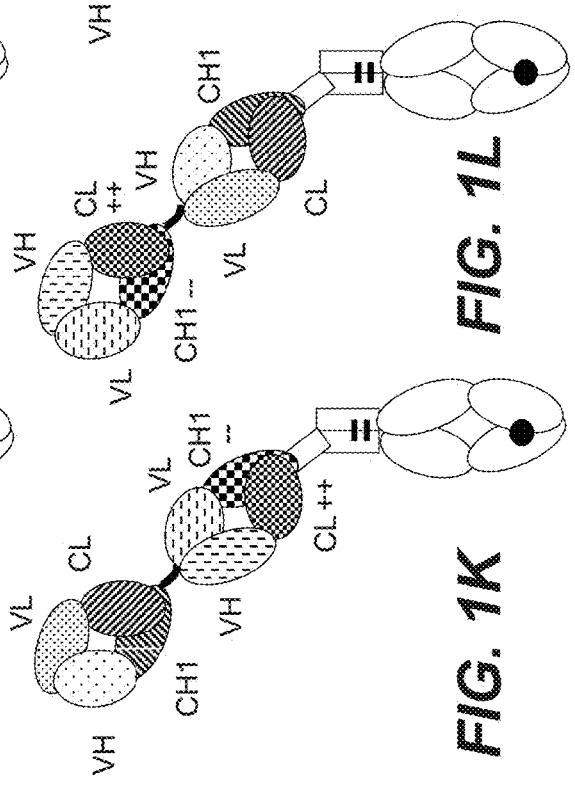

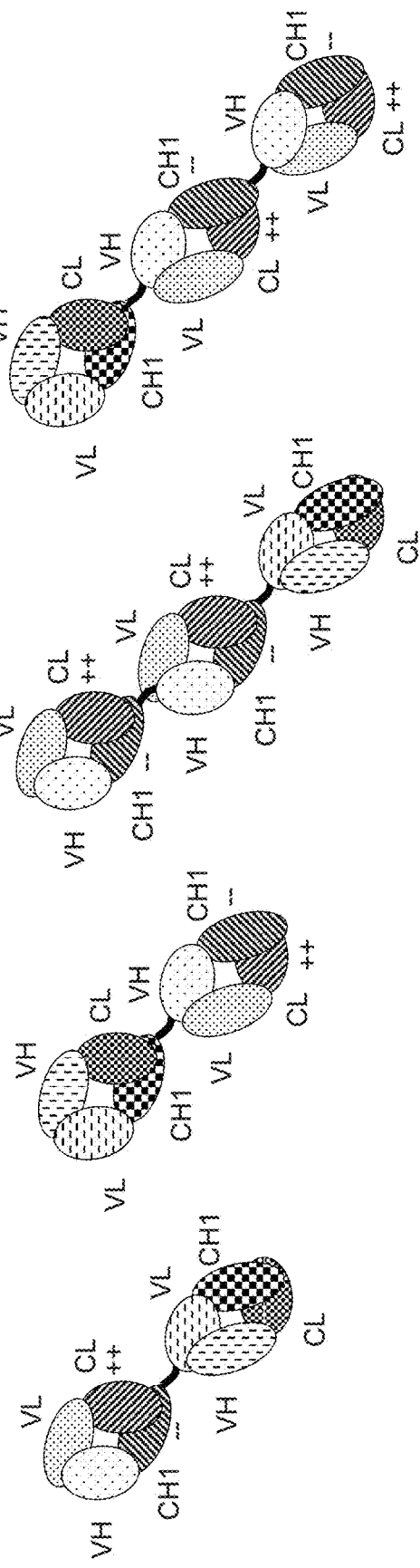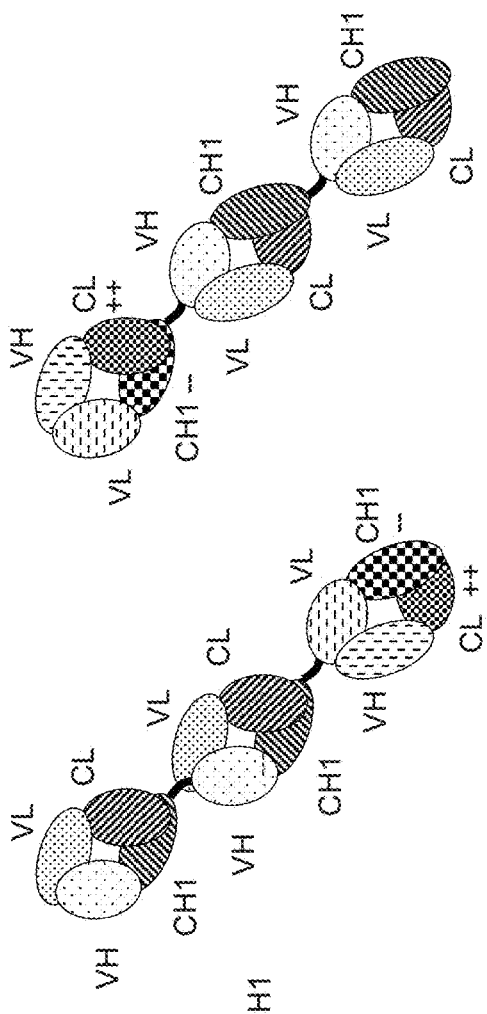

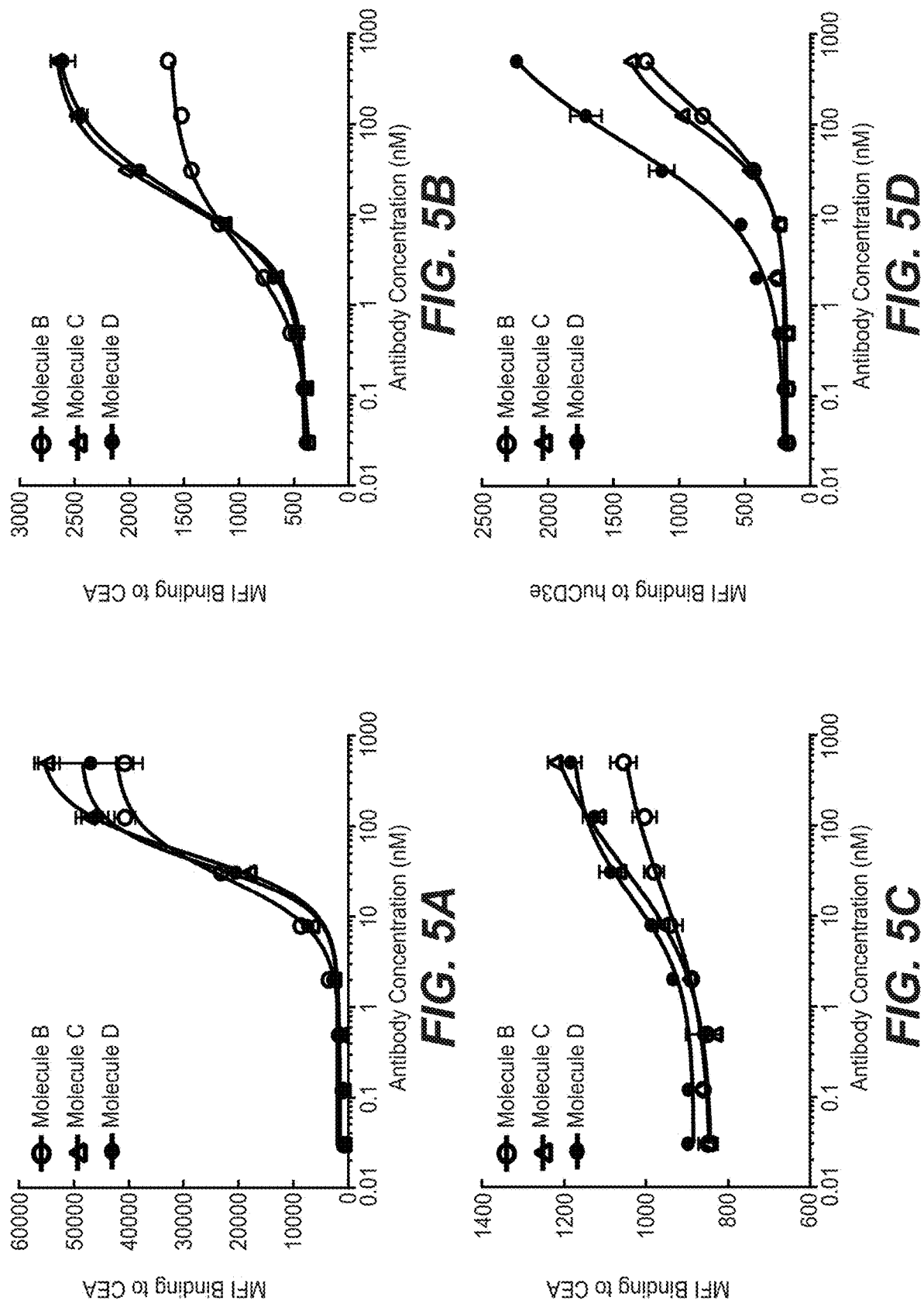

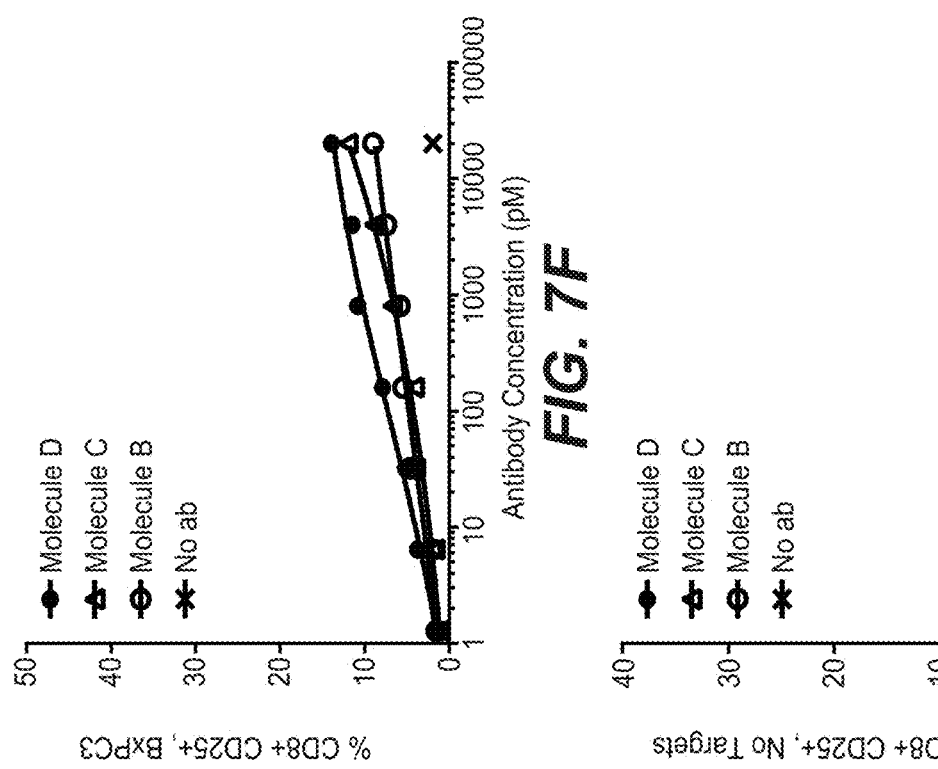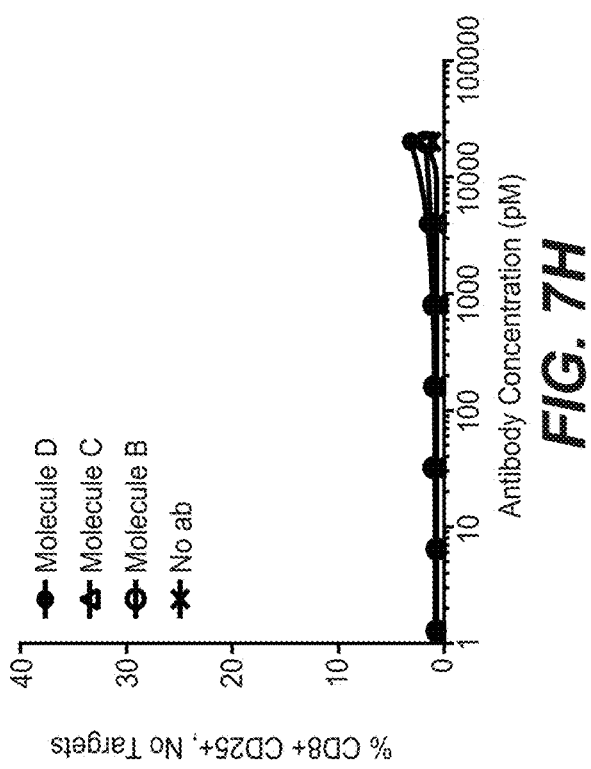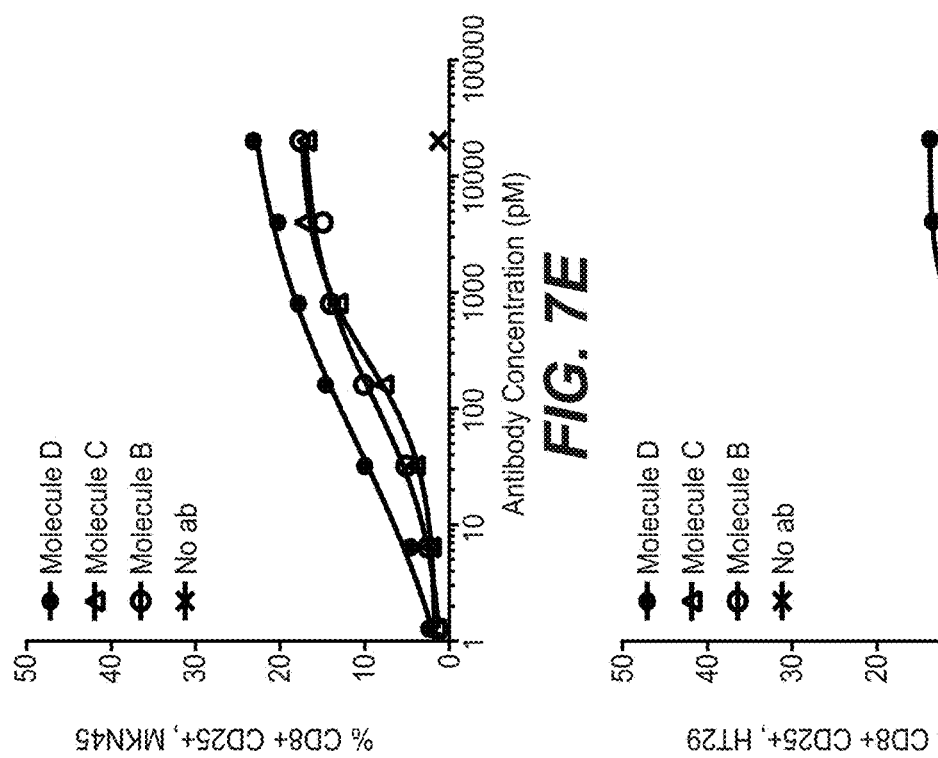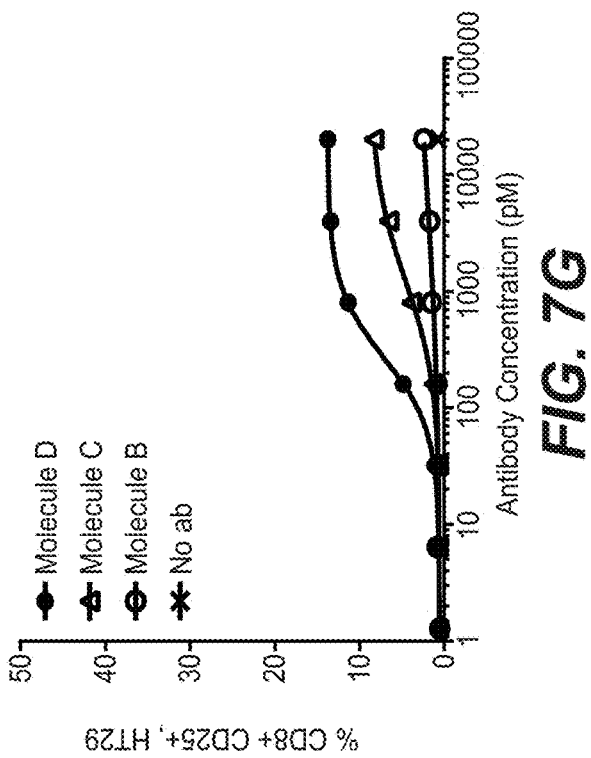

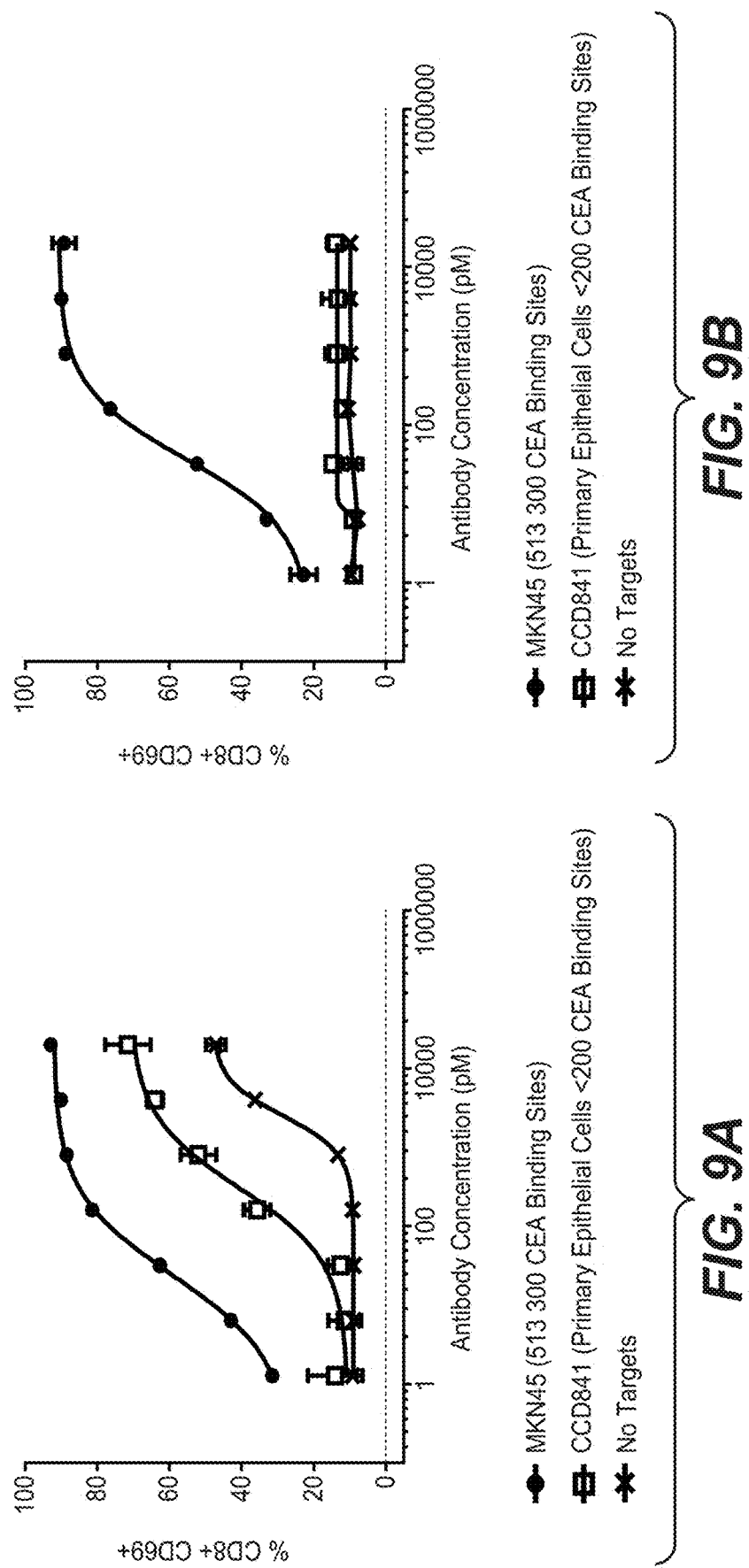

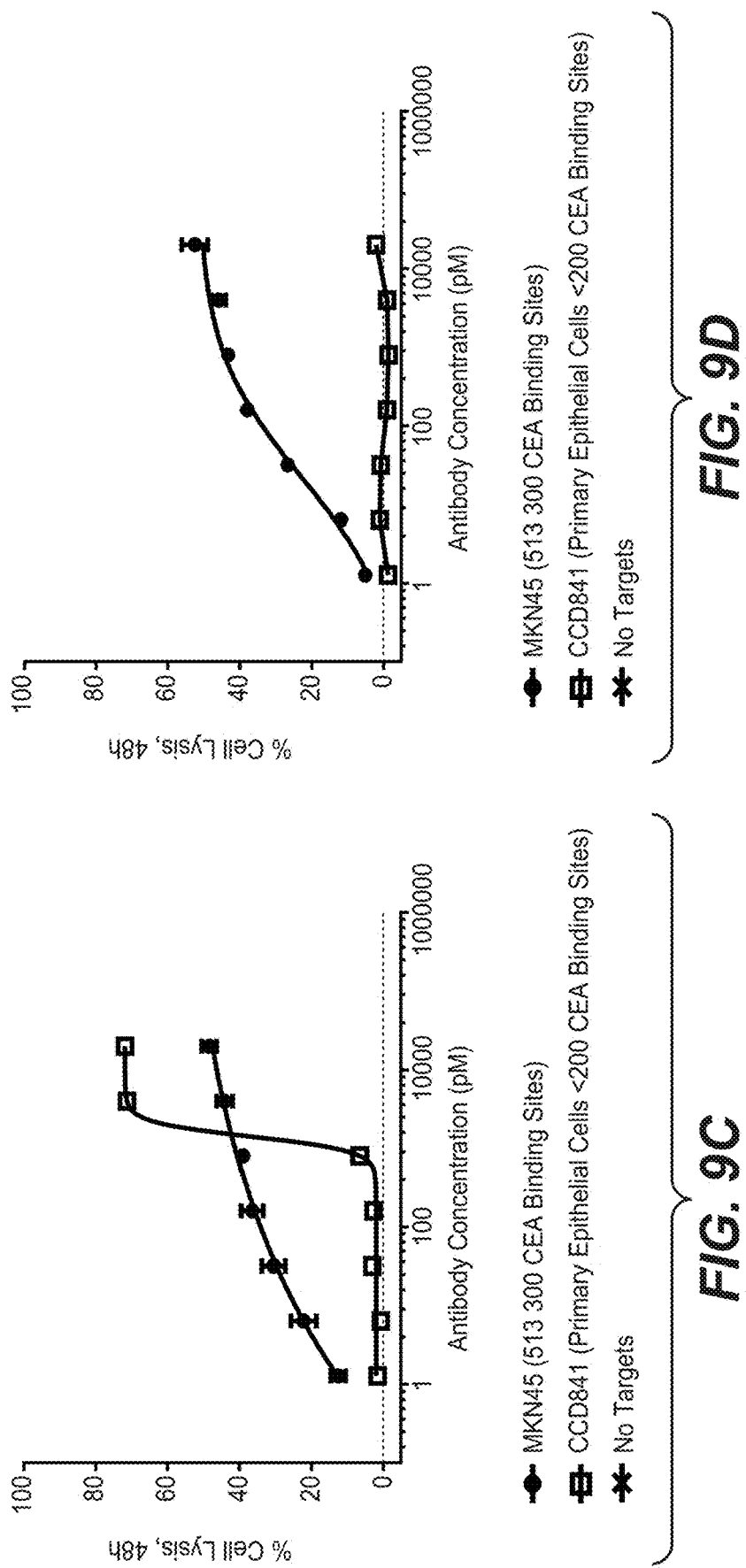

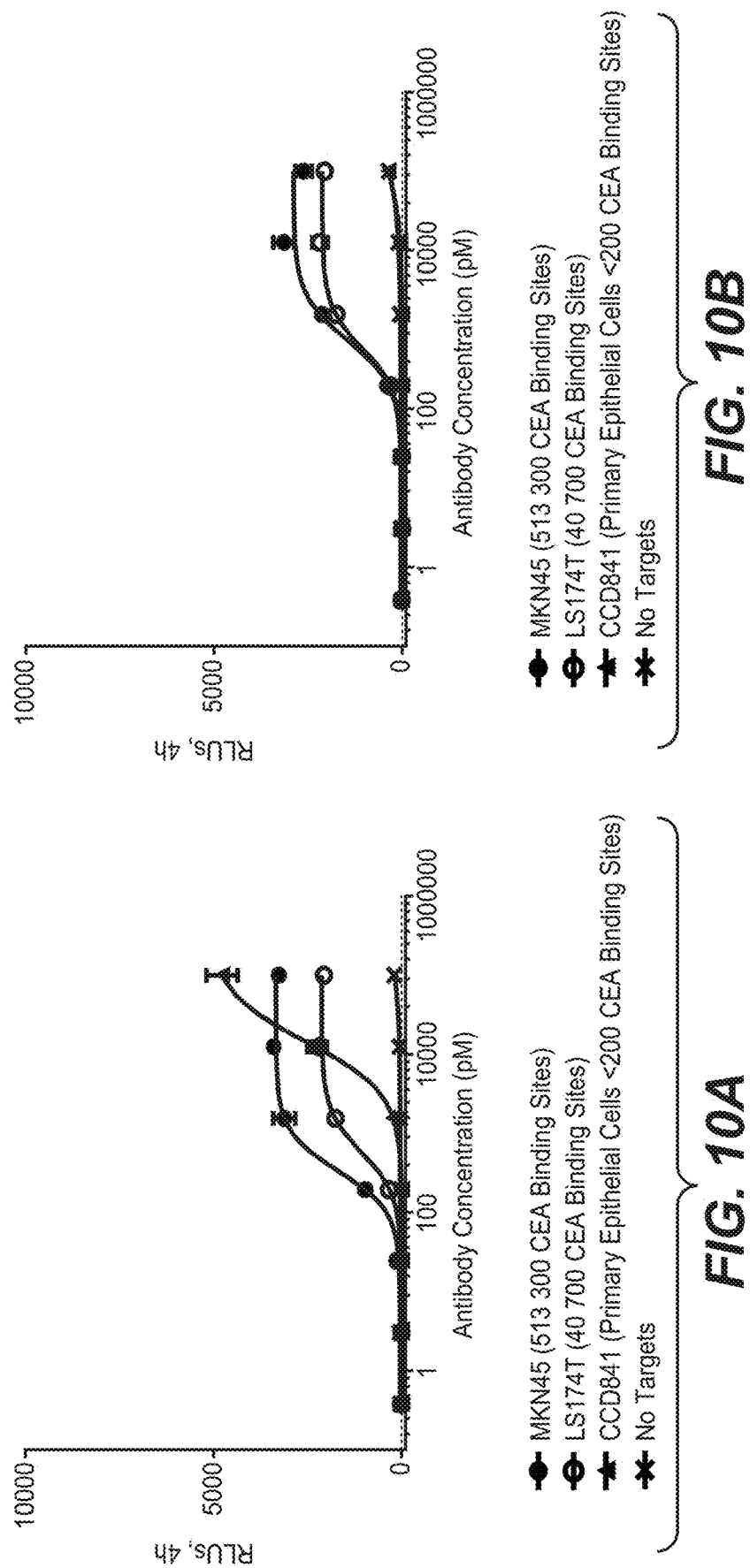

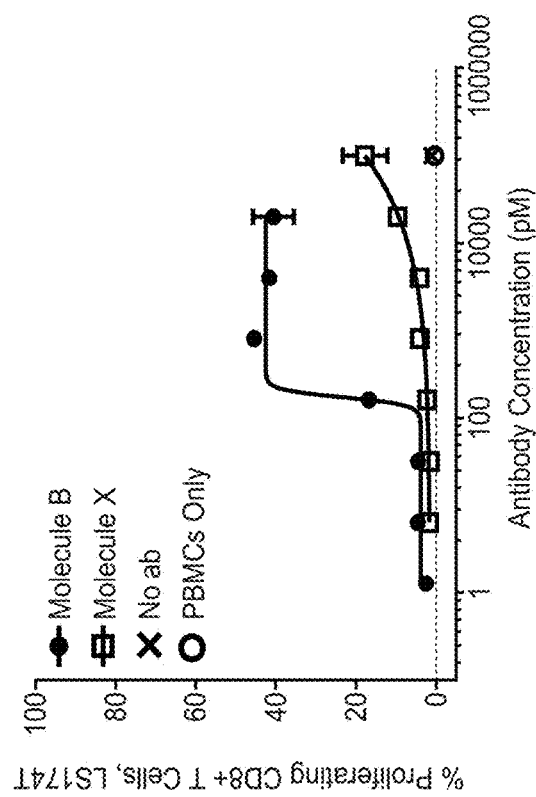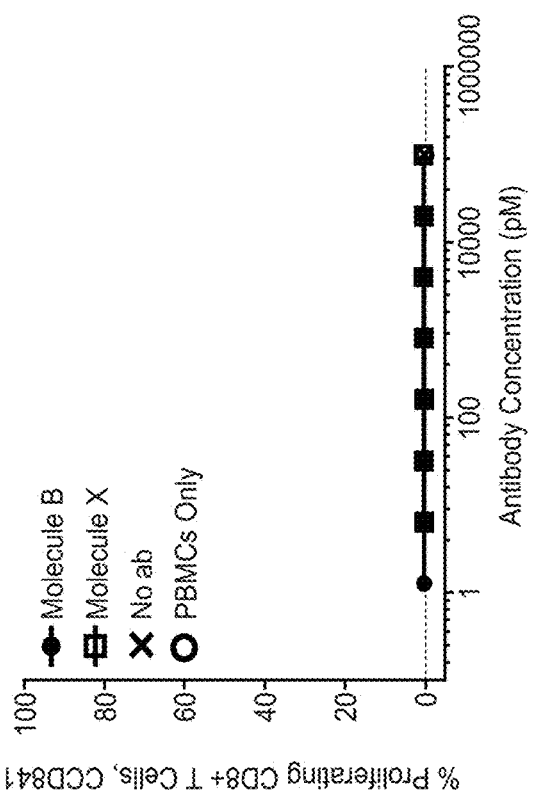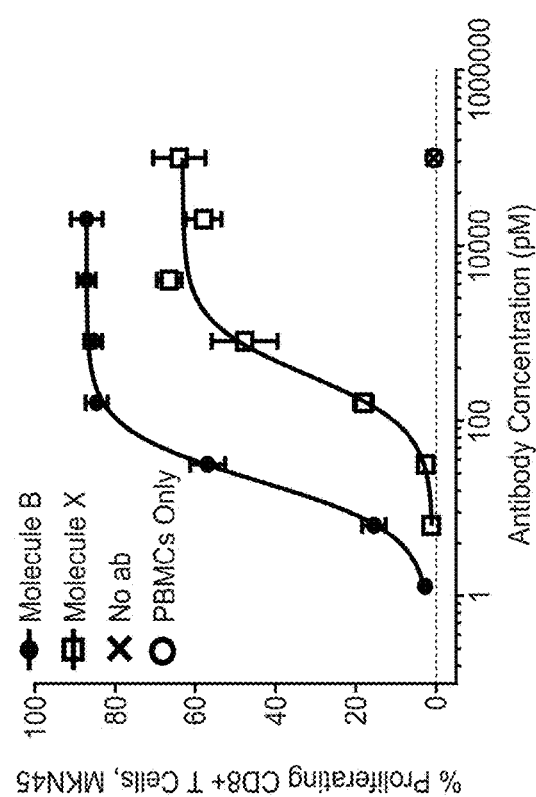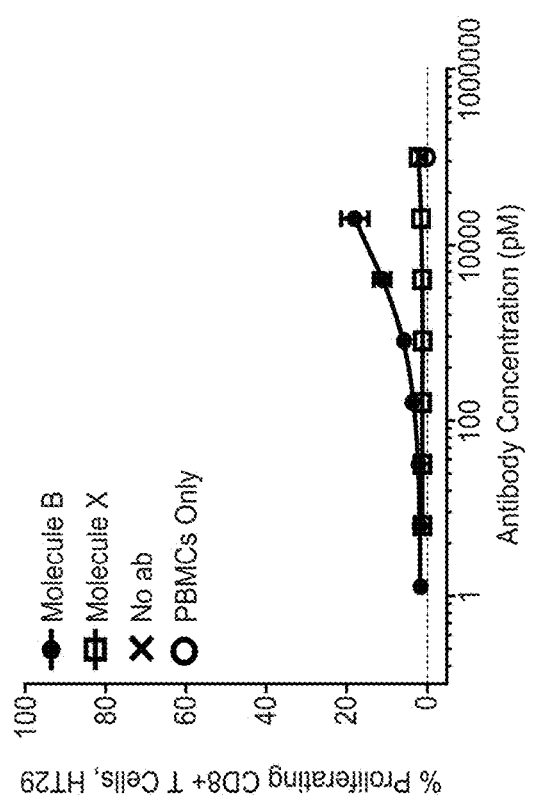

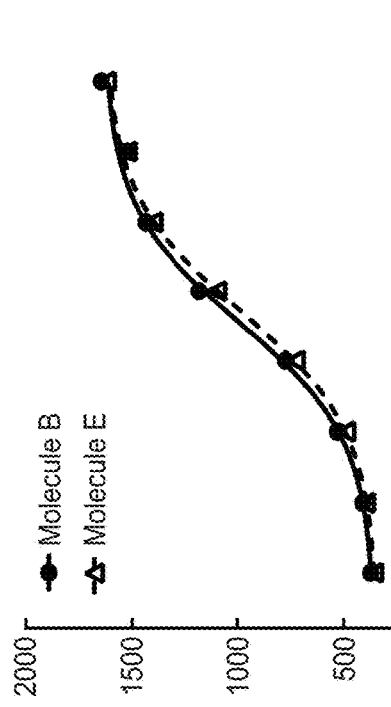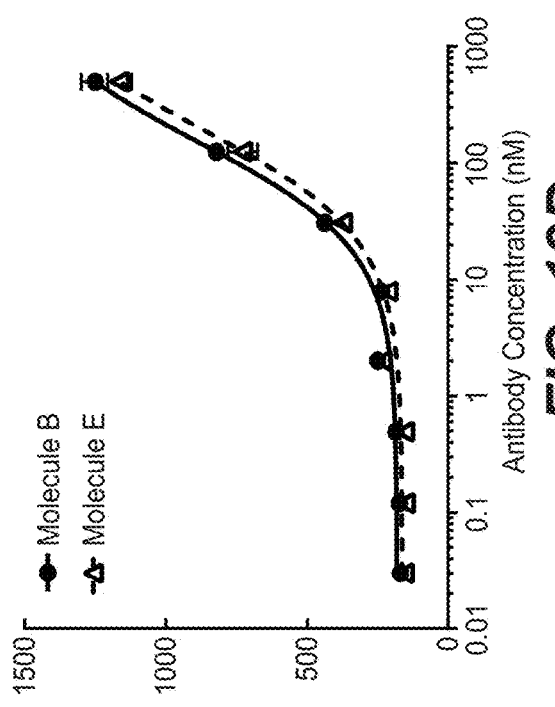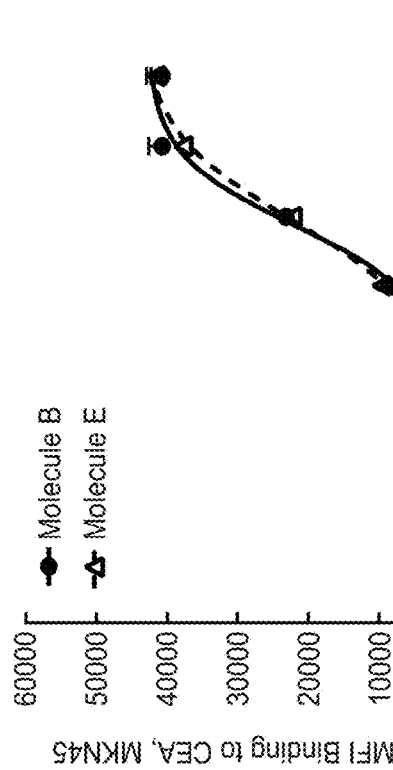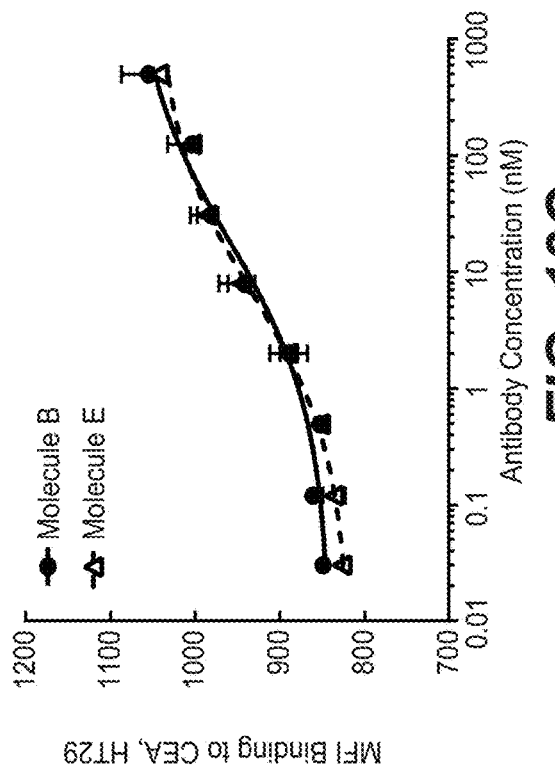

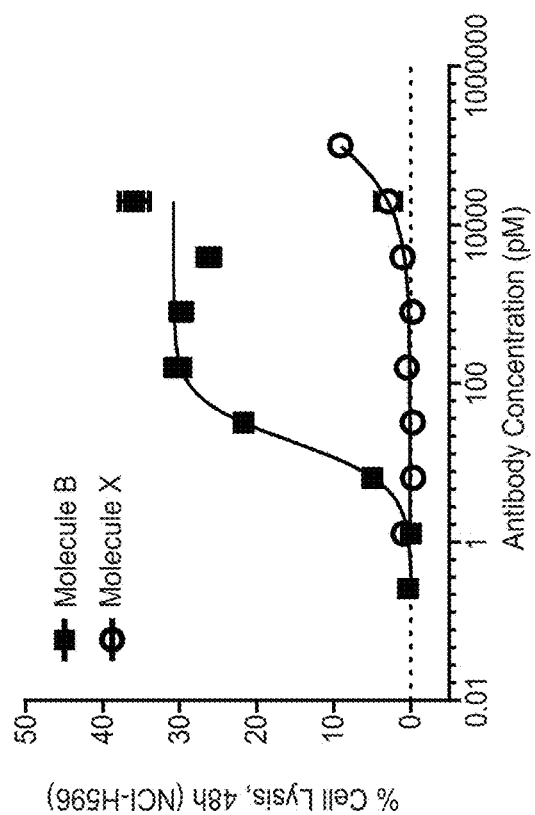
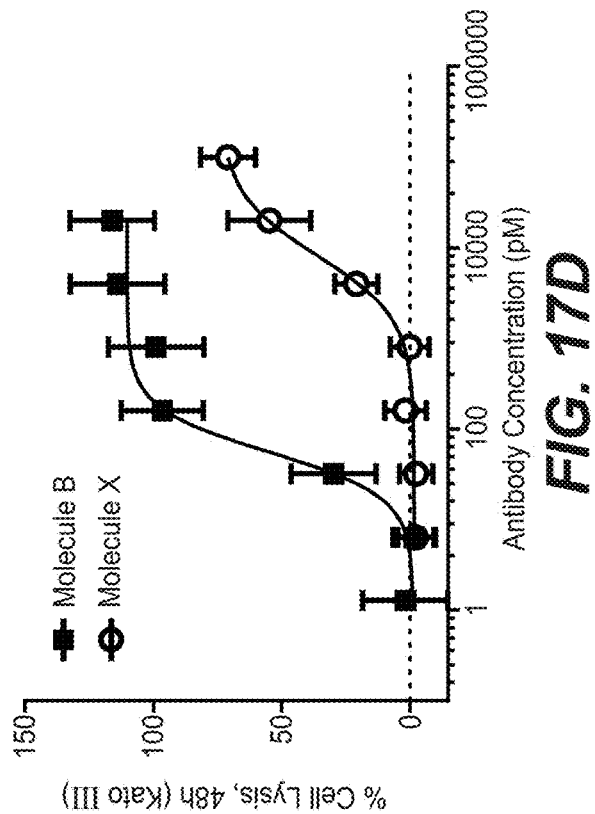
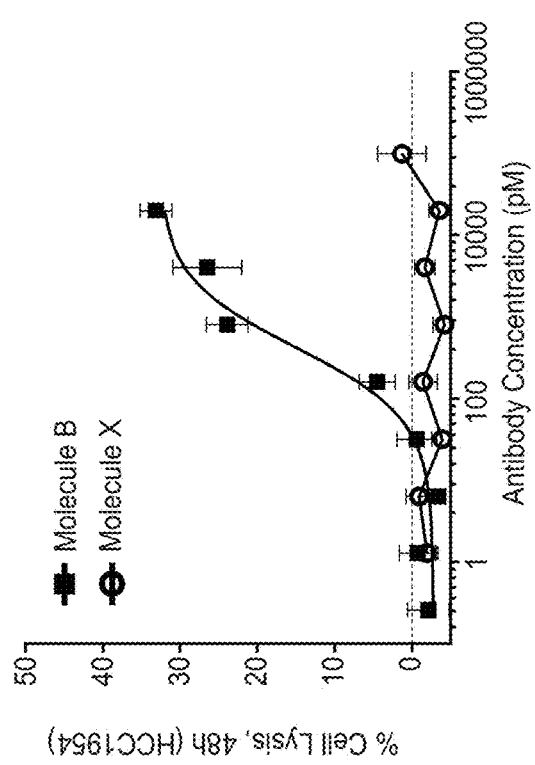
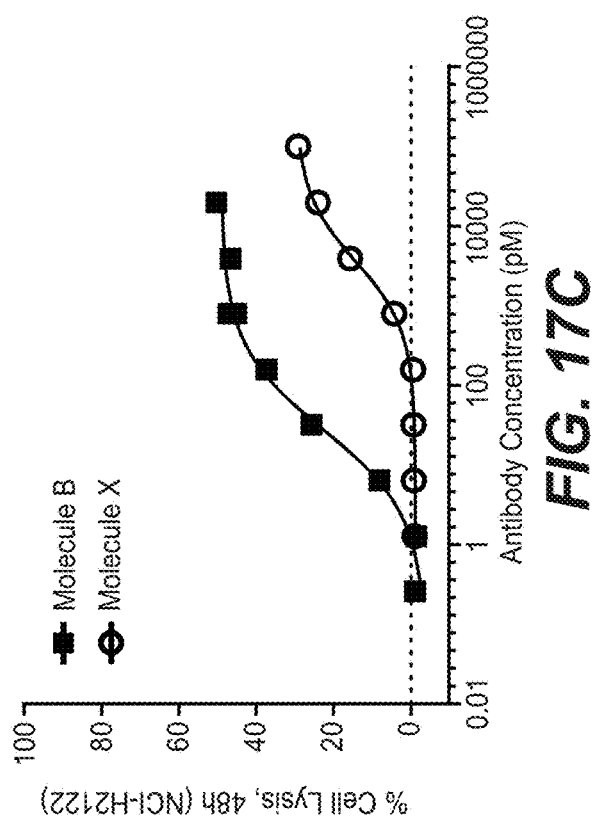
FIG. 17A
FIG. 17B
FIG. 17C
FIG. 17D

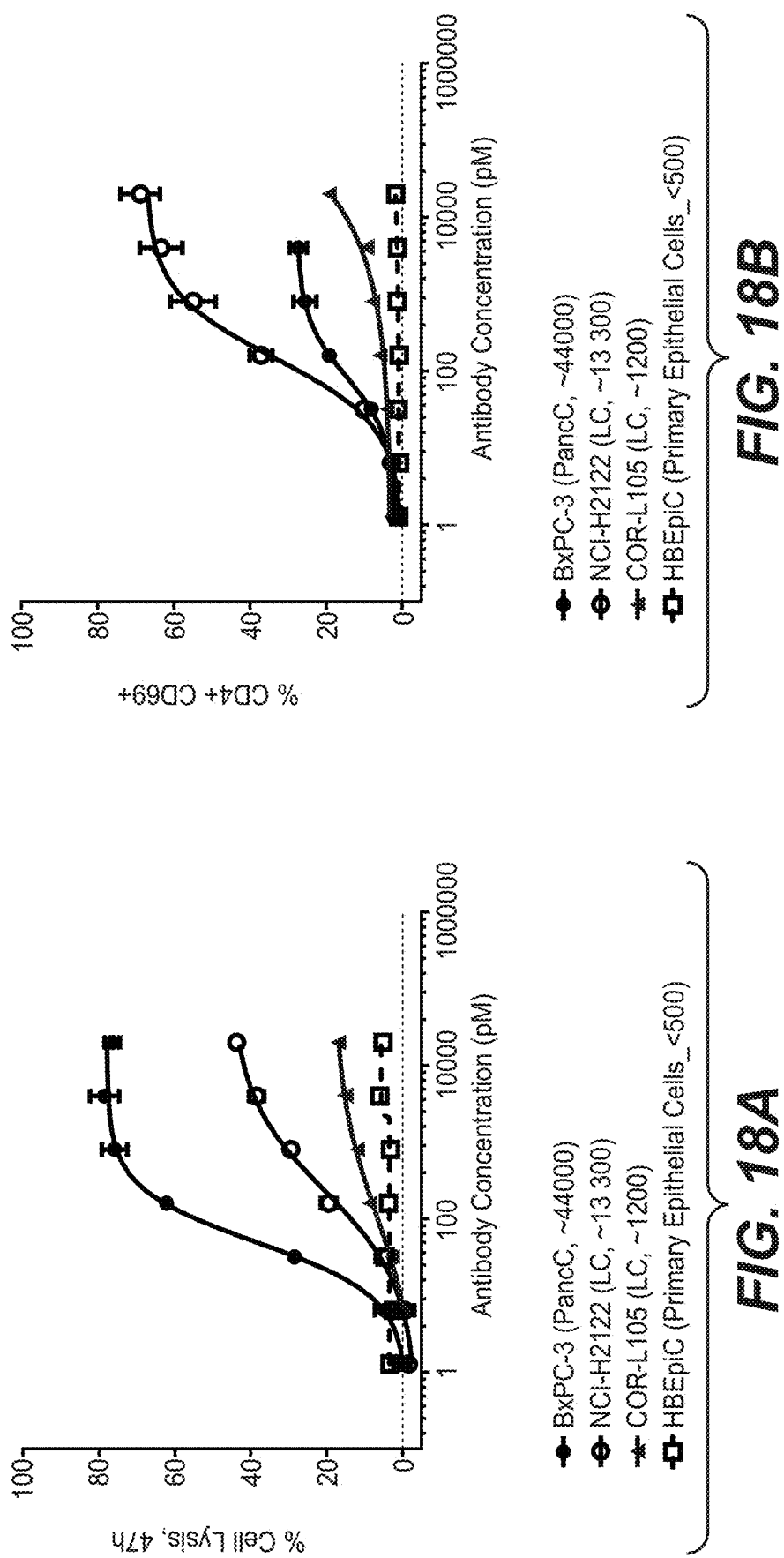

| Treatment 1 vs. Treatment 2 | Statistical Power |
|---|---|
| vehicle vs. molecule X 0.5 mg/kg twice/week | **** |
| vehicle vs. molecule X 2.5 mg/kg twice/week | **** |
| vehicle vs. molecule X 12.5 mg/kg twice/week | **** |
| vehicle vs. molecule B 0.1 mg/kg once/week | **** |
| vehicle vs. molecule B 0.5 mg/kg once/week | **** |
| vehicle vs. molecule B 2.5 mg/kg once/week | **** |
| molecule X 0.5 mg/kg twice/week vs. molecule X 2.5 mg/kg twice/week | ** |
| molecule X 0.5 mg/kg twice/week vs. molecule X 12.5 mg/kg twice/week | *** |
| molecule X 0.5 mg/kg twice/week vs. molecule B 0.1 mg/kg once/week | ns |
| molecule X 0.5 mg/kg twice/week vs. molecule B 0.5 mg/kg once/week | **** |
| molecule X 0.5 mg/kg twice/week vs. molecule B 2.5 mg/kg once/week | **** |
| molecule X 2.5 mg/kg twice/week vs. molecule X 12.5 mg/kg twice/week | ns |
| molecule X 2.5 mg/kg twice/week vs. molecule B 0.1 mg/kg once/week | ns |
| molecule X 2.5 mg/kg twice/week vs. molecule B 0.5 mg/kg once/week | *** |
| molecule X 2.5 mg/kg twice/week vs. molecule B 2.5 mg/kg once/week | **** |
| molecule X 12.5 mg/kg twice/week vs. molecule B 0.1 mg/kg once/week | * |
| molecule X 12.5 mg/kg twice/week vs. molecule B 0.5 mg/kg once/week | ** |
| molecule X 12.5 mg/kg twice/week vs. molecule B 2.5 mg/kg once/week | **** |
| molecule B 0.1 mg/kg once/week vs. molecule B 0.5 mg/kg once/week | **** |
| molecule B 0.1 mg/kg once/week vs. molecule B 2.5 mg/kg once/week | **** |
| molecule B 0.5 mg/kg once/week vs. molecule B 2.5 mg/kg once/week | * |

FIG. 23B

SEQUENCE LISTING

```
<160> NUMBER OF SEQ ID NOS: 52

<210> SEQ ID NO 1
<211> LENGTH: 207
<212> TYPE: PRT
<213> ORGANISM: Homo sapiens

<400> SEQUENCE: 1

Met Gln Ser Gly Thr His Trp Arg Val Leu Gly Leu Cys Leu Leu Ser
1               5                   10                  15

Val Gly Val Trp Gly Gln Asp Gly Asn Glu Glu Met Gly Gly Ile Thr
            20                  25                  30

Gln Thr Pro Tyr Lys Val Ser Ile Ser Gly Thr Thr Val Ile Leu Thr
        35                  40                  45

Cys Pro Gln Tyr Pro Gly Ser Glu Ile Leu Trp Gln His Asn Asp Lys
    50                  55                  60

Asn Ile Gly Gly Asp Glu Asp Asp Lys Asn Ile Gly Ser Asp Glu Asp
65                  70                  75                  80

His Leu Ser Leu Lys Glu Phe Ser Glu Leu Glu Gln Ser Gly Tyr Tyr
                85                  90                  95

Val Cys Tyr Pro Arg Gly Ser Lys Pro Glu Asp Ala Asn Phe Tyr Leu
            100                 105                 110

Tyr Leu Arg Ala Arg Val Cys Glu Asn Cys Met Glu Met Asp Val Met
        115                 120                 125

Ser Val Ala Thr Ile Val Ile Val Asp Ile Cys Ile Thr Gly Gly Leu
    130                 135                 140

Leu Leu Leu Val Tyr Tyr Trp Ser Lys Asn Arg Lys Ala Lys Ala Lys
145                 150                 155                 160

Pro Val Thr Arg Gly Ala Gly Ala Gly Gly Arg Gln Arg Gly Gln Asn
                165                 170                 175

Lys Glu Arg Pro Pro Pro Val Pro Asn Pro Asp Tyr Glu Pro Ile Arg
            180                 185                 190

Lys Gly Gln Arg Asp Leu Tyr Ser Gly Leu Asn Gln Arg Arg Ile
        195                 200                 205

<210> SEQ ID NO 2
```

```
<211> LENGTH: 198
<212> TYPE: PRT
<213> ORGANISM: Macaca fascicularis

<400> SEQUENCE: 2

Met Gln Ser Gly Thr Arg Trp Arg Val Leu Gly Leu Cys Leu Leu Ser
1               5                   10                  15

Ile Gly Val Trp Gly Gln Asp Gly Asn Glu Glu Met Gly Ser Ile Thr
            20                  25                  30

Gln Thr Pro Tyr Gln Val Ser Ile Ser Gly Thr Thr Val Ile Leu Thr
        35                  40                  45

Cys Ser Gln His Leu Gly Ser Glu Ala Gln Trp Gln His Asn Gly Lys
    50                  55                  60

Asn Lys Glu Asp Ser Gly Asp Arg Leu Phe Leu Pro Glu Phe Ser Glu
65                  70                  75                  80

Met Glu Gln Ser Gly Tyr Tyr Val Cys Tyr Pro Arg Gly Ser Asn Pro
                85                  90                  95

Glu Asp Ala Ser His His Leu Tyr Leu Lys Ala Arg Val Cys Glu Asn
            100                 105                 110

Cys Met Glu Met Asp Val Met Ala Val Ala Thr Ile Val Ile Val Asp
        115                 120                 125

Ile Cys Ile Thr Leu Gly Leu Leu Leu Val Tyr Tyr Trp Ser Lys
    130                 135                 140

Asn Arg Lys Ala Lys Ala Lys Pro Val Thr Arg Gly Ala Gly Ala Gly
145                 150                 155                 160

Gly Arg Gln Arg Gly Gln Asn Lys Glu Arg Pro Pro Pro Val Pro Asn
                165                 170                 175

Pro Asp Tyr Glu Pro Ile Arg Lys Gly Gln Gln Asp Leu Tyr Ser Gly
            180                 185                 190

Leu Asn Gln Arg Arg Ile
            195

<210> SEQ ID NO 3
<211> LENGTH: 125
<212> TYPE: PRT
<213> ORGANISM: Artificial Sequence
<220> FEATURE:
<223> OTHER INFORMATION: CD3 VH

<400> SEQUENCE: 3

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125
```

<210> SEQ ID NO 4
<211> LENGTH: 5
<212> TYPE: PRT
<213> ORGANISM: Artificial Sequence
<220> FEATURE:
<223> OTHER INFORMATION: CD3 HCDR1

<400> SEQUENCE: 4

Thr Tyr Ala Met Asn
1               5

<210> SEQ ID NO 5
<211> LENGTH: 19
<212> TYPE: PRT
<213> ORGANISM: Artificial Sequence
<220> FEATURE:
<223> OTHER INFORMATION: CD3 HCDR2

<400> SEQUENCE: 5

Arg Ile Arg Ser Lys Tyr Asn Asn Tyr Ala Thr Tyr Tyr Ala Asp Ser
1               5                   10                  15

Val Lys Gly

<210> SEQ ID NO 6
<211> LENGTH: 14
<212> TYPE: PRT
<213> ORGANISM: Artificial Sequence
<220> FEATURE:
<223> OTHER INFORMATION: CD3 HCDR3

<400> SEQUENCE: 6

His Gly Asn Phe Gly Asn Ser Tyr Val Ser Trp Phe Ala Tyr
1               5                   10

<210> SEQ ID NO 7
<211> LENGTH: 109
<212> TYPE: PRT
<213> ORGANISM: Artificial Sequence
<220> FEATURE:
<223> OTHER INFORMATION: CD3 VL

<400> SEQUENCE: 7

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
                20                  25                  30

Asn Tyr Ala Asn Trp Val Gln Glu Lys Pro Gly Gln Ala Phe Arg Gly
            35                  40                  45

Leu Ile Gly Gly Thr Asn Lys Arg Ala Pro Gly Thr Pro Ala Arg Phe
        50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu
            100                 105

<210> SEQ ID NO 8
<211> LENGTH: 14
<212> TYPE: PRT
<213> ORGANISM: Artificial Sequence
<220> FEATURE:
<223> OTHER INFORMATION: CD3 LCDR1

```
<400> SEQUENCE: 8

Gly Ser Ser Thr Gly Ala Val Thr Thr Ser Asn Tyr Ala Asn
1               5                   10

<210> SEQ ID NO 9
<211> LENGTH: 7
<212> TYPE: PRT
<213> ORGANISM: Artificial Sequence
<220> FEATURE:
<223> OTHER INFORMATION: CD3 LCDR2

<400> SEQUENCE: 9

Gly Thr Asn Lys Arg Ala Pro
1               5

<210> SEQ ID NO 10
<211> LENGTH: 9
<212> TYPE: PRT
<213> ORGANISM: Artificial Sequence
<220> FEATURE:
<223> OTHER INFORMATION: CD3 LCDR3

<400> SEQUENCE: 10

Ala Leu Trp Tyr Ser Asn Leu Trp Val
1               5

<210> SEQ ID NO 11
<211> LENGTH: 10
<212> TYPE: PRT
<213> ORGANISM: Artificial Sequence
<220> FEATURE:
<223> OTHER INFORMATION: linker

<400> SEQUENCE: 11

Gly Gly Gly Gly Ser Gly Gly Gly Gly Ser
1               5                   10

<210> SEQ ID NO 12
<211> LENGTH: 11
<212> TYPE: PRT
<213> ORGANISM: Artificial Sequence
<220> FEATURE:
<223> OTHER INFORMATION: linker

<400> SEQUENCE: 12

Asp Gly Gly Gly Gly Ser Gly Gly Gly Gly Ser
1               5                   10

<210> SEQ ID NO 13
<211> LENGTH: 225
<212> TYPE: PRT
<213> ORGANISM: Homo sapiens

<400> SEQUENCE: 13

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Asn Ser Thr Tyr
```

-continued

```
            65                  70                  75                  80
Arg Val Val Ser Val Leu Thr Val Leu His Gln Asp Trp Leu Asn Gly
                    85                  90                  95
Lys Glu Tyr Lys Cys Lys Val Ser Asn Lys Ala Leu Pro Ala Pro Ile
                100                 105                 110
Glu Lys Thr Ile Ser Lys Ala Lys Gly Gln Pro Arg Glu Pro Gln Val
            115                 120                 125
Tyr Thr Leu Pro Pro Ser Arg Asp Glu Leu Thr Lys Asn Gln Val Ser
        130                 135                 140
Leu Thr Cys Leu Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Asp Ser Asp Gly Ser Phe Phe Leu Tyr Ser Lys Leu Thr Val
                180                 185                 190
Asp Lys Ser Arg Trp Gln Gln Gly Asn Val Phe Ser Cys Ser Val Met
                195                 200                 205
His Glu Ala Leu His Asn His Tyr Thr Gln Lys Ser Leu Ser Leu Ser
            210                 215                 220
Pro
225

<210> SEQ ID NO 14
<211> LENGTH: 5
<212> TYPE: PRT
<213> ORGANISM: Mus musculus

<400> SEQUENCE: 14

Asp Thr Tyr Met His
1               5

<210> SEQ ID NO 15
<211> LENGTH: 17
<212> TYPE: PRT
<213> ORGANISM: Mus musculus

<400> SEQUENCE: 15

Arg Ile Asp Pro Ala Asn Gly Asn Ser Lys Tyr Val Pro Lys Phe Gln
1               5                   10                  15
Gly

<210> SEQ ID NO 16
<211> LENGTH: 12
<212> TYPE: PRT
<213> ORGANISM: Mus musculus

<400> SEQUENCE: 16

Phe Gly Tyr Tyr Val Ser Asp Tyr Ala Met Ala Tyr
1               5                   10

<210> SEQ ID NO 17
<211> LENGTH: 15
<212> TYPE: PRT
<213> ORGANISM: Mus musculus

<400> SEQUENCE: 17

Arg Ala Gly Glu Ser Val Asp Ile Phe Gly Val Gly Phe Leu His
1               5                   10                  15
```

```
<210> SEQ ID NO 18
<211> LENGTH: 7
<212> TYPE: PRT
<213> ORGANISM: Mus musculus

<400> SEQUENCE: 18

Arg Ala Ser Asn Arg Ala Thr
1               5

<210> SEQ ID NO 19
<211> LENGTH: 9
<212> TYPE: PRT
<213> ORGANISM: Mus musculus

<400> SEQUENCE: 19

Gln Gln Thr Asn Glu Asp Pro Tyr Thr
1               5

<210> SEQ ID NO 20
<211> LENGTH: 121
<212> TYPE: PRT
<213> ORGANISM: Mus musculus

<400> SEQUENCE: 20

Glu Val Gln Leu Gln Gln Ser Gly Ala Glu Leu Val Glu Pro Gly Ala
1               5                   10                  15

Ser Val Lys Leu Ser Cys Thr Ala Ser Gly Phe Asn Ile Lys Asp Thr
            20                  25                  30

Tyr Met His Trp Val Lys Gln Arg Pro Glu Gln Gly Leu Glu Trp Ile
        35                  40                  45

Gly Arg Ile Asp Pro Ala Asn Gly Asn Ser Lys Tyr Val Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Thr Ser Leu Thr Ser Glu Asp Thr Ala Val Tyr Tyr Cys
                85                  90                  95

Ala Pro Phe Gly Tyr Tyr Val Ser Asp Tyr Ala Met Ala Tyr Trp Gly
            100                 105                 110

Gln Gly Thr Ser Val Thr Val Ser Ser
        115                 120

<210> SEQ ID NO 21
<211> LENGTH: 111
<212> TYPE: PRT
<213> ORGANISM: Mus musculus

<400> SEQUENCE: 21

Asp Ile Val Leu Thr Gln Ser Pro Ala Ser Leu Ala Val Ser Leu Gly
1               5                   10                  15

Gln Arg Ala Thr Met Ser Cys Arg Ala Gly Glu Ser Val Asp Ile Phe
            20                  25                  30

Gly Val Gly Phe Leu His Trp Tyr Gln Gln Lys Pro Gly Gln Pro Pro
        35                  40                  45

Lys Leu Leu Ile Tyr Arg Ala Ser Asn Leu Glu Ser Gly Ile Pro Val
    50                  55                  60

Arg Phe Ser Gly Thr Gly Ser Arg Thr Asp Phe Thr Leu Ile Ile Asp
65                  70                  75                  80

Pro Val Glu Ala Asp Asp Val Ala Thr Tyr Tyr Cys Gln Gln Thr Asn
                85                  90                  95
```

Glu Asp Pro Tyr Thr Phe Gly Gly Gly Thr Lys Leu Glu Ile Lys
            100                 105                 110

<210> SEQ ID NO 22
<211> LENGTH: 121
<212> TYPE: PRT
<213> ORGANISM: Artificial Sequence
<220> FEATURE:
<223> OTHER INFORMATION: Humanized CEA binder VH

<400> SEQUENCE: 22

Gln Val Gln Leu Val Gln Ser Gly Ala Glu Val Lys Lys Pro Gly Ser
1               5                   10                  15

Ser Val Lys Val Ser Cys Lys Ala Ser Gly Phe Asn Ile Lys Asp Thr
            20                  25                  30

Tyr Met His Trp Val Arg Gln Ala Pro Gly Gln Gly Leu Glu Trp Met
        35                  40                  45

Gly Arg Ile Asp Pro Ala Asn Gly Asn Ser Lys Tyr Val Pro Lys Phe
    50                  55                  60

Gln Gly Arg Val Thr Ile Thr Ala Asp Thr Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Pro Phe Gly Tyr Tyr Val Ser Asp Tyr Ala Met Ala Tyr Trp Gly
            100                 105                 110

Gln Gly Thr Leu Val Thr Val Ser Ser
        115                 120

<210> SEQ ID NO 23
<211> LENGTH: 111
<212> TYPE: PRT
<213> ORGANISM: Artificial Sequence
<220> FEATURE:
<223> OTHER INFORMATION: Humanized CEA binder VL

<400> SEQUENCE: 23

Glu Ile Val Leu Thr Gln Ser Pro Ala Thr Leu Ser Leu Ser Pro Gly
1               5                   10                  15

Glu Arg Ala Thr Leu Ser Cys Arg Ala Gly Glu Ser Val Asp Ile Phe
            20                  25                  30

Gly Val Gly Phe Leu His Trp Tyr Gln Gln Lys Pro Gly Gln Ala Pro
        35                  40                  45

Arg Leu Leu Ile Tyr Arg Ala Ser Asn Arg Ala Thr Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln Gln Thr Asn
                85                  90                  95

Glu Asp Pro Tyr Thr Phe Gly Gln Gly Thr Lys Leu Glu Ile Lys
            100                 105                 110

<210> SEQ ID NO 24
<211> LENGTH: 5
<212> TYPE: PRT
<213> ORGANISM: Artificial Sequence
<220> FEATURE:
<223> OTHER INFORMATION: CEA HCDR1

<400> SEQUENCE: 24

Glu Phe Gly Met Asn

```
<210> SEQ ID NO 25
<211> LENGTH: 17
<212> TYPE: PRT
<213> ORGANISM: Artificial Sequence
<220> FEATURE:
<223> OTHER INFORMATION: CEA HCDR2

<400> SEQUENCE: 25

Trp Ile Asn Thr Lys Thr Gly Glu Ala Thr Tyr Val Glu Glu Phe Lys
1               5                   10                  15
Gly

<210> SEQ ID NO 26
<211> LENGTH: 12
<212> TYPE: PRT
<213> ORGANISM: Artificial Sequence
<220> FEATURE:
<223> OTHER INFORMATION: CEA HCDR3

<400> SEQUENCE: 26

Trp Asp Phe Ala Tyr Tyr Val Glu Ala Met Asp Tyr
1               5                   10

<210> SEQ ID NO 27
<211> LENGTH: 11
<212> TYPE: PRT
<213> ORGANISM: Artificial Sequence
<220> FEATURE:
<223> OTHER INFORMATION: CEA LCDR1

<400> SEQUENCE: 27

Lys Ala Ser Ala Ala Val Gly Thr Tyr Val Ala
1               5                   10

<210> SEQ ID NO 28
<211> LENGTH: 7
<212> TYPE: PRT
<213> ORGANISM: Artificial Sequence
<220> FEATURE:
<223> OTHER INFORMATION: CEA LCDR2

<400> SEQUENCE: 28

Ser Ala Ser Tyr Arg Lys Arg
1               5

<210> SEQ ID NO 29
<211> LENGTH: 10
<212> TYPE: PRT
<213> ORGANISM: Artificial Sequence
<220> FEATURE:
<223> OTHER INFORMATION: CEA LCDR3

<400> SEQUENCE: 29

His Gln Tyr Tyr Thr Tyr Pro Leu Phe Thr
1               5                   10

<210> SEQ ID NO 30
<211> LENGTH: 121
<212> TYPE: PRT
<213> ORGANISM: Artificial Sequence
<220> FEATURE:
<223> OTHER INFORMATION: CEA VH

<400> SEQUENCE: 30
```

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Phe
            20                  25                  30

Gly Met Asn Trp Val Arg Gln Ala Pro Gly Gln Gly Leu Glu Trp Met
        35                  40                  45

Gly Trp Ile Asn Thr Lys Thr Gly Glu Ala Thr Tyr Val Glu Glu Phe
    50                  55                  60

Lys Gly Arg Val Thr Phe Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Trp Asp Phe Ala Tyr Tyr Val Glu Ala Met Asp Tyr Trp Gly
            100                 105                 110

Gln Gly Thr Thr Val Thr Val Ser Ser
            115                 120
```

<210> SEQ ID NO 31
<211> LENGTH: 108
<212> TYPE: PRT
<213> ORGANISM: Artificial Sequence
<220> FEATURE:
<223> OTHER INFORMATION: CEA VL

<400> SEQUENCE: 31

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Ala Ala Val Gly Thr Tyr
            20                  25                  30

Val Ala Trp Tyr Gln Gln Lys Pro Gly Lys Ala Pro Lys Leu Leu Ile
        35                  40                  45

Tyr Ser Ala Ser Tyr Arg Lys Arg Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys His Gln Tyr Tyr Thr Tyr Pro Leu
                85                  90                  95

Phe Thr Phe Gly Gln Gly Thr Lys Leu Glu Ile Lys
            100                 105
```

<210> SEQ ID NO 32
<211> LENGTH: 449
<212> TYPE: PRT
<213> ORGANISM: Artificial Sequence
<220> FEATURE:
<223> OTHER INFORMATION: parental CEA VH-CH1(EE)-Fc (hole, P329G LALA)

<400> SEQUENCE: 32

```
Glu Val Gln Leu Gln Gln Ser Gly Ala Glu Leu Val Glu Pro Gly Ala
1               5                   10                  15

Ser Val Lys Leu Ser Cys Thr Ala Ser Gly Phe Asn Ile Lys Asp Thr
            20                  25                  30

Tyr Met His Trp Val Lys Gln Arg Pro Glu Gln Gly Leu Glu Trp Ile
        35                  40                  45

Gly Arg Ile Asp Pro Ala Asn Gly Asn Ser Lys Tyr Val Pro Lys Phe
    50                  55                  60

Gln Gly Lys Ala Thr Ile Thr Ala Asp Thr Ser Ser Asn Thr Ala Tyr
65                  70                  75                  80
```

Leu Gln Leu Thr Ser Leu Thr Ser Glu Asp Thr Ala Val Tyr Tyr Cys
                85                  90                  95

Ala Pro Phe Gly Tyr Tyr Val Ser Asp Tyr Ala Met Ala Tyr Trp Gly
            100                 105                 110

Gln Gly Thr Ser Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Glu Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Glu Lys Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Gly Ala Pro Ile
                325                 330                 335

Glu Lys Thr Ile Ser Lys Ala Lys Gly Gln Pro Arg Glu Pro Gln Val
            340                 345                 350

Cys Thr Leu Pro Pro Ser Arg Asp Glu Leu Thr Lys Asn Gln Val Ser
        355                 360                 365

Leu Ser Cys Ala Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Val Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro

<210> SEQ ID NO 33
<211> LENGTH: 674
<212> TYPE: PRT
<213> ORGANISM: Artificial Sequence
<220> FEATURE:
<223> OTHER INFORMATION: parental CEA VH-CH1(EE)-CD3 VL-CH1-Fc (knob,

P329G LALA)

<400> SEQUENCE: 33

| | | | | | | | | | | | | | | |
|---|---|---|---|---|---|---|---|---|---|---|---|---|---|---|
| Glu | Val | Gln | Leu | Gln | Gln | Ser | Gly | Ala | Glu | Leu | Val | Glu | Pro | Gly | Ala |
| 1 | | | | 5 | | | | | 10 | | | | | 15 | |
| Ser | Val | Lys | Leu | Ser | Cys | Thr | Ala | Ser | Gly | Phe | Asn | Ile | Lys | Asp | Thr |
| | | | 20 | | | | | 25 | | | | | 30 | | |
| Tyr | Met | His | Trp | Val | Lys | Gln | Arg | Pro | Glu | Gln | Gly | Leu | Glu | Trp | Ile |
| | | 35 | | | | | 40 | | | | | 45 | | | |
| Gly | Arg | Ile | Asp | Pro | Ala | Asn | Gly | Asn | Ser | Lys | Tyr | Val | Pro | Lys | Phe |
| | 50 | | | | | 55 | | | | | 60 | | | | |
| Gln | Gly | Lys | Ala | Thr | Ile | Thr | Ala | Asp | Thr | Ser | Ser | Asn | Thr | Ala | Tyr |
| 65 | | | | | 70 | | | | | 75 | | | | | 80 |
| Leu | Gln | Leu | Thr | Ser | Leu | Thr | Ser | Glu | Asp | Thr | Ala | Val | Tyr | Tyr | Cys |
| | | | | 85 | | | | | 90 | | | | | 95 | |
| Ala | Pro | Phe | Gly | Tyr | Tyr | Val | Ser | Asp | Tyr | Ala | Met | Ala | Tyr | Trp | Gly |
| | | | 100 | | | | | 105 | | | | | 110 | | |
| Gln | Gly | Thr | Ser | Val | Thr | Val | Ser | Ser | Ala | Ser | Thr | Lys | Gly | Pro | Ser |
| | | 115 | | | | | 120 | | | | | 125 | | | |
| Val | Phe | Pro | Leu | Ala | Pro | Ser | Ser | Lys | Ser | Thr | Ser | Gly | Gly | Thr | Ala |
| | 130 | | | | | 135 | | | | | 140 | | | | |
| Ala | Leu | Gly | Cys | Leu | Val | Glu | Asp | Tyr | Phe | Pro | Glu | Pro | Val | Thr | Val |
| 145 | | | | | 150 | | | | | 155 | | | | | 160 |
| Ser | Trp | Asn | Ser | Gly | Ala | Leu | Thr | Ser | Gly | Val | His | Thr | Phe | Pro | Ala |
| | | | | 165 | | | | | 170 | | | | | 175 | |
| Val | Leu | Gln | Ser | Ser | Gly | Leu | Tyr | Ser | Leu | Ser | Ser | Val | Val | Thr | Val |
| | | | | 180 | | | | | 185 | | | | | 190 | |
| Pro | Ser | Ser | Ser | Leu | Gly | Thr | Gln | Thr | Tyr | Ile | Cys | Asn | Val | Asn | His |
| | | | 195 | | | | | 200 | | | | | 205 | | |
| Lys | Pro | Ser | Asn | Thr | Lys | Val | Asp | Glu | Lys | Val | Glu | Pro | Lys | Ser | Cys |
| | 210 | | | | | 215 | | | | | 220 | | | | |
| Asp | Gly | Gly | Gly | Gly | Ser | Gly | Gly | Gly | Gly | Ser | Gln | Ala | Val | Val | Thr |
| 225 | | | | | 230 | | | | | 235 | | | | | 240 |
| Gln | Glu | Pro | Ser | Leu | Thr | Val | Ser | Pro | Gly | Gly | Thr | Val | Thr | Leu | Thr |
| | | | | 245 | | | | | 250 | | | | | 255 | |
| Cys | Gly | Ser | Ser | Thr | Gly | Ala | Val | Thr | Thr | Ser | Asn | Tyr | Ala | Asn | Trp |
| | | | | 260 | | | | | 265 | | | | | 270 | |
| Val | Gln | Glu | Lys | Pro | Gly | Gln | Ala | Phe | Arg | Gly | Leu | Ile | Gly | Gly | Thr |
| | | | 275 | | | | | 280 | | | | | 285 | | |
| Asn | Lys | Arg | Ala | Pro | Gly | Thr | Pro | Ala | Arg | Phe | Ser | Gly | Ser | Leu | Leu |
| | | 290 | | | | | 295 | | | | | 300 | | | |
| Gly | Gly | Lys | Ala | Ala | Leu | Thr | Leu | Ser | Gly | Ala | Gln | Pro | Glu | Asp | Glu |
| 305 | | | | | 310 | | | | | 315 | | | | | 320 |
| Ala | Glu | Tyr | Tyr | Cys | Ala | Leu | Trp | Tyr | Ser | Asn | Leu | Trp | Val | Phe | Gly |
| | | | | 325 | | | | | 330 | | | | | 335 | |
| Gly | Gly | Thr | Lys | Leu | Thr | Val | Leu | Ser | Ser | Ala | Ser | Thr | Lys | Gly | Pro |
| | | | 340 | | | | | 345 | | | | | 350 | | |
| Ser | Val | Phe | Pro | Leu | Ala | Pro | Ser | Ser | Lys | Ser | Thr | Ser | Gly | Gly | Thr |
| | | | 355 | | | | | 360 | | | | | 365 | | |
| Ala | Ala | Leu | Gly | Cys | Leu | Val | Lys | Asp | Tyr | Phe | Pro | Glu | Pro | Val | Thr |
| | | 370 | | | | | 375 | | | | | 380 | | | |
| Val | Ser | Trp | Asn | Ser | Gly | Ala | Leu | Thr | Ser | Gly | Val | His | Thr | Phe | Pro |
| 385 | | | | | 390 | | | | | 395 | | | | | 400 |

```
Ala Val Leu Gln Ser Ser Gly Leu Tyr Ser Leu Ser Ser Val Val Thr
                405                 410                 415
Val Pro Ser Ser Ser Leu Gly Thr Gln Thr Tyr Ile Cys Asn Val Asn
                420                 425                 430
His Lys Pro Ser Asn Thr Lys Val Asp Lys Lys Val Glu Pro Lys Ser
                435                 440                 445
Cys Asp Lys Thr His Thr Cys Pro Pro Cys Pro Ala Pro Glu Ala Ala
                450                 455                 460
Gly Gly Pro Ser Val Phe Leu Phe Pro Pro Lys Pro Lys Asp Thr Leu
465                 470                 475                 480
Met Ile Ser Arg Thr Pro Glu Val Thr Cys Val Val Val Asp Val Ser
                485                 490                 495
His Glu Asp Pro Glu Val Lys Phe Asn Trp Tyr Val Asp Gly Val Glu
                500                 505                 510
Val His Asn Ala Lys Thr Lys Pro Arg Glu Glu Gln Tyr Asn Ser Thr
                515                 520                 525
Tyr Arg Val Val Ser Val Leu Thr Val Leu His Gln Asp Trp Leu Asn
                530                 535                 540
Gly Lys Glu Tyr Lys Cys Lys Val Ser Asn Lys Ala Leu Gly Ala Pro
545                 550                 555                 560
Ile Glu Lys Thr Ile Ser Lys Ala Lys Gly Gln Pro Arg Glu Pro Gln
                565                 570                 575
Val Tyr Thr Leu Pro Pro Cys Arg Asp Glu Leu Thr Lys Asn Gln Val
                580                 585                 590
Ser Leu Trp Cys Leu Val Lys Gly Phe Tyr Pro Ser Asp Ile Ala Val
                595                 600                 605
Glu Trp Glu Ser Asn Gly Gln Pro Glu Asn Asn Tyr Lys Thr Thr Pro
                610                 615                 620
Pro Val Leu Asp Ser Asp Gly Ser Phe Phe Leu Tyr Ser Lys Leu Thr
625                 630                 635                 640
Val Asp Lys Ser Arg Trp Gln Gln Gly Asn Val Phe Ser Cys Ser Val
                645                 650                 655
Met His Glu Ala Leu His Asn His Tyr Thr Gln Lys Ser Leu Ser Leu
                660                 665                 670
Ser Pro

<210> SEQ ID NO 34
<211> LENGTH: 232
<212> TYPE: PRT
<213> ORGANISM: Artificial Sequence
<220> FEATURE:
<223> OTHER INFORMATION: CD3 VH-CL

<400> SEQUENCE: 34

Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Thr Tyr
                20                  25                  30
Ala Met Asn Trp Val Arg Gln Ala Pro Gly Lys Gly Leu Glu Trp Val
                35                  40                  45
Ser Arg Ile Arg Ser Lys Tyr Asn Asn Tyr Ala Thr Tyr Tyr Ala Asp
                50                  55                  60
Ser Val Lys Gly Arg Phe Thr Ile Ser Arg Asp Asp Ser Lys Asn Thr
65                  70                  75                  80
Leu Tyr Leu Gln Met Asn Ser Leu Arg Ala Glu Asp Thr Ala Val Tyr
```

```
                    85                  90                  95
Tyr Cys Val Arg His Gly Asn Phe Gly Asn Ser Tyr Val Ser Trp Phe
                100                 105                 110

Ala Tyr Trp Gly Gln Gly Thr Leu Val Thr Val Ser Ser Ala Ser Val
            115                 120                 125

Ala Ala Pro Ser Val Phe Ile Phe Pro Pro Ser Asp Glu Gln Leu Lys
        130                 135                 140

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
                165                 170                 175

Ser Gln Glu Ser Val Thr Glu Gln Asp Ser Lys Asp Ser Thr Tyr Ser
            180                 185                 190

Leu Ser Ser Thr Leu Thr Leu Ser Lys Ala Asp Tyr Glu Lys His Lys
        195                 200                 205

Val Tyr Ala Cys Glu Val Thr His Gln Gly Leu Ser Ser Pro Val Thr
    210                 215                 220

Lys Ser Phe Asn Arg Gly Glu Cys
225                 230

<210> SEQ ID NO 35
<211> LENGTH: 218
<212> TYPE: PRT
<213> ORGANISM: Artificial Sequence
<220> FEATURE:
<223> OTHER INFORMATION: parental CEA VL-CL(RK)

<400> SEQUENCE: 35

Asp Ile Val Leu Thr Gln Ser Pro Ala Ser Leu Ala Val Ser Leu Gly
1               5                   10                  15

Gln Arg Ala Thr Met Ser Cys Arg Ala Gly Glu Ser Val Asp Ile Phe
            20                  25                  30

Gly Val Gly Phe Leu His Trp Tyr Gln Gln Lys Pro Gly Gln Pro Pro
        35                  40                  45

Lys Leu Leu Ile Tyr Arg Ala Ser Asn Leu Glu Ser Gly Ile Pro Val
50                  55                  60

Arg Phe Ser Gly Thr Gly Ser Arg Thr Asp Phe Thr Leu Ile Ile Asp
65                  70                  75                  80

Pro Val Glu Ala Asp Asp Val Ala Thr Tyr Tyr Cys Gln Gln Thr Asn
                85                  90                  95

Glu Asp Pro Tyr Thr Phe Gly Gly Gly Thr Lys Leu Glu Ile Lys Arg
            100                 105                 110

Thr Val Ala Ala Pro Ser Val Phe Ile Phe Pro Pro Ser Asp Arg Lys
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
```

<210> SEQ ID NO 36
<211> LENGTH: 449
<212> TYPE: PRT
<213> ORGANISM: Artificial Sequence
<220> FEATURE:
<223> OTHER INFORMATION: humanized CEA VH-CH1(EE)-Fc (hole, P329G LALA)

<400> SEQUENCE: 36

```
Gln Val Gln Leu Val Gln Ser Gly Ala Glu Val Lys Lys Pro Gly Ser
1               5                   10                  15
Ser Val Lys Val Ser Cys Lys Ala Ser Gly Phe Asn Ile Lys Asp Thr
            20                  25                  30
Tyr Met His Trp Val Arg Gln Ala Pro Gly Gln Gly Leu Glu Trp Met
        35                  40                  45
Gly Arg Ile Asp Pro Ala Asn Gly Asn Ser Lys Tyr Val Pro Lys Phe
    50                  55                  60
Gln Gly Arg Val Thr Ile Thr Ala Asp Thr Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Pro Phe Gly Tyr Tyr Val Ser Asp Tyr Ala Met Ala Tyr Trp Gly
            100                 105                 110
Gln Gly Thr Leu Val Thr Val Ser Ser Ala Ser Thr Lys Gly Pro Ser
        115                 120                 125
Val Phe Pro Leu Ala Pro Ser Ser Lys Ser Thr Ser Gly Gly Thr Ala
    130                 135                 140
Ala Leu Gly Cys Leu Val Glu Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Gln Thr Tyr Ile Cys Asn Val Asn His
        195                 200                 205
Lys Pro Ser Asn Thr Lys Val Asp Glu Lys Val Glu Pro Lys Ser Cys
    210                 215                 220
Asp Lys Thr His Thr Cys Pro Pro Cys Pro Ala Pro Glu Ala Ala Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
            260                 265                 270
Glu Asp Pro Glu Val Lys Phe Asn Trp Tyr Val Asp Gly Val Glu Val
        275                 280                 285
His Asn Ala Lys Thr Lys Pro Arg Glu Glu Gln Tyr Asn Ser Thr Tyr
    290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Gly Ala Pro Ile
                325                 330                 335
Glu Lys Thr Ile Ser Lys Ala Lys Gly Gln Pro Arg Glu Pro Gln Val
            340                 345                 350
Cys Thr Leu Pro Pro Ser Arg Asp Glu Leu Thr Lys Asn Gln Val Ser
```

```
                355                 360                 365
Leu Ser Cys Ala Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Val Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro

<210> SEQ ID NO 37
<211> LENGTH: 674
<212> TYPE: PRT
<213> ORGANISM: Artificial Sequence
<220> FEATURE:
<223> OTHER INFORMATION: humanized CEA VH-CH1(EE)-CD3 VL-CH1-Fc (knob,
      P329G LALA)

<400> SEQUENCE: 37

Gln Val Gln Leu Val Gln Ser Gly Ala Glu Val Lys Lys Pro Gly Ser
1               5                   10                  15

Ser Val Lys Val Ser Cys Lys Ala Ser Gly Phe Asn Ile Lys Asp Thr
                20                  25                  30

Tyr Met His Trp Val Arg Gln Ala Pro Gly Gln Gly Leu Glu Trp Met
            35                  40                  45

Gly Arg Ile Asp Pro Ala Asn Gly Asn Ser Lys Tyr Val Pro Lys Phe
        50                  55                  60

Gln Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Pro Phe Gly Tyr Tyr Val Ser Asp Tyr Ala Met Ala Tyr Trp Gly
                100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Glu Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
            195                 200                 205

Lys Pro Ser Asn Thr Lys Val Asp Glu Lys Val Glu Pro Lys Ser Cys
        210                 215                 220

Asp Gly Gly Gly Gly Ser Gly Gly Gly Ser Gln Ala Val Val Thr
225                 230                 235                 240

Gln Glu Pro Ser Leu Thr Val Ser Pro Gly Gly Thr Val Thr Leu Thr
                245                 250                 255

Cys Gly Ser Ser Thr Gly Ala Val Thr Thr Ser Asn Tyr Ala Asn Trp
```

```
                260             265             270
Val Gln Glu Lys Pro Gly Gln Ala Phe Arg Gly Leu Ile Gly Gly Thr
            275             280             285

Asn Lys Arg Ala Pro Gly Thr Pro Ala Arg Phe Ser Gly Ser Leu Leu
290             295             300

Gly Gly Lys Ala Ala Leu Thr Leu Ser Gly Ala Gln Pro Glu Asp Glu
305             310             315             320

Ala Glu Tyr Tyr Cys Ala Leu Trp Tyr Ser Asn Leu Trp Val Phe Gly
            325             330             335

Gly Gly Thr Lys Leu Thr Val Leu Ser Ser Ala Ser Thr Lys Gly Pro
            340             345             350

Ser Val Phe Pro Leu Ala Pro Ser Ser Lys Ser Thr Ser Gly Gly Thr
            355             360             365

Ala Ala Leu Gly Cys Leu Val Lys Asp Tyr Phe Pro Glu Pro Val Thr
            370             375             380

Val Ser Trp Asn Ser Gly Ala Leu Thr Ser Gly Val His Thr Phe Pro
385             390             395             400

Ala Val Leu Gln Ser Ser Gly Leu Tyr Ser Leu Ser Ser Val Val Thr
            405             410             415

Val Pro Ser Ser Ser Leu Gly Thr Gln Thr Tyr Ile Cys Asn Val Asn
            420             425             430

His Lys Pro Ser Asn Thr Lys Val Asp Lys Lys Val Glu Pro Lys Ser
            435             440             445

Cys Asp Lys Thr His Thr Cys Pro Pro Cys Pro Ala Pro Glu Ala Ala
            450             455             460

Gly Gly Pro Ser Val Phe Leu Phe Pro Pro Lys Pro Lys Asp Thr Leu
465             470             475             480

Met Ile Ser Arg Thr Pro Glu Val Thr Cys Val Val Val Asp Val Ser
            485             490             495

His Glu Asp Pro Glu Val Lys Phe Asn Trp Tyr Val Asp Gly Val Glu
            500             505             510

Val His Asn Ala Lys Thr Lys Pro Arg Glu Glu Gln Tyr Asn Ser Thr
            515             520             525

Tyr Arg Val Val Ser Val Leu Thr Val Leu His Gln Asp Trp Leu Asn
            530             535             540

Gly Lys Glu Tyr Lys Cys Lys Val Ser Asn Lys Ala Leu Gly Ala Pro
545             550             555             560

Ile Glu Lys Thr Ile Ser Lys Ala Lys Gly Gln Pro Arg Glu Pro Gln
            565             570             575

Val Tyr Thr Leu Pro Pro Cys Arg Asp Glu Leu Thr Lys Asn Gln Val
            580             585             590

Ser Leu Trp Cys Leu Val Lys Gly Phe Tyr Pro Ser Asp Ile Ala Val
            595             600             605

Glu Trp Glu Ser Asn Gly Gln Pro Glu Asn Asn Tyr Lys Thr Thr Pro
            610             615             620

Pro Val Leu Asp Ser Asp Gly Ser Phe Phe Leu Tyr Ser Lys Leu Thr
625             630             635             640

Val Asp Lys Ser Arg Trp Gln Gln Gly Asn Val Phe Ser Cys Ser Val
            645             650             655

Met His Glu Ala Leu His Asn His Tyr Thr Gln Lys Ser Leu Ser Leu
            660             665             670

Ser Pro
```

-continued

<210> SEQ ID NO 38
<211> LENGTH: 218
<212> TYPE: PRT
<213> ORGANISM: Artificial Sequence
<220> FEATURE:
<223> OTHER INFORMATION: humanized CEA VL-CL(RK)

<400> SEQUENCE: 38

```
Glu Ile Val Leu Thr Gln Ser Pro Ala Thr Leu Ser Leu Ser Pro Gly
1               5                   10                  15

Glu Arg Ala Thr Leu Ser Cys Arg Ala Gly Glu Ser Val Asp Ile Phe
            20                  25                  30

Gly Val Gly Phe Leu His Trp Tyr Gln Gln Lys Pro Gly Gln Ala Pro
        35                  40                  45

Arg Leu Leu Ile Tyr Arg Ala Ser Asn Arg Ala Thr Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln Gln Thr Asn
                85                  90                  95

Glu Asp Pro Tyr Thr Phe Gly Gln Gly Thr Lys Leu Glu Ile Lys Arg
            100                 105                 110

Thr Val Ala Ala Pro Ser Val Phe Ile Phe Pro Pro Ser Asp Arg Lys
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 39
<211> LENGTH: 225
<212> TYPE: PRT
<213> ORGANISM: Artificial Sequence
<220> FEATURE:
<223> OTHER INFORMATION: Fc (hole, P329G LALA)

<400> SEQUENCE: 39

```
Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95
```

```
Lys Glu Tyr Lys Cys Lys Val Ser Asn Lys Ala Leu Gly Ala Pro Ile
                100                 105                 110
Glu Lys Thr Ile Ser Lys Ala Lys Gly Gln Pro Arg Glu Pro Gln Val
            115                 120                 125
Cys Thr Leu Pro Pro Ser Arg Asp Glu Leu Thr Lys Asn Gln Val Ser
        130                 135                 140
Leu Ser Cys Ala Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Asp Ser Asp Gly Ser Phe Phe Leu Val Ser Lys Leu Thr Val
            180                 185                 190
Asp Lys Ser Arg Trp Gln Gln Gly Asn Val Phe Ser Cys Ser Val Met
        195                 200                 205
His Glu Ala Leu His Asn His Tyr Thr Gln Lys Ser Leu Ser Leu Ser
    210                 215                 220
Pro
225

<210> SEQ ID NO 40
<211> LENGTH: 439
<212> TYPE: PRT
<213> ORGANISM: Artificial Sequence
<220> FEATURE:
<223> OTHER INFORMATION: CD3 VL-CH1-Fc (knob, P329G LALA)

<400> SEQUENCE: 40

Gln Ala Val Val Thr Gln Glu Pro Ser Leu Thr Val Ser Pro Gly Gly
1               5                   10                  15
Thr Val Thr Leu Thr Cys Gly Ser Ser Thr Gly Ala Val Thr Thr Ser
            20                  25                  30
Asn Tyr Ala Asn Trp Val Gln Glu Lys Pro Gly Gln Ala Phe Arg Gly
        35                  40                  45
Leu Ile Gly Gly Thr Asn Lys Arg Ala Pro Gly Thr Pro Ala Arg Phe
    50                  55                  60
Ser Gly Ser Leu Leu Gly Gly Lys Ala Ala Leu Thr Leu Ser Gly Ala
65                  70                  75                  80
Gln Pro Glu Asp Glu Ala Glu Tyr Tyr Cys Ala Leu Trp Tyr Ser Asn
                85                  90                  95
Leu Trp Val Phe Gly Gly Gly Thr Lys Leu Thr Val Leu Ser Ser Ala
            100                 105                 110
Ser Thr Lys Gly Pro Ser Val Phe Pro Leu Ala Pro Ser Ser Lys Ser
        115                 120                 125
Thr Ser Gly Gly Thr Ala Ala Leu Gly Cys Leu Val Lys Asp Tyr Phe
    130                 135                 140
Pro Glu Pro Val Thr Val Ser Trp Asn Ser Gly Ala Leu Thr Ser Gly
145                 150                 155                 160
Val His Thr Phe Pro Ala Val Leu Gln Ser Ser Gly Leu Tyr Ser Leu
                165                 170                 175
Ser Ser Val Val Thr Val Pro Ser Ser Ser Leu Gly Thr Gln Thr Tyr
            180                 185                 190
Ile Cys Asn Val Asn His Lys Pro Ser Asn Thr Lys Val Asp Lys Lys
        195                 200                 205
Val Glu Pro Lys Ser Cys Asp Lys Thr His Thr Cys Pro Pro Cys Pro
    210                 215                 220
```

Ala Pro Glu Ala Ala Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
            245                 250                 255

Val Val Asp Val Ser His Glu Asp Pro Glu Val Lys Phe Asn Trp Tyr
        260                 265                 270

Val Asp Gly Val Glu Val His Asn Ala Lys Thr Lys Pro Arg Glu Glu
            275                 280                 285

Gln Tyr Asn Ser Thr Tyr Arg Val Val Ser Val Leu Thr Val Leu His
    290                 295                 300

Gln Asp Trp Leu Asn Gly Lys Glu Tyr Lys Cys Lys Val Ser Asn Lys
305                 310                 315                 320

Ala Leu Gly Ala Pro Ile Glu Lys Thr Ile Ser Lys Ala Lys Gly Gln
                325                 330                 335

Pro Arg Glu Pro Gln Val Tyr Thr Leu Pro Pro Cys Arg Asp Glu Leu
            340                 345                 350

Thr Lys Asn Gln Val Ser Leu Trp Cys Leu Val Lys Gly Phe Tyr Pro
        355                 360                 365

Ser Asp Ile Ala Val Glu Trp Glu Ser Asn Gly Gln Pro Glu Asn Asn
370                 375                 380

Tyr Lys Thr Thr Pro Pro Val Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
            420                 425                 430

Lys Ser Leu Ser Leu Ser Pro
        435

<210> SEQ ID NO 41
<211> LENGTH: 684
<212> TYPE: PRT
<213> ORGANISM: Artificial Sequence
<220> FEATURE:
<223> OTHER INFORMATION: humanized CEA VH-CH1(EE)-CD3 VL-CH1-Fc (knob,
      P329G LALA) (longer linker)

<400> SEQUENCE: 41

Gln Val Gln Leu Val Gln Ser Gly Ala Glu Val Lys Lys Pro Gly Ser
1               5                   10                  15

Ser Val Lys Val Ser Cys Lys Ala Ser Gly Phe Asn Ile Lys Asp Thr
            20                  25                  30

Tyr Met His Trp Val Arg Gln Ala Pro Gly Gln Gly Leu Glu Trp Met
        35                  40                  45

Gly Arg Ile Asp Pro Ala Asn Gly Asn Ser Lys Tyr Val Pro Lys Phe
    50                  55                  60

Gln Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Pro Phe Gly Tyr Tyr Val Ser Asp Tyr Ala Met Ala Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala

```
            130                 135                 140
Ala Leu Gly Cys Leu Val Glu Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Glu Lys Val Glu Pro Lys Ser Cys
    210                 215                 220

Asp Gly Gly Gly Ser Gly Gly Gly Ser Gly Gly Gly Gly Ser
225                 230                 235                 240

Gly Gly Gly Gly Ser Gln Ala Val Val Thr Gln Glu Pro Ser Leu Thr
                245                 250                 255

Val Ser Pro Gly Gly Thr Val Thr Leu Thr Cys Gly Ser Ser Thr Gly
            260                 265                 270

Ala Val Thr Thr Ser Asn Tyr Ala Asn Trp Val Gln Glu Lys Pro Gly
        275                 280                 285

Gln Ala Phe Arg Gly Leu Ile Gly Gly Thr Asn Lys Arg Ala Pro Gly
    290                 295                 300

Thr Pro Ala Arg Phe Ser Gly Ser Leu Leu Gly Gly Lys Ala Ala Leu
305                 310                 315                 320

Thr Leu Ser Gly Ala Gln Pro Glu Asp Glu Ala Glu Tyr Tyr Cys Ala
                325                 330                 335

Leu Trp Tyr Ser Asn Leu Trp Val Phe Gly Gly Gly Thr Lys Leu Thr
            340                 345                 350

Val Leu Ser Ser Ala Ser Thr Lys Gly Pro Ser Val Phe Pro Leu Ala
        355                 360                 365

Pro Ser Ser Lys Ser Thr Ser Gly Gly Thr Ala Ala Leu Gly Cys Leu
    370                 375                 380

Val Lys Asp Tyr Phe Pro Glu Pro Val Thr Val Ser Trp Asn Ser Gly
385                 390                 395                 400

Ala Leu Thr Ser Gly Val His Thr Phe Pro Ala Val Leu Gln Ser Ser
                405                 410                 415

Gly Leu Tyr Ser Leu Ser Ser Val Val Thr Val Pro Ser Ser Ser Leu
            420                 425                 430

Gly Thr Gln Thr Tyr Ile Cys Asn Val Asn His Lys Pro Ser Asn Thr
        435                 440                 445

Lys Val Asp Lys Lys Val Glu Pro Lys Ser Cys Asp Lys Thr His Thr
    450                 455                 460

Cys Pro Pro Cys Pro Ala Pro Glu Ala Ala Gly Gly Pro Ser Val Phe
465                 470                 475                 480

Leu Phe Pro Pro Lys Pro Lys Asp Thr Leu Met Ile Ser Arg Thr Pro
                485                 490                 495

Glu Val Thr Cys Val Val Val Asp Val Ser His Glu Asp Pro Glu Val
            500                 505                 510

Lys Phe Asn Trp Tyr Val Asp Gly Val Glu Val His Asn Ala Lys Thr
        515                 520                 525

Lys Pro Arg Glu Glu Gln Tyr Asn Ser Thr Tyr Arg Val Val Ser Val
    530                 535                 540

Leu Thr Val Leu His Gln Asp Trp Leu Asn Gly Lys Glu Tyr Lys Cys
545                 550                 555                 560
```

```
Lys Val Ser Asn Lys Ala Leu Gly Ala Pro Ile Glu Lys Thr Ile Ser
            565                 570                 575

Lys Ala Lys Gly Gln Pro Arg Glu Pro Gln Val Tyr Thr Leu Pro Pro
            580                 585                 590

Cys Arg Asp Glu Leu Thr Lys Asn Gln Val Ser Leu Trp Cys Leu Val
            595                 600                 605

Lys Gly Phe Tyr Pro Ser Asp Ile Ala Val Glu Trp Glu Ser Asn Gly
            610                 615                 620

Gln Pro Glu Asn Asn Tyr Lys Thr Thr Pro Pro Val Leu Asp Ser Asp
625                 630                 635                 640

Gly Ser Phe Phe Leu Tyr Ser Lys Leu Thr Val Asp Lys Ser Arg Trp
            645                 650                 655

Gln Gln Gly Asn Val Phe Ser Cys Ser Val Met His Glu Ala Leu His
            660                 665                 670

Asn His Tyr Thr Gln Lys Ser Leu Ser Leu Ser Pro
            675                 680

<210> SEQ ID NO 42
<211> LENGTH: 694
<212> TYPE: PRT
<213> ORGANISM: Artificial Sequence
<220> FEATURE:
<223> OTHER INFORMATION: CEA VH-CH1-CD3 VH-CL-Fc (knob, P329G LALA)

<400> SEQUENCE: 42

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Phe
            20                  25                  30

Gly Met Asn Trp Val Arg Gln Ala Pro Gly Gln Gly Leu Glu Trp Met
            35                  40                  45

Gly Trp Ile Asn Thr Lys Thr Gly Glu Ala Thr Tyr Val Glu Glu Phe
    50                  55                  60

Lys Gly Arg Val Thr Phe Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
            85                  90                  95

Ala Arg Trp Asp Phe Ala Tyr Tyr Val Glu Ala Met Asp Tyr Trp Gly
            100                 105                 110

Gln Gly Thr Thr Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
            130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
            210                 215                 220

Asp Gly Gly Gly Gly Ser Gly Gly Gly Gly Ser Glu Val Gln Leu Leu
225                 230                 235                 240
```

```
Glu Ser Gly Gly Gly Leu Val Gln Pro Gly Gly Ser Leu Arg Leu Ser
                245                 250                 255

Cys Ala Ala Ser Gly Phe Thr Phe Ser Thr Tyr Ala Met Asn Trp Val
            260                 265                 270

Arg Gln Ala Pro Gly Lys Gly Leu Glu Trp Val Ser Arg Ile Arg Ser
        275                 280                 285

Lys Tyr Asn Asn Tyr Ala Thr Tyr Tyr Ala Asp Ser Val Lys Gly Arg
    290                 295                 300

Phe Thr Ile Ser Arg Asp Asp Ser Lys Asn Thr Leu Tyr Leu Gln Met
305                 310                 315                 320

Asn Ser Leu Arg Ala Glu Asp Thr Ala Val Tyr Tyr Cys Val Arg His
                325                 330                 335

Gly Asn Phe Gly Asn Ser Tyr Val Ser Trp Phe Ala Tyr Trp Gly Gln
            340                 345                 350

Gly Thr Leu Val Thr Val Ser Ser Ala Ser Val Ala Ala Pro Ser Val
        355                 360                 365

Phe Ile Phe Pro Pro Ser Asp Glu Gln Leu Lys Ser Gly Thr Ala Ser
    370                 375                 380

Val Val Cys Leu Leu Asn Asn Phe Tyr Pro Arg Glu Ala Lys Val Gln
385                 390                 395                 400

Trp Lys Val Asp Asn Ala Leu Gln Ser Gly Asn Ser Gln Glu Ser Val
                405                 410                 415

Thr Glu Gln Asp Ser Lys Asp Ser Thr Tyr Ser Leu Ser Ser Thr Leu
            420                 425                 430

Thr Leu Ser Lys Ala Asp Tyr Glu Lys His Lys Val Tyr Ala Cys Glu
        435                 440                 445

Val Thr His Gln Gly Leu Ser Ser Pro Val Thr Lys Ser Phe Asn Arg
    450                 455                 460

Gly Glu Cys Asp Lys Thr His Thr Cys Pro Pro Cys Pro Ala Pro Glu
465                 470                 475                 480

Ala Ala Gly Gly Pro Ser Val Phe Leu Phe Pro Pro Lys Pro Lys Asp
                485                 490                 495

Thr Leu Met Ile Ser Arg Thr Pro Glu Val Thr Cys Val Val Val Asp
            500                 505                 510

Val Ser His Glu Asp Pro Glu Val Lys Phe Asn Trp Tyr Val Asp Gly
        515                 520                 525

Val Glu Val His Asn Ala Lys Thr Lys Pro Arg Glu Glu Gln Tyr Asn
    530                 535                 540

Ser Thr Tyr Arg Val Val Ser Val Leu Thr Val Leu His Gln Asp Trp
545                 550                 555                 560

Leu Asn Gly Lys Glu Tyr Lys Cys Lys Val Ser Asn Lys Ala Leu Gly
                565                 570                 575

Ala Pro Ile Glu Lys Thr Ile Ser Lys Ala Lys Gly Gln Pro Arg Glu
            580                 585                 590

Pro Gln Val Tyr Thr Leu Pro Pro Cys Arg Asp Glu Leu Thr Lys Asn
        595                 600                 605

Gln Val Ser Leu Trp Cys Leu Val Lys Gly Phe Tyr Pro Ser Asp Ile
    610                 615                 620

Ala Val Glu Trp Glu Ser Asn Gly Gln Pro Glu Asn Asn Tyr Lys Thr
625                 630                 635                 640

Thr Pro Pro Val Leu Asp Ser Asp Gly Ser Phe Phe Leu Tyr Ser Lys
                645                 650                 655
```

```
Leu Thr Val Asp Lys Ser Arg Trp Gln Gln Gly Asn Val Phe Ser Cys
                660                 665                 670

Ser Val Met His Glu Ala Leu His Asn His Tyr Thr Gln Lys Ser Leu
            675                 680                 685

Ser Leu Ser Pro Gly Lys
        690

<210> SEQ ID NO 43
<211> LENGTH: 451
<212> TYPE: PRT
<213> ORGANISM: Artificial Sequence
<220> FEATURE:
<223> OTHER INFORMATION: CEA VH-CH1-Fc (hole, P329G LALA)

<400> SEQUENCE: 43

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Phe
            20                  25                  30

Gly Met Asn Trp Val Arg Gln Ala Pro Gly Gln Gly Leu Glu Trp Met
        35                  40                  45

Gly Trp Ile Asn Thr Lys Thr Gly Glu Ala Thr Tyr Val Glu Glu Phe
    50                  55                  60

Lys Gly Arg Val Thr Phe Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Trp Asp Phe Ala Tyr Tyr Val Glu Ala Met Asp Tyr Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320
```

Lys Glu Tyr Lys Cys Lys Val Ser Asn Lys Ala Leu Gly Ala Pro Ile
                325                 330                 335

Glu Lys Thr Ile Ser Lys Ala Lys Gly Gln Pro Arg Glu Pro Gln Val
            340                 345                 350

Cys Thr Leu Pro Pro Ser Arg Asp Glu Leu Thr Lys Asn Gln Val Ser
            355                 360                 365

Leu Ser Cys Ala Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Val Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 44
<211> LENGTH: 214
<212> TYPE: PRT
<213> ORGANISM: Artificial Sequence
<220> FEATURE:
<223> OTHER INFORMATION: CD3 VL-CH1

<400> SEQUENCE: 44

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Glu Lys Pro Gly Gln Ala Phe Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Ser Ser Ala
            100                 105                 110

Ser Thr Lys Gly Pro Ser Val Phe Pro Leu Ala Pro Ser Ser Lys Ser
        115                 120                 125

Thr Ser Gly Gly Thr Ala Ala Leu Gly Cys Leu Val Lys Asp Tyr Phe
    130                 135                 140

Pro Glu Pro Val Thr Val Ser Trp Asn Ser Gly Ala Leu Thr Ser Gly
145                 150                 155                 160

Val His Thr Phe Pro Ala Val Leu Gln Ser Ser Gly Leu Tyr Ser Leu
                165                 170                 175

Ser Ser Val Val Thr Val Pro Ser Ser Ser Leu Gly Thr Gln Thr Tyr
            180                 185                 190

Ile Cys Asn Val Asn His Lys Pro Ser Asn Thr Lys Val Asp Lys Lys
        195                 200                 205

Val Glu Pro Lys Ser Cys
    210

```
<210> SEQ ID NO 45
<211> LENGTH: 215
<212> TYPE: PRT
<213> ORGANISM: Artificial Sequence
<220> FEATURE:
<223> OTHER INFORMATION: CEA VL-CL

<400> SEQUENCE: 45

Asp Ile Gln Met Thr Gln Ser Pro Ser Ser Leu Ser Ala Ser Val Gly
1               5                   10                  15

Asp Arg Val Thr Ile Thr Cys Lys Ala Ser Ala Ala Val Gly Thr Tyr
            20                  25                  30

Val Ala Trp Tyr Gln Gln Lys Pro Gly Lys Ala Pro Lys Leu Leu Ile
        35                  40                  45

Tyr Ser Ala Ser Tyr Arg Lys Arg Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys His Gln Tyr Tyr Thr Tyr Pro Leu
                85                  90                  95

Phe Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 46
<211> LENGTH: 19
<212> TYPE: PRT
<213> ORGANISM: Artificial Sequence
<220> FEATURE:
<223> OTHER INFORMATION: CD3 HCDR2

<400> SEQUENCE: 46

Arg Ile Arg Ser Lys Tyr Asn Asn Tyr Ala Thr Tyr Tyr Ala Asp Ser
1               5                   10                  15

Val Lys Asp

<210> SEQ ID NO 47
<211> LENGTH: 14
<212> TYPE: PRT
<213> ORGANISM: Artificial Sequence
<220> FEATURE:
<223> OTHER INFORMATION: CD3 LCDR1

<400> SEQUENCE: 47

Arg Ser Ser Thr Gly Ala Val Thr Thr Ser Asn Tyr Ala Asn
1               5                   10
```

-continued

```
<210> SEQ ID NO 48
<211> LENGTH: 125
<212> TYPE: PRT
<213> ORGANISM: Artificial Sequence
<220> FEATURE:
<223> OTHER INFORMATION: CD3 VH

<400> SEQUENCE: 48

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 49
<211> LENGTH: 109
<212> TYPE: PRT
<213> ORGANISM: Artificial Sequence
<220> FEATURE:
<223> OTHER INFORMATION: CD3 VL

<400> SEQUENCE: 49

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Gly Gln Ala Phe Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu
            100                 105

<210> SEQ ID NO 50
<211> LENGTH: 674
<212> TYPE: PRT
<213> ORGANISM: Artificial Sequence
<220> FEATURE:
<223> OTHER INFORMATION: humanized CEA VH-CH1-CD3 VL-CH1-Fc (knob, P329G
      LALA)

<400> SEQUENCE: 50

Gln Val Gln Leu Val Gln Ser Gly Ala Glu Val Lys Lys Pro Gly Ser
1               5                   10                  15
```

Ser Val Lys Val Ser Cys Lys Ala Ser Gly Phe Asn Ile Lys Asp Thr
            20                  25                  30

Tyr Met His Trp Val Arg Gln Ala Pro Gly Gln Gly Leu Glu Trp Met
        35                  40                  45

Gly Arg Ile Asp Pro Ala Asn Gly Asn Ser Lys Tyr Val Pro Lys Phe
    50                  55                  60

Gln Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Pro Phe Gly Tyr Tyr Val Ser Asp Tyr Ala Met Ala Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Gly Gly Gly Ser Gly Gly Gly Ser Gln Ala Val Val Thr
225                 230                 235                 240

Gln Glu Pro Ser Leu Thr Val Ser Pro Gly Gly Thr Val Thr Leu Thr
                245                 250                 255

Cys Gly Ser Ser Thr Gly Ala Val Thr Thr Ser Asn Tyr Ala Asn Trp
            260                 265                 270

Val Gln Glu Lys Pro Gly Gln Ala Phe Arg Gly Leu Ile Gly Gly Thr
        275                 280                 285

Asn Lys Arg Ala Pro Gly Thr Pro Ala Arg Phe Ser Gly Ser Leu Leu
    290                 295                 300

Gly Gly Lys Ala Ala Leu Thr Leu Ser Gly Ala Gln Pro Glu Asp Glu
305                 310                 315                 320

Ala Glu Tyr Tyr Cys Ala Leu Trp Tyr Ser Asn Leu Trp Val Phe Gly
                325                 330                 335

Gly Gly Thr Lys Leu Thr Val Leu Ser Ser Ala Ser Thr Lys Gly Pro
            340                 345                 350

Ser Val Phe Pro Leu Ala Pro Ser Ser Lys Ser Thr Ser Gly Gly Thr
        355                 360                 365

Ala Ala Leu Gly Cys Leu Val Lys Asp Tyr Phe Pro Glu Pro Val Thr
    370                 375                 380

Val Ser Trp Asn Ser Gly Ala Leu Thr Ser Gly Val His Thr Phe Pro
385                 390                 395                 400

Ala Val Leu Gln Ser Ser Gly Leu Tyr Ser Leu Ser Ser Val Val Thr
                405                 410                 415

Val Pro Ser Ser Ser Leu Gly Thr Gln Thr Tyr Ile Cys Asn Val Asn
            420                 425                 430

```
His Lys Pro Ser Asn Thr Lys Val Asp Lys Lys Val Glu Pro Lys Ser
            435                 440                 445

Cys Asp Lys Thr His Thr Cys Pro Pro Cys Pro Ala Pro Glu Ala Ala
450                 455                 460

Gly Gly Pro Ser Val Phe Leu Phe Pro Pro Lys Pro Lys Asp Thr Leu
465                 470                 475                 480

Met Ile Ser Arg Thr Pro Glu Val Thr Cys Val Val Val Asp Val Ser
                485                 490                 495

His Glu Asp Pro Glu Val Lys Phe Asn Trp Tyr Val Asp Gly Val Glu
            500                 505                 510

Val His Asn Ala Lys Thr Lys Pro Arg Glu Glu Gln Tyr Asn Ser Thr
        515                 520                 525

Tyr Arg Val Val Ser Val Leu Thr Val Leu His Gln Asp Trp Leu Asn
530                 535                 540

Gly Lys Glu Tyr Lys Cys Lys Val Ser Asn Lys Ala Leu Gly Ala Pro
545                 550                 555                 560

Ile Glu Lys Thr Ile Ser Lys Ala Lys Gly Gln Pro Arg Glu Pro Gln
                565                 570                 575

Val Tyr Thr Leu Pro Pro Cys Arg Asp Glu Leu Thr Lys Asn Gln Val
            580                 585                 590

Ser Leu Trp Cys Leu Val Lys Gly Phe Tyr Pro Ser Asp Ile Ala Val
        595                 600                 605

Glu Trp Glu Ser Asn Gly Gln Pro Glu Asn Asn Tyr Lys Thr Thr Pro
610                 615                 620

Pro Val Leu Asp Ser Asp Gly Ser Phe Phe Leu Tyr Ser Lys Leu Thr
625                 630                 635                 640

Val Asp Lys Ser Arg Trp Gln Gln Gly Asn Val Phe Ser Cys Ser Val
                645                 650                 655

Met His Glu Ala Leu His Asn His Tyr Thr Gln Lys Ser Leu Ser Leu
            660                 665                 670

Ser Pro

<210> SEQ ID NO 51
<211> LENGTH: 449
<212> TYPE: PRT
<213> ORGANISM: Artificial Sequence
<220> FEATURE:
<223> OTHER INFORMATION: humanized CEA VH-CH1-Fc (hole, P329G LALA)

<400> SEQUENCE: 51

Gln Val Gln Leu Val Gln Ser Gly Ala Glu Val Lys Lys Pro Gly Ser
1               5                   10                  15

Ser Val Lys Val Ser Cys Lys Ala Ser Gly Phe Asn Ile Lys Asp Thr
            20                  25                  30

Tyr Met His Trp Val Arg Gln Ala Pro Gly Gln Gly Leu Glu Trp Met
        35                  40                  45

Gly Arg Ile Asp Pro Ala Asn Gly Asn Ser Lys Tyr Val Pro Lys Phe
    50                  55                  60

Gln Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Pro Phe Gly Tyr Tyr Val Ser Asp Tyr Ala Met Ala Tyr Trp Gly
            100                 105                 110

Gln Gly Thr Leu Val Thr Val Ser Ser Ala Ser Thr Lys Gly Pro Ser
```

```
                115                 120                 125
Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
        180                 185                 190

Pro Ser Ser Ser Leu Gly Thr Gln Thr Tyr Ile Cys Asn Val Asn His
                195                 200                 205

Lys Pro Ser Asn Thr Lys Val Asp Lys Lys Val Glu Pro Lys Ser Cys
        210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
        260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Gly Ala Pro Ile
                325                 330                 335

Glu Lys Thr Ile Ser Lys Ala Lys Gly Gln Pro Arg Glu Pro Gln Val
        340                 345                 350

Cys Thr Leu Pro Pro Ser Arg Asp Glu Leu Thr Lys Asn Gln Val Ser
        355                 360                 365

Leu Ser Cys Ala Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Val Ser Lys Leu Thr Val
                405                 410                 415

Asp Lys Ser Arg Trp Gln Gln Gly Asn Val Phe Ser Cys Ser Val Met
        420                 425                 430

His Glu Ala Leu His Asn His Tyr Thr Gln Lys Ser Leu Ser Leu Ser
        435                 440                 445

Pro

<210> SEQ ID NO 52
<211> LENGTH: 218
<212> TYPE: PRT
<213> ORGANISM: Artificial Sequence
<220> FEATURE:
<223> OTHER INFORMATION: humanized CEA VL-CL

<400> SEQUENCE: 52

Glu Ile Val Leu Thr Gln Ser Pro Ala Thr Leu Ser Leu Ser Pro Gly
1               5                   10                  15

Glu Arg Ala Thr Leu Ser Cys Arg Ala Gly Glu Ser Val Asp Ile Phe
            20                  25                  30
```

```
Gly Val Gly Phe Leu His Trp Tyr Gln Gln Lys Pro Gly Gln Ala Pro
        35                  40                  45

Arg Leu Leu Ile Tyr Arg Ala Ser Asn Arg Ala Thr Gly Ile Pro Ala
        50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln Gln Thr Asn
                85                  90                  95

Glu Asp Pro Tyr Thr Phe Gly Gln Gly Thr Lys Leu Glu Ile Lys Arg
                100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
        210                 215
```

BISPECIFIC T CELL ACTIVATING ANTIGEN BINDING MOLECULES

CROSS REFERENCE TO RELATED APPLICATIONS

This application claims priority to European Patent Application No. EP 15188035.8, filed Oct. 2, 2015, the disclosure of which is incorporated herein by reference in its entirety.

SEQUENCE LISTING

The present application contains a Sequence Listing which has been submitted in ASCII format via EFS-Web and is hereby incorporated by reference in its entirety. Said ASCII copy, created on Sep. 27, 2016, is named P33120 US_ST25.txt and is 84,302 bytes in size.

FIELD OF THE INVENTION

The present invention generally relates to bispecific antigen binding molecules for activating T cells. In addition, the present invention relates to polynucleotides encoding such bispecific antigen binding molecules, and vectors and host cells comprising such polynucleotides. The invention further relates to methods for producing the bispecific antigen binding molecules of the invention, and to methods of using these bispecific antigen binding molecules in the treatment of disease.

BACKGROUND

The selective destruction of an individual cell or a specific cell type is often desirable in a variety of clinical settings. For example, it is a primary goal of cancer therapy to specifically destroy tumor cells, while leaving healthy cells and tissues intact and undamaged.

An attractive way of achieving this is by inducing an immune response against the tumor, to make immune effector cells such as natural killer (NK) cells or cytotoxic T lymphocytes (CTLs) attack and destroy tumor cells. CTLs constitute the most potent effector cells of the immune system, however they cannot be activated by the effector mechanism mediated by the Fc domain of conventional therapeutic antibodies.

In this regard, bispecific antibodies designed to bind with one "arm" to a surface antigen on target cells, and with the second "arm" to an activating, invariant component of the T cell receptor (TCR) complex, have become of interest in recent years. The simultaneous binding of such an antibody to both of its targets will force a temporary interaction between target cell and T cell, causing activation of any cytotoxic T cell and subsequent lysis of the target cell. Hence, the immune response is re-directed to the target cells and is independent of peptide antigen presentation by the target cell or the specificity of the T cell as would be relevant for normal MHC-restricted activation of CTLs. In this context it is crucial that CTLs are only activated when a target cell is presenting the bispecific antibody to them, i.e. the immunological synapse is mimicked. Particularly desirable are bispecific antibodies that do not require lymphocyte preconditioning or co-stimulation in order to elicit efficient lysis of target cells.

Several bispecific antibody formats have been developed and their suitability for T cell mediated immunotherapy investigated. Out of these, the so-called BiTE (bispecific T cell engager) molecules have been very well characterized and already shown some promise in the clinic (reviewed in Nagorsen and Bauerle, Exp Cell Res 317, 1255-1260 (2011)). BiTEs are tandem scFv molecules wherein two scFv molecules are fused by a flexible linker. Further bispecific formats being evaluated for T cell engagement include diabodies (Holliger et al., Prot Eng 9, 299-305 (1996)) and derivatives thereof, such as tandem diabodies (Kipriyanov et al., J Mol Biol 293, 41-66 (1999)). A more recent development are the so-called DART (dual affinity retargeting) molecules, which are based on the diabody format but feature a C-terminal disulfide bridge for additional stabilization (Moore et al., Blood 117, 4542-51 (2011)). The so-called triomabs, which are whole hybrid mouse/rat IgG molecules and also currently being evaluated in clinical trials, represent a larger sized format (reviewed in Seimetz et al., Cancer Treat Rev 36, 458-467 (2010)).

The variety of formats that are being developed shows the great potential attributed to T cell re-direction and activation in immunotherapy. The task of generating bispecific antibodies suitable therefor is, however, by no means trivial, but involves a number of challenges that have to be met related to efficacy, toxicity, applicability and produceability of the antibodies.

Small constructs such as, for example, BiTE molecules— while being able to efficiently crosslink effector and target cells—have a very short serum half life requiring them to be administered to patients by continuous infusion. IgG-like formats on the other hand—while having the great benefit of a long half life—suffer from toxicity associated with the native effector functions inherent to IgG molecules. Their immunogenic potential constitutes another unfavorable feature of IgG-like bispecific antibodies, especially non-human formats, for successful therapeutic development. Finally, a major challenge in the general development of bispecific antibodies has been the production of bispecific antibody constructs at a clinically sufficient quantity and purity, due to the mispairing of antibody heavy and light chains of different specificities upon co-expression, which decreases the yield of the correctly assembled construct and results in a number of non-functional side products from which the desired bispecific antibody may be difficult to separate.

Different approaches have been taken to overcome the chain association issue in bispecific antibodies (see e.g. Klein et al., mAbs 6, 653-663 (2012)). For example, the 'knobs-into-holes' strategy aims at forcing the pairing of two different antibody heavy chains by introducing mutations into the CH3 domains to modify the contact interface. On one chain bulky amino acids are replaced by amino acids with short side chains to create a 'hole'. Conversely, amino acids with large side chains are introduced into the other CH3 domain, to create a 'knob'. By coexpressing these two heavy chains (and two identical light chains, which have to be appropriate for both heavy chains), high yields of heterodimer ('knob-hole') versus homodimer ('hole-hole' or 'knob-knob') are observed (Ridgway, J. B., et al., Protein Eng. 9 (1996) 617-621; and WO 96/027011). The percentage of heterodimer could be further increased by remodeling the interaction surfaces of the two CH3 domains using a phage display approach and the introduction of a disulfide bridge to stabilize the heterodimers (Merchant, A. M., et al., Nature Biotech. 16 (1998) 677-681; Atwell, S., et al., J. Mol. Biol. 270 (1997) 26-35). New approaches for the knobs-into-holes technology are described in e.g. in EP 1870459 A1.

The 'knobs-into-holes' strategy does, however, not solve the problem of heavy chain-light chain mispairing, which occurs in bispecific antibodies comprising different light chains for binding to the different target antigens.

A strategy to prevent heavy chain-light chain mispairing is to exchange domains between the heavy and light chains of one of the binding arms of a bispecific antibody (see WO 2009/080251, WO 2009/080252, WO 2009/080253, WO 2009/080254 and Schaefer, W. et al, PNAS, 108 (2011) 11187-11191, which relate to bispecific IgG antibodies with a domain crossover).

Exchanging the heavy and light chain variable domains VH and VL in one of the binding arms of the bispecific antibody (WO2009/080252, see also Schaefer, W. et al, PNAS, 108 (2011) 11187-11191) clearly reduces the side products caused by the mispairing of a light chain against a first antigen with the wrong heavy chain against the second antigen (compared to approaches without such domain exchange). Nevertheless, these antibody preparations are not completely free of side products. The main side product is based on a Bence Jones-type interaction (Schaefer, W. et al, PNAS, 108 (2011) 11187-11191; in Fig. S1I of the Supplement). A further reduction of such side products is thus desirable to improve e.g. the yield of such bispecific antibodies.

The choice of target antigens and appropriate binders for both the T cell antigen and the target cell antigen is a further crucial aspect in the generation of T cell bispecific (TCB) antibodies for therapeutic application. Carcinoembryonic antigen (CEA) is an attractive target antigen as the prevalence of CEA expression is generally high in tumors, but low in normal tissues. Accordingly, numerous antibodies have been raised against this target, one of which is the murine antibody T84.66 (Wagener et al., J Immunol 130, 2308 (1983), Neumaier et al., J Immunol 135, 3604 (1985)), which has also been chimerized (WO 1991/01990) and humanized (WO 2005/086875). WO 2007/071426 or WO 2014/131712 describe bispecific antibodies targeting CD3 on T cells and carcinoembryonic antigen (CEA) on target cells.

The present invention provides novel, improved bispecific antigen binding molecules designed for T cell activation and re-direction, targeting CD3 and CEA, that combine good efficacy and produceability with low toxicity and favorable pharmacokinetic properties.

SUMMARY OF THE INVENTION

The present inventors have developed a novel T cell activating bispecific antigen binding molecule with unexpected, improved properties using a novel humanized anti-CEA antibody.

Thus, in a first aspect the present invention provides a T cell activating bispecific antigen binding molecule comprising
(a) a first antigen binding moiety which specifically binds to a first antigen;
(b) a second antigen binding moiety which specifically binds to a second antigen;
wherein the first antigen is an activating T cell antigen and the second antigen is CEA, or the first antigen is CEA and the second antigen is an activating T cell antigen; and
wherein the antigen binding moiety which specifically binds to CEA comprises a heavy chain variable region, particularly a humanized heavy chain variable region, comprising the heavy chain complementarity determining region (HCDR) 1 of SEQ ID NO: 14, the HCDR 2 of SEQ ID NO: 15 and the HCDR 3 of SEQ ID NO: 16, and a light chain variable region, particularly a humanized light chain variable region, comprising the light chain complementarity determining region (LCDR) 1 of SEQ ID NO: 17, the LCDR 2 of SEQ ID NO: 18 and the LCDR 3 of SEQ ID NO: 19.

In one embodiment, the antigen binding moiety which specifically binds to CEA comprises a heavy chain variable region comprising an amino acid sequence that is at least about 95%, 96%, 97%, 98%, 99% or 100% identical to the amino acid sequence of SEQ ID NO: 22 and a light chain variable region comprising an amino acid sequence that is at least about 95%, 96%, 97%, 98%, 99% or 100% identical to the amino acid sequence of SEQ ID NO: 23.

In particular embodiments, the first and/or the second antigen binding moiety is a Fab molecule. In a particular embodiment, the second antigen binding moiety is a Fab molecule which specifically binds to a second antigen, and wherein the variable domains VL and VH or the constant domains CL and CH1 of the Fab light chain and the Fab heavy chain are replaced by each other (i.e. according to such embodiment, the second Fab molecule is a crossover Fab molecule wherein the variable or constant domains of the Fab light chain and the Fab heavy chain are exchanged).

In particular embodiments, the first (and the third, if any) Fab molecule is a conventional Fab molecule. In a further particular embodiment, not more than one Fab molecule capable of specific binding to an activating T cell antigen is present in the T cell activating bispecific antigen binding molecule (i.e. the T cell activating bispecific antigen binding molecule provides monovalent binding to the activating T cell antigen).

In one embodiment, the first antigen is CEA and the second antigen is an activating T cell antigen. In a more specific embodiment, the activating T cell antigen is CD3, particularly CD3 epsilon.

In a particular embodiment, the T cell activating bispecific antigen binding molecule of the invention comprises
(a) a first Fab molecule which specifically binds to a first antigen;
(b) a second Fab molecule which specifically binds to a second antigen, and wherein the variable domains VL and VH or the constant domains CL and CH1 of the Fab light chain and the Fab heavy chain are replaced by each other;
wherein the first antigen is CEA and the second antigen is an activating T cell antigen;
wherein the first Fab molecule under (a) comprises a heavy chain variable region, particularly a humanized heavy chain variable region, comprising the heavy chain complementarity determining region (HCDR) 1 of SEQ ID NO: 14, the HCDR 2 of SEQ ID NO: 15 and the HCDR 3 of SEQ ID NO: 16, and a light chain variable region, particularly a humanized light chain variable region, comprising the light chain complementarity determining region (LCDR) 1 of SEQ ID NO: 17, the LCDR 2 of SEQ ID NO: 18 and the LCDR 3 of SEQ ID NO: 19.

According to a further aspect of the invention, the ratio of a desired bispecific antibody compared to undesired side products, in particular Bence Jones-type side products occurring in bispecific antibodies with a VH/VL domain exchange in one of their binding arms, can be improved by the introduction of charged amino acids with opposite charges at specific amino acid positions in the CH1 and CL domains (sometimes referred to herein as "charge modifications").

Thus, in some embodiments the first antigen binding moiety under (a) is a first Fab molecule which specifically binds to a first antigen, the second antigen binding moiety under (b) is a second Fab molecule which specifically binds to a second antigen wherein the variable domains VL and VH of the Fab light chain and the Fab heavy chain are replaced by each other;
and i) in the constant domain CL of the first Fab molecule under a) the amino acid at position 124 is substituted independently by lysine (K), arginine (R) or histidine (H) (numbering according to Kabat), and wherein in the constant domain CH1 of the first Fab molecule under a) the amino acid at position 147 or the amino acid at position 213 is substituted independently by glutamic acid (E), or aspartic acid (D) (numbering according to Kabat EU index); or ii) in the constant domain CL of the second Fab molecule under b) the amino acid at position 124 is substituted independently by lysine (K), arginine (R) or histidine (H) (numbering according to Kabat), and wherein in the constant domain CH1 of the second Fab molecule under b) the amino acid at position 147 or the amino acid at position 213 is substituted independently by glutamic acid (E), or aspartic acid (D) (numbering according to Kabat EU index).

In one such embodiment, in the constant domain CL of the first Fab molecule under a) the amino acid at position 124 is substituted independently by lysine (K), arginine (R) or histidine (H) (numbering according to Kabat) (in one preferred embodiment independently by lysine (K) or arginine (R)), and in the constant domain CH1 of the first Fab molecule under a) the amino acid at position 147 or the amino acid at position 213 is substituted independently by glutamic acid (E), or aspartic acid (D) (numbering according to Kabat EU index).

In a further embodiment, in the constant domain CL of the first Fab molecule under a) the amino acid at position 124 is substituted independently by lysine (K), arginine (R) or histidine (H) (numbering according to Kabat), and in the constant domain CH1 of the first Fab molecule under a) the amino acid at position 147 is substituted independently by glutamic acid (E), or aspartic acid (D) (numbering according to Kabat EU index).

In yet another embodiment, in the constant domain CL of the first Fab molecule under a) the amino acid at position 124 is substituted independently by lysine (K), arginine (R) or histidine (H) (numbering according to Kabat) (in one preferred embodiment independently by lysine (K) or arginine (R)) and the amino acid at position 123 is substituted independently by lysine (K), arginine (R) or histidine (H) (numbering according to Kabat) (in one preferred embodiment independently by lysine (K) or arginine (R)), and in the constant domain CH1 of the first Fab molecule under a) the amino acid at position 147 is substituted independently by glutamic acid (E), or aspartic acid (D) (numbering according to Kabat EU index) and the amino acid at position 213 is substituted independently by glutamic acid (E), or aspartic acid (D) (numbering according to Kabat EU index). In a particular embodiment, in the constant domain CL of the first Fab molecule under a) the amino acid at position 124 is substituted by lysine (K) (numbering according to Kabat) and the amino acid at position 123 is substituted by lysine (K) (numbering according to Kabat), and in the constant domain CH1 of the first Fab molecule under a) the amino acid at position 147 is substituted by glutamic acid (E) (numbering according to Kabat EU index) and the amino acid at position 213 is substituted by glutamic acid (E) (numbering according to Kabat EU index).

In another particular embodiment, in the constant domain CL of the first Fab molecule under a) the amino acid at position 124 is substituted by lysine (K) (numbering according to Kabat) and the amino acid at position 123 is substituted by arginine (R) (numbering according to Kabat), and in the constant domain CH1 of the first Fab molecule under a) the amino acid at position 147 is substituted by glutamic acid (E) (numbering according to Kabat EU index) and the amino acid at position 213 is substituted by glutamic acid (E) (numbering according to Kabat EU index).

In an alternative embodiment, in the constant domain CL of the second Fab molecule under b) the amino acid at position 124 is substituted independently by lysine (K), arginine (R) or histidine (H) (numbering according to Kabat) (in one preferred embodiment independently by lysine (K) or arginine (R)), and in the constant domain CH1 of the second Fab molecule under b) the amino acid at position 147 or the amino acid at position 213 is substituted independently by glutamic acid (E), or aspartic acid (D) (numbering according to Kabat EU index).

In a further embodiment, in the constant domain CL of the second Fab molecule under b) the amino acid at position 124 is substituted independently by lysine (K), arginine (R) or histidine (H) (numbering according to Kabat), and in the constant domain CH1 of the second Fab molecule under b) the amino acid at position 147 is substituted independently by glutamic acid (E), or aspartic acid (D) (numbering according to Kabat EU index).

In still another embodiment, in the constant domain CL of the second Fab molecule under b) the amino acid at position 124 is substituted independently by lysine (K), arginine (R) or histidine (H) (numbering according to Kabat) (in one preferred embodiment independently by lysine (K) or arginine (R)) and the amino acid at position 123 is substituted independently by lysine (K), arginine (R) or histidine (H) (numbering according to Kabat) (in one preferred embodiment independently by lysine (K) or arginine (R)), and in the constant domain CH1 of the second Fab molecule under b) the amino acid at position 147 is substituted independently by glutamic acid (E), or aspartic acid (D) (numbering according to Kabat EU index) and the amino acid at position 213 is substituted independently by glutamic acid (E), or aspartic acid (D) (numbering according to Kabat EU index).

In one embodiment, in the constant domain CL of the second Fab molecule under b) the amino acid at position 124 is substituted by lysine (K) (numbering according to Kabat) and the amino acid at position 123 is substituted by lysine (K) (numbering according to Kabat), and in the constant domain CH1 of the second Fab molecule under b) the amino acid at position 147 is substituted by glutamic acid (E) (numbering according to Kabat EU index) and the amino acid at position 213 is substituted by glutamic acid (E) (numbering according to Kabat EU index).

In another embodiment, in the constant domain CL of the second Fab molecule under b) the amino acid at position 124 is substituted by lysine (K) (numbering according to Kabat) and the amino acid at position 123 is substituted by arginine (R) (numbering according to Kabat), and in the constant domain CH1 of the second Fab molecule under b) the amino acid at position 147 is substituted by glutamic acid (E) (numbering according to Kabat EU index) and the amino acid at position 213 is substituted by glutamic acid (E) (numbering according to Kabat EU index).

In a particular embodiment, the T cell activating bispecific antigen binding molecule of the invention comprises
(a) a first Fab molecule which specifically binds to a first antigen;
(b) a second Fab molecule which specifically binds to a second antigen, and wherein the variable domains VL and VH of the Fab light chain and the Fab heavy chain are replaced by each other; wherein the first antigen is CEA and the second antigen is an activating T cell antigen; wherein the first Fab molecule under (a) comprises a heavy chain variable region, particularly a humanized heavy chain variable region, comprising the heavy chain complementarity determining region (HCDR) 1 of SEQ ID NO: 14, the HCDR 2 of SEQ ID NO: 15 and the HCDR 3 of SEQ ID NO: 16, and a light chain variable region, particularly a humanized light chain variable region, comprising the light chain complementarity determining region (LCDR) 1 of SEQ ID NO: 17, the LCDR 2 of SEQ ID NO: 18 and the LCDR 3 of SEQ ID NO: 19; and wherein in the constant domain CL of the first Fab molecule under a) the amino acid at position 124 is substituted independently by lysine (K), arginine (R) or histidine (H) (numbering according to Kabat) (in one preferred embodiment independently by lysine (K) or arginine (R)) and the amino acid at position 123 is substituted independently by lysine (K), arginine (R) or histidine (H) (numbering according to Kabat) (in one preferred embodiment independently by lysine (K) or arginine (R)), and in the constant domain CH1 of the first Fab molecule under a) the amino acid at position 147 is substituted independently by glutamic acid (E), or aspartic acid (D) (numbering according to Kabat EU index) and the amino acid at position 213 is substituted independently by glutamic acid (E), or aspartic acid (D) (numbering according to Kabat EU index).

In some embodiments, the T cell activating bispecific antigen binding molecule according to the invention further comprises a third antigen binding moiety which specifically binds to the first antigen. In particular embodiments, the third antigen binding moiety is identical to the first antigen binding moiety. In one embodiment, the third antigen binding moiety is a Fab molecule.

In particular embodiments, the third and the first antigen binding moiety are each a Fab molecule and the third Fab molecule is identical to the first Fab molecule. In these embodiments, the third Fab molecule thus comprises the same amino acid substitutions, if any, as the first Fab molecule. Like the first Fab molecule, the third Fab molecule particularly is a conventional Fab molecule.

If a third antigen binding moiety is present, in a particular embodiment the first and the third antigen moiety specifically bind to CEA, and the second antigen binding moiety specifically binds to an activating T cell antigen, particularly CD3, more particularly CD3 epsilon.

In some embodiments of the T cell activating bispecific antigen binding molecule according to the invention the first antigen binding moiety under a) and the second antigen binding moiety under b) are fused to each other, optionally via a peptide linker. In particular embodiments, the first and the second antigen binding moiety are each a Fab molecule. In a specific such embodiment, the second Fab molecule is fused at the C-terminus of the Fab heavy chain to the N-terminus of the Fab heavy chain of the first Fab molecule. In an alternative such embodiment, the first Fab molecule is fused at the C-terminus of the Fab heavy chain to the N-terminus of the Fab heavy chain of the second Fab molecule. In embodiments wherein either (i) the second Fab molecule is fused at the C-terminus of the Fab heavy chain to the N-terminus of the Fab heavy chain of the first Fab molecule or (ii) the first Fab molecule is fused at the C-terminus of the Fab heavy chain to the N-terminus of the Fab heavy chain of the second Fab molecule, additionally the Fab light chain of the Fab molecule and the Fab light chain of the second Fab molecule may be fused to each other, optionally via a peptide linker.

In particular embodiments, the T cell activating bispecific antigen binding molecule according to the invention additionally comprises an Fc domain composed of a first and a second subunit capable of stable association.

The T cell activating bispecific antigen binding molecule according to the invention can have different configurations, i.e. the first, second (and optionally third) antigen binding moiety may be fused to each other and to the Fc domain in different ways. The components may be fused to each other directly or, preferably, via one or more suitable peptide linkers. Where fusion of a Fab molecule is to the N-terminus of a subunit of the Fc domain, it is typically via an immunoglobulin hinge region.

In one embodiment, the first and the second antigen binding moiety are each a Fab molecule and the second antigen binding moiety is fused at the C-terminus of the Fab heavy chain to the N-terminus of the first or the second subunit of the Fc domain. In such embodiment, the first antigen binding moiety may be fused at the C-terminus of the Fab heavy chain to the N-terminus of the Fab heavy chain of the second antigen binding moiety or to the N-terminus of the other one of the subunits of the Fc domain.

In one embodiment, the first and the second antigen binding moiety are each a Fab molecule and the first and the second antigen binding moiety are each fused at the C-terminus of the Fab heavy chain to the N-terminus of one of the subunits of the Fc domain. In this embodiment, the T cell activating bispecific antigen binding molecule essentially comprises an immunoglobulin molecule, wherein in one of the Fab arms the heavy and light chain variable regions VH and VL (or the constant regions CH1 and CL in embodiments wherein no charge modifications as described herein are introduced in CH1 and CL domains) are exchanged/replaced by each other (see FIG. 1A, D).

In alternative embodiments, a third antigen binding moiety, particularly a third Fab molecule, is fused at the C-terminus of the Fab heavy chain to the N-terminus of the first or second subunit of the Fc domain. In a particular such embodiment, the second and the third antigen binding moiety are each fused at the C-terminus of the Fab heavy chain to the N-terminus of one of the subunits of the Fc domain, and the first antigen binding moiety is fused at the C-terminus of the Fab heavy chain to the N-terminus of the Fab heavy chain of the second Fab molecule. In this embodiment, the T cell activating bispecific antigen binding molecule essentially comprises an immunoglobulin molecule, wherein in one of the Fab arms the heavy and light chain variable regions VH and VL (or the constant regions CH1 and CL in embodiments wherein no charge modifications as described herein are introduced in CH1 and CL domains) are exchanged/replaced by each other, and wherein an additional (conventional) Fab molecule is N-terminally fused to said Fab arm (see FIG. 1B, E). In another such embodiment, the first and the third antigen binding moiety are each fused at the C-terminus of the Fab heavy chain to the N-terminus of one of the subunits of the Fc domain, and the second antigen binding moiety is fused at the C-terminus of the Fab heavy chain to the N-terminus of the Fab heavy chain of the first antigen binding moiety. In this embodiment, the T cell activating bispecific antigen binding molecule essentially comprises an immunoglobulin molecule with an additional Fab molecule N-terminally fused to one of the immunoglobulin Fab arms, wherein in said additional Fab molecule the heavy and light chain variable regions VH and VL (or the constant regions CH1 and CL in embodiments wherein no charge modifications as described herein are introduced in CH1 and CL domains) are exchanged/replaced by each other (see FIG. 1C, F).

In a particular embodiment, the immunoglobulin molecule comprised in the T cell activating bispecific antigen binding molecule according to the invention is an IgG class immunoglobulin. In an even more particular embodiment the immunoglobulin is an $IgG_1$ subclass immunoglobulin. In another embodiment, the immunoglobulin is an $IgG_4$ subclass immunoglobulin.

In a particular embodiment, the invention provides a T cell activating bispecific antigen binding molecule comprising a) a first Fab molecule which specifically binds to a first antigen;
b) a second Fab molecule which specifically binds to a second antigen, and wherein the variable domains VL and VH or the constant domains CL and CH1 of the Fab light chain and the Fab heavy chain are replaced by each other;
c) a third Fab molecule which specifically binds to the first antigen; and
d) an Fc domain composed of a first and a second subunit capable of stable association; wherein the first antigen is CEA and the second antigen is an activating T cell antigen, particularly CD3, more particularly CD3 epsilon;
 wherein the third Fab molecule under c) is identical to the first Fab molecule under a);
 wherein
(i) the first Fab molecule under a) is fused at the C-terminus of the Fab heavy chain to the N-terminus of the Fab heavy chain of the second Fab molecule under b), and the second Fab molecule under b) and the third Fab molecule under c) are each fused at the C-terminus of the Fab heavy chain to the N-terminus of one of the subunits of the Fc domain under d), or
(ii) the second Fab molecule under b) is fused at the C-terminus of the Fab heavy chain to the N-terminus of the Fab heavy chain of the first Fab molecule under a), and the first Fab molecule under a) and the third Fab molecule under c) are each fused at the C-terminus of the Fab heavy chain to the N-terminus of one of the subunits of the Fc domain under d); and
wherein the first Fab molecule under a) and the third Fab molecule under c) comprise a heavy chain variable region, particularly a humanized heavy chain variable region, comprising the heavy chain complementarity determining region (HCDR) 1 of SEQ ID NO: 14, the HCDR 2 of SEQ ID NO: 15 and the HCDR 3 of SEQ ID NO: 16, and a light chain variable region, particularly a humanized light chain variable region, comprising the light chain complementarity determining region (LCDR) 1 of SEQ ID NO: 17, the LCDR 2 of SEQ ID NO: 18 and the LCDR 3 of SEQ ID NO: 19.

In another embodiment, the invention provides a T cell activating bispecific antigen binding molecule comprising
a) a first Fab molecule which specifically binds to a first antigen;
b) a second Fab molecule which specifically binds to a second antigen, and wherein the variable domains VL and VH or the constant domains CL and CH1 of the Fab light chain and the Fab heavy chain are replaced by each other;
c) an Fc domain composed of a first and a second subunit capable of stable association; wherein the first antigen is CEA and the second antigen is an activating T cell antigen, particularly CD3, more particularly CD3 epsilon;
wherein
(i) the first Fab molecule under a) is fused at the C-terminus of the Fab heavy chain to the N-terminus of the Fab heavy chain of the second Fab molecule under b), and the second Fab molecule under b) is fused at the C-terminus of the Fab heavy chain to the N-terminus of one of the subunits of the Fc domain under c), or
(ii) the second Fab molecule under b) is fused at the C-terminus of the Fab heavy chain to the N-terminus of the Fab heavy chain of the first Fab molecule under a), and the first Fab molecule under a) is fused at the C-terminus of the Fab heavy chain to the N-terminus of one of the subunits of the Fc domain under c); and
wherein the first Fab molecule under a) comprises a heavy chain variable region, particularly a humanized heavy chain variable region, comprising the heavy chain complementarity determining region (HCDR) 1 of SEQ ID NO: 14, the HCDR 2 of SEQ ID NO: 15 and the HCDR 3 of SEQ ID NO: 16, and a light chain variable region, particularly a humanized light chain variable region, comprising the light chain complementarity determining region (LCDR) 1 of SEQ ID NO: 17, the LCDR 2 of SEQ ID NO: 18 and the LCDR 3 of SEQ ID NO: 19.

In a further embodiment, the invention provides a T cell activating bispecific antigen binding molecule comprising
a) a first Fab molecule which specifically binds to a first antigen;
b) a second Fab molecule which specifically binds to a second antigen, and wherein the variable domains VL and VH or the constant domains CL and CH1 of the Fab light chain and the Fab heavy chain are replaced by each other; and
c) an Fc domain composed of a first and a second subunit capable of stable association; wherein
(i) the first antigen is CEA and the second antigen is an activating T cell antigen, particularly CD3, more particularly CD3 epsilon; or
(ii) the second antigen is CEA and the first antigen is an activating T cell antigen, particularly CD3, more particularly CD3 epsilon;
wherein the first Fab molecule under a) and the second Fab molecule under b) are each fused at the C-terminus of the Fab heavy chain to the N-terminus of one of the subunits of the Fc domain under c); and
wherein the Fab molecule which specifically binds to CEA comprises a heavy chain variable region, particularly a humanized heavy chain variable region, comprising the heavy chain complementarity determining region (HCDR) 1 of SEQ ID NO: 14, the HCDR 2 of SEQ ID NO: 15 and the HCDR 3 of SEQ ID NO: 16, and a light chain variable region, particularly a humanized light chain variable region, comprising the light chain complementarity determining region (LCDR) 1 of SEQ ID NO: 17, the LCDR 2 of SEQ ID NO: 18 and the LCDR 3 of SEQ ID NO: 19.

In all of the different configurations of the T cell activating bispecific antigen binding molecule according to the invention, the amino acid substitutions described herein, if present, may either be in the CH1 and CL domains of the first and (if present) the third Fab molecule, or in the CH1 and CL domains of the second Fab molecule. Preferably, they are in the CH1 and CL domains of the first and (if present) the third Fab molecule. In accordance with the concept of the invention, if amino acid substitutions as described herein are made in the first (and, if present, the third) Fab molecule, no such amino acid substitutions are made in the second Fab molecule. Conversely, if amino acid substitutions as described herein are made in the second Fab molecule, no such amino acid substitutions are made in the first (and, if present, the third) Fab molecule. No amino acid substitutions are made in T cell activating bispecific antigen binding molecules comprising a Fab molecule wherein the constant domains CL and CH1 of the Fab light chain and the Fab heavy chain are replaced by each other.

In particular embodiments of the T cell activating bispecific antigen binding molecule according to the invention, particularly wherein amino acid substitutions as described herein are made in the first (and, if present, the third) Fab molecule, the constant domain CL of the first (and, if present, the third) Fab molecule is of kappa isotype. In other embodiments of the T cell activating bispecific antigen binding molecule according to the invention, particularly wherein amino acid substitutions as described herein are made in the second Fab molecule, the constant domain CL of the second Fab molecule is of kappa isotype. In some embodiments, the constant domain CL of the first (and, if present, the third) Fab molecule and the constant domain CL of the second Fab molecule are of kappa isotype.

In a particular embodiment, the invention provides a T cell activating bispecific antigen binding molecule comprising
a) a first Fab molecule which specifically binds to a first antigen;
b) a second Fab molecule which specifically binds to a second antigen, and wherein the variable domains VL and VH of the Fab light chain and the Fab heavy chain are replaced by each other;
c) a third Fab molecule which specifically binds to the first antigen; and
d) an Fc domain composed of a first and a second subunit capable of stable association; wherein the first antigen is CEA and the second antigen is an activating T cell antigen, particularly CD3, more particularly CD3 epsilon;
wherein the third Fab molecule under c) is identical to the first Fab molecule under a);
wherein in the constant domain CL of the first Fab molecule under a) and the third Fab molecule under c) the amino acid at position 124 is substituted by lysine (K) (numbering according to Kabat) and the amino acid at position 123 is substituted by lysine (K) or arginine (R) (numbering according to Kabat), and wherein in the constant domain CH1 of the first Fab molecule under a) and the third Fab molecule under c) the amino acid at position 147 is substituted by glutamic acid (E) (numbering according to Kabat EU index) and the amino acid at position 213 is substituted by glutamic acid (E) (numbering according to Kabat EU index);
wherein
(i) the first Fab molecule under a) is fused at the C-terminus of the Fab heavy chain to the N-terminus of the Fab heavy chain of the second Fab molecule under b), and the second Fab molecule under b) and the third Fab molecule under c) are each fused at the C-terminus of the Fab heavy chain to the N-terminus of one of the subunits of the Fc domain under d), or
(ii) the second Fab molecule under b) is fused at the C-terminus of the Fab heavy chain to the N-terminus of the Fab heavy chain of the first Fab molecule under a), and the first Fab molecule under a) and the third Fab molecule under c) are each fused at the C-terminus of the Fab heavy chain to the N-terminus of one of the subunits of the Fc domain under d); and
wherein the first Fab molecule under a) and the third Fab molecule under c) comprise a heavy chain variable region, particularly a humanized heavy chain variable region, comprising the heavy chain complementarity determining region (HCDR) 1 of SEQ ID NO: 14, the HCDR 2 of SEQ ID NO: 15 and the HCDR 3 of SEQ ID NO: 16, and a light chain variable region, particularly a humanized light chain variable region, comprising the light chain complementarity determining region (LCDR) 1 of SEQ ID NO: 17, the LCDR 2 of SEQ ID NO: 18 and the LCDR 3 of SEQ ID NO: 19.

In an even more particular embodiment, the invention provides a T cell activating bispecific antigen binding molecule comprising
a) a first Fab molecule which specifically binds to a first antigen;
b) a second Fab molecule which specifically binds to a second antigen, and wherein the variable domains VL and VH of the Fab light chain and the Fab heavy chain are replaced by each other;
c) a third Fab molecule which specifically binds to the first antigen; and
d) an Fc domain composed of a first and a second subunit capable of stable association;
wherein the first antigen is CEA and the second antigen is an activating T cell antigen, particularly CD3, more particularly CD3 epsilon;
wherein the third Fab molecule under c) is identical to the first Fab molecule under a);
wherein in the constant domain CL of the first Fab molecule under a) and the third Fab molecule under c) the amino acid at position 124 is substituted by lysine (K) (numbering according to Kabat) and the amino acid at position 123 is substituted by arginine (R) (numbering according to Kabat), and wherein in the constant domain CH1 of the first Fab molecule under a) and the third Fab molecule under c) the amino acid at position 147 is substituted by glutamic acid (E) (numbering according to Kabat EU index) and the amino acid at position 213 is substituted by glutamic acid (E) (numbering according to Kabat EU index);
wherein the first Fab molecule under a) is fused at the C-terminus of the Fab heavy chain to the N-terminus of the Fab heavy chain of the second Fab molecule under b), and the second Fab molecule under b) and the third Fab molecule under c) are each fused at the C-terminus of the Fab heavy chain to the N-terminus of one of the subunits of the Fc domain under d); and
wherein the first Fab molecule under a) and the third Fab molecule under c) comprise a heavy chain variable region, particularly a humanized heavy chain variable region, comprising the heavy chain complementarity determining region (HCDR) 1 of SEQ ID NO: 14, the HCDR 2 of SEQ ID NO: 15 and the HCDR 3 of SEQ ID NO: 16, and a light chain variable region, particularly a humanized light chain variable region, comprising the light chain complementarity determining region (LCDR) 1 of SEQ ID NO: 17, the LCDR 2 of SEQ ID NO: 18 and the LCDR 3 of SEQ ID NO: 19.

In another embodiment, the invention provides a T cell activating bispecific antigen binding molecule comprising
a) a first Fab molecule which specifically binds to a first antigen;
b) a second Fab molecule which specifically binds to a second antigen, and wherein the variable domains VL and VH of the Fab light chain and the Fab heavy chain are replaced by each other;
c) an Fc domain composed of a first and a second subunit capable of stable association; wherein the first antigen is CEA and the second antigen is an activating T cell antigen, particularly CD3, more particularly CD3 epsilon;
wherein in the constant domain CL of the first Fab molecule under a) the amino acid at position 124 is substituted by lysine (K) (numbering according to Kabat) and the amino acid at position 123 is substituted by lysine (K) or arginine (R) (numbering according to Kabat), and wherein in the constant domain CH1 of the first Fab molecule under a) the amino acid at position 147 is substituted by glutamic acid (E) (numbering according to Kabat EU index) and the amino acid at position 213 is substituted by glutamic acid (E) (numbering according to Kabat EU index);
wherein
(i) the first Fab molecule under a) is fused at the C-terminus of the Fab heavy chain to the N-terminus of the Fab heavy chain of the second Fab molecule under b), and the second Fab molecule under b) is fused at the C-terminus of the Fab heavy chain to the N-terminus of one of the subunits of the Fc domain under c), or
(ii) the second Fab molecule under b) is fused at the C-terminus of the Fab heavy chain to the N-terminus of the Fab heavy chain of the first Fab molecule under a), and the first Fab molecule under a) is fused at the C-terminus of the Fab heavy chain to the N-terminus of one of the subunits of the Fc domain under c); and
wherein the first Fab molecule under a) comprises a heavy chain variable region, particularly a humanized heavy chain variable region, comprising the heavy chain complementarity determining region (HCDR) 1 of SEQ ID NO: 14, the HCDR 2 of SEQ ID NO: 15 and the HCDR 3 of SEQ ID NO: 16, and a light chain variable region, particularly a humanized light chain variable region, comprising the light chain complementarity determining region (LCDR) 1 of SEQ ID NO: 17, the LCDR 2 of SEQ ID NO: 18 and the LCDR 3 of SEQ ID NO: 19.

In a further embodiment, the invention provides a T cell activating bispecific antigen binding molecule comprising
a) a first Fab molecule which specifically binds to a first antigen;
b) a second Fab molecule which specifically binds to a second antigen, and wherein the variable domains VL and VH of the Fab light chain and the Fab heavy chain are replaced by each other; and
c) an Fc domain composed of a first and a second subunit capable of stable association;
wherein
(i) the first antigen is CEA and the second antigen is an activating T cell antigen, particularly CD3, more particularly CD3 epsilon; or
(ii) the second antigen is CEA and the first antigen is an activating T cell antigen, particularly CD3, more particularly CD3 epsilon;
wherein in the constant domain CL of the first Fab molecule under a) the amino acid at position 124 is substituted by lysine (K) (numbering according to Kabat) and the amino acid at position 123 is substituted by lysine (K) or arginine (R) (numbering according to Kabat), and wherein in the constant domain CH1 of the first Fab molecule under a) the amino acid at position 147 is substituted by glutamic acid (E) (numbering according to Kabat EU index) and the amino acid at position 213 is substituted by glutamic acid (E) (numbering according to Kabat EU index);
wherein the first Fab molecule under a) and the second Fab molecule under b) are each fused at the C-terminus of the Fab heavy chain to the N-terminus of one of the subunits of the Fc domain under c); and
wherein the Fab molecule which specifically binds to CEA comprises a heavy chain variable region, particularly a humanized heavy chain variable region, comprising the heavy chain complementarity determining region (HCDR) 1 of SEQ ID NO: 14, the HCDR 2 of SEQ ID NO: 15 and the HCDR 3 of SEQ ID NO: 16, and a light chain variable region, particularly a humanized light chain variable region, comprising the light chain complementarity determining region (LCDR) 1 of SEQ ID NO: 17, the LCDR 2 of SEQ ID NO: 18 and the LCDR 3 of SEQ ID NO: 19.

In particular embodiments of the T cell activating bispecific antigen binding molecule, the Fc domain is an IgG Fc domain. In a specific embodiment, the Fc domain is an IgG$_1$ Fc domain. In another specific embodiment, the Fc domain is an IgG$_4$ Fc domain. In an even more specific embodiment, the Fc domain is an IgG$_4$ Fc domain comprising the amino acid substitution S228P (Kabat numbering). In particular embodiments the Fc domain is a human Fc domain.

In particular embodiments, the Fc domain comprises a modification promoting the association of the first and the second Fc domain subunit. In a specific such embodiment, an amino acid residue in the CH3 domain of the first subunit of the Fc domain is replaced with an amino acid residue having a larger side chain volume, thereby generating a protuberance within the CH3 domain of the first subunit which is positionable in a cavity within the CH3 domain of the second subunit, and an amino acid residue in the CH3 domain of the second subunit of the Fc domain is replaced with an amino acid residue having a smaller side chain volume, thereby generating a cavity within the CH3 domain of the second subunit within which the protuberance within the CH3 domain of the first subunit is positionable.

In a particular embodiment the Fc domain exhibits reduced binding affinity to an Fc receptor and/or reduced effector function, as compared to a native IgG$_1$ Fc domain. In certain embodiments the Fc domain is engineered to have reduced binding affinity to an Fc receptor and/or reduced effector function, as compared to a non-engineered Fc domain. In one embodiment, the Fc domain comprises one or more amino acid substitution that reduces binding to an Fc receptor and/or effector function.

In one embodiment, the one or more amino acid substitution in the Fc domain that reduces binding to an Fc receptor and/or effector function is at one or more position selected from the group of L234, L235, and P329 (Kabat EU index numbering). In particular embodiments, each subunit of the Fc domain comprises three amino acid substitutions that reduce binding to an Fc receptor and/or effector function wherein said amino acid substitutions are L234A, L235A and P329G (Kabat EU index numbering). In one such embodiment, the Fc domain is an IgG$_1$ Fc domain, particularly a human IgG$_1$ Fc domain. In other embodiments, each subunit of the Fc domain comprises two amino acid substitutions that reduce binding to an Fc receptor and/or effector function wherein said amino acid substitutions are L235E and P329G (Kabat EU index numbering). In one such embodiment, the Fc domain is an IgG$_4$ Fc domain, particularly a human IgG$_4$ Fc domain. In one embodiment, the Fc domain of the T cell activating bispecific antigen binding molecule is an IgG$_4$ Fc domain and comprises the amino acid substitutions L235E and S228P (SPLE) (Kabat EU index numbering).

In one embodiment the Fc receptor is an Fcγ receptor. In one embodiment the Fc receptor is a human Fc receptor. In one embodiment, the Fc receptor is an activating Fc receptor. In a specific embodiment, the Fc receptor is human FcγRIIa, FcγRI, and/or FcγRIIIa. In one embodiment, the effector function is antibody-dependent cell-mediated cytotoxicity (ADCC).

In a specific embodiment of the T cell activating bispecific antigen binding molecule according to the invention, the antigen binding moiety which specifically binds to an activating T cell antigen, particularly CD3, more particularly CD3 epsilon, comprises a heavy chain variable region comprising the heavy chain complementarity determining region (HCDR) 1 of SEQ ID NO: 4, the HCDR 2 of SEQ ID NO: 5, the HCDR 3 of SEQ ID NO: 6, and a light chain variable region comprising the light chain complementarity determining region (LCDR) 1 of SEQ ID NO: 8, the LCDR 2 of SEQ ID NO: 9 and the LCDR 3 of SEQ ID NO: 10. In an even more specific embodiment, the antigen binding moiety which specifically binds to an activating T cell antigen, particularly CD3, more particularly CD3 epsilon, comprises a heavy chain variable region comprising an amino acid sequence that is at least about 95%, 96%, 97%, 98%, 99% or 100% identical to the amino acid sequence of SEQ ID NO: 3 and a light chain variable region comprising an amino acid sequence that is at least about 95%, 96%, 97%, 98%, 99% or 100% identical to the amino acid sequence of SEQ ID NO: 7. In some embodiments, the antigen binding moiety which specifically binds to an activating T cell antigen is a Fab molecule. In one specific embodiment, the second antigen binding moiety, particularly Fab molecule, comprised in the T cell activating bispecific antigen binding molecule according to the invention specifically binds to CD3, more particularly CD3 epsilon, and comprises the heavy chain complementarity determining region (CDR) 1 of SEQ ID NO: 4, the heavy chain CDR 2 of SEQ ID NO: 5, the heavy chain CDR 3 of SEQ ID NO: 6, the light chain CDR 1 of SEQ ID NO: 8, the light chain CDR 2 of SEQ ID NO: 9 and the light chain CDR 3 of SEQ ID NO: 10. In an even more specific embodiment, said second antigen binding moiety, particularly Fab molecule, comprises a heavy chain variable region comprising the amino acid sequence of SEQ ID NO: 3 and a light chain variable region comprising the amino acid sequence of SEQ ID NO: 7.

In a further specific embodiment of the T cell activating bispecific antigen binding molecule according to the invention, the antigen binding moiety, particularly Fab molecule, which specifically binds to CEA comprises the heavy chain complementarity determining region (CDR) 1 of SEQ ID NO: 14, the heavy chain CDR 2 of SEQ ID NO: 15, the heavy chain CDR 3 of SEQ ID NO: 16, the light chain CDR 1 of SEQ ID NO: 17, the light chain CDR 2 of SEQ ID NO: 18 and the light chain CDR 3 of SEQ ID NO: 19. In an even more specific embodiment, the antigen binding moiety, particularly Fab molecule, which specifically binds to CEA comprises a heavy chain variable region comprising an amino acid sequence that is at least about 95%, 96%, 97%, 98%, 99% or 100% identical to the amino acid sequence of SEQ ID NO: 22 and a light chain variable region comprising an amino acid sequence that is at least about 95%, 96%, 97%, 98%, 99% or 100% identical to the amino acid sequence of SEQ ID NO: 23. In one specific embodiment, the first (and, if present, the third) antigen binding moiety, particularly Fab molecule, comprised in the T cell activating bispecific antigen binding molecule according to the invention specifically binds to CEA, and comprises the heavy chain complementarity determining region (CDR) 1 of SEQ ID NO: 14, the heavy chain CDR 2 of SEQ ID NO: 15, the heavy chain CDR 3 of SEQ ID NO: 16, the light chain CDR 1 of SEQ ID NO: 17, the light chain CDR 2 of SEQ ID NO: 18 and the light chain CDR 3 of SEQ ID NO: 19. In an even more specific embodiment, said first (and, if present, said third) antigen binding moiety, particularly Fab molecule, comprises a heavy chain variable region comprising the amino acid sequence of SEQ ID NO: 22 and a light chain variable region comprising the amino acid sequence of SEQ ID NO: 23.

In a particular aspect, the invention provides a T cell activating bispecific antigen binding molecule comprising a) a first Fab molecule which specifically binds to a first antigen;
b) a second Fab molecule which specifically binds to a second antigen, and wherein the variable domains VL and VH or the constant domains CL and CH1 of the Fab light chain and the Fab heavy chain are replaced by each other;
c) a third Fab molecule which specifically binds to the first antigen; and
d) an Fc domain composed of a first and a second subunit capable of stable association;
wherein
(i) the first antigen is CEA and the second antigen is CD3, particularly CD3 epsilon;
(ii) the first Fab molecule under a) and the third Fab molecule under c) each comprise the heavy chain complementarity determining region (CDR) 1 of SEQ ID NO: 14, the heavy chain CDR 2 of SEQ ID NO: 15, the heavy chain CDR 3 of SEQ ID NO: 16, the light chain CDR 1 of SEQ ID NO: 17, the light chain CDR 2 of SEQ ID NO: 18 and the light chain CDR 3 of SEQ ID NO: 19, and the second Fab molecule under b) comprises the heavy chain CDR 1 of SEQ ID NO: 4, the heavy chain CDR 2 of SEQ ID NO: 5, the heavy chain CDR 3 of SEQ ID NO: 6, the light chain CDR 1 of SEQ ID NO: 8, the light chain CDR 2 of SEQ ID NO: 9 and the light chain CDR 3 of SEQ ID NO: 10; and
(iii) the first Fab molecule under a) is fused at the C-terminus of the Fab heavy chain to the N-terminus of the Fab heavy chain of the second Fab molecule under b), and the second Fab molecule under b) and the third Fab molecule under c) are each fused at the C-terminus of the Fab heavy chain to the N-terminus of one of the subunits of the Fc domain under d).

In one embodiment, in the second Fab molecule under b) the variable domains VL and VH are replaced by each other and further (iv) in the constant domain CL of the first Fab molecule under a) and the third Fab molecule under c) the amino acid at position 124 is substituted by lysine (K) (numbering according to Kabat) and the amino acid at position 123 is substituted by lysine (K) or arginine (R), particularly by arginine (R) (numbering according to Kabat), and in the constant domain CH1 of the first Fab molecule under a) and the third Fab molecule under c) the amino acid at position 147 is substituted by glutamic acid (E) (numbering according to Kabat EU index) and the amino acid at position 213 is substituted by glutamic acid (E) (numbering according to Kabat EU index).

According to another aspect of the invention there is provided one or more isolated polynucleotide(s) encoding a T cell activating bispecific antigen binding molecule of the invention. The invention further provides one or more expression vector(s) comprising the isolated polynucleotide(s) of the invention, and a host cell comprising the isolated polynucleotide(s) or the expression vector(s) of the invention. In some embodiments the host cell is a eukaryotic cell, particularly a mammalian cell.

In another aspect is provided a method of producing the T cell activating bispecific antigen binding molecule of the invention, comprising the steps of a) culturing the host cell of the invention under conditions suitable for the expression of the T cell activating bispecific antigen binding molecule and b) recovering the T cell activating bispecific antigen binding molecule. The invention also encompasses a T cell activating bispecific antigen binding molecule produced by the method of the invention.

The invention further provides a pharmaceutical composition comprising the T cell activating bispecific antigen binding molecule of the invention and a pharmaceutically acceptable carrier.

Also encompassed by the invention are methods of using the T cell activating bispecific antigen binding molecule and pharmaceutical composition of the invention. In one aspect the invention provides a T cell activating bispecific antigen binding molecule or a pharmaceutical composition of the invention for use as a medicament. In one aspect is provided a T cell activating bispecific antigen binding molecule or a pharmaceutical composition according to the invention for use in the treatment of a disease in an individual in need thereof. In a specific embodiment the disease is cancer.

Also provided is the use of a T cell activating bispecific antigen binding molecule of the invention for the manufacture of a medicament for the treatment of a disease in an individual in need thereof; as well as a method of treating a disease in an individual, comprising administering to said individual a therapeutically effective amount of a composition comprising the T cell activating bispecific antigen binding molecule according to the invention in a pharmaceutically acceptable form. In a specific embodiment the disease is cancer. In any of the above embodiments the individual preferably is a mammal, particularly a human.

The invention also provides a method for inducing lysis of a target cell, particularly a tumor cell, comprising contacting a target cell with a T cell activating bispecific antigen binding molecule of the invention in the presence of a T cell, particularly a cytotoxic T cell.

BRIEF DESCRIPTION OF THE DRAWINGS

FIGS. 5A-D. Binding of different CEA TCB formats to cells, expressing either high levels of CEA (MKN45; A), medium levels of CEA (LS174T; B) or low levels of CEA (HT29; C), or human CD3 (Jurkat cells; D). Median Fluorescence intensities (MFI) are depicted. Error bars indicate SD of triplicates.

FIGS. 7A-H. Up-regulation of CD25 on human CD4+(A-D) and CD8+(E-H) T cells after T cell-mediated lysis of CEA-expressing tumor cells induced by different CEA CD3 TCB molecules. Human PBMCs were used as effector cells and MKN45 (A, E), BxPC-3 (B, F) or HT29 (C, G) cells were used as target cells, at a final effector to target cell ratio of 10:1. Results without target cells are shown in (D) and (H). Percentage of CD25-positive T cells was determined by FACS after 48 h. Depicted are triplicates with SD.

FIGS. 9A-D. T cell activation and tumor cell lysis induced by different CEA CD3 TCB molecules, as measured by FACS (percent of CD69-positive CD8+ T cells (A, B)), or LDH (C, D) after 48 h. Human PBMCs were used as effector cells at a final effector to target cell ratio of 10:1. Target cells were either high CEA expressing MKN45 or low CEA-expressing primary epithelial cells CCD841 CoN. In addition, T cell activation was assessed in the absence of targets ("no targets"). Depicted are triplicates with SD. A, C: CEA CD3 TCB with parental chimeric T84.66 CEA binder (molecule A), B, D: CEA CD3 TCB with humanized CEA binder (humanized variant 1; molecule B).

FIGS. 10A-B. Jurkat-NFAT reporter cell assay to determine early CD3-mediated activation of Jurkats upon simultaneous binding of different CEA CD3 TCB molecules to target and Jurkat effector cells. The intensity of CD3-mediated activation and signaling was detected by measuring the relative luminescence signal (RLUs). Depicted are triplicates with SD. (A) CEA CD3 TCB with parental chimeric T84.66 CEA binder (molecule A), (B) CEA CD3 TCB with humanized CEA binder (humanized variant 1; molecule B).

FIGS. 12A-H. Proliferation of CD8+(A-D) and CD4+(E-H) T cells, induced by different CEA CD3 TCB molecules, as measured by FACS after 5 days. Human PBMCs were used as effector cells at a final effector to target cell ratio of 10:1. Target cells were either high CEA expressing MKN45 (A, E), medium CEA expressing LS174T (B, F), low CEA-expressing HT29 (C, G) cells or very low CEA expressing primary epithelial cells CCD841 CoN (D, H). Depicted are triplicates with SD.

FIGS. 13A-D. Binding of different CEA CD3 TCB molecules (molecule B and molecule E) to MKN45 (A), LS174T (B), HT29 (C) and Jurkat (D) cells, as measured by FACS.

FIGS. 17A-E. Determination of antigen-dependent tumor cell lysis, induced by different CEA CD3 TCB molecules in the presence of various CEA-positive tumor cells: (A) HCC1954, (B) NCI-H596, (C) NCI-H2122, (D) Kato III, (E) CX-1. Tumor cell lysis was determined by quantification of LDH released from apoptotic/necrotic tumor cells. Depicted are triplicates with SD. EC50 values of tumor cell lysis were calculated by Graph Pad Prism and are presented in Table 7.

FIGS. 18A-B. Antigen-dependent T cell activation and tumor lysis induced by CEA CD3 TCB molecule B in the presence of CEA-positive tumor cells, but not in the presence of low CEA-expressing primary epithelia cells. Tumor cell lysis was determined by quantification of LDH released from apoptotic/necrotic tumor cells (A). T cell activation was determined by FACS measurement of up-regulation of the early activation marker CD69 on CD4+ effector cells (B). Depicted are triplicates with SD. EC50 values of tumor cell lysis and T-cell activation were calculated by Graph Pad Prism and are presented in Table 9 and Table 11.

FIGS. 23A-B. (A) Anti-tumor activity of CEA CD3 TCB molecule B versus CEA CD3 TCB molecule X in the MKN45 model in fully humanized NSG mice. Different doses and schedules of administration were tested. Black arrow indicates start of therapy. Treatment was administered for 4 weeks. (B) 2-way ANOVA multiple comparison analysis at study termination (day 38). *p<0.05 p<0.01; *p<0.001; ****p<0.0001 (9<n<14).

DETAILED DESCRIPTION OF THE INVENTION

Definitions

Figures 1C, 1F:
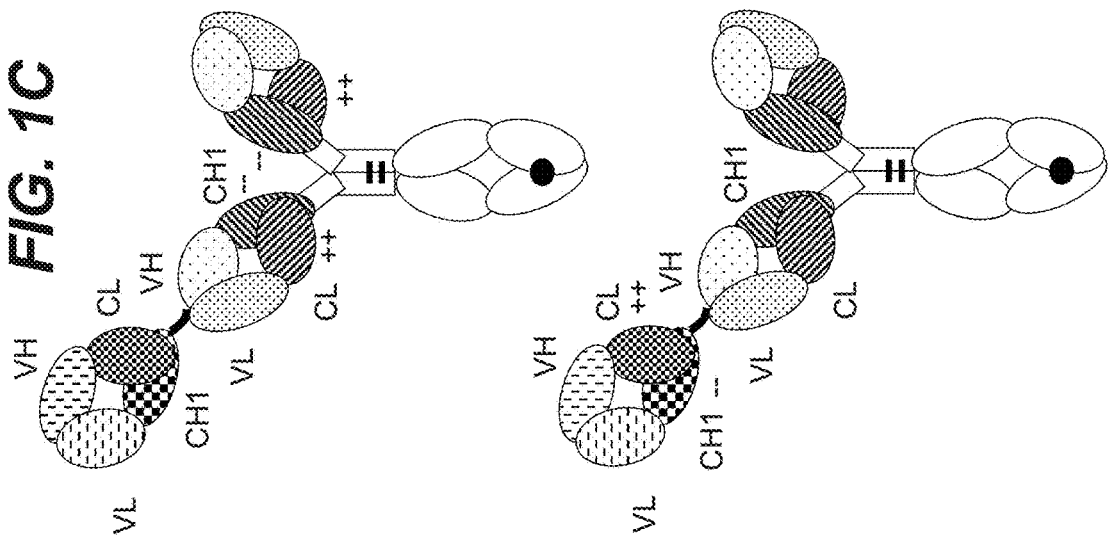
FIGS. 1A-Z. Exemplary configurations of the T cell activating bispecific antigen binding molecules (TCBs) of the invention. (A, D) Illustration of the "1+1 CrossMab" molecule. (B, E) Illustration of the "2+1 IgG Crossfab" molecule with alternative order of Crossfab and Fab components ("inverted"). (C, F) Illustration of the "2+1 IgG Crossfab" molecule. (G, K) Illustration of the "1+1 IgG Crossfab" molecule with alternative order of Crossfab and Fab components ("inverted"). (H, L) Illustration of the "1+1 IgG Crossfab" molecule. (I, M) Illustration of the "2+1 IgG Crossfab" molecule with two CrossFabs. (J, N) Illustration of the "2+1 IgG Crossfab" molecule with two CrossFabs and alternative order of Crossfab and Fab components ("inverted"). (0, S) Illustration of the "Fab-Crossfab" molecule. (P, T) Illustration of the "Crossfab-Fab" molecule. (Q, U) Illustration of the "(Fab)$_2$-Crossfab" molecule. (R, V) Illustration of the "Crossfab-(Fab)$_2$" molecule. (W, Y) Illustration of the "Fab-(Crossfab)$_2$" molecule. (X, Z) Illustration of the "(Crossfab)$_2$-Fab" molecule. Black dot: optional modification in the Fc domain promoting heterodimerization. ++, --: amino acids of opposite charges optionally introduced in the CH1 and CL domains. Crossfab molecules are depicted as comprising an exchange of VH and VL regions, but may—in embodiments wherein no charge modifications are introduced in CH1 and CL domains—alternatively comprise an exchange of the CH1 and CL domains.

Terms are used herein as generally used in the art, unless otherwise defined in the following.

As used herein, the term "antigen binding molecule" refers in its broadest sense to a molecule that specifically binds an antigenic determinant. Examples of antigen binding molecules are immunoglobulins and derivatives, e.g. fragments, thereof.

The term "bispecific" means that the antigen binding molecule is able to specifically bind to at least two distinct antigenic determinants. Typically, a bispecific antigen binding molecule comprises two antigen binding sites, each of which is specific for a different antigenic determinant. In certain embodiments the bispecific antigen binding molecule is capable of simultaneously binding two antigenic determinants, particularly two antigenic determinants expressed on two distinct cells.

The term "valent" as used herein denotes the presence of a specified number of antigen binding sites in an antigen binding molecule. As such, the term "monovalent binding to an antigen" denotes the presence of one (and not more than one) antigen binding site specific for the antigen in the antigen binding molecule.

An "antigen binding site" refers to the site, i.e. one or more amino acid residues, of an antigen binding molecule which provides interaction with the antigen. For example, the antigen binding site of an antibody comprises amino acid residues from the complementarity determining regions (CDRs). A native immunoglobulin molecule typically has two antigen binding sites, a Fab molecule typically has a single antigen binding site.

As used herein, the term "antigen binding moiety" refers to a polypeptide molecule that specifically binds to an antigenic determinant. In one embodiment, an antigen binding moiety is able to direct the entity to which it is attached (e.g. a second antigen binding moiety) to a target site, for example to a specific type of tumor cell or tumor stroma bearing the antigenic determinant. In another embodiment an antigen binding moiety is able to activate signaling through its target antigen, for example a T cell receptor complex antigen. Antigen binding moieties include antibodies and fragments thereof as further defined herein. Particular antigen binding moieties include an antigen binding domain of an antibody, comprising an antibody heavy chain variable region and an antibody light chain variable region. In certain embodiments, the antigen binding moieties may comprise antibody constant regions as further defined herein and known in the art. Useful heavy chain constant regions include any of the five isotypes: α, δ, ε, γ, or μ. Useful light chain constant regions include any of the two isotypes: κ and λ.

As used herein, the term "antigenic determinant" is synonymous with "antigen" and "epitope," and refers to a site (e.g. a contiguous stretch of amino acids or a conformational configuration made up of different regions of non-contiguous amino acids) on a polypeptide macromolecule to which an antigen binding moiety binds, forming an antigen binding moiety-antigen complex. Useful antigenic determinants can be found, for example, on the surfaces of tumor cells, on the surfaces of virus-infected cells, on the surfaces of other diseased cells, on the surface of immune cells, free in blood serum, and/or in the extracellular matrix (ECM). The proteins referred to as antigens herein (e.g. CD3) can be any native form the proteins from any vertebrate source, including mammals such as primates (e.g. humans) and rodents (e.g. mice and rats), unless otherwise indicated. In a particular embodiment the antigen is a human protein. Where reference is made to a specific protein herein, the term encompasses the "full-length", unprocessed protein as well as any form of the protein that results from processing in the cell. The term also encompasses naturally occurring variants of the protein, e.g. splice variants or allelic variants. An exemplary human protein useful as antigen is CD3, particularly the epsilon subunit of CD3 (see UniProt no. P07766 (version 130), NCBI RefSeq no. NP_000724.1, SEQ ID NO: 1 for the human sequence; or UniProt no. Q95LI5 (version 49), NCBI GENBANK® no. BAB71849.1, SEQ ID NO: 2 for the cynomolgus [*Macaca fascicularis*] sequence), or Carcinoembroynic antigen (CEA), also known as Carcinoembryonic antigen-related cell adhesion molecule 5 (CEACAM5, UniProt no. P06731 (version 119), NCBI RefSeq no. NP_004354.2). In certain embodiments the T cell activating bispecific antigen binding molecule of the invention binds to an epitope of CD3 or CEA that is conserved among the CD3 or CEA antigens from different species.

By "specific binding" is meant that the binding is selective for the antigen and can be discriminated from unwanted or non-specific interactions. The ability of an antigen binding moiety to bind to a specific antigenic determinant can be measured either through an enzyme-linked immunosorbent assay (ELISA) or other techniques familiar to one of skill in the art, e.g. surface plasmon resonance (SPR) technique (analyzed on a BIACORE® instrument) (Liljeblad et al., Glyco J 17, 323-329 (2000)), and traditional binding assays (Heeley, Endocr Res 28, 217-229 (2002)). In one embodiment, the extent of binding of an antigen binding moiety to an unrelated protein is less than about 10% of the binding of the antigen binding moiety to the antigen as measured, e.g., by SPR. In certain embodiments, an antigen binding moiety that binds to the antigen, or an antigen binding molecule comprising that antigen binding moiety, has a dissociation constant ($K_D$) of ≤1 μM, ≤100 nM, ≤10 nM, ≤1 nM, ≤0.1 nM, ≤0.01 nM, or ≤0.001 nM (e.g. $10^{-8}$M or less, e.g. from $10^{-8}$M to $10^{-13}$M, e.g., from $10^{-9}$M to $10^{-13}$ M).

"Affinity" refers to the strength of the sum total of non-covalent interactions between a single binding site of a molecule (e.g., a receptor) and its binding partner (e.g., a ligand). Unless indicated otherwise, as used herein, "binding affinity" refers to intrinsic binding affinity which reflects a 1:1 interaction between members of a binding pair (e.g., an antigen binding moiety and an antigen, or a receptor and its ligand). The affinity of a molecule X for its partner Y can generally be represented by the dissociation constant ($K_D$), which is the ratio of dissociation and association rate constants ($k_{off}$ and $k_{on}$, respectively). Thus, equivalent affinities may comprise different rate constants, as long as the ratio of the rate constants remains the same. Affinity can be measured by well established methods known in the art, including those described herein. A particular method for measuring affinity is Surface Plasmon Resonance (SPR).

"Reduced binding", for example reduced binding to an Fc receptor, refers to a decrease in affinity for the respective interaction, as measured for example by SPR. For clarity the term includes also reduction of the affinity to zero (or below the detection limit of the analytic method), i.e. complete abolishment of the interaction. Conversely, "increased binding" refers to an increase in binding affinity for the respective interaction.

An "activating T cell antigen" as used herein refers to an antigenic determinant expressed on the surface of a T lymphocyte, particularly a cytotoxic T lymphocyte, which is capable of inducing T cell activation upon interaction with an antigen binding molecule. Specifically, interaction of an antigen binding molecule with an activating T cell antigen may induce T cell activation by triggering the signaling cascade of the T cell receptor complex. In a particular embodiment the activating T cell antigen is CD3, particularly the epsilon subunit of CD3 (see UniProt no. P07766 (version 130), NCBI RefSeq no. NP_000724.1, SEQ ID NO: 1 for the human sequence; or UniProt no. Q95LI5 (version 49), NCBI GENBANK® no. BAB71849.1, SEQ ID NO: 2 for the cynomolgus [Macaca fascicularis] sequence).

"T cell activation" as used herein refers to one or more cellular response of a T lymphocyte, particularly a cytotoxic T lymphocyte, selected from: proliferation, differentiation, cytokine secretion, cytotoxic effector molecule release, cytotoxic activity, and expression of activation markers. The T cell activating bispecific antigen binding molecules of the invention are capable of inducing T cell activation. Suitable assays to measure T cell activation are known in the art described herein.

A "target cell antigen" as used herein refers to an antigenic determinant presented on the surface of a target cell, for example a cell in a tumor such as a cancer cell or a cell of the tumor stroma. In a particular embodiment, the target cell antigen is CEA, particularly human CEA.

As used herein, the terms "first", "second" or "third" with respect to Fab molecules etc., are used for convenience of distinguishing when there is more than one of each type of moiety. Use of these terms is not intended to confer a specific order or orientation of the T cell activating bispecific antigen binding molecule unless explicitly so stated.

A "Fab molecule" refers to a protein consisting of the VH and CH1 domain of the heavy chain (the "Fab heavy chain") and the VL and CL domain of the light chain (the "Fab light chain") of an immunoglobulin.

By "fused" is meant that the components (e.g. a Fab molecule and an Fc domain subunit) are linked by peptide bonds, either directly or via one or more peptide linkers.

As used herein, the term "single-chain" refers to a molecule comprising amino acid monomers linearly linked by peptide bonds. In certain embodiments, one of the antigen binding moieties is a single-chain Fab molecule, i.e. a Fab molecule wherein the Fab light chain and the Fab heavy chain are connected by a peptide linker to form a single peptide chain. In a particular such embodiment, the C-terminus of the Fab light chain is connected to the N-terminus of the Fab heavy chain in the single-chain Fab molecule.

By a "crossover" Fab molecule (also termed "Crossfab") is meant a Fab molecule wherein the variable domains or the constant domains of the Fab heavy and light chain are exchanged (i.e. replaced by each other), i.e. the crossover Fab molecule comprises a peptide chain composed of the light chain variable domain VL and the heavy chain constant domain 1 CH1 (VL-CH1, in N- to C-terminal direction), and a peptide chain composed of the heavy chain variable domain VH and the light chain constant domain CL (VH-CL, in N- to C-terminal direction). For clarity, in a crossover Fab molecule wherein the variable domains of the Fab light chain and the Fab heavy chain are exchanged, the peptide chain comprising the heavy chain constant domain 1 CH1 is referred to herein as the "heavy chain" of the (crossover) Fab molecule. Conversely, in a crossover Fab molecule wherein the constant domains of the Fab light chain and the Fab heavy chain are exchanged, the peptide chain comprising the heavy chain variable domain VH is referred to herein as the "heavy chain" of the (crossover) Fab molecule.

In contrast thereto, by a "conventional" Fab molecule is meant a Fab molecule in its natural format, i.e. comprising a heavy chain composed of the heavy chain variable and constant domains (VH-CH1, in N- to C-terminal direction), and a light chain composed of the light chain variable and constant domains (VL-CL, in N- to C-terminal direction).

The term "immunoglobulin molecule" refers to a protein having the structure of a naturally occurring antibody. For example, immunoglobulins of the IgG class are heterotetrameric glycoproteins of about 150,000 daltons, composed of two light chains and two heavy chains that are disulfide-bonded. From N- to C-terminus, each heavy chain has a variable domain (VH), also called a variable heavy domain or a heavy chain variable region, followed by three constant domains (CH1, CH2, and CH3), also called a heavy chain constant region. Similarly, from N- to C-terminus, each light chain has a variable domain (VL), also called a variable light domain or a light chain variable region, followed by a constant light (CL) domain, also called a light chain constant region. The heavy chain of an immunoglobulin may be assigned to one of five types, called α (IgA), δ (IgD), ε (IgE), γ (IgG), or μ (IgM), some of which may be further divided into subtypes, e.g. $\gamma_1$ (IgG$_1$), $\gamma_2$ (IgG$_2$), $\gamma_3$ (IgG$_3$), $\gamma_4$ (IgG$_4$), $\alpha_1$ (IgA$_1$) and $\alpha_2$ (IgA$_2$). The light chain of an immunoglobulin may be assigned to one of two types, called kappa (κ) and lambda (λ), based on the amino acid sequence of its constant domain. An immunoglobulin essentially consists of two Fab molecules and an Fc domain, linked via the immunoglobulin hinge region.

The term "antibody" herein is used in the broadest sense and encompasses various antibody structures, including but not limited to monoclonal antibodies, polyclonal antibodies, and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$, diabodies, linear antibodies, single-chain antibody molecules (e.g. scFv), and single-domain antibodies. For a review of certain antibody fragments, see Hudson et al., Nat Med 9, 129-134 (2003). For a review of scFv fragments, see e.g. Plückthun, in The Pharmacology of Monoclonal Antibodies, vol. 113, Rosenburg and Moore eds., Springer-Verlag, New York, pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046. Diabodies are antibody fragments with two antigen-binding sites that may be bivalent or bispecific. See, for example, EP 404,097; WO 1993/01161; Hudson et al., Nat Med 9, 129-134 (2003); and Hollinger et al., Proc Natl Acad Sci USA 90, 6444-6448 (1993). Triabodies and tetrabodies are also described in Hudson et al., Nat Med 9, 129-134 (2003). Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see e.g. U.S. Pat. No. 6,248,516 B1). Antibody fragments can be made by various techniques, including but not limited to proteolytic digestion of an intact antibody as well as production by recombinant host cells (e.g. E. coli or phage), as described herein.

The term "antigen binding domain" refers to the part of an antibody that comprises the area which specifically binds to and is complementary to part or all of an antigen. An antigen binding domain may be provided by, for example, one or more antibody variable domains (also called antibody variable regions). Particularly, an antigen binding domain comprises an antibody light chain variable domain (VL) and an antibody heavy chain variable domain (VH).

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). See, e.g., Kindt et al., Kuby Immunology, 6th ed., W.H. Freeman and Co., page 91 (2007). A single VH or VL domain may be sufficient to confer antigen-binding specificity.

The term "hypervariable region" or "HVR", as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the complementarity determining regions (CDRs), the latter being of highest sequence variability and/or involved in antigen recognition. With the exception of CDR1 in VH, CDRs generally comprise the amino acid residues that form the hypervariable loops. Hypervariable regions (HVRs) are also referred to as "complementarity determining regions" (CDRs), and these terms are used herein interchangeably in reference to portions of the variable region that form the antigen binding regions. This particular region has been described by Kabat et al., Sequences of Proteins of Immunological Interest, 5th Ed. Public Health Service, National Institutes of Health, Bethesda, Md. (1991) and by Chothia et al., J Mol Biol 196:901-917 (1987), where the definitions include overlapping or subsets of amino acid residues when compared against each other. Nevertheless, application of either definition to refer to a CDR of an antibody or variants thereof is intended to be within the scope of the term as defined and used herein. The appropriate amino acid residues which encompass the CDRs as defined by each of the above cited references are set forth below in Table A as a comparison. The exact residue numbers which encompass a particular CDR will vary depending on the sequence and size of the CDR. Those skilled in the art can routinely determine which residues comprise a particular CDR given the variable region amino acid sequence of the antibody. The CDR sequences given herein are generally according to the Kabat definition.

TABLE A

| CDR Definitions[1] | | | |
|---|---|---|---|
| CDR | Kabat | Chothia | AbM[2] |
| $V_H$ CDR1 | 31-35 | 26-32 | 26-35 |
| $V_H$ CDR2 | 50-65 | 52-58 | 50-58 |
| $V_H$ CDR3 | 95-102 | 95-102 | 95-102 |

TABLE A-continued

| CDR Definitions[1] | | | |
|---|---|---|---|
| CDR | Kabat | Chothia | AbM[2] |
| $V_L$ CDR1 | 24-34 | 26-32 | 24-34 |
| $V_L$ CDR2 | 50-56 | 50-52 | 50-56 |
| $V_L$ CDR3 | 89-97 | 91-96 | 89-97 |

[1]Numbering of all CDR definitions in Table A is according to the numbering conventions set forth by Kabat et al. (see below).
[2]"AbM" with a lowercase "b" as used in Table A refers to the CDRs as defined by Oxford Molecular's "AbM" antibody modeling software.

Kabat et al. also defined a numbering system for variable region sequences that is applicable to any antibody. One of ordinary skill in the art can unambiguously assign this system of "Kabat numbering" to any variable region sequence, without reliance on any experimental data beyond the sequence itself. As used herein in connection with variable region seqeunces, "Kabat numbering" refers to the numbering system set forth by Kabat et al., Sequences of Proteins of Immunological Interest, 5th Ed. Public Health Service, National Institutes of Health, Bethesda, Md. (1991). Unless otherwise specified, references to the numbering of specific amino acid residue positions in an antibody variable region are according to the Kabat numbering system.

As used herein, the amino acid positions of all constant regions and domains of the heavy and light chain are numbered according to the Kabat numbering system described in Kabat, et al., Sequences of Proteins of Immunological Interest, 5th ed., Public Health Service, National Institutes of Health, Bethesda, Md. (1991) and is referred to as "numbering according to Kabat" or "Kabat numbering" herein. Specifically the Kabat numbering system (see pages 647-660 of Kabat, et al., Sequences of Proteins of Immunological Interest, 5th ed., Public Health Service, National Institutes of Health, Bethesda, Md. (1991)) is used for the light chain constant domain CL of kappa and lambda isotype and the Kabat EU index numbering system (see pages 661-723) is used for the heavy chain constant domains (CH1, Hinge, CH2 and CH3), which is herein further clarified by referring to "numbering according to Kabat EU index" in this case.

The polypeptide sequences of the sequence listing are not numbered according to the Kabat numbering system. However, it is well within the ordinary skill of one in the art to convert the numbering of the sequences of the Sequence Listing to Kabat numbering.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1 (L1)-FR2-H2(L2)-FR3-H3 (L3)-FR4.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. Such variable domains are referred to herein as "humanized variable region". A humanized antibody optionally may comprise at least a portion of an antibody constant region derived from a human antibody. A "humanized form" of an antibody, e.g., a non-human antibody, refers to an antibody that has undergone humanization. Other forms of "humanized antibodies" encompassed by the present invention are those in which the constant region has been additionally modified or changed from that of the original antibody to generate the properties according to the invention, especially in regard to C1q binding and/or Fc receptor (FcR) binding.

The "class" of an antibody or immunoglobulin refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called α, δ, ε, γ, and μ, respectively.

The term "Fc domain" or "Fc region" herein is used to define a C-terminal region of an immunoglobulin heavy chain that contains at least a portion of the constant region. The term includes native sequence Fc regions and variant Fc regions. Although the boundaries of the Fc region of an IgG heavy chain might vary slightly, the human IgG heavy chain Fc region is usually defined to extend from Cys226, or from Pro230, to the carboxyl-terminus of the heavy chain. However, antibodies produced by host cells may undergo post-translational cleavage of one or more, particularly one or two, amino acids from the C-terminus of the heavy chain. Therefore an antibody produced by a host cell by expression of a specific nucleic acid molecule encoding a full-length heavy chain may include the full-length heavy chain, or it may include a cleaved variant of the full-length heavy chain (also referred to herein as a "cleaved variant heavy chain"). This may be the case where the final two C-terminal amino acids of the heavy chain are glycine (G446) and lysine (K447, numbering according to Kabat EU index). Therefore, the C-terminal lysine (Lys447), or the C-terminal glycine (Gly$_{446}$) and lysine (K447), of the Fc region may or may not be present. Amino acid sequences of heavy chains including Fc domains (or a subunit of an Fc domain as defined herein) are denoted herein without C-terminal glycine-lysine dipeptide if not indicated otherwise. In one embodiment of the invention, a heavy chain including a subunit of an Fc domain as specified herein, comprised in a T cell activating bispecific antigen binding molecule according to the invention, comprises an additional C-terminal glycine-lysine dipeptide (G446 and K447, numbering according to EU index of Kabat). In one embodiment of the invention, a heavy chain including a subunit of an Fc domain as specified herein, comprised in a T cell activating bispecific antigen binding molecule according to the invention, comprises an additional C-terminal glycine residue (G446, numbering according to EU index of Kabat). Compositions of the invention, such as the pharmaceutical compositions described herein, comprise a population of T cell activating bispecific antigen binding molecules of the invention. The population of T cell activating bispecific antigen binding molecule may comprise molecules having a full-length heavy chain and molecules having a cleaved variant heavy chain. The population of T cell activating bispecific antigen binding molecules may consist of a mixture of molecules having a full-length heavy chain and molecules having a cleaved variant heavy chain, wherein at least 50%, at least 60%, at least 70%, at least 80% or at least 90% of the T cell activating bispecific antigen binding molecules have a cleaved variant heavy chain. In one embodiment of the invention a composition comprising a population of T cell activating bispecific antigen binding molecules of the invention comprises an T cell activating bispecific antigen binding molecule comprising a heavy chain including a subunit of an Fc domain as specified herein with an additional C-terminal glycine-lysine dipeptide (G446 and K447, numbering according to EU index of Kabat). In one embodiment of the invention a composition comprising a population of T cell activating bispecific antigen binding molecules of the invention comprises an T cell activating bispecific antigen binding molecule comprising a heavy chain including a subunit of an Fc domain as specified herein with an additional C-terminal glycine residue (G446, numbering according to EU index of Kabat). In one embodiment of the invention such a composition comprises a population of T cell activating bispecific antigen binding molecules comprised of molecules comprising a heavy chain including a subunit of an Fc domain as specified herein; molecules comprising a heavy chain including a subunit of a Fc domain as specified herein with an additional C-terminal glycine residue (G446, numbering according to EU index of Kabat); and molecules comprising a heavy chain including a subunit of an Fc domain as specified herein with an additional C-terminal glycine-lysine dipeptide (G446 and K447, numbering according to EU index of Kabat). Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, Md., 1991 (see also above). A "subunit" of an Fc domain as used herein refers to one of the two polypeptides forming the dimeric Fc domain, i.e. a polypeptide comprising C-terminal constant regions of an immunoglobulin heavy chain, capable of stable self-association. For example, a subunit of an IgG Fc domain comprises an IgG CH2 and an IgG CH3 constant domain.

A "modification promoting the association of the first and the second subunit of the Fc domain" is a manipulation of the peptide backbone or the post-translational modifications of an Fc domain subunit that reduces or prevents the association of a polypeptide comprising the Fc domain subunit with an identical polypeptide to form a homodimer. A modification promoting association as used herein particularly includes separate modifications made to each of the two Fc domain subunits desired to associate (i.e. the first and the second subunit of the Fc domain), wherein the modifications are complementary to each other so as to promote association of the two Fc domain subunits. For example, a modification promoting association may alter the structure or charge of one or both of the Fc domain subunits so as to make their association sterically or electrostatically favorable, respectively. Thus, (hetero)dimerization occurs between a polypeptide comprising the first Fc domain subunit and a polypeptide comprising the second Fc domain subunit, which might be non-identical in the sense that further components fused to each of the subunits (e.g. antigen binding moieties) are not the same. In some embodiments the modification promoting association comprises an amino acid mutation in the Fc domain, specifically an amino acid substitution. In a particular embodiment, the modification promoting association comprises a separate amino acid mutation, specifically an amino acid substitution, in each of the two subunits of the Fc domain.

The term "effector functions" refers to those biological activities attributable to the Fc region of an antibody, which vary with the antibody isotype. Examples of antibody effector functions include: C1q binding and complement dependent cytotoxicity (CDC), Fc receptor binding, antibody-dependent cell-mediated cytotoxicity (ADCC), antibody-dependent cellular phagocytosis (ADCP), cytokine secretion, immune complex-mediated antigen uptake by antigen presenting cells, down regulation of cell surface receptors (e.g. B cell receptor), and B cell activation.

As used herein, the terms "engineer, engineered, engineering", are considered to include any manipulation of the peptide backbone or the post-translational modifications of a naturally occurring or recombinant polypeptide or fragment thereof. Engineering includes modifications of the amino acid sequence, of the glycosylation pattern, or of the side chain group of individual amino acids, as well as combinations of these approaches.

The term "amino acid mutation" as used herein is meant to encompass amino acid substitutions, deletions, insertions, and modifications. Any combination of substitution, deletion, insertion, and modification can be made to arrive at the final construct, provided that the final construct possesses the desired characteristics, e.g., reduced binding to an Fc receptor, or increased association with another peptide. Amino acid sequence deletions and insertions include amino- and/or carboxy-terminal deletions and insertions of amino acids. Particular amino acid mutations are amino acid substitutions. For the purpose of altering e.g. the binding characteristics of an Fc region, non-conservative amino acid substitutions, i.e. replacing one amino acid with another amino acid having different structural and/or chemical properties, are particularly preferred. Amino acid substitutions include replacement by non-naturally occurring amino acids or by naturally occurring amino acid derivatives of the twenty standard amino acids (e.g. 4-hydroxyproline, 3-methylhistidine, ornithine, homoserine, 5-hydroxylysine). Amino acid mutations can be generated using genetic or chemical methods well known in the art. Genetic methods may include site-directed mutagenesis, PCR, gene synthesis and the like. It is contemplated that methods of altering the side chain group of an amino acid by methods other than genetic engineering, such as chemical modification, may also be useful. Various designations may be used herein to indicate the same amino acid mutation. For example, a substitution from proline at position 329 of the Fc domain to glycine can be indicated as 329G, G329, $G_{329}$, P329G, or Pro329Gly.

As used herein, term "polypeptide" refers to a molecule composed of monomers (amino acids) linearly linked by amide bonds (also known as peptide bonds). The term "polypeptide" refers to any chain of two or more amino acids, and does not refer to a specific length of the product. Thus, peptides, dipeptides, tripeptides, oligopeptides, "protein," "amino acid chain," or any other term used to refer to a chain of two or more amino acids, are included within the definition of "polypeptide," and the term "polypeptide" may be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis. A polypeptide of the invention may be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides may have a defined three-dimensional structure, although they do not necessarily have such structure. Polypeptides with a defined three-dimensional structure are referred to as folded, and polypeptides which do not possess a defined three-dimensional structure, but rather can adopt a large number of different conformations, and are referred to as unfolded.

By an "isolated" polypeptide or a variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated for the purpose of the invention, as are native or recombinant polypeptides which have been separated, fractionated, or partially or substantially purified by any suitable technique.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary. In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "polynucleotide" refers to an isolated nucleic acid molecule or construct, e.g. messenger RNA (mRNA), virally-derived RNA, or plasmid DNA (pDNA). A polynucleotide may comprise a conventional phosphodiester bond or a non-conventional bond (e.g. an amide bond, such as found in peptide nucleic acids (PNA). The term "nucleic acid molecule" refers to any one or more nucleic acid segments, e.g. DNA or RNA fragments, present in a polynucleotide.

By "isolated" nucleic acid molecule or polynucleotide is intended a nucleic acid molecule, DNA or RNA, which has been removed from its native environment. For example, a recombinant polynucleotide encoding a polypeptide contained in a vector is considered isolated for the purposes of the present invention. Further examples of an isolated polynucleotide include recombinant polynucleotides maintained in heterologous host cells or purified (partially or substantially) polynucleotides in solution. An isolated polynucleotide includes a polynucleotide molecule contained in cells that ordinarily contain the polynucleotide molecule, but the polynucleotide molecule is present extrachromosomally or at a chromosomal location that is different from its natural chromosomal location. Isolated RNA molecules include in vivo or in vitro RNA transcripts of the present invention, as well as positive and negative strand forms, and double-stranded forms. Isolated polynucleotides or nucleic acids according to the present invention further include such molecules produced synthetically. In addition, a polynucleotide or a nucleic acid may be or may include a regulatory element such as a promoter, ribosome binding site, or a transcription terminator. By a nucleic acid or polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These alterations of the reference sequence may occur at the 5' or 3' terminal positions of the reference nucleotide sequence or anywhere between those terminal positions, interspersed either individually among residues in the reference sequence or in one or more contiguous groups within the reference sequence. As a practical matter, whether any particular polynucleotide sequence is at least 80%, 85%, 90%, 95%, 96%, 97%, 98% or 99% identical to a nucleotide sequence of the present invention can be determined conventionally using known computer programs, such as the ones discussed above for polypeptides (e.g. ALIGN-2).

The term "expression cassette" refers to a polynucleotide generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter. In certain embodiments, the expression cassette of the invention comprises polynucleotide sequences that encode bispecific antigen binding molecules of the invention or fragments thereof.

The term "vector" or "expression vector" is synonymous with "expression construct" and refers to a DNA molecule that is used to introduce and direct the expression of a specific gene to which it is operably associated in a target cell. The term includes the vector as a self-replicating nucleic acid structure as well as the vector incorporated into the genome of a host cell into which it has been introduced. The expression vector of the present invention comprises an expression cassette. Expression vectors allow transcription of large amounts of stable mRNA. Once the expression vector is inside the target cell, the ribonucleic acid molecule or protein that is encoded by the gene is produced by the cellular transcription and/or translation machinery. In one embodiment, the expression vector of the invention comprises an expression cassette that comprises polynucleotide sequences that encode bispecific antigen binding molecules of the invention or fragments thereof. The terms "host cell", "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein. A host cell is any type of cellular system that can be used to generate the bispecific antigen binding molecules of the present invention. Host cells include cultured cells, e.g. mammalian cultured cells, such as CHO cells, BHK cells, NS0 cells, SP2/0 cells, YO myeloma cells, P3X63 mouse myeloma cells, PER cells, PER.C6 cells or hybridoma cells, yeast cells, insect cells, and plant cells, to name only a few, but also cells comprised within a transgenic animal, transgenic plant or cultured plant or animal tissue.

An "activating Fc receptor" is an Fc receptor that following engagement by an Fc domain of an antibody elicits signaling events that stimulate the receptor-bearing cell to perform effector functions. Human activating Fc receptors include FcγRIIIa (CD16a), FcγRI (CD64), FcγRIIa (CD32), and FcαRI (CD89).

Antibody-dependent cell-mediated cytotoxicity (ADCC) is an immune mechanism leading to the lysis of antibody-coated target cells by immune effector cells. The target cells are cells to which antibodies or derivatives thereof comprising an Fc region specifically bind, generally via the protein part that is N-terminal to the Fc region. As used herein, the term "reduced ADCC" is defined as either a reduction in the number of target cells that are lysed in a given time, at a given concentration of antibody in the medium surrounding the target cells, by the mechanism of ADCC defined above, and/or an increase in the concentration of antibody in the medium surrounding the target cells, required to achieve the lysis of a given number of target cells in a given time, by the mechanism of ADCC. The reduction in ADCC is relative to the ADCC mediated by the same antibody produced by the same type of host cells, using the same standard production, purification, formulation and storage methods (which are known to those skilled in the art), but that has not been engineered. For example the reduction in ADCC mediated by an antibody comprising in its Fc domain an amino acid substitution that reduces ADCC, is relative to the ADCC mediated by the same antibody without this amino acid substitution in the Fc domain. Suitable assays to measure ADCC are well known in the art (see e.g. PCT publication no. WO 2006/082515 or PCT publication no. WO 2012/130831).

An "effective amount" of an agent refers to the amount that is necessary to result in a physiological change in the cell or tissue to which it is administered.

A "therapeutically effective amount" of an agent, e.g. a pharmaceutical composition, refers to an amount effective, at dosages and for periods of time necessary, to achieve the desired therapeutic or prophylactic result. A therapeutically effective amount of an agent for example eliminates, decreases, delays, minimizes or prevents adverse effects of a disease.

An "individual" or "subject" is a mammal. Mammals include, but are not limited to, domesticated animals (e.g. cows, sheep, cats, dogs, and horses), primates (e.g. humans and non-human primates such as monkeys), rabbits, and rodents (e.g. mice and rats). Particularly, the individual or subject is a human.

The term "pharmaceutical composition" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical composition, other than an active ingredient, which is nontoxic to a subject. A pharmaceutically acceptable carrier includes, but is not limited to, a buffer, excipient, stabilizer, or preservative.

As used herein, "treatment" (and grammatical variations thereof such as "treat" or "treating") refers to clinical intervention in an attempt to alter the natural course of a disease in the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, T cell activating bispecific antigen binding molecules of the invention are used to delay development of a disease or to slow the progression of a disease.

The term "package insert" is used to refer to instructions customarily included in commercial packages of therapeutic products, that contain information about the indications, usage, dosage, administration, combination therapy, contraindications and/or warnings concerning the use of such therapeutic products.

DETAILED DESCRIPTION OF THE EMBODIMENTS

The invention provides a T cell activating bispecific antigen binding molecule with favorable properties for therapeutic application, in particular with improved efficacy and safety (e.g. with respect to unspecific activation of T cells or selectivity towards tumor cells over normal cells), and improved produceability (e.g. with respect to purity, yield).

The inventors have discovered that T cell activating bispecific antigen binding molecules comprising an antigen binding moiety with the binding specificity of the anti-CEA antibody T84.66 (Wagener et al., J Immunol 130, 2308-(1983), Neumaier et al., J Immunol 135, 3604 (1985)) provide unexpectedly high potency in mediating killing of CEA-expressing tumor cells by T cells. Moreover, T cell activating bispecific antigen binding molecules comprising a novel humanized version of antibody T84.66 were surprisingly found to exhibit improved selectivity towards tumor cells over normal cells as compared to a T cell activating bispecific antigen binding molecule comprising the parental T84.66 binder.

Charge Modifications

The T cell activating bispecific antigen binding molecules of the invention may comprise amino acid substitutions in Fab molecules comprised therein which are particularly efficient in reducing mispairing of light chains with non-matching heavy chains (Bence-Jones-type side products), which can occur in the production of Fab-based bi-/multi-specific antigen binding molecules with a VH/VL exchange in one (or more, in case of molecules comprising more than two antigen-binding Fab molecules) of their binding arms (see also PCT publication no. WO 2015/150447, particularly the examples therein, incorporated herein by reference in its entirety).

Accordingly, in particular embodiments, the T cell activating bispecific antigen binding molecule of the invention comprises (a) a first Fab molecule which specifically binds to a first antigen (b) a second Fab molecule which specifically binds to a second antigen, and wherein the variable domains VL and VH of the Fab light chain and the Fab heavy chain are replaced by each other, wherein the first antigen is an activating T cell antigen and the second antigen is CEA, or the first antigen is CEA and the second antigen is an activating T cell antigen; and wherein i) in the constant domain CL of the first Fab molecule under
   a) the amino acid at position 124 is substituted by a positively charged amino acid (numbering according to Kabat), and wherein in the constant domain CH1 of the first Fab molecule under a) the amino acid at position 147 or the amino acid at position 213 is substituted by a negatively charged amino acid (numbering according to Kabat EU index); or ii) in the constant domain CL of the second Fab molecule under b) the amino acid at position 124 is substituted by a positively charged amino acid (numbering according to Kabat), and wherein in the constant domain CH1 of the second Fab molecule under b) the amino acid at position 147 or the amino acid at position 213 is substituted by a negatively charged amino acid (numbering according to Kabat EU index).

The T cell activating bispecific antigen binding molecule does not comprise both modifications mentioned under i) and ii). The constant domains CL and CH1 of the second Fab molecule are not replaced by each other (i.e. remain unexchanged).

In one embodiment of the T cell activating bispecific antigen binding molecule according to the invention, in the constant domain CL of the first Fab molecule under a) the amino acid at position 124 is substituted independently by lysine (K), arginine (R) or histidine (H) (numbering according to Kabat) (in one preferred embodiment independently by lysine (K) or arginine (R)), and in the constant domain CH1 of the first Fab molecule under a) the amino acid at position 147 or the amino acid at position 213 is substituted independently by glutamic acid (E), or aspartic acid (D) (numbering according to Kabat EU index).

In a further embodiment, in the constant domain CL of the first Fab molecule under a) the amino acid at position 124 is substituted independently by lysine (K), arginine (R) or histidine (H) (numbering according to Kabat), and in the constant domain CH1 of the first Fab molecule under a) the amino acid at position 147 is substituted independently by glutamic acid (E), or aspartic acid (D) (numbering according to Kabat EU index).

In a particular embodiment, in the constant domain CL of the first Fab molecule under a) the amino acid at position 124 is substituted independently by lysine (K), arginine (R) or histidine (H) (numbering according to Kabat) (in one preferred embodiment independently by lysine (K) or arginine (R)) and the amino acid at position 123 is substituted independently by lysine (K), arginine (R) or histidine (H) (numbering according to Kabat) (in one preferred embodiment independently by lysine (K) or arginine (R)), and in the constant domain CH1 of the first Fab molecule under a) the amino acid at position 147 is substituted independently by glutamic acid (E), or aspartic acid (D) (numbering according to Kabat EU index) and the amino acid at position 213 is substituted independently by glutamic acid (E), or aspartic acid (D) (numbering according to Kabat EU index).

In a more particular embodiment, in the constant domain CL of the first Fab molecule under a) the amino acid at position 124 is substituted by lysine (K) (numbering according to Kabat) and the amino acid at position 123 is substituted by lysine (K) or arginine (R) (numbering according to Kabat), and in the constant domain CH1 of the first Fab molecule under a) the amino acid at position 147 is substituted by glutamic acid (E) (numbering according to Kabat EU index) and the amino acid at position 213 is substituted by glutamic acid (E) (numbering according to Kabat EU index).

In an even more particular embodiment, in the constant domain CL of the first Fab molecule under a) the amino acid at position 124 is substituted by lysine (K) (numbering according to Kabat) and the amino acid at position 123 is substituted by arginine (R) (numbering according to Kabat), and in the constant domain CH1 of the first Fab molecule under a) the amino acid at position 147 is substituted by glutamic acid (E) (numbering according to Kabat EU index) and the amino acid at position 213 is substituted by glutamic acid (E) (numbering according to Kabat EU index).

In particular embodiments, the constant domain CL of the first Fab molecule under a) is of kappa isotype.

Alternatively, the amino acid substitutions according to the above embodiments may be made in the constant domain CL and the constant domain CH1 of the second Fab molecule under b) instead of in the constant domain CL and the constant domain CH1 of the first Fab molecule under a). In particular such embodiments, the constant domain CL of the second Fab molecule under b) is of kappa isotype.

The T cell activating bispecific antigen binding molecule according to the invention may further comprise a third Fab molecule which specifically binds to the first antigen. In particular embodiments, said third Fab molecule is identical to the first Fab molecule under a). In these embodiments, the amino acid substitutions according to the above embodiments will be made in the constant domain CL and the constant domain CH1 of each of the first Fab molecule and the third Fab molecule. Alternatively, the amino acid substitutions according to the above embodiments may be made in the constant domain CL and the constant domain CH1 of the second Fab molecule under b), but not in the constant domain CL and the constant domain CH1 of the first Fab molecule and the third Fab molecule.

In particular embodiments, the T cell activating bispecific antigen binding molecule according to the invention further comprises an Fc domain composed of a first and a second subunit capable of stable association.

T Cell Activating Bispecific Antigen Binding Molecule Formats

The components of the T cell activating bispecific antigen binding molecule can be fused to each other in a variety of configurations. Exemplary configurations are depicted in FIG. 1.

In particular embodiments, the antigen binding moieties comprised in the T cell activating bispecific antigen binding molecule are Fab molecules. In such embodiments, the first, second, third etc. antigen binding moiety may be referred to herein as first, second, third etc. Fab molecule, respectively. Furthermore, in particular embodiments, the T cell activating bispecific antigen binding molecule comprises an Fc domain composed of a first and a second subunit capable of stable association.

In some embodiments, the second Fab molecule is fused at the C-terminus of the Fab heavy chain to the N-terminus of the first or the second subunit of the Fc domain.

In one such embodiment, the first Fab molecule is fused at the C-terminus of the Fab heavy chain to the N-terminus of the Fab heavy chain of the second Fab molecule. In a specific such embodiment, the T cell activating bispecific antigen binding molecule essentially consists of the first and the second Fab molecule, the Fc domain composed of a first and a second subunit, and optionally one or more peptide linkers, wherein the first Fab molecule is fused at the C-terminus of the Fab heavy chain to the N-terminus of the Fab heavy chain of the second Fab molecule, and the second Fab molecule is fused at the C-terminus of the Fab heavy chain to the N-terminus of the first or the second subunit of the Fc domain. Such a configuration is schematically depicted in FIGS. 1G and 1K. Optionally, the Fab light chain of the first Fab molecule and the Fab light chain of the second Fab molecule may additionally be fused to each other.

In another such embodiment, the first Fab molecule is fused at the C-terminus of the Fab heavy chain to the N-terminus of the first or second subunit of the Fc domain. In a specific such embodiment, the T cell activating bispecific antigen binding molecule essentially consists of the first and the second Fab molecule, the Fc domain composed of a first and a second subunit, and optionally one or more peptide linkers, wherein the first and the second Fab molecule are each fused at the C-terminus of the Fab heavy chain to the N-terminus of one of the subunits of the Fc domain.

Figures 1B, 1E:
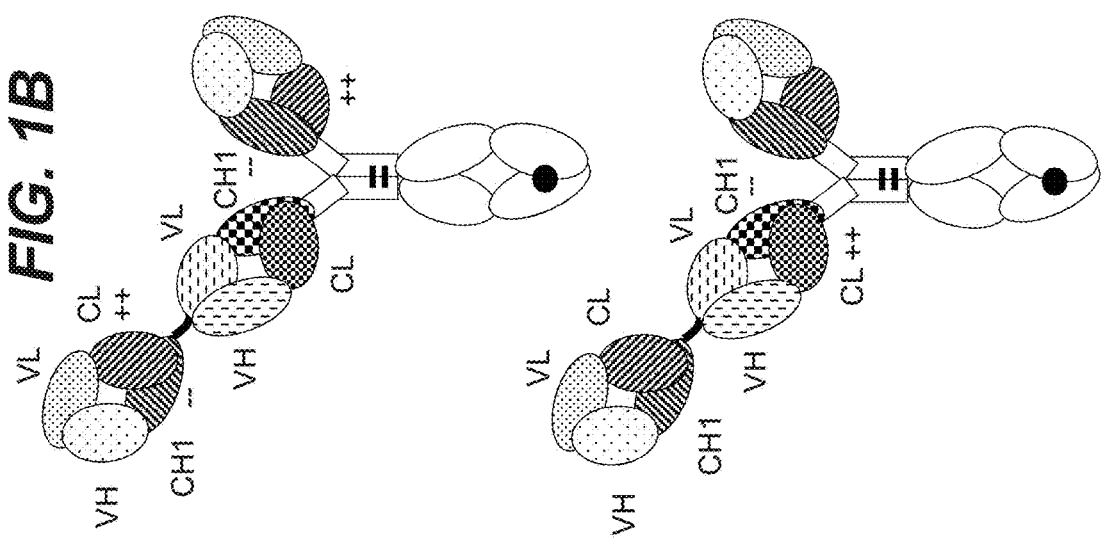
Figures 1A, 1D:
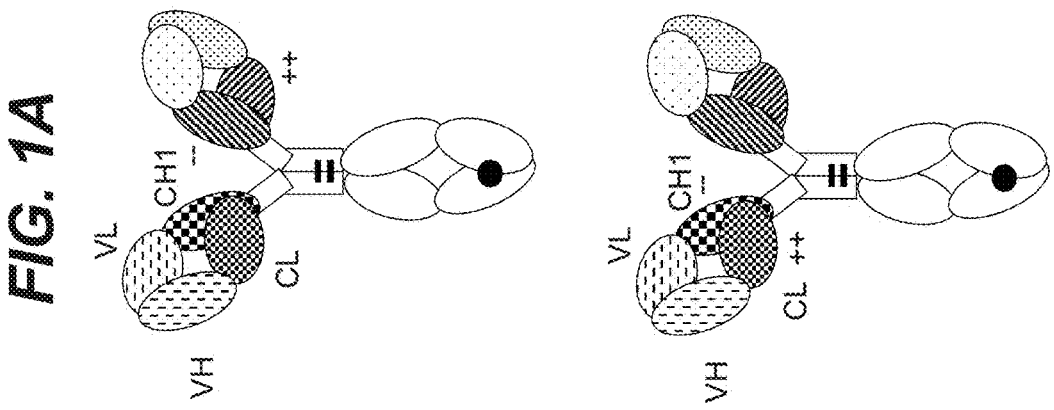

Such a configuration is schematically depicted in FIGS. 1A and 1D. The first and the second Fab molecule may be fused to the Fc domain directly or through a peptide linker. In a particular embodiment the first and the second Fab molecule are each fused to the Fc domain through an immunoglobulin hinge region. In a specific embodiment, the immunoglobulin hinge region is a human IgG$_1$ hinge region, particularly where the Fc domain is an IgG$_1$ Fc domain.

In other embodiments, the first Fab molecule is fused at the C-terminus of the Fab heavy chain to the N-terminus of the first or second subunit of the Fc domain.

In one such embodiment, the second Fab molecule is fused at the C-terminus of the Fab heavy chain to the N-terminus of the Fab heavy chain of the first Fab molecule. In a specific such embodiment, the T cell activating bispecific antigen binding molecule essentially consists of the first and the second Fab molecule, the Fc domain composed of a first and a second subunit, and optionally one or more peptide linkers, wherein the second Fab molecule is fused at the C-terminus of the Fab heavy chain to the N-terminus of the Fab heavy chain of the first Fab molecule, and the first Fab molecule is fused at the C-terminus of the Fab heavy chain to the N-terminus of the first or the second subunit of the Fc domain. Such a configuration is schematically depicted in FIGS. 1H and 1L. Optionally, the Fab light chain of the first Fab molecule and the Fab light chain of the second Fab molecule may additionally be fused to each other.

The Fab molecules may be fused to the Fc domain or to each other directly or through a peptide linker, comprising one or more amino acids, typically about 2-20 amino acids. Peptide linkers are known in the art and are described herein. Suitable, non-immunogenic peptide linkers include, for example, $(G_4S)_n$, $(SG_4)_n$, $(G_4S)_n$ or $G_4(SG_4)_n$ peptide linkers. "n" is generally an integer from 1 to 10, typically from 2 to 4. In one embodiment said peptide linker has a length of at least 5 amino acids, in one embodiment a length of 5 to 100, in a further embodiment of 10 to 50 amino acids. In one embodiment said peptide linker is $(GxS)_n$ or $(GxS)_nG_m$ with G=glycine, S=serine, and (x=3, n=3, 4, 5 or 6, and m=0, 1, 2 or 3) or (x=4, n=2, 3, 4 or 5 and m=0, 1, 2 or 3), in one embodiment x=4 and n=2 or 3, in a further embodiment x=4 and n=2. In one embodiment said peptide linker is $(G_4S)_2$. A particularly suitable peptide linker for fusing the Fab light chains of the first and the second Fab molecule to each other is $(G_4S)_2$. An exemplary peptide linker suitable for connecting the Fab heavy chains of the first and the second Fab fragments comprises the sequence (D)-$(G_4S)_2$ (SEQ ID NOs 11 and 12). Another suitable such linker comprises the sequence $(G_4S)_4$. Additionally, linkers may comprise (a portion of) an immunoglobulin hinge region. Particularly where a Fab molecule is fused to the N-terminus of an Fc domain subunit, it may be fused via an immunoglobulin hinge region or a portion thereof, with or without an additional peptide linker.

A T cell activating bispecific antigen binding molecule with a single antigen binding moiety (such as a Fab molecule) capable of specific binding to a target cell antigen (for example as shown in FIG. 1A, D, G, H, K, L) is useful, particularly in cases where internalization of the target cell antigen is to be expected following binding of a high affinity antigen binding moiety. In such cases, the presence of more than one antigen binding moiety specific for the target cell antigen may enhance internalization of the target cell antigen, thereby reducing its availability.

In many other cases, however, it will be advantageous to have a T cell activating bispecific antigen binding molecule comprising two or more antigen binding moieties (such as Fab molecules) specific for a target cell antigen (see examples shown in FIG. 1B, 1C, 1E, 1F, 1I, 1J. 1M or 1N), for example to optimize targeting to the target site or to allow crosslinking of target cell antigens. Accordingly, in particular embodiments, the T cell activating bispecific antigen binding molecule of the invention further comprises a third Fab molecule which specifically binds to the first antigen. The first antigen preferably is the target cell antigen, i.e. CEA. In one embodiment, the third Fab molecule is a conventional Fab molecule. In one embodiment, the third Fab molecule is identical to the first Fab molecule (i.e. the first and the third Fab molecule comprise the same heavy and light chain amino acid sequences and have the same arrangement of domains (i.e. conventional or crossover)). In a particular embodiment, the second Fab molecule specifically binds to an activating T cell antigen, particularly CD3, and the first and third Fab molecule specifically bind to CEA.

In alternative embodiments, the T cell activating bispecific antigen binding molecule of the invention further comprises a third Fab molecule which specifically binds to the second antigen. In these embodiments, the second antigen preferably is the target cell antigen, i.e. CEA. In one such embodiment, the third Fab molecule is a crossover Fab molecule (a Fab molecule wherein the variable domains VH and VL or the constant domains CL and CH1 of the Fab heavy and light chains are exchanged/replaced by each other). In one such embodiment, the third Fab molecule is identical to the second Fab molecule (i.e. the second and the third Fab molecule comprise the same heavy and light chain amino acid sequences and have the same arrangement of domains (i.e. conventional or crossover)). In one such embodiment, the first Fab molecule specifically binds to an activating T cell antigen, particularly CD3, and the second and third Fab molecule specifically bind to CEA.

In one embodiment, the third Fab molecule is fused at the C-terminus of the Fab heavy chain to the N-terminus of the first or second subunit of the Fc domain.

In a particular embodiment, the second and the third Fab molecule are each fused at the C-terminus of the Fab heavy chain to the N-terminus of one of the subunits of the Fc domain, and the first Fab molecule is fused at the C-terminus of the Fab heavy chain to the N-terminus of the Fab heavy chain of the second Fab molecule. In a specific such embodiment, the T cell activating bispecific antigen binding molecule essentially consists of the first, the second and the third Fab molecule, the Fc domain composed of a first and a second subunit, and optionally one or more peptide linkers, wherein the first Fab molecule is fused at the C-terminus of the Fab heavy chain to the N-terminus of the Fab heavy chain of the second Fab molecule, and the second Fab molecule is fused at the C-terminus of the Fab heavy chain to the N-terminus of the first subunit of the Fc domain, and wherein the third Fab molecule is fused at the C-terminus of the Fab heavy chain to the N-terminus of the second subunit of the Fc domain. Such a configuration is schematically depicted in FIGS. 1B and 1E (particular embodiments, wherein the third Fab molecule is a conventional Fab molecule and preferably identical to the first Fab molecule), and FIGS. 1I and 1M (alternative embodiments, wherein the third Fab molecule is a crossover Fab molecule and preferably identical to the second Fab molecule). The second and the third Fab molecule may be fused to the Fc domain directly or through a peptide linker. In a particular embodiment the second and the third Fab molecule are each fused to the Fc domain through an immunoglobulin hinge region. In a specific embodiment, the immunoglobulin hinge region is a human $IgG_1$ hinge region, particularly where the Fc domain is an $IgG_1$ Fc domain. Optionally, the Fab light chain of the first Fab molecule and the Fab light chain of the second Fab molecule may additionally be fused to each other.

In another embodiment, the first and the third Fab molecule are each fused at the C-terminus of the Fab heavy chain to the N-terminus of one of the subunits of the Fc domain, and the second Fab molecule is fused at the C-terminus of the Fab heavy chain to the N-terminus of the Fab heavy chain of the first Fab molecule. In a specific such embodiment, the T cell activating bispecific antigen binding molecule essentially consists of the first, the second and the third Fab molecule, the Fc domain composed of a first and a second subunit, and optionally one or more peptide linkers, wherein the second Fab molecule is fused at the C-terminus of the Fab heavy chain to the N-terminus of the Fab heavy chain of the first Fab molecule, and the first Fab molecule is fused at the C-terminus of the Fab heavy chain to the N-terminus of the first subunit of the Fc domain, and wherein the third Fab molecule is fused at the C-terminus of the Fab heavy chain to the N-terminus of the second subunit of the Fc domain. Such a configuration is schematically depicted in FIGS. 1C and 1F (particular embodiments, wherein the third Fab molecule is a conventional Fab molecule and preferably identical to the first Fab molecule) and in FIGS. 1J and 1N (alternative embodiments, wherein the third Fab molecule is a crossover Fab molecule and preferably identical to the second Fab molecule). The first and the third Fab molecule may be fused to the Fc domain directly or through a peptide linker. In a particular embodiment the first and the third Fab molecule are each fused to the Fc domain through an immunoglobulin hinge region. In a specific embodiment, the immunoglobulin hinge region is a human IgG$_1$ hinge region, particularly where the Fc domain is an IgG$_1$ Fc domain. Optionally, the Fab light chain of the first Fab molecule and the Fab light chain of the second Fab molecule may additionally be fused to each other.

In configurations of the T cell activating bispecific antigen binding molecule wherein a Fab molecule is fused at the C-terminus of the Fab heavy chain to the N-terminus of each of the subunits of the Fc domain through an immunoglobulin hinge regions, the two Fab molecules, the hinge regions and the Fc domain essentially form an immunoglobulin molecule. In a particular embodiment the immunoglobulin molecule is an IgG class immunoglobulin. In an even more particular embodiment the immunoglobulin is an IgG$_1$ subclass immunoglobulin. In another embodiment the immunoglobulin is an IgG$_4$ subclass immunoglobulin. In a further particular embodiment the immunoglobulin is a human immunoglobulin. In other embodiments the immunoglobulin is a chimeric immunoglobulin or a humanized immunoglobulin.

In some of the T cell activating bispecific antigen binding molecule of the invention, the Fab light chain of the first Fab molecule and the Fab light chain of the second Fab molecule are fused to each other, optionally via a peptide lnker. Depending on the configuration of the first and the second Fab molecule, the Fab light chain of the first Fab molecule may be fused at its C-terminus to the N-terminus of the Fab light chain of the second Fab molecule, or the Fab light chain of the second Fab molecule may be fused at its C-terminus to the N-terminus of the Fab light chain of the first Fab molecule. Fusion of the Fab light chains of the first and the second Fab molecule further reduces mispairing of unmatched Fab heavy and light chains, and also reduces the number of plasmids needed for expression of some of the T cell activating bispecific antigen binding molecules of the invention.

In certain embodiments the T cell activating bispecific antigen binding molecule according to the invention comprises a polypeptide wherein the Fab light chain variable region of the second Fab molecule shares a carboxy-terminal peptide bond with the Fab heavy chain constant region of the second Fab molecule (i.e. the second Fab molecule comprises a crossover Fab heavy chain, wherein the heavy chain variable region is replaced by a light chain variable region), which in turn shares a carboxy-terminal peptide bond with an Fc domain subunit (VL$_{(2)}$-CH1$_{(2)}$-CH2-CH3(-CH4)), and a polypeptide wherein the Fab heavy chain of the first Fab molecule shares a carboxy-terminal peptide bond with an Fc domain subunit (VH$_{(1)}$-CH1$_{(1)}$-CH2-CH3(-CH4)). In some embodiments the T cell activating bispecific antigen binding molecule further comprises a polypeptide wherein the Fab heavy chain variable region of the second Fab molecule shares a carboxy-terminal peptide bond with the Fab light chain constant region of the second Fab molecule (VH$_{(2)}$-CL$_{(2)}$) and the Fab light chain polypeptide of the first Fab molecule (VL$_{(1)}$-CL$_{(1)}$). In certain embodiments the polypeptides are covalently linked, e.g., by a disulfide bond.

In certain embodiments the T cell activating bispecific antigen binding molecule according to the invention comprises a polypeptide wherein the Fab heavy chain variable region of the second Fab molecule shares a carboxy-terminal peptide bond with the Fab light chain constant region of the second Fab molecule (i.e. the second Fab molecule comprises a crossover Fab heavy chain, wherein the heavy chain constant region is replaced by a light chain constant region), which in turn shares a carboxy-terminal peptide bond with an Fc domain subunit (VH$_{(2)}$-CL$_{(2)}$-CH2-CH3(-CH4)), and a polypeptide wherein the Fab heavy chain of the first Fab molecule shares a carboxy-terminal peptide bond with an Fc domain subunit (VH$_{(1)}$-CH1$_{(1)}$-CH2-CH3(-CH4)). In some embodiments the T cell activating bispecific antigen binding molecule further comprises a polypeptide wherein the Fab light chain variable region of the second Fab molecule shares a carboxy-terminal peptide bond with the Fab heavy chain constant region of the second Fab molecule (VL$_{(2)}$-CH1$_{(2)}$) and the Fab light chain polypeptide of the first Fab molecule (VL$_{(1)}$-CL$_{(1)}$). In certain embodiments the polypeptides are covalently linked, e.g., by a disulfide bond.

In some embodiments, the T cell activating bispecific antigen binding molecule comprises a polypeptide wherein the Fab light chain variable region of the second Fab molecule shares a carboxy-terminal peptide bond with the Fab heavy chain constant region of the second Fab molecule (i.e. the second Fab molecule comprises a crossover Fab heavy chain, wherein the heavy chain variable region is replaced by a light chain variable region), which in turn shares a carboxy-terminal peptide bond with the Fab heavy chain of the first Fab molecule, which in turn shares a carboxy-terminal peptide bond with an Fc domain subunit (VL$_{(2)}$-CH1$_{(2)}$-VH$_{(1)}$-CH1$_{(1)}$-CH2-CH3 (-CH4)). In other embodiments, the T cell activating bispecific antigen binding molecule comprises a polypeptide wherein the Fab heavy chain of the first Fab molecule shares a carboxy-terminal peptide bond with the Fab light chain variable region of the second Fab molecule which in turn shares a carboxy-terminal peptide bond with the Fab heavy chain constant region of the second Fab molecule (i.e. the second Fab molecule comprises a crossover Fab heavy chain, wherein the heavy chain variable region is replaced by a light chain variable region), which in turn shares a carboxy-terminal peptide bond with an Fc domain subunit (VH$_{(1)}$-CH1$_{(1)}$-VL$_{(2)}$-CH1$_{(2)}$-CH2-CH3(-CH4)).

In some of these embodiments the T cell activating bispecific antigen binding molecule further comprises a crossover Fab light chain polypeptide of the second Fab molecule, wherein the Fab heavy chain variable region of the second Fab molecule shares a carboxy-terminal peptide bond with the Fab light chain constant region of the second Fab molecule (VH$_{(2)}$-CL$_{(2)}$), and the Fab light chain polypeptide of the first Fab molecule (VL$_{(1)}$-CL$_{(1)}$). In others of these embodiments the T cell activating bispecific antigen binding molecule further comprises a polypeptide wherein the Fab heavy chain variable region of the second Fab molecule shares a carboxy-terminal peptide bond with the Fab light chain constant region of the second Fab molecule which in turn shares a carboxy-terminal peptide bond with the Fab light chain polypeptide of the first Fab molecule (VH$_{(2)}$-CL$_{(2)}$-VL$_{(1)}$-CL$_{(1)}$), or a polypeptide wherein the Fab light chain polypeptide of the first Fab molecule shares a carboxy-terminal peptide bond with the Fab heavy chain variable region of the second Fab molecule which in turn shares a carboxy-terminal peptide bond with the Fab light chain constant region of the second Fab molecule (VL$_{(1)}$-CL$_{(1)}$-VH$_{(2)}$-CL$_{(2)}$), as appropriate.

The T cell activating bispecific antigen binding molecule according to these embodiments may further comprise (i) an Fc domain subunit polypeptide (CH2-CH3(-CH4)), or (ii) a polypeptide wherein the Fab heavy chain of a third Fab molecule shares a carboxy-terminal peptide bond with an Fc domain subunit (VH$_{(3)}$-CH1$_{(3)}$-CH2-CH3(-CH4)) and the Fab light chain polypeptide of a third Fab molecule (VL$_{(3)}$-CL$_{(3)}$). In certain embodiments the polypeptides are covalently linked, e.g., by a disulfide bond.

In some embodiments, the T cell activating bispecific antigen binding molecule comprises a polypeptide wherein the Fab heavy chain variable region of the second Fab molecule shares a carboxy-terminal peptide bond with the Fab light chain constant region of the second Fab molecule (i.e. the second Fab molecule comprises a crossover Fab heavy chain, wherein the heavy chain constant region is replaced by a light chain constant region), which in turn shares a carboxy-terminal peptide bond with the Fab heavy chain of the first Fab molecule, which in turn shares a carboxy-terminal peptide bond with an Fc domain subunit (VH$_{(2)}$-CL$_{(2)}$-VH$_{(1)}$-CH1$_{(1)}$-CH2-CH3(-CH4)). In other embodiments, the T cell activating bispecific antigen binding molecule comprises a polypeptide wherein the Fab heavy chain of the first Fab molecule shares a carboxy-terminal peptide bond with the Fab heavy chain variable region of the second Fab molecule which in turn shares a carboxy-terminal peptide bond with the Fab light chain constant region of the second Fab molecule (i.e. the second Fab molecule comprises a crossover Fab heavy chain, wherein the heavy chain constant region is replaced by a light chain constant region), which in turn shares a carboxy-terminal peptide bond with an Fc domain subunit (VH$_{(1)}$-CH1$_{(1)}$-VH$_{(2)}$-CL$_{(2)}$-CH2-CH3(-CH4)).

In some of these embodiments the T cell activating bispecific antigen binding molecule further comprises a crossover Fab light chain polypeptide of the second Fab molecule, wherein the Fab light chain variable region of the second Fab molecule shares a carboxy-terminal peptide bond with the Fab heavy chain constant region of the second Fab molecule (VL$_{(2)}$-CH1$_{(2)}$), and the Fab light chain polypeptide of the first Fab molecule (VL$_{(1)}$-CL$_{(1)}$). In others of these embodiments the T cell activating bispecific antigen binding molecule further comprises a polypeptide wherein the Fab light chain variable region of the second Fab molecule shares a carboxy-terminal peptide bond with the Fab heavy chain constant region of the second Fab molecule which in turn shares a carboxy-terminal peptide bond with the Fab light chain polypeptide of the first Fab molecule (VL$_{(2)}$-CH1$_{(2)}$-VL$_{(1)}$-CL$_{(1)}$), or a polypeptide wherein the Fab light chain polypeptide of the first Fab molecule shares a carboxy-terminal peptide bond with the Fab heavy chain variable region of the second Fab molecule which in turn shares a carboxy-terminal peptide bond with the Fab light chain constant region of the second Fab molecule (VL$_{(1)}$-CL$_{(1)}$-VH$_{(2)}$-CL$_{(2)}$), as appropriate.

The T cell activating bispecific antigen binding molecule according to these embodiments may further comprise (i) an Fc domain subunit polypeptide (CH2-CH3(-CH4)), or (ii) a polypeptide wherein the Fab heavy chain of a third Fab molecule shares a carboxy-terminal peptide bond with an Fc domain subunit (VH$_{(3)}$-CH1$_{(3)}$-CH2-CH3(-CH4)) and the Fab light chain polypeptide of a third Fab molecule (VL$_{(3)}$-CL$_{(3)}$). In certain embodiments the polypeptides are covalently linked, e.g., by a disulfide bond.

In some embodiments, the first Fab molecule is fused at the C-terminus of the Fab heavy chain to the N-terminus of the Fab heavy chain of the second Fab molecule. In certain such embodiments, the T cell activating bispecific antigen binding molecule does not comprise an Fc domain. In certain embodiments, the T cell activating bispecific antigen binding molecule essentially consists of the first and the second Fab molecule, and optionally one or more peptide linkers, wherein the first Fab molecule is fused at the C-terminus of the Fab heavy chain to the N-terminus of the Fab heavy chain of the second Fab molecule. Such a configuration is schematically depicted in FIGS. 1O and 1S.

In other embodiments, the second Fab molecule is fused at the C-terminus of the Fab heavy chain to the N-terminus of the Fab heavy chain of the first Fab molecule. In certain such embodiments, the T cell activating bispecific antigen binding molecule does not comprise an Fc domain. In certain embodiments, the T cell activating bispecific antigen binding molecule essentially consists of the first and the second Fab molecule, and optionally one or more peptide linkers, wherein the second Fab molecule is fused at the C-terminus of the Fab heavy chain to the N-terminus of the Fab heavy chain of the first Fab molecule. Such a configuration is schematically depicted in FIGS. 1P and 1T. In some embodiments, the first Fab molecule is fused at the C-terminus of the Fab heavy chain to the N-terminus of the Fab heavy chain of the second Fab molecule, and the T cell activating bispecific antigen binding molecule further comprises a third Fab molecule, wherein said third Fab molecule is fused at the C-terminus of the Fab heavy chain to the N-terminus of the Fab heavy chain of the first Fab molecule. In particular such embodiments, said third Fab molecule is a conventional Fab molecule. In other such embodiments, said third Fab molecule is a crossover Fab molecule as described herein, i.e. a Fab molecule wherein the variable domains VH and VL or the constant domains CL and CH1 of the Fab heavy and light chains are exchanged/replaced by each other. In certain such embodiments, the T cell activating bispecific antigen binding molecule essentially consists of the first, the second and the third Fab molecule, and optionally one or more peptide linkers, wherein the first Fab molecule is fused at the C-terminus of the Fab heavy chain to the N-terminus of the Fab heavy chain of the second Fab molecule, and the third Fab molecule is fused at the C-terminus of the Fab heavy chain to the N-terminus of the Fab heavy chain of the first Fab molecule. Such a configuration is schematically depicted in FIGS. 1Q and 1U (particular embodiments, wherein the third Fab molecule is a conventional Fab molecule and preferably identical to the first Fab molecule).

Figure 1X:
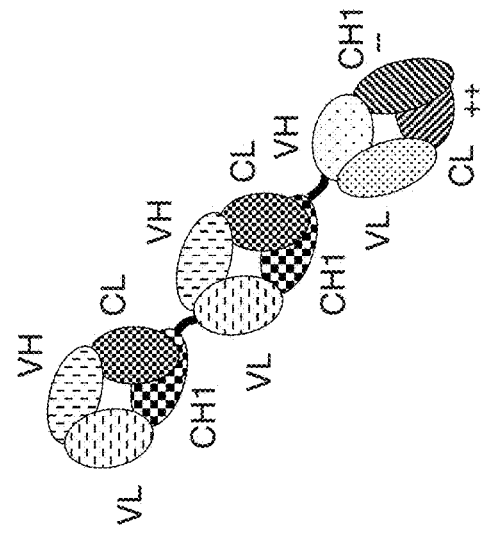
Figure 1Z:
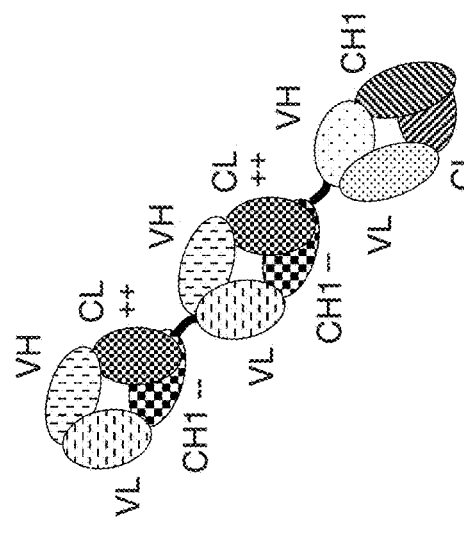
Figure 1W:
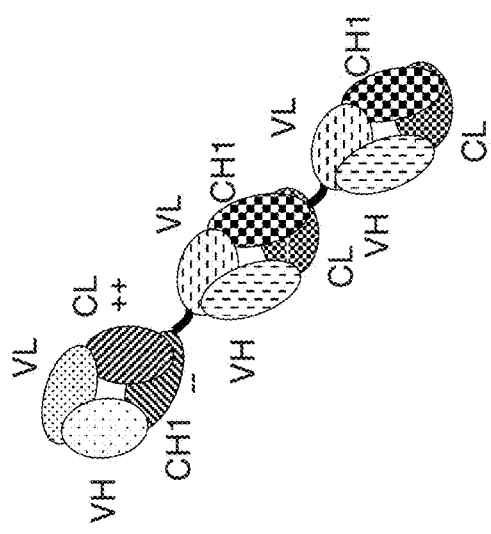
Figure 1Y:
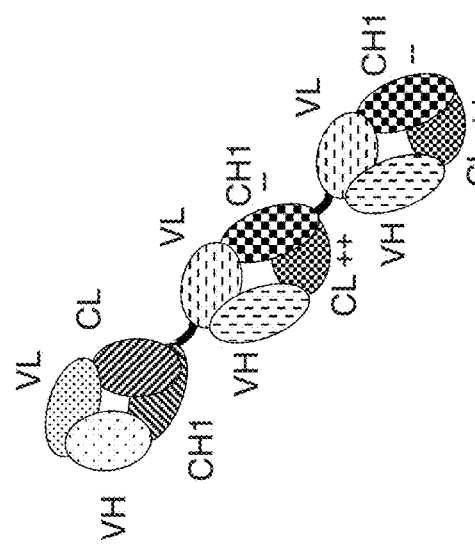

In some embodiments, the first Fab molecule is fused at the C-terminus of the Fab heavy chain to the N-terminus of the Fab heavy chain of the second Fab molecule, and the T cell activating bispecific antigen binding molecule further comprises a third Fab molecule, wherein said third Fab molecule is fused at the N-terminus of the Fab heavy chain to the C-terminus of the Fab heavy chain of the second Fab molecule. In particular such embodiments, said third Fab molecule is a crossover Fab molecule as described herein, i.e. a Fab molecule wherein the variable domains VH and VL or the constant domains CH1 and CL of the Fab heavy and light chains are exchanged/replaced by each other. In other such embodiments, said third Fab molecule is a conventional Fab molecule. In certain such embodiments, the T cell activating bispecific antigen binding molecule essentially consists of the first, the second and the third Fab molecule, and optionally one or more peptide linkers, wherein the first Fab molecule is fused at the C-terminus of the Fab heavy chain to the N-terminus of the Fab heavy chain of the second Fab molecule, and the third Fab molecule is fused at the N-terminus of the Fab heavy chain to the C-terminus of the Fab heavy chain of the second Fab molecule. Such a configuration is schematically depicted in FIGS. 1W and 1Y (particular embodiments, wherein the third Fab molecule is a crossover Fab molecule and preferably identical to the second Fab molecule).

In some embodiments, the second Fab molecule is fused at the C-terminus of the Fab heavy chain to the N-terminus of the Fab heavy chain of the first Fab molecule, and the T cell activating bispecific antigen binding molecule further comprises a third Fab molecule, wherein said third Fab molecule is fused at the N-terminus of the Fab heavy chain to the C-terminus of the Fab heavy chain of the first Fab molecule. In particular such embodiments, said third Fab molecule is a conventional Fab molecule. In other such embodiments, said third Fab molecule is a crossover Fab molecule as described herein, i.e. a Fab molecule wherein the variable domains VH and VL or the constant domains CH1 and CL of the Fab heavy and light chains are exchanged/replaced by each other. In certain such embodiments, the T cell activating bispecific antigen binding molecule essentially consists of the first, the second and the third Fab molecule, and optionally one or more peptide linkers, wherein the second Fab molecule is fused at the C-terminus of the Fab heavy chain to the N-terminus of the Fab heavy chain of the first Fab molecule, and the third Fab molecule is fused at the N-terminus of the Fab heavy chain to the C-terminus of the Fab heavy chain of the first Fab molecule. Such a configuration is schematically depicted in FIGS. 1R and 1V (particular embodiments, wherein the third Fab molecule is a conventional Fab molecule and preferably identical to the first Fab molecule).

In some embodiments, the second Fab molecule is fused at the C-terminus of the Fab heavy chain to the N-terminus of the Fab heavy chain of the first Fab molecule, and the T cell activating bispecific antigen binding molecule further comprises a third Fab molecule, wherein said third Fab molecule is fused at the C-terminus of the Fab heavy chain to the N-terminus of the Fab heavy chain of the second Fab molecule. In particular such embodiments, said third Fab molecule is a crossover Fab molecule as described herein, i.e. a Fab molecule wherein the variable domains VH and VL or the constant domains CH1 and CL of the Fab heavy and light chains are exchanged/replaced by each other. In other such embodiments, said third Fab molecule is a conventional Fab molecule. In certain such embodiments, the T cell activating bispecific antigen binding molecule essentially consists of the first, the second and the third Fab molecule, and optionally one or more peptide linkers, wherein the second Fab molecule is fused at the C-terminus of the Fab heavy chain to the N-terminus of the Fab heavy chain of the first Fab molecule, and the third Fab molecule is fused at the C-terminus of the Fab heavy chain to the N-terminus of the Fab heavy chain of the second Fab molecule. Such a configuration is schematically depicted in FIGS. 1X and 1Z (particular embodiments, wherein the third Fab molecule is a crossover Fab molecule and preferably identical to the first Fab molecule).

In certain embodiments the T cell activating bispecific antigen binding molecule according to the invention comprises a polypeptide wherein the Fab heavy chain of the first Fab molecule shares a carboxy-terminal peptide bond with the Fab light chain variable region of the second Fab molecule, which in turn shares a carboxy-terminal peptide bond with the Fab heavy chain constant region of the second Fab molecule (i.e. the second Fab molecule comprises a crossover Fab heavy chain, wherein the heavy chain variable region is replaced by a light chain variable region) ($VH_{(1)}$-$CH1_{(1)}$-$VL_{(2)}$-$CH1_{(2)}$). In some embodiments the T cell activating bispecific antigen binding molecule further comprises a polypeptide wherein the Fab heavy chain variable region of the second Fab molecule shares a carboxy-terminal peptide bond with the Fab light chain constant region of the second Fab molecule ($VH_{(2)}$-$CL_{(2)}$) and the Fab light chain polypeptide of the first Fab molecule ($VL_{(1)}$-$CL_{(1)}$).

In certain embodiments the T cell activating bispecific antigen binding molecule according to the invention comprises a polypeptide wherein the Fab light chain variable region of the second Fab molecule shares a carboxy-terminal peptide bond with the Fab heavy chain constant region of the second Fab molecule (i.e. the second Fab molecule comprises a crossover Fab heavy chain, wherein the heavy chain variable region is replaced by a light chain variable region), which in turn shares a carboxy-terminal peptide bond with the Fab heavy chain of the first Fab molecule ($VL_{(2)}$-$CH1_{(2)}$-$VH_{(1)}$-$CH1_{(1)}$). In some embodiments the T cell activating bispecific antigen binding molecule further comprises a polypeptide wherein the Fab heavy chain variable region of the second Fab molecule shares a carboxy-terminal peptide bond with the Fab light chain constant region of the second Fab molecule ($VH_{(2)}$-$CL_{(2)}$) and the Fab light chain polypeptide of the first Fab molecule ($VL_{(1)}$-$CL_{(1)}$).

In certain embodiments the T cell activating bispecific antigen binding molecule according to the invention comprises a polypeptide wherein the Fab heavy chain variable region of the second Fab molecule shares a carboxy-terminal peptide bond with the Fab light chain constant region of the second Fab molecule (i.e. the second Fab molecule comprises a crossover Fab heavy chain, wherein the heavy chain constant region is replaced by a light chain constant region), which in turn shares a carboxy-terminal peptide bond with the Fab heavy chain of the first Fab molecule ($VH_{(2)}$-$CL_{(2)}$-$VH_{(1)}$-$CH1_{(1)}$). In some embodiments the T cell activating bispecific antigen binding molecule further comprises a polypeptide wherein the Fab light chain variable region of the second Fab molecule shares a carboxy-terminal peptide bond with the Fab heavy chain constant region of the second Fab molecule ($VL_{(2)}$-$CH1_{(2)}$) and the Fab light chain polypeptide of the first Fab molecule ($VL_{(1)}$-$CL_{(1)}$).

In certain embodiments the T cell activating bispecific antigen binding molecule according to the invention comprises a polypeptide wherein the Fab heavy chain of a third Fab molecule shares a carboxy-terminal peptide bond with the Fab heavy chain of the first Fab molecule, which in turn shares a carboxy-terminal peptide bond with the Fab light chain variable region of the second Fab molecule, which in turn shares a carboxy-terminal peptide bond with the Fab heavy chain constant region of the second Fab molecule (i.e. the second Fab molecule comprises a crossover Fab heavy chain, wherein the heavy chain variable region is replaced by a light chain variable region) ($VH_{(3)}$-$CH1_{(3)}$-$VH_{(1)}$-$CH1_{(1)}$-$VL_{(2)}$-$CH1_{(2)}$). In some embodiments the T cell activating bispecific antigen binding molecule further comprises a polypeptide wherein the Fab heavy chain variable region of the second Fab molecule shares a carboxy-terminal peptide bond with the Fab light chain constant region of the second Fab molecule ($VH_{(2)}$-$CL_{(2)}$) and the Fab light chain polypeptide of the first Fab molecule ($VL_{(1)}$-$CL_{(1)}$). In some embodiments the T cell activating bispecific antigen binding molecule further comprises the Fab light chain polypeptide of a third Fab molecule ($VL_{(3)}$-$CL_{(3)}$).

In certain embodiments the T cell activating bispecific antigen binding molecule according to the invention comprises a polypeptide wherein the Fab heavy chain of a third Fab molecule shares a carboxy-terminal peptide bond with the Fab heavy chain of the first Fab molecule, which in turn shares a carboxy-terminal peptide bond with the Fab heavy chain variable region of the second Fab molecule, which in turn shares a carboxy-terminal peptide bond with the Fab light chain constant region of the second Fab molecule (i.e. the second Fab molecule comprises a crossover Fab heavy chain, wherein the heavy chain constant region is replaced by a light chain constant region) ($VH_{(3)}$-$CH1_{(3)}$-$VH_{(1)}$-$CH1_{(1)}$-$VH_{(2)}$-$CL_{(2)}$). In some embodiments the T cell activating bispecific antigen binding molecule further comprises a polypeptide wherein the Fab light chain variable region of the second Fab molecule shares a carboxy-terminal peptide bond with the Fab heavy chain constant region of the second Fab molecule ($VL_{(2)}$-$CH1_{(2)}$) and the Fab light chain polypeptide of the first Fab molecule ($VL_{(1)}$-$CL_{(1)}$). In some embodiments the T cell activating bispecific antigen binding molecule further comprises the Fab light chain polypeptide of a third Fab molecule ($VL_{(3)}$-$CL_{(3)}$).

In certain embodiments the T cell activating bispecific antigen binding molecule according to the invention comprises a polypeptide wherein the Fab light chain variable region of the second Fab molecule shares a carboxy-terminal peptide bond with the Fab heavy chain constant region of the second Fab molecule (i.e. the second Fab molecule comprises a crossover Fab heavy chain, wherein the heavy chain variable region is replaced by a light chain variable region), which in turn shares a carboxy-terminal peptide bond with the Fab heavy chain of the first Fab molecule, which in turn shares a carboxy-terminal peptide bond with the Fab heavy chain of a third Fab molecule ($VL_{(2)}$-$CH1_{(2)}$-$VH_{(1)}$-$CH1_{(1)}$-$VH_{(3)}$-$CH1_{(3)}$). In some embodiments the T cell activating bispecific antigen binding molecule further comprises a polypeptide wherein the Fab heavy chain variable region of the second Fab molecule shares a carboxy-terminal peptide bond with the Fab light chain constant region of the second Fab molecule ($VH_{(2)}$-$CL_{(2)}$) and the Fab light chain polypeptide of the first Fab molecule ($VL_{(1)}$-$CL_{(1)}$). In some embodiments the T cell activating bispecific antigen binding molecule further comprises the Fab light chain polypeptide of a third Fab molecule ($VL_{(3)}$-$CL_{(3)}$).

In certain embodiments the T cell activating bispecific antigen binding molecule according to the invention comprises a polypeptide wherein the Fab light chain variable region of the second Fab molecule shares a carboxy-terminal peptide bond with the Fab heavy chain constant region of the second Fab molecule ($VL_{(2)}$-$CH1_{(2)}$) and the Fab light chain polypeptide of the first Fab molecule ($VL_{(1)}$-$CL_{(1)}$). In some embodiments the T cell activating bispecific antigen binding molecule further comprises the Fab light chain polypeptide of a third Fab molecule ($VL_{(3)}$-$CL_{(3)}$).

In certain embodiments the T cell activating bispecific antigen binding molecule according to the invention comprises a polypeptide wherein the Fab heavy chain of the first Fab molecule shares a carboxy-terminal peptide bond with the Fab light chain variable region of the second Fab molecule, which in turn shares a carboxy-terminal peptide bond with the Fab heavy chain constant region of the second Fab molecule (i.e. the second Fab molecule comprises a crossover Fab heavy chain, wherein the heavy chain variable region is replaced by a light chain variable region), which in turn shares a carboxy-terminal peptide bond with the Fab light chain variable region of a third Fab molecule, which in turn shares a carboxy-terminal peptide bond with the Fab heavy chain constant region of a third Fab molecule (i.e. the third Fab molecule comprises a crossover Fab heavy chain, wherein the heavy chain variable region is replaced by a light chain variable region) ($VH_{(1)}$-$CH1_{(1)}$-$VL_{(2)}$-$CH1_{(2)}$-$VL_{(3)}$-$CH1_{(3)}$). In some embodiments the T cell activating bispecific antigen binding molecule further comprises a polypeptide wherein the Fab heavy chain variable region of the second Fab molecule shares a carboxy-terminal peptide bond with the Fab light chain constant region of the second Fab molecule ($VH_{(2)}$-$CL_{(2)}$) and the Fab light chain polypeptide of the first Fab molecule ($VL_{(1)}$-$CL_{(1)}$). In some embodiments the T cell activating bispecific antigen binding molecule further comprises a polypeptide wherein the Fab heavy chain variable region of a third Fab molecule shares a carboxy-terminal peptide bond with the Fab light chain constant region of a third Fab molecule ($VH_{(3)}$-$CL_{(3)}$).

In certain embodiments the T cell activating bispecific antigen binding molecule according to the invention comprises a polypeptide wherein the Fab heavy chain of the first Fab molecule shares a carboxy-terminal peptide bond with the Fab heavy chain variable region of the second Fab molecule, which in turn shares a carboxy-terminal peptide bond with the Fab light chain constant region of the second Fab molecule (i.e. the second Fab molecule comprises a crossover Fab heavy chain, wherein the heavy chain constant region is replaced by a light chain constant region), which in turn shares a carboxy-terminal peptide bond with the Fab heavy chain variable region of a third Fab molecule, which in turn shares a carboxy-terminal peptide bond with the Fab light chain constant region of a third Fab molecule (i.e. the third Fab molecule comprises a crossover Fab heavy chain, wherein the heavy chain constant region is replaced by a light chain constant region) ($VH_{(1)}$-$CH1_{(1)}$-$VH_{(2)}$-$CL_{(2)}$-$VH_{(3)}$-$CL_{(3)}$). In some embodiments the T cell activating bispecific antigen binding molecule further comprises a polypeptide wherein the Fab light chain variable region of the second Fab molecule shares a carboxy-terminal peptide bond with the Fab heavy chain constant region of the second Fab molecule ($VL_{(2)}$-$CH1_{(2)}$) and the Fab light chain polypeptide of the first Fab molecule ($VL_{(1)}$-$CL_{(1)}$). In some embodiments the T cell activating bispecific antigen binding molecule further comprises a polypeptide wherein the Fab light chain variable region of a third Fab molecule shares a carboxy-terminal peptide bond with the Fab heavy chain constant region of a third Fab molecule ($VL_{(3)}$-$CH1_{(3)}$).

In certain embodiments the T cell activating bispecific antigen binding molecule according to the invention comprises a polypeptide wherein the Fab light chain variable region of a third Fab molecule shares a carboxy-terminal peptide bond with the Fab heavy chain constant region of a third Fab molecule (i.e. the third Fab molecule comprises a crossover Fab heavy chain, wherein the heavy chain variable region is replaced by a light chain variable region), which in turn shares a carboxy-terminal peptide bond with the Fab light chain variable region of the second Fab molecule, which in turn shares a carboxy-terminal peptide bond with the Fab heavy chain constant region of the second Fab molecule (i.e. the second Fab molecule comprises a crossover Fab heavy chain, wherein the heavy chain variable region is replaced by a light chain variable region), which in turn shares a carboxy-terminal peptide bond with the Fab heavy chain of the first Fab molecule ($VL_{(3)}$-$CH1_{(3)}$-$VL_{(2)}$-$CH1_{(2)}$-$VH_{(1)}$-$CH1_{(1)}$). In some embodiments the T cell activating bispecific antigen binding molecule further comprises a polypeptide wherein the Fab heavy chain variable region of the second Fab molecule shares a carboxy-terminal peptide bond with the Fab light chain constant region of the second Fab molecule ($VH_{(2)}$-$CL_{(2)}$) and the Fab light chain polypeptide of the first Fab molecule ($VL_{(1)}$-$CL_{(1)}$). In some embodiments the T cell activating bispecific antigen binding molecule further comprises a polypeptide wherein the Fab heavy chain variable region of a third Fab molecule shares a carboxy-terminal peptide bond with the Fab light chain constant region of a third Fab molecule ($VH_{(3)}$-$CL_{(3)}$).

In certain embodiments the T cell activating bispecific antigen binding molecule according to the invention comprises a polypeptide wherein the Fab heavy chain variable region of a third Fab molecule shares a carboxy-terminal peptide bond with the Fab light chain constant region of a third Fab molecule (i.e. the third Fab molecule comprises a crossover Fab heavy chain, wherein the heavy chain constant region is replaced by a light chain constant region), which in turn shares a carboxy-terminal peptide bond with the Fab heavy chain variable region of the second Fab molecule, which in turn shares a carboxy-terminal peptide bond with the Fab light chain constant region of the second Fab molecule (i.e. the second Fab molecule comprises a crossover Fab heavy chain, wherein the heavy chain constant region is replaced by a light chain constant region), which in turn shares a carboxy-terminal peptide bond with the Fab heavy chain of the first Fab molecule ($VH_{(3)}$-$CL_{(3)}$-$VH_{(2)}$-$CL_{(2)}$-$VH_{(1)}$-$CH1_{(1)}$). In some embodiments the T cell activating bispecific antigen binding molecule further comprises a polypeptide wherein the Fab light chain variable region of the second Fab molecule shares a carboxy-terminal peptide bond with the Fab heavy chain constant region of the second Fab molecule ($VL_{(2)}$-$CH1_{(2)}$) and the Fab light chain polypeptide of the first Fab molecule ($VL_{(1)}$-$CL_{(1)}$). In some embodiments the T cell activating bispecific antigen binding molecule further comprises a polypeptide wherein the Fab light chain variable region of a third Fab molecule shares a carboxy-terminal peptide bond with the Fab heavy chain constant region of a third Fab molecule ($VL_{(3)}$-$CH1_{(3)}$).

According to any of the above embodiments, components of the T cell activating bispecific antigen binding molecule (e.g. Fab molecules, Fc domain) may be fused directly or through various linkers, particularly peptide linkers comprising one or more amino acids, typically about 2-20 amino acids, that are described herein or are known in the art. Suitable, non-immunogenic peptide linkers include, for example, $(G_4S)_n$, $(SG_4)_n$, $(G_4S)_n$ or $G_4(SG_4)_n$ peptide linkers, wherein n is generally an integer from 1 to 10, typically from 2 to 4.

Fc Domain

The Fc domain of the T cell activating bispecific antigen binding molecule consists of a pair of polypeptide chains comprising heavy chain domains of an immunoglobulin molecule. For example, the Fc domain of an immunoglobulin G (IgG) molecule is a dimer, each subunit of which comprises the CH2 and CH3 IgG heavy chain constant domains. The two subunits of the Fc domain are capable of stable association with each other. In one embodiment the T cell activating bispecific antigen binding molecule of the invention comprises not more than one Fc domain.

In one embodiment according the invention the Fc domain of the T cell activating bispecific antigen binding molecule is an IgG Fc domain. In a particular embodiment the Fc domain is an $IgG_1$ Fc domain. In another embodiment the Fc domain is an $IgG_4$ Fc domain. In a more specific embodiment, the Fc domain is an $IgG_4$ Fc domain comprising an amino acid substitution at position S228 (Kabat numbering), particularly the amino acid substitution S228P. This amino acid substitution reduces in vivo Fab arm exchange of $IgG_4$ antibodies (see Stubenrauch et al., Drug Metabolism and Disposition 38, 84-91 (2010)). In a further particular embodiment the Fc domain is human. An exemplary sequence of a human $IgG_1$ Fc region is given in SEQ ID NO: 13.

Fc Domain Modifications Promoting Heterodimerization

T cell activating bispecific antigen binding molecules according to the invention comprise different Fab molecules, fused to one or the other of the two subunits of the Fc domain, thus the two subunits of the Fc domain are typically comprised in two non-identical polypeptide chains. Recombinant co-expression of these polypeptides and subsequent dimerization leads to several possible combinations of the two polypeptides. To improve the yield and purity of T cell activating bispecific antigen binding molecules in recombinant production, it will thus be advantageous to introduce in the Fc domain of the T cell activating bispecific antigen binding molecule a modification promoting the association of the desired polypeptides.

Accordingly, in particular embodiments the Fc domain of the T cell activating bispecific antigen binding molecule according to the invention comprises a modification promoting the association of the first and the second subunit of the Fc domain. The site of most extensive protein-protein interaction between the two subunits of a human IgG Fc domain is in the CH3 domain of the Fc domain. Thus, in one embodiment said modification is in the CH3 domain of the Fc domain.

There exist several approaches for modifications in the CH3 domain of the Fc domain in order to enforce heterodimerization, which are well described e.g. in WO 96/27011, WO 98/050431, EP 1870459, WO 2007/110205, WO 2007/147901, WO 2009/089004, WO 2010/129304, WO 2011/90754, WO 2011/143545, WO 2012058768, WO 2013157954, WO 2013096291. Typically, in all such approaches the CH3 domain of the first subunit of the Fc domain and the CH3 domain of the second subunit of the Fc domain are both engineered in a complementary manner so that each CH3 domain (or the heavy chain comprising it) can no longer homodimerize with itself but is forced to heterodimerize with the complementarily engineered other CH3 domain (so that the first and second CH3 domain heterodimerize and no homdimers between the two first or the two second CH3 domains are formed). These different approaches for improved heavy chain heterodimerization are contemplated as different alternatives in combination with the heavy-light chain modifications (VH and VL exchange/replacement in one binding arm and the introduction of substitutions of charged amino acids with opposite charges in the CH1/CL interface) in the T cell activating bispecific antigen binding molecule according to the invention which reduce light chain mispairing and Bence Jones-type side products.

In a specific embodiment said modification promoting the association of the first and the second subunit of the Fc domain is a so-called "knob-into-hole" modification, comprising a "knob" modification in one of the two subunits of the Fc domain and a "hole" modification in the other one of the two subunits of the Fc domain.

The knob-into-hole technology is described e.g. in U.S. Pat. Nos. 5,731,168; 7,695,936; Ridgway et al., Prot Eng 9, 617-621 (1996) and Carter, J Immunol Meth 248, 7-15 (2001). Generally, the method involves introducing a protuberance ("knob") at the interface of a first polypeptide and a corresponding cavity ("hole") in the interface of a second polypeptide, such that the protuberance can be positioned in the cavity so as to promote heterodimer formation and hinder homodimer formation. Protuberances are constructed by replacing small amino acid side chains from the interface of the first polypeptide with larger side chains (e.g. tyrosine or tryptophan). Compensatory cavities of identical or similar size to the protuberances are created in the interface of the second polypeptide by replacing large amino acid side chains with smaller ones (e.g. alanine or threonine). Accordingly, in a particular embodiment, in the CH3 domain of the first subunit of the Fc domain of the T cell activating bispecific antigen binding molecule an amino acid residue is replaced with an amino acid residue having a larger side chain volume, thereby generating a protuberance within the CH3 domain of the first subunit which is positionable in a cavity within the CH3 domain of the second subunit, and in the CH3 domain of the second subunit of the Fc domain an amino acid residue is replaced with an amino acid residue having a smaller side chain volume, thereby generating a cavity within the CH3 domain of the second subunit within which the protuberance within the CH3 domain of the first subunit is positionable.

Preferably said amino acid residue having a larger side chain volume is selected from the group consisting of arginine (R), phenylalanine (F), tyrosine (Y), and tryptophan (W).

Preferably said amino acid residue having a smaller side chain volume is selected from the group consisting of alanine (A), serine (S), threonine (T), and valine (V).

The protuberance and cavity can be made by altering the nucleic acid encoding the polypeptides, e.g. by site-specific mutagenesis, or by peptide synthesis.

In a specific embodiment, in the CH3 domain of the first subunit of the Fc domain (the "knobs" subunit) the threonine residue at position 366 is replaced with a tryptophan residue (T366W), and in the CH3 domain of the second subunit of the Fc domain (the "hole" subunit) the tyrosine residue at position 407 is replaced with a valine residue (Y407V). In one embodiment, in the second subunit of the Fc domain additionally the threonine residue at position 366 is replaced with a serine residue (T366S) and the leucine residue at position 368 is replaced with an alanine residue (L368A) (numberings according to Kabat EU index).

In yet a further embodiment, in the first subunit of the Fc domain additionally the serine residue at position 354 is replaced with a cysteine residue (S354C) or the glutamic acid residue at position 356 is replaced with a cysteine residue (E356C), and in the second subunit of the Fc domain additionally the tyrosine residue at position 349 is replaced by a cysteine residue (Y349C) (numberings according to Kabat EU index). Introduction of these two cysteine residues results in formation of a disulfide bridge between the two subunits of the Fc domain, further stabilizing the dimer (Carter, J Immunol Methods 248, 7-15 (2001)).

In a particular embodiment, the first subunit of the Fc domain comprises amino acid substitutions S354C and T366W, and the second subunit of the Fc domain comprises amino acid substitutions Y349C, T366S, L368A and Y407V (numbering according to Kabat EU index).

In a particular embodiment the Fab molecule which specifically binds an activating T cell antigen is fused (optionally via a Fab molecule which specifically binds to a target cell antigen) to the first subunit of the Fc domain (comprising the "knob" modification). Without wishing to be bound by theory, fusion of the Fab molecule which specifically binds an activating T cell antigen to the knob-containing subunit of the Fc domain will (further) minimize the generation of antigen binding molecules comprising two Fab molecules which bind to an activating T cell antigen (steric clash of two knob-containing polypeptides).

Other techniques of CH3-modification for enforcing the heterodimerization are contemplated as alternatives according to the invention and are described e.g. in WO 96/27011, WO 98/050431, EP 1870459, WO 2007/110205, WO 2007/147901, WO 2009/089004, WO 2010/129304, WO 2011/90754, WO 2011/143545, WO 2012/058768, WO 2013/157954, WO 2013/096291.

In one embodiment the heterodimerization approach described in EP 1870459 A1, is used alternatively. This approach is based on the introduction of charged amino acids with opposite charges at specific amino acid positions in the CH3/CH3 domain interface between the two subunits of the Fc domain. One preferred embodiment for the T cell activating bispecific antigen binding molecule of the invention are amino acid mutations R409D; K370E in one of the two CH3 domains (of the Fc domain) and amino acid mutations D399K; E357K in the other one of the CH3 domains of the Fc domain (numbering according to Kabat EU index).

In another embodiment the T cell activating bispecific antigen binding molecule of the invention comprises amino acid mutation T366W in the CH3 domain of the first subunit of the Fc domain and amino acid mutations T366S, L368A, Y407V in the CH3 domain of the second subunit of the Fc domain, and additionally amino acid mutations R409D; K370E in the CH3 domain of the first subunit of the Fc domain and amino acid mutations D399K; E357K in the CH3 domain of the second subunit of the Fc domain (numberings according to Kabat EU index).

In another embodiment T cell activating bispecific antigen binding molecule of the invention comprises amino acid mutations S354C, T366W in the CH3 domain of the first subunit of the Fc domain and amino acid mutations Y349C, T366S, L368A, Y407V in the CH3 domain of the second subunit of the Fc domain, or said T cell activating bispecific antigen binding molecule comprises amino acid mutations Y349C, T366W in the CH3 domain of the first subunit of the Fc domain and amino acid mutations S354C, T366S, L368A, Y407V in the CH3 domains of the second subunit of the Fc domain and additionally amino acid mutations R409D; K370E in the CH3 domain of the first subunit of the Fc domain and amino acid mutations D399K; E357K in the CH3 domain of the second subunit of the Fc domain (all numberings according to Kabat EU index).

In one embodiment the heterodimerization approach described in WO 2013/157953 is used alternatively. In one embodiment a first CH3 domain comprises amino acid mutation T366K and a second CH3 domain comprises amino acid mutation L351D (numberings according to Kabat EU index). In a further embodiment the first CH3 domain comprises further amino acid mutation L351K. In a further embodiment the second CH3 domain comprises further an amino acid mutation selected from Y349E, Y349D and L368E (preferably L368E) (numberings according to Kabat EU index).

In one embodiment the heterodimerization approach described in WO 2012/058768 is used alternatively. In one embodiment a first CH3 domain comprises amino acid mutations L351Y, Y407A and a second CH3 domain comprises amino acid mutations T366A, K409F. In a further embodiment the second CH3 domain comprises a further amino acid mutation at position T411, D399, 5400, F405, N390, or K392, e.g. selected from a) T411N, T411R, T411Q, T411K, T411D, T411E or T411W, b) D399R, D399W, D399Y or D399K, c) S400E, S400D, S400R, or S400K, d) F405I, F405M, F405T, F405S, F405V or F405W, e) N390R, N390K or N390D, f) K392V, K392M, K392R, K392L, K392F or K392E (numberings according to Kabat EU index). In a further embodiment a first CH3 domain comprises amino acid mutations L351Y, Y407A and a second CH3 domain comprises amino acid mutations T366V, K409F. In a further embodiment a first CH3 domain comprises amino acid mutation Y407A and a second CH3 domain comprises amino acid mutations T366A, K409F. In a further embodiment the second CH3 domain further comprises amino acid mutations K392E, T411E, D399R and S400R (numberings according to Kabat EU index).

In one embodiment the heterodimerization approach described in WO 2011/143545 is used alternatively, e.g. with the amino acid modification at a position selected from the group consisting of 368 and 409 (numbering according to Kabat EU index).

In one embodiment the heterodimerization approach described in WO 2011/090762, which also uses the knobs-into-holes technology described above, is used alternatively. In one embodiment a first CH3 domain comprises amino acid mutation T366W and a second CH3 domain comprises amino acid mutation Y407A. In one embodiment a first CH3 domain comprises amino acid mutation T366Y and a second CH3 domain comprises amino acid mutation Y407T (numberings according to Kabat EU index).

In one embodiment the T cell activating bispecific antigen binding molecule or its Fc domain is of $IgG_2$ subclass and the heterodimerization approach described in WO 2010/129304 is used alternatively.

In an alternative embodiment a modification promoting association of the first and the second subunit of the Fc domain comprises a modification mediating electrostatic steering effects, e.g. as described in PCT publication no. WO 2009/089004. Generally, this method involves replacement of one or more amino acid residues at the interface of the two Fc domain subunits by charged amino acid residues so that homodimer formation becomes electrostatically unfavorable but heterodimerization electrostatically favorable. In one such embodiment a first CH3 domain comprises amino acid substitution of K392 or N392 with a negatively charged amino acid (e.g. glutamic acid (E), or aspartic acid (D), preferably K392D or N392D) and a second CH3 domain comprises amino acid substitution of D399, E356, D356, or E357 with a positively charged amino acid (e.g. lysine (K) or arginine (R), preferably D399K, E356K, D356K, or E357K, and more preferably D399K and E356K). In a further embodiment the first CH3 domain further comprises amino acid substitution of K409 or R409 with a negatively charged amino acid (e.g. glutamic acid (E), or aspartic acid (D), preferably K409D or R409D). In a further embodiment the first CH3 domain further or alternatively comprises amino acid substitution of K439 and/or K370 with a negatively charged amino acid (e.g. glutamic acid (E), or aspartic acid (D)) (all numberings according to Kabat EU index).

In yet a further embodiment the heterodimerization approach described in WO 2007/147901 is used alternatively. In one embodiment a first CH3 domain comprises amino acid mutations K253E, D282K, and K322D and a second CH3 domain comprises amino acid mutations D239K, E240K, and K292D (numberings according to Kabat EU index).

In still another embodiment the heterodimerization approach described in WO 2007/110205 can be used alternatively.

In one embodiment, the first subunit of the Fc domain comprises amino acid substitutions K392D and K409D, and the second subunit of the Fc domain comprises amino acid substitutions D356K and D399K (numbering according to Kabat EU index).

Fc Domain Modifications Reducing Fc Receptor Binding and/or Effector Function

The Fc domain confers to the T cell activating bispecific antigen binding molecule favorable pharmacokinetic properties, including a long serum half-life which contributes to good accumulation in the target tissue and a favorable tissue-blood distribution ratio. At the same time it may, however, lead to undesirable targeting of the T cell activating bispecific antigen binding molecule to cells expressing Fc receptors rather than to the preferred antigen-bearing cells. Moreover, the co-activation of Fc receptor signaling pathways may lead to cytokine release which, in combination with the T cell activating properties and the long half-life of the antigen binding molecule, results in excessive activation of cytokine receptors and severe side effects upon systemic administration. Activation of (Fc receptor-bearing) immune cells other than T cells may even reduce efficacy of the T cell activating bispecific antigen binding molecule due to the potential destruction of T cells e.g. by NK cells.

Accordingly, in particular embodiments, the Fc domain of the T cell activating bispecific antigen binding molecules according to the invention exhibits reduced binding affinity to an Fc receptor and/or reduced effector function, as compared to a native $IgG_1$ Fc domain. In one such embodiment the Fc domain (or the T cell activating bispecific antigen binding molecule comprising said Fc domain) exhibits less than 50%, preferably less than 20%, more preferably less than 10% and most preferably less than 5% of the binding affinity to an Fc receptor, as compared to a native $IgG_1$ Fc domain (or a T cell activating bispecific antigen binding molecule comprising a native $IgG_1$ Fc domain), and/or less than 50%, preferably less than 20%, more preferably less than 10% and most preferably less than 5% of the effector function, as compared to a native $IgG_1$ Fc domain domain (or a T cell activating bispecific antigen binding molecule comprising a native $IgG_1$ Fc domain). In one embodiment, the Fc domain domain (or the T cell activating bispecific antigen binding molecule comprising said Fc domain) does not substantially bind to an Fc receptor and/or induce effector function. In a particular embodiment the Fc receptor is an Fcγ receptor. In one embodiment the Fc receptor is a human Fc receptor. In one embodiment the Fc receptor is an activating Fc receptor. In a specific embodiment the Fc receptor is an activating human Fcγ receptor, more specifically human FcγRIIIa, FcγRI or FcγRIIa, most specifically human FcγRIIIa. In one embodiment the effector function is one or more selected from the group of CDC, ADCC, ADCP, and cytokine secretion. In a particular embodiment the effector function is ADCC. In one embodiment the Fc domain domain exhibits substantially similar binding affinity to neonatal Fc receptor (FcRn), as compared to a native IgG$_1$ Fc domain domain. Substantially similar binding to FcRn is achieved when the Fc domain (or the T cell activating bispecific antigen binding molecule comprising said Fc domain) exhibits greater than about 70%, particularly greater than about 80%, more particularly greater than about 90% of the binding affinity of a native IgG$_1$ Fc domain (or the T cell activating bispecific antigen binding molecule comprising a native IgG$_1$ Fc domain) to FcRn.

In certain embodiments the Fc domain is engineered to have reduced binding affinity to an Fc receptor and/or reduced effector function, as compared to a non-engineered Fc domain. In particular embodiments, the Fc domain of the T cell activating bispecific antigen binding molecule comprises one or more amino acid mutation that reduces the binding affinity of the Fc domain to an Fc receptor and/or effector function. Typically, the same one or more amino acid mutation is present in each of the two subunits of the Fc domain. In one embodiment the amino acid mutation reduces the binding affinity of the Fc domain to an Fc receptor. In one embodiment the amino acid mutation reduces the binding affinity of the Fc domain to an Fc receptor by at least 2-fold, at least 5-fold, or at least 10-fold. In embodiments where there is more than one amino acid mutation that reduces the binding affinity of the Fc domain to the Fc receptor, the combination of these amino acid mutations may reduce the binding affinity of the Fc domain to an Fc receptor by at least 10-fold, at least 20-fold, or even at least 50-fold. In one embodiment the T cell activating bispecific antigen binding molecule comprising an engineered Fc domain exhibits less than 20%, particularly less than 10%, more particularly less than 5% of the binding affinity to an Fc receptor as compared to a T cell activating bispecific antigen binding molecule comprising a non-engineered Fc domain. In a particular embodiment the Fc receptor is an Fcγ receptor. In some embodiments the Fc receptor is a human Fc receptor. In some embodiments the Fc receptor is an activating Fc receptor. In a specific embodiment the Fc receptor is an activating human Fcγ receptor, more specifically human FcγRIIIa, FcγRI or FcγRIIa, most specifically human FcγRIIIa. Preferably, binding to each of these receptors is reduced. In some embodiments binding affinity to a complement component, specifically binding affinity to C1q, is also reduced. In one embodiment binding affinity to neonatal Fc receptor (FcRn) is not reduced. Substantially similar binding to FcRn, i.e. preservation of the binding affinity of the Fc domain to said receptor, is achieved when the Fc domain (or the T cell activating bispecific antigen binding molecule comprising said Fc domain) exhibits greater than about 70% of the binding affinity of a non-engineered form of the Fc domain (or the T cell activating bispecific antigen binding molecule comprising said non-engineered form of the Fc domain) to FcRn. The Fc domain, or T cell activating bispecific antigen binding molecules of the invention comprising said Fc domain, may exhibit greater than about 80% and even greater than about 90% of such affinity. In certain embodiments the Fc domain of the T cell activating bispecific antigen binding molecule is engineered to have reduced effector function, as compared to a non-engineered Fc domain. The reduced effector function can include, but is not limited to, one or more of the following: reduced complement dependent cytotoxicity (CDC), reduced antibody-dependent cell-mediated cytotoxicity (ADCC), reduced antibody-dependent cellular phagocytosis (ADCP), reduced cytokine secretion, reduced immune complex-mediated antigen uptake by antigen-presenting cells, reduced binding to NK cells, reduced binding to macrophages, reduced binding to monocytes, reduced binding to polymorphonuclear cells, reduced direct signaling inducing apoptosis, reduced crosslinking of target-bound antibodies, reduced dendritic cell maturation, or reduced T cell priming. In one embodiment the reduced effector function is one or more selected from the group of reduced CDC, reduced ADCC, reduced ADCP, and reduced cytokine secretion. In a particular embodiment the reduced effector function is reduced ADCC. In one embodiment the reduced ADCC is less than 20% of the ADCC induced by a non-engineered Fc domain (or a T cell activating bispecific antigen binding molecule comprising a non-engineered Fc domain).

In one embodiment the amino acid mutation that reduces the binding affinity of the Fc domain to an Fc receptor and/or effector function is an amino acid substitution. In one embodiment the Fc domain comprises an amino acid substitution at a position selected from the group of E233, L234, L235, N297, P331 and P329 (numberings according to Kabat EU index). In a more specific embodiment the Fc domain comprises an amino acid substitution at a position selected from the group of L234, L235 and P329 (numberings according to Kabat EU index). In some embodiments the Fc domain comprises the amino acid substitutions L234A and L235A (numberings according to Kabat EU index). In one such embodiment, the Fc domain is an IgG$_1$ Fc domain, particularly a human IgG$_1$ Fc domain. In one embodiment the Fc domain comprises an amino acid substitution at position P329. In a more specific embodiment the amino acid substitution is P329A or P329G, particularly P329G (numberings according to Kabat EU index). In one embodiment the Fc domain comprises an amino acid substitution at position P329 and a further amino acid substitution at a position selected from E233, L234, L235, N297 and P331 (numberings according to Kabat EU index). In a more specific embodiment the further amino acid substitution is E233P, L234A, L235A, L235E, N297A, N297D or P331S. In particular embodiments the Fc domain comprises amino acid substitutions at positions P329, L234 and L235 (numberings according to Kabat EU index). In more particular embodiments the Fc domain comprises the amino acid mutations L234A, L235A and P329G ("P329G LALA"). In one such embodiment, the Fc domain is an IgG$_1$ Fc domain, particularly a human IgG$_1$ Fc domain. The "P329G LALA" combination of amino acid substitutions almost completely abolishes Fcγ receptor (as well as complement) binding of a human IgG$_1$ Fc domain, as described in PCT publication no. WO 2012/130831, incorporated herein by reference in its entirety. WO 2012/130831 also describes methods of preparing such mutant Fc domains and methods for determining its properties such as Fc receptor binding or effector functions.

IgG$_4$ antibodies exhibit reduced binding affinity to Fc receptors and reduced effector functions as compared to IgG$_1$ antibodies. Hence, in some embodiments the Fc domain of the T cell activating bispecific antigen binding molecules of the invention is an IgG$_4$ Fc domain, particularly a human IgG$_4$ Fc domain. In one embodiment the IgG$_4$ Fc domain comprises amino acid substitutions at position S228, specifically the amino acid substitution S228P (numberings according to Kabat EU index). To further reduce its binding affinity to an Fc receptor and/or its effector function, in one embodiment the IgG$_4$ Fc domain comprises an amino acid substitution at position L235, specifically the amino acid substitution L235E (numberings according to Kabat EU index). In another embodiment, the IgG$_4$ Fc domain comprises an amino acid substitution at position P329, specifically the amino acid substitution P329G (numberings according to Kabat EU index). In a particular embodiment, the IgG$_4$ Fc domain comprises amino acid substitutions at positions S228, L235 and P329, specifically amino acid substitutions S228P, L235E and P329G (numberings according to Kabat EU index). Such IgG$_4$ Fc domain mutants and their Fcγ receptor binding properties are described in PCT publication no. WO 2012/130831, incorporated herein by reference in its entirety. In a particular embodiment the Fc domain exhibiting reduced binding affinity to an Fc receptor and/or reduced effector function, as compared to a native IgG$_1$ Fc domain, is a human IgG$_1$ Fc domain comprising the amino acid substitutions L234A, L235A and optionally P329G, or a human IgG$_4$ Fc domain comprising the amino acid substitutions S228P, L235E and optionally P329G (numberings according to Kabat EU index).

In certain embodiments N-glycosylation of the Fc domain has been eliminated. In one such embodiment the Fc domain comprises an amino acid mutation at position N297, particularly an amino acid substitution replacing asparagine by alanine (N297A) or aspartic acid (N297D) (numberings according to Kabat EU index).

In addition to the Fc domains described hereinabove and in PCT publication no. WO 2012/130831, Fc domains with reduced Fc receptor binding and/or effector function also include those with substitution of one or more of Fc domain residues 238, 265, 269, 270, 297, 327 and 329 (U.S. Pat. No. 6,737,056) (numberings according to Kabat EU index). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Mutant Fc domains can be prepared by amino acid deletion, substitution, insertion or modification using genetic or chemical methods well known in the art. Genetic methods may include site-specific mutagenesis of the encoding DNA sequence, PCR, gene synthesis, and the like. The correct nucleotide changes can be verified for example by sequencing.

Binding to Fc receptors can be easily determined e.g. by ELISA, or by Surface Plasmon Resonance (SPR) using standard instrumentation such as a BIACORE® instrument (GE Healthcare), and Fc receptors such as may be obtained by recombinant expression. A suitable such binding assay is described herein. Alternatively, binding affinity of Fc domains or cell activating bispecific antigen binding molecules comprising an Fc domain for Fc receptors may be evaluated using cell lines known to express particular Fc receptors, such as human NK cells expressing FcγIIIa receptor. Effector function of an Fc domain, or a T cell activating bispecific antigen binding molecule comprising an Fc domain, can be measured by methods known in the art. A suitable assay for measuring ADCC is described herein. Other examples of in vitro assays to assess ADCC activity of a molecule of interest are described in U.S. Pat. No. 5,500,362; Hellstrom et al. Proc Natl Acad Sci USA 83, 7059-7063 (1986) and Hellstrom et al., Proc Natl Acad Sci USA 82, 1499-1502 (1985); U.S. Pat. No. 5,821,337; Bruggemann et al., J Exp Med 166, 1351-1361 (1987). Alternatively, non-radioactive assays methods may be employed (see, for example, ACTI™ non-radioactive cytotoxicity assay for flow cytometry (CellTechnology, Inc. Mountain View, Calif.); and CytoTox 96® non-radioactive cytotoxicity assay (Promega, Madison, Wis.)). Useful effector cells for such assays include peripheral blood mononuclear cells (PBMC) and Natural Killer (NK) cells. Alternatively, or additionally, ADCC activity of the molecule of interest may be assessed in vivo, e.g. in a animal model such as that disclosed in Clynes et al., Proc Natl Acad Sci USA 95, 652-656 (1998).

In some embodiments, binding of the Fc domain to a complement component, specifically to C1q, is reduced. Accordingly, in some embodiments wherein the Fc domain is engineered to have reduced effector function, said reduced effector function includes reduced CDC. C1q binding assays may be carried out to determine whether the T cell activating bispecific antigen binding molecule is able to bind C1q and hence has CDC activity. See e.g., C1q and C3c binding ELISA in WO 2006/029879 and WO 2005/100402. To assess complement activation, a CDC assay may be performed (see, for example, Gazzano-Santoro et al., J Immunol Methods 202, 163 (1996); Cragg et al., Blood 101, 1045-1052 (2003); and Cragg and Glennie, Blood 103, 2738-2743 (2004)).

Antigen Binding Moieties

The antigen binding molecule of the invention is bispecific, i.e. it comprises at least two antigen binding moieties capable of specific binding to two distinct antigenic determinants. According to particular embodiments of the invention, the antigen binding moieties are Fab molecules (i.e. antigen binding domains composed of a heavy and a light chain, each comprising a variable and a constant domain). In one embodiment said Fab molecules are human. In another embodiment said Fab molecules are humanized. In yet another embodiment said Fab molecules comprise human heavy and light chain constant domains.

Preferably, at least one of the antigen binding moieties is a crossover Fab molecule. Such modification reduces mispairing of heavy and light chains from different Fab molecules, thereby improving the yield and purity of the T cell activating bispecific antigen binding molecule of the invention in recombinant production. In a particular crossover Fab molecule useful for the T cell activating bispecific antigen binding molecule of the invention, the variable domains of the Fab light chain and the Fab heavy chain (VL and VH, respectively) are exchanged. Even with this domain exchange, however, the preparation of the T cell activating bispecific antigen binding molecule may comprise certain side products due to a so-called Bence Jones-type interaction between mispaired heavy and light chains (see Schaefer et al, PNAS, 108 (2011) 11187-11191). To further reduce mispairing of heavy and light chains from different Fab molecules and thus increase the purity and yield of the desired T cell activating bispecific antigen binding molecule, according to the present invention charged amino acids with opposite charges may be introduced at specific amino acid positions in the CH1 and CL domains of either the Fab molecule(s) specifically binding to a target cell antigen, or the Fab molecule specifically binding to an activating T cell antigen. Charge modifications are made either in the conventional Fab molecule(s) comprised in the T cell activating bispecific antigen binding molecule (such as shown e.g. in FIGS. 1 A-C, G-J), or in the VH/VL crossover Fab molecule(s) comprised in the T cell activating bispecific antigen binding molecule (such as shown e.g. in FIG. 1 D-F, K-N) (but not in both). In particular embodiments, the charge modifications are made in the conventional Fab molecule(s) comprised in the T cell activating bispecific antigen binding molecule (which in particular embodiments specifically bind(s) to the target cell antigen).

In a particular embodiment according to the invention, the T cell activating bispecific antigen binding molecule is capable of simultaneous binding to a target cell antigen, particularly a tumor cell antigen, and an activating T cell antigen, particularly CD3. In one embodiment, the T cell activating bispecific antigen binding molecule is capable of crosslinking a T cell and a target cell by simultaneous binding to a target cell antigen and an activating T cell antigen. In an even more particular embodiment, such simultaneous binding results in lysis of the target cell, particularly a tumor cell. In one embodiment, such simultaneous binding results in activation of the T cell. In other embodiments, such simultaneous binding results in a cellular response of a T lymphocyte, particularly a cytotoxic T lymphocyte, selected from the group of: proliferation, differentiation, cytokine secretion, cytotoxic effector molecule release, cytotoxic activity, and expression of activation markers. In one embodiment, binding of the T cell activating bispecific antigen binding molecule to the activating T cell antigen, particularly CD3, without simultaneous binding to the target cell antigen does not result in T cell activation.

In one embodiment, the T cell activating bispecific antigen binding molecule is capable of re-directing cytotoxic activity of a T cell to a target cell. In a particular embodiment, said re-direction is independent of MHC-mediated peptide antigen presentation by the target cell and and/or specificity of the T cell.

Particularly, a T cell according to any of the embodiments of the invention is a cytotoxic T cell. In some embodiments the T cell is a CD4$^+$ or a CD8$^+$ T cell, particularly a CD8$^+$ T cell.

Activating T Cell Antigen Binding Moiety

The T cell activating bispecific antigen binding molecule of the invention comprises at least one antigen binding moiety, particularly a Fab molecule, which specifically binds to an activating T cell antigen (also referred to herein as an "activating T cell antigen binding moiety, or activating T cell antigen binding Fab molecule"). In a particular embodiment, the T cell activating bispecific antigen binding molecule comprises not more than one antigen binding moiety capable of specific binding to an activating T cell antigen. In one embodiment the T cell activating bispecific antigen binding molecule provides monovalent binding to the activating T cell antigen.

In particular embodiments, the antigen binding moiety which specifically binds an activating T cell antigen is a crossover Fab molecule as described herein, i.e. a Fab molecule wherein the variable domains VH and VL or the constant domains CH1 and CL of the Fab heavy and light chains are exchanged/replaced by each other. In such embodiments, the antigen binding moiety(ies) which specifically binds a target cell antigen is preferably a conventional Fab molecule. In embodiments where there is more than one antigen binding moiety, particularly Fab molecule, which specifically binds to a target cell antigen comprised in the T cell activating bispecific antigen binding molecule, the antigen binding moiety which specifically binds to an activating T cell antigen preferably is a crossover Fab molecule and the antigen binding moieties which specifically bind to a target cell antigen are conventional Fab molecules.

In alternative embodiments, the antigen binding moiety which specifically binds an activating T cell antigen is a conventional Fab molecule. In such embodiments, the antigen binding moiety(ies) which specifically binds a target cell antigen is a crossover Fab molecule as described herein, i.e. a Fab molecule wherein the variable domains VH and VL or the constant domains CH1 and CL of the Fab heavy and light chains are exchanged/replaced by each other.

In a particular embodiment the activating T cell antigen is CD3, particularly human CD3 (SEQ ID NO: 1) or cynomolgus CD3 (SEQ ID NO: 2), most particularly human CD3. In a particular embodiment the activating T cell antigen binding moiety is cross-reactive for (i.e. specifically binds to) human and cynomolgus CD3. In some embodiments, the activating T cell antigen is the epsilon subunit of CD3 (CD3 epsilon).

In some embodiments, the activating T cell antigen binding moiety specifically binds to CD3, particularly CD3 epsilon, and comprises at least one heavy chain complementarity determining region (CDR) selected from the group consisting of SEQ ID NO: 4, SEQ ID NO: 5 and SEQ ID NO: 6 and at least one light chain CDR selected from the group of SEQ ID NO: 8, SEQ ID NO: 9, SEQ ID NO: 10.

In one embodiment the CD3 binding antigen binding moiety, particularly Fab molecule, comprises a heavy chain variable region comprising the heavy chain CDR1 of SEQ ID NO: 4, the heavy chain CDR2 of SEQ ID NO: 5, the heavy chain CDR3 of SEQ ID NO: 6, and a light chain variable region comprising the light chain CDR1 of SEQ ID NO: 8, the light chain CDR2 of SEQ ID NO: 9, and the light chain CDR3 of SEQ ID NO: 10.

In another embodiment the CD3 binding antigen binding moiety, particularly Fab molecule, comprises a heavy chain variable region comprising the heavy chain CDR1 of SEQ ID NO: 4, the heavy chain CDR2 of SEQ ID NO: 46, the heavy chain CDR3 of SEQ ID NO: 6, and a light chain variable region comprising the light chain CDR1 of SEQ ID NO: 47, the light chain CDR2 of SEQ ID NO: 9, and the light chain CDR3 of SEQ ID NO: 10.

In one embodiment the CD3 binding antigen binding moiety, particularly Fab molecule, comprises a heavy chain variable region sequence that is at least about 95%, 96%, 97%, 98%, 99% or 100% identical to SEQ ID NO: 3 and a light chain variable region sequence that is at least about 95%, 96%, 97%, 98%, 99% or 100% identical to SEQ ID NO: 7.

In one embodiment the CD3 binding antigen binding moiety, particularly Fab molecule, comprises a heavy chain variable region comprising the amino acid sequence of SEQ ID NO: 3 and a light chain variable region comprising the amino acid sequence of SEQ ID NO: 7.

In one embodiment the CD3 binding antigen binding moiety, particularly Fab molecule, comprises the heavy chain variable region sequence of SEQ ID NO: 3 and the light chain variable region sequence of SEQ ID NO: 7.

In one embodiment the CD3 binding antigen binding moiety, particularly Fab molecule, comprises a heavy chain variable region sequence that is at least about 95%, 96%, 97%, 98%, 99% or 100% identical to SEQ ID NO: 48 and a light chain variable region sequence that is at least about 95%, 96%, 97%, 98%, 99% or 100% identical to SEQ ID NO: 49.

In one embodiment the CD3 binding antigen binding moiety, particularly Fab molecule, comprises a heavy chain variable region comprising the amino acid sequence of SEQ ID NO: 48 and a light chain variable region comprising the amino acid sequence of SEQ ID NO: 49.

In one embodiment the CD3 binding antigen binding moiety, particularly Fab molecule, comprises the heavy chain variable region sequence of SEQ ID NO: 48 and the light chain variable region sequence of SEQ ID NO: 49.

Target Cell Antigen Binding Moiety

The T cell activating bispecific antigen binding molecule of the invention comprises at least one antigen binding moiety, particularly a Fab molecule, which specifically binds to CEA (target cell antigen). In certain embodiments, the T cell activating bispecific antigen binding molecule comprises two antigen binding moieties, particularly Fab molecules, which specifically bind to CEA.

In a particular such embodiment, each of these antigen binding moieties specifically binds to the same antigenic determinant. In an even more particular embodiment, all of these antigen binding moieties are identical, i.e. they comprise the same amino acid sequences including the same amino acid substitutions in the CH1 and CL domain as described herein (if any). In one embodiment, the T cell activating bispecific antigen binding molecule comprises an immunoglobulin molecule which specifically binds to CEA. In one embodiment the T cell activating bispecific antigen binding molecule comprises not more than two antigen binding moieties, particularly Fab molecules, which specifically bind to CEA.

In particular embodiments, the antigen binding moiety(ies) which specifically bind to CEA is/are a conventional Fab molecule. In such embodiments, the antigen binding moiety(ies) which specifically binds an activating T cell antigen is a crossover Fab molecule as described herein, i.e. a Fab molecule wherein the variable domains VH and VL or the constant domains CH1 and CL of the Fab heavy and light chains are exchanged/replaced by each other.

In alternative embodiments, the antigen binding moiety(ies) which specifically bind to CEA is/are a crossover Fab molecule as described herein, i.e. a Fab molecule wherein the variable domains VH and VL or the constant domains CH1 and CL of the Fab heavy and light chains are exchanged/replaced by each other. In such embodiments, the antigen binding moiety(ies) which specifically binds an activating T cell antigen is a conventional Fab molecule.

The CEA binding moiety is able to direct the T cell activating bispecific antigen binding molecule to a target site, for example to a specific type of tumor cell that expresses CEA.

In one embodiment, the antigen binding moiety, particularly Fab molecule, which specifically binds to CEA comprises a heavy chain variable region comprising the heavy chain complementarity determining region (CDR) 1 of SEQ ID NO: 14, the heavy chain CDR 2 of SEQ ID NO: 15, and the heavy chain CDR 3 of SEQ ID NO: 16, and a light chain variable region comprising the light chain CDR 1 of SEQ ID NO: 17, the light chain CDR 2 of SEQ ID NO: 18 and the light chain CDR 3 of SEQ ID NO: 19. In a further embodiment, the antigen binding moiety, particularly Fab molecule, which specifically binds to CEA comprises a heavy chain variable region that is at least 95%, 96%, 97%, 98%, or 99% identical to the sequence of SEQ ID NO: 22, and a light chain variable region that is at least 95%, 96%, 97%, 98%, or 99% identical to the sequence of SEQ ID NO: 23. In still a further embodiment, the antigen binding moiety, particularly Fab molecule, which specifically binds to CEA comprises the heavy chain variable region sequence of SEQ ID NO: 22, and the light chain variable region sequence of SEQ ID NO: 23. In a particular embodiment, the T cell activating bispecific antigen binding molecule comprises a polypeptide that is at least 95%, 96%, 97%, 98%, or 99% identical to the sequence of SEQ ID NO: 34, a polypeptide that is at least 95%, 96%, 97%, 98%, or 99% identical to the sequence of SEQ ID NO: 36, a polypeptide that is at least 95%, 96%, 97%, 98%, or 99% identical to the sequence of SEQ ID NO: 37, and a polypeptide that is at least 95%, 96%, 97%, 98%, or 99% identical to the sequence of SEQ ID NO: 38. In a further particular embodiment, the T cell activating bispecific antigen binding molecule comprises a polypeptide sequence of SEQ ID NO: 34, a polypeptide sequence of SEQ ID NO: 36, a polypeptide sequence of SEQ ID NO: 37 and a polypeptide sequence of SEQ ID NO: 38. In another embodiment, the T cell activating bispecific antigen binding molecule comprises a polypeptide that is at least 95%, 96%, 97%, 98%, or 99% identical to the sequence of SEQ ID NO: 34, a polypeptide that is at least 95%, 96%, 97%, 98%, or 99% identical to the sequence of SEQ ID NO: 37, a polypeptide that is at least 95%, 96%, 97%, 98%, or 99% identical to the sequence of SEQ ID NO: 38, and a polypeptide that is at least 95%, 96%, 97%, 98%, or 99% identical to the sequence of SEQ ID NO: 39. In a further embodiment, the the T cell activating bispecific antigen binding molecule comprises a polypeptide sequence of SEQ ID NO: 34, a polypeptide sequence of SEQ ID NO: 37, a polypeptide sequence of SEQ ID NO: 38 and a polypeptide sequence of SEQ ID NO: 39. In still another embodiment, the T cell activating bispecific antigen binding molecule comprises a polypeptide that is at least 95%, 96%, 97%, 98%, or 99% identical to the sequence of SEQ ID NO: 34, a polypeptide that is at least 95%, 96%, 97%, 98%, or 99% identical to the sequence of SEQ ID NO: 36, a polypeptide that is at least 95%, 96%, 97%, 98%, or 99% identical to the sequence of SEQ ID NO: 38, and a polypeptide that is at least 95%, 96%, 97%, 98%, or 99% identical to the sequence of SEQ ID NO: 40. In a further embodiment, the the T cell activating bispecific antigen binding molecule comprises a polypeptide sequence of SEQ ID NO: 34, a polypeptide sequence of SEQ ID NO: 36, a polypeptide sequence of SEQ ID NO: 38 and a polypeptide sequence of SEQ ID NO: 40. In a further embodiment, the T cell activating bispecific antigen binding molecule comprises a polypeptide that is at least 95%, 96%, 97%, 98%, or 99% identical to the sequence of SEQ ID NO: 34, a polypeptide that is at least 95%, 96%, 97%, 98%, or 99% identical to the sequence of SEQ ID NO: 36, a polypeptide that is at least 95%, 96%, 97%, 98%, or 99% identical to the sequence of SEQ ID NO: 38, and a polypeptide that is at least 95%, 96%, 97%, 98%, or 99% identical to the sequence of SEQ ID NO: 41. In a further embodiment, the the T cell activating bispecific antigen binding molecule comprises a polypeptide sequence of SEQ ID NO: 34, a polypeptide sequence of SEQ ID NO: 36, a polypeptide sequence of SEQ ID NO: 38 and a polypeptide sequence of SEQ ID NO: 41. In yet another embodiment, the T cell activating bispecific antigen binding molecule comprises a polypeptide that is at least 95%, 96%, 97%, 98%, or 99% identical to the sequence of SEQ ID NO: 34, a polypeptide that is at least 95%, 96%, 97%, 98%, or 99% identical to the sequence of SEQ ID NO: 50, a polypeptide that is at least 95%, 96%, 97%, 98%, or 99% identical to the sequence of SEQ ID NO: 51, and a polypeptide that is at least 95%, 96%, 97%, 98%, or 99% identical to the sequence of SEQ ID NO: 52. In a further embodiment, the the T cell activating bispecific antigen binding molecule comprises a polypeptide sequence of SEQ ID NO: 34, a polypeptide sequence of SEQ ID NO: 50, a polypeptide sequence of SEQ ID NO: 51 and a polypeptide sequence of SEQ ID NO: 52.

CEA Antibodies

In one aspect the invention provides an antibody, particularly a humanized antibody, which specifically binds to CEA, wherein said antibody comprises a heavy chain variable region comprising the heavy chain complementarity determining region (CDR) 1 of SEQ ID NO: 14, the heavy chain CDR 2 of SEQ ID NO: 15, and the heavy chain CDR 3 of SEQ ID NO: 16, and a light chain variable region comprising the light chain CDR 1 of SEQ ID NO: 17, the light chain CDR 2 of SEQ ID NO: 18 and the light chain CDR 3 of SEQ ID NO: 19. In one embodiment, the antibody comprises a heavy chain variable region that is at least 95%, 96%, 97%, 98%, or 99% identical to the sequence of SEQ ID NO: 22, and a light chain variable region that is at least 95%, 96%, 97%, 98%, or 99% identical to the sequence of SEQ ID NO: 23. In a further embodiment, the antigen binding moiety, particularly Fab molecule, which specifically binds to CEA comprises the heavy chain variable region sequence of SEQ ID NO: 22, and the light chain variable region sequence of SEQ ID NO: 23. In one embodiment, the antibody is a Fab molecule.

Polynucleotides

The invention further provides isolated polynucleotides encoding a T cell activating bispecific antigen binding molecule as described herein or a fragment thereof. In some embodiments, said fragment is an antigen binding fragment.

The polynucleotides encoding T cell activating bispecific antigen binding molecules of the invention may be expressed as a single polynucleotide that encodes the entire T cell activating bispecific antigen binding molecule or as multiple (e.g., two or more) polynucleotides that are co-expressed. Polypeptides encoded by polynucleotides that are co-expressed may associate through, e.g., disulfide bonds or other means to form a functional T cell activating bispecific antigen binding molecule. For example, the light chain portion of a Fab molecule may be encoded by a separate polynucleotide from the portion of the T cell activating bispecific antigen binding molecule comprising the heavy chain portion of the Fab molecule, an Fc domain subunit and optionally (part of) another Fab molecule. When co-expressed, the heavy chain polypeptides will associate with the light chain polypeptides to form the Fab molecule. In another example, the portion of the T cell activating bispecific antigen binding molecule comprising one of the two Fc domain subunits and optionally (part of) one or more Fab molecules could be encoded by a separate polynucleotide from the portion of the T cell activating bispecific antigen binding molecule comprising the the other of the two Fc domain subunits and optionally (part of) a Fab molecule. When co-expressed, the Fc domain subunits will associate to form the Fc domain.

In some embodiments, the isolated polynucleotide encodes the entire T cell activating bispecific antigen binding molecule according to the invention as described herein. In other embodiments, the isolated polynucleotide encodes a polypeptides comprised in the T cell activating bispecific antigen binding molecule according to the invention as described herein.

In certain embodiments the polynucleotide or nucleic acid is DNA. In other embodiments, a polynucleotide of the present invention is RNA, for example, in the form of messenger RNA (mRNA). RNA of the present invention may be single stranded or double stranded.

Recombinant Methods

T cell activating bispecific antigen binding molecules of the invention may be obtained, for example, by solid-state peptide synthesis (e.g. Merrifield solid phase synthesis) or recombinant production. For recombinant production one or more polynucleotide encoding the T cell activating bispecific antigen binding molecule (fragment), e.g., as described above, is isolated and inserted into one or more vectors for further cloning and/or expression in a host cell. Such polynucleotide may be readily isolated and sequenced using conventional procedures. In one embodiment a vector, preferably an expression vector, comprising one or more of the polynucleotides of the invention is provided. Methods which are well known to those skilled in the art can be used to construct expression vectors containing the coding sequence of a T cell activating bispecific antigen binding molecule (fragment) along with appropriate transcriptional/translational control signals. These methods include in vitro recombinant DNA techniques, synthetic techniques and in vivo recombination/genetic recombination. See, for example, the techniques described in Maniatis et al., MOLECULAR CLONING: A LABORATORY MANUAL, Cold Spring Harbor Laboratory, N.Y. (1989); and Ausubel et al., CURRENT PROTOCOLS IN MOLECULAR BIOLOGY, Greene Publishing Associates and Wiley Interscience, N.Y (1989). The expression vector can be part of a plasmid, virus, or may be a nucleic acid fragment. The expression vector includes an expression cassette into which the polynucleotide encoding the T cell activating bispecific antigen binding molecule (fragment) (i.e. the coding region) is cloned in operable association with a promoter and/or other transcription or translation control elements. As used herein, a "coding region" is a portion of nucleic acid which consists of codons translated into amino acids. Although a "stop codon" (TAG, TGA, or TAA) is not translated into an amino acid, it may be considered to be part of a coding region, if present, but any flanking sequences, for example promoters, ribosome binding sites, transcriptional terminators, introns, 5' and 3' untranslated regions, and the like, are not part of a coding region. Two or more coding regions can be present in a single polynucleotide construct, e.g. on a single vector, or in separate polynucleotide constructs, e.g. on separate (different) vectors. Furthermore, any vector may contain a single coding region, or may comprise two or more coding regions, e.g. a vector of the present invention may encode one or more polypeptides, which are post- or co-translationally separated into the final proteins via proteolytic cleavage. In addition, a vector, polynucleotide, or nucleic acid of the invention may encode heterologous coding regions, either fused or unfused to a polynucleotide encoding the T cell activating bispecific antigen binding molecule (fragment) of the invention, or variant or derivative thereof. Heterologous coding regions include without limitation specialized elements or motifs, such as a secretory signal peptide or a heterologous functional domain. An operable association is when a coding region for a gene product, e.g. a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter may be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription. Suitable promoters and other transcription control regions are disclosed herein. A variety of transcription control regions are known to those skilled in the art. These include, without limitation, transcription control regions, which function in vertebrate cells, such as, but not limited to, promoter and enhancer segments from cytomegaloviruses (e.g. the immediate early promoter, in conjunction with intron-A), simian virus 40 (e.g. the early promoter), and retroviruses (such as, e.g. Rous sarcoma virus). Other transcription control regions include those derived from vertebrate genes such as actin, heat shock protein, bovine growth hormone and rabbit â-globin, as well as other sequences capable of controlling gene expression in eukaryotic cells. Additional suitable transcription control regions include tissue-specific promoters and enhancers as well as inducible promoters (e.g. promoters inducible tetracyclins). Similarly, a variety of translation control elements are known to those of ordinary skill in the art. These include, but are not limited to ribosome binding sites, translation initiation and termination codons, and elements derived from viral systems (particularly an internal ribosome entry site, or IRES, also referred to as a CITE sequence). The expression cassette may also include other features such as an origin of replication, and/or chromosome integration elements such as retroviral long terminal repeats (LTRs), or adeno-associated viral (AAV) inverted terminal repeats (ITRs).

Polynucleotide and nucleic acid coding regions of the present invention may be associated with additional coding regions which encode secretory or signal peptides, which direct the secretion of a polypeptide encoded by a polynucleotide of the present invention. For example, if secretion of the T cell activating bispecific antigen binding molecule is desired, DNA encoding a signal sequence may be placed upstream of the nucleic acid encoding a T cell activating bispecific antigen binding molecule of the invention or a fragment thereof. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the translated polypeptide to produce a secreted or "mature" form of the polypeptide. In certain embodiments, the native signal peptide, e.g. an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, may be used. For example, the wild-type leader sequence may be substituted with the leader sequence of human tissue plasminogen activator (TPA) or mouse β-glucuronidase.

DNA encoding a short protein sequence that could be used to facilitate later purification (e.g. a histidine tag) or assist in labeling the T cell activating bispecific antigen binding molecule may be included within or at the ends of the T cell activating bispecific antigen binding molecule (fragment) encoding polynucleotide.

In a further embodiment, a host cell comprising one or more polynucleotides of the invention is provided. In certain embodiments a host cell comprising one or more vectors of the invention is provided. The polynucleotides and vectors may incorporate any of the features, singly or in combination, described herein in relation to polynucleotides and vectors, respectively. In one such embodiment a host cell comprises (e.g. has been transformed or transfected with) a vector comprising a polynucleotide that encodes (part of) a T cell activating bispecific antigen binding molecule of the invention. As used herein, the term "host cell" refers to any kind of cellular system which can be engineered to generate the T cell activating bispecific antigen binding molecules of the invention or fragments thereof. Host cells suitable for replicating and for supporting expression of T cell activating bispecific antigen binding molecules are well known in the art. Such cells may be transfected or transduced as appropriate with the particular expression vector and large quantities of vector containing cells can be grown for seeding large scale fermenters to obtain sufficient quantities of the T cell activating bispecific antigen binding molecule for clinical applications. Suitable host cells include prokaryotic microorganisms, such as E. coli, or various eukaryotic cells, such as Chinese hamster ovary cells (CHO), insect cells, or the like. For example, polypeptides may be produced in bacteria in particular when glycosylation is not needed. After expression, the polypeptide may be isolated from the bacterial cell paste in a soluble fraction and can be further purified. In addition to prokaryotes, eukaryotic microbes such as filamentous fungi or yeast are suitable cloning or expression hosts for polypeptide-encoding vectors, including fungi and yeast strains whose glycosylation pathways have been "humanized", resulting in the production of a polypeptide with a partially or fully human glycosylation pattern. See Gerngross, Nat Biotech 22, 1409-1414 (2004), and Li et al., Nat Biotech 24, 210-215 (2006). Suitable host cells for the expression of (glycosylated) polypeptides are also derived from multicellular organisms (invertebrates and vertebrates). Examples of invertebrate cells include plant and insect cells. Numerous baculoviral strains have been identified which may be used in conjunction with insect cells, particularly for transfection of Spodoptera frugiperda cells. Plant cell cultures can also be utilized as hosts. See e.g. U.S. Pat. Nos. 5,959,177, 6,040,498, 6,420,548, 7,125,978, and 6,417,429 (describing PLANTIBODIES™ technology for producing antibodies in transgenic plants). Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293T cells as described, e.g., in Graham et al., J Gen Virol 36, 59 (1977)), baby hamster kidney cells (BHK), mouse sertoli cells (TM4 cells as described, e.g., in Mather, Biol Reprod 23, 243-251 (1980)), monkey kidney cells (CV1), African green monkey kidney cells (VERO-76), human cervical carcinoma cells (HELA), canine kidney cells (MDCK), buffalo rat liver cells (BRL 3A), human lung cells (W138), human liver cells (Hep G2), mouse mammary tumor cells (MMT 060562), TRI cells (as described, e.g., in Mather et al., Annals N.Y. Acad Sci 383, 44-68 (1982)), MRC 5 cells, and FS4 cells. Other useful mammalian host cell lines include Chinese hamster ovary (CHO) cells, including dhfr⁻ CHO cells (Urlaub et al., Proc Natl Acad Sci USA 77, 4216 (1980)); and myeloma cell lines such as YO, NSO, P3X63 and Sp2/0. For a review of certain mammalian host cell lines suitable for protein production, see, e.g., Yazaki and Wu, Methods in Molecular Biology, Vol. 248 (B.K.C. Lo, ed., Humana Press, Totowa, N.J.), pp. 255-268 (2003). Host cells include cultured cells, e.g., mammalian cultured cells, yeast cells, insect cells, bacterial cells and plant cells, to name only a few, but also cells comprised within a transgenic animal, transgenic plant or cultured plant or animal tissue. In one embodiment, the host cell is a eukaryotic cell, preferably a mammalian cell, such as a Chinese Hamster Ovary (CHO) cell, a human embryonic kidney (HEK) cell or a lymphoid cell (e.g., YO, NSO, Sp20 cell).

Standard technologies are known in the art to express foreign genes in these systems. Cells expressing a polypeptide comprising either the heavy or the light chain of an antigen binding domain such as an antibody, may be engineered so as to also express the other of the antibody chains such that the expressed product is an antibody that has both a heavy and a light chain.

In one embodiment, a method of producing a T cell activating bispecific antigen binding molecule according to the invention is provided, wherein the method comprises culturing a host cell comprising a polynucleotide encoding the T cell activating bispecific antigen binding molecule, as provided herein, under conditions suitable for expression of the T cell activating bispecific antigen binding molecule, and recovering the T cell activating bispecific antigen binding molecule from the host cell (or host cell culture medium).

The components of the T cell activating bispecific antigen binding molecule are genetically fused to each other. T cell activating bispecific antigen binding molecule can be designed such that its components are fused directly to each other or indirectly through a linker sequence. The composition and length of the linker may be determined in accordance with methods well known in the art and may be tested for efficacy. Examples of linker sequences between different components of T cell activating bispecific antigen binding molecules are found in the sequences provided herein. Additional sequences may also be included to incorporate a cleavage site to separate the individual components of the fusion if desired, for example an endopeptidase recognition sequence.

In certain embodiments the one or more antigen binding moieties of the T cell activating bispecific antigen binding molecules comprise at least an antibody variable region capable of binding an antigenic determinant. Variable regions can form part of and be derived from naturally or non-naturally occurring antibodies and fragments thereof. Methods to produce polyclonal antibodies and monoclonal antibodies are well known in the art (see e.g. Harlow and Lane, "Antibodies, a laboratory manual", Cold Spring Harbor Laboratory, 1988). Non-naturally occurring antibodies can be constructed using solid phase-peptide synthesis, can be produced recombinantly (e.g. as described in U.S. Pat. No. 4,186,567) or can be obtained, for example, by screening combinatorial libraries comprising variable heavy chains and variable light chains (see e.g. U.S. Pat. No. 5,969,108 to McCafferty).

Any animal species of antibody, antibody fragment, antigen binding domain or variable region can be used in the T cell activating bispecific antigen binding molecules of the invention. Non-limiting antibodies, antibody fragments, antigen binding domains or variable regions useful in the present invention can be of murine, primate, or human origin. If the T cell activating bispecific antigen binding molecule is intended for human use, a chimeric form of antibody may be used wherein the constant regions of the antibody are from a human. A humanized or fully human form of the antibody can also be prepared in accordance with methods well known in the art (see e. g. U.S. Pat. No. 5,565,332 to Winter). Humanization may be achieved by various methods including, but not limited to (a) grafting the non-human (e.g., donor antibody) CDRs onto human (e.g. recipient antibody) framework and constant regions with or without retention of critical framework residues (e.g. those that are important for retaining good antigen binding affinity or antibody functions), (b) grafting only the non-human specificity-determining regions (SDRs or a-CDRs; the residues critical for the antibody-antigen interaction) onto human framework and constant regions, or (c) transplanting the entire non-human variable domains, but "cloaking" them with a human-like section by replacement of surface residues. Humanized antibodies and methods of making them are reviewed, e.g., in Almagro and Fransson, Front Biosci 13, 1619-1633 (2008), and are further described, e.g., in Riechmann et al., Nature 332, 323-329 (1988); Queen et al., Proc Natl Acad Sci USA 86, 10029-10033 (1989); U.S. Pat. Nos. 5,821,337, 7,527,791, 6,982,321, and 7,087,409; Jones et al., Nature 321, 522-525 (1986); Morrison et al., Proc Natl Acad Sci 81, 6851-6855 (1984); Morrison and Oi, Adv Immunol 44, 65-92 (1988); Verhoeyen et al., Science 239, 1534-1536 (1988); Padlan, Molec Immun 31(3), 169-217 (1994); Kashmiri et al., Methods 36, 25-34 (2005) (describing SDR (a-CDR) grafting); Padlan, Mol Immunol 28, 489-498 (1991) (describing "resurfacing"); Dall'Acqua et al., Methods 36, 43-60 (2005) (describing "FR shuffling"); and Osbourn et al., Methods 36, 61-68 (2005) and Klimka et al., Br J Cancer 83, 252-260 (2000) (describing the "guided selection" approach to FR shuffling). Human antibodies and human variable regions can be produced using various techniques known in the art. Human antibodies are described generally in van Dijk and van de Winkel, Curr Opin Pharmacol 5, 368-74 (2001) and Lonberg, Curr Opin Immunol 20, 450-459 (2008). Human variable regions can form part of and be derived from human monoclonal antibodies made by the hybridoma method (see e.g. Monoclonal Antibody Production Techniques and Applications, pp. 51-63 (Marcel Dekker, Inc., New York, 1987)). Human antibodies and human variable regions may also be prepared by administering an immunogen to a transgenic animal that has been modified to produce intact human antibodies or intact antibodies with human variable regions in response to antigenic challenge (see e.g. Lonberg, Nat Biotech 23, 1117-1125 (2005). Human antibodies and human variable regions may also be generated by isolating Fv clone variable region sequences selected from human-derived phage display libraries (see e.g., Hoogenboom et al. in Methods in Molecular Biology 178, 1-37 (O'Brien et al., ed., Human Press, Totowa, N.J., 2001); and McCafferty et al., Nature 348, 552-554; Clackson et al., Nature 352, 624-628 (1991)). Phage typically display antibody fragments, either as single-chain Fv (scFv) fragments or as Fab fragments.

In certain embodiments, the antigen binding moieties useful in the present invention are engineered to have enhanced binding affinity according to, for example, the methods disclosed in U.S. Pat. Appl. Publ. No. 2004/0132066, the entire contents of which are hereby incorporated by reference. The ability of the T cell activating bispecific antigen binding molecule of the invention to bind to a specific antigenic determinant can be measured either through an enzyme-linked immunosorbent assay (ELISA) or other techniques familiar to one of skill in the art, e.g. surface plasmon resonance technique (analyzed on a BIACORE® T100 system) (Liljeblad, et al., Glyco J 17, 323-329 (2000)), and traditional binding assays (Heeley, Endocr Res 28, 217-229 (2002)). Competition assays may be used to identify an antibody, antibody fragment, antigen binding domain or variable domain that competes with a reference antibody for binding to a particular antigen, e.g. an antibody that competes with the V9 antibody for binding to CD3. In certain embodiments, such a competing antibody binds to the same epitope (e.g. a linear or a conformational epitope) that is bound by the reference antibody. Detailed exemplary methods for mapping an epitope to which an antibody binds are provided in Morris (1996) "Epitope Mapping Protocols," in Methods in Molecular Biology vol. 66 (Humana Press, Totowa, N.J.). In an exemplary competition assay, immobilized antigen (e.g. CD3) is incubated in a solution comprising a first labeled antibody that binds to the antigen (e.g. V9 antibody, described in U.S. Pat. No. 6,054,297) and a second unlabeled antibody that is being tested for its ability to compete with the first antibody for binding to the antigen. The second antibody may be present in a hybridoma supernatant. As a control, immobilized antigen is incubated in a solution comprising the first labeled antibody but not the second unlabeled antibody. After incubation under conditions permissive for binding of the first antibody to the antigen, excess unbound antibody is removed, and the amount of label associated with immobilized antigen is measured. If the amount of label associated with immobilized antigen is substantially reduced in the test sample relative to the control sample, then that indicates that the second antibody is competing with the first antibody for binding to the antigen. See Harlow and Lane (1988) Antibodies: A Laboratory Manual ch.14 (Cold Spring Harbor Laboratory, Cold Spring Harbor, N.Y.).

T cell activating bispecific antigen binding molecules prepared as described herein may be purified by art-known techniques such as high performance liquid chromatography, ion exchange chromatography, gel electrophoresis, affinity chromatography, size exclusion chromatography, and the like. The actual conditions used to purify a particular protein will depend, in part, on factors such as net charge, hydrophobicity, hydrophilicity etc., and will be apparent to those having skill in the art. For affinity chromatography purification an antibody, ligand, receptor or antigen can be used to which the T cell activating bispecific antigen binding molecule binds. For example, for affinity chromatography purification of T cell activating bispecific antigen binding molecules of the invention, a matrix with protein A or protein G may be used. Sequential Protein A or G affinity chromatography and size exclusion chromatography can be used to isolate a T cell activating bispecific antigen binding molecule essentially as described in the Examples. The purity of the T cell activating bispecific antigen binding molecule can be determined by any of a variety of well known analytical methods including gel electrophoresis, high pressure liquid chromatography, and the like. For example, the heavy chain fusion proteins expressed as described in the Examples were shown to be intact and properly assembled as demonstrated by reducing SDS-PAGE (see e.g. FIG. 4). Three bands were resolved at approximately Mr 25,000, Mr 50,000 and Mr 75,000, corresponding to the predicted molecular weights of the T cell activating bispecific antigen binding molecule light chain, heavy chain and heavy chain/light chain fusion protein.

Assays

T cell activating bispecific antigen binding molecules provided herein may be identified, screened for, or characterized for their physical/chemical properties and/or biological activities by various assays known in the art.

Affinity Assays

The affinity of the T cell activating bispecific antigen binding molecule for an Fc receptor or a target antigen can be determined in accordance with the methods set forth in the Examples by surface plasmon resonance (SPR), using standard instrumentation such as a BIACORE® instrument (GE Healthcare), and receptors or target proteins such as may be obtained by recombinant expression. Alternatively, binding of T cell activating bispecific antigen binding molecules for different receptors or target antigens may be evaluated using cell lines expressing the particular receptor or target antigen, for example by flow cytometry (FACS). A specific illustrative and exemplary embodiment for measuring binding affinity is described in the following and in the Examples below. According to one embodiment, $K_D$ is measured by surface plasmon resonance using a BIACORE® T100 machine (GE Healthcare) at 25° C.

To analyze the interaction between the Fc-portion and Fc receptors, His-tagged recombinant Fc-receptor is captured by an anti-Penta His antibody (Qiagen) immobilized on CM5 chips and the bispecific constructs are used as analytes. Briefly, carboxymethylated dextran biosensor chips (CM5, GE Healthcare) are activated with N-ethyl-N'-(3-dimethylaminopropyl)-carbodiimide hydrochloride (EDC) and N-hydroxysuccinimide (NHS) according to the supplier's instructions. Anti Penta-His antibody is diluted with 10 mM sodium acetate, pH 5.0, to 40 µg/ml before injection at a flow rate of 5 µl/min to achieve approximately 6500 response units (RU) of coupled protein. Following the injection of the ligand, 1 M ethanolamine is injected to block unreacted groups. Subsequently the Fc-receptor is captured for 60 s at 4 or 10 nM. For kinetic measurements, four-fold serial dilutions of the bispecific construct (range between 500 nM and 4000 nM) are injected in HBS-EP (GE Healthcare, 10 mM HEPES, 150 mM NaCl, 3 mM EDTA, 0.05% Surfactant P20, pH 7.4) at 25° C. at a flow rate of 30 µl/min for 120 s.

To determine the affinity to the target antigen, bispecific constructs are captured by an anti human Fab specific antibody (GE Healthcare) that is immobilized on an activated CM5-sensor chip surface as described for the anti Penta-His antibody. The final amount of coupled protein is is approximately 12000 R U. The bispecific constructs are captured for 90 s at 300 nM. The target antigens are passed through the flow cells for 180 s at a concentration range from 250 to 1000 nM with a flowrate of 30 µl/min. The dissociation is monitored for 180 s.

Bulk refractive index differences are corrected for by subtracting the response obtained on reference flow cell. The steady state response was used to derive the dissociation constant $K_D$ by non-linear curve fitting of the Langmuir binding isotherm. Association rates ($k_{on}$) and dissociation rates ($k_{off}$) are calculated using a simple one-to-one Langmuir binding model (BIACORE® T100 Evaluation Software version 1.1.1) by simultaneously fitting the association and dissociation sensorgrams. The equilibrium dissociation constant ($K_D$) is calculated as the ratio $k_{off}/k_{on}$. See, e.g., Chen et al., J Mol Biol 293, 865-881 (1999).

Activity Assays

Biological activity of the T cell activating bispecific antigen binding molecules of the invention can be measured by various assays as described in the Examples. Biological activities may for example include the induction of proliferation of T cells, the induction of signaling in T cells, the induction of expression of activation markers in T cells, the induction of cytokine secretion by T cells, the induction of lysis of target cells such as tumor cells, and the induction of tumor regression and/or the improvement of survival.

Compositions, Formulations, and Routes of Administration

In a further aspect, the invention provides pharmaceutical compositions comprising any of the T cell activating bispecific antigen binding molecules provided herein, e.g., for use in any of the below therapeutic methods. In one embodiment, a pharmaceutical composition comprises any of the T cell activating bispecific antigen binding molecules provided herein and a pharmaceutically acceptable carrier. In another embodiment, a pharmaceutical composition comprises any of the T cell activating bispecific antigen binding molecules provided herein and at least one additional therapeutic agent, e.g., as described below.

Further provided is a method of producing a T cell activating bispecific antigen binding molecule of the invention in a form suitable for administration in vivo, the method comprising (a) obtaining a T cell activating bispecific antigen binding molecule according to the invention, and (b) formulating the T cell activating bispecific antigen binding molecule with at least one pharmaceutically acceptable carrier, whereby a preparation of T cell activating bispecific antigen binding molecule is formulated for administration in vivo.

Pharmaceutical compositions of the present invention comprise a therapeutically effective amount of one or more T cell activating bispecific antigen binding molecule dissolved or dispersed in a pharmaceutically acceptable carrier. The phrases "pharmaceutical or pharmacologically acceptable" refers to molecular entities and compositions that are generally non-toxic to recipients at the dosages and concentrations employed, i.e. do not produce an adverse, allergic or other untoward reaction when administered to an animal, such as, for example, a human, as appropriate. The preparation of a pharmaceutical composition that contains at least one T cell activating bispecific antigen binding molecule and optionally an additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards or corresponding authorities in other countries. Preferred compositions are lyophilized formulations or aqueous solutions. As used herein, "pharmaceutically acceptable carrier" includes any and all solvents, buffers, dispersion media, coatings, surfactants, antioxidants, preservatives (e.g. antibacterial agents, antifungal agents), isotonic agents, absorption delaying agents, salts, preservatives, antioxidants, proteins, drugs, drug stabilizers, polymers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

The composition may comprise different types of carriers depending on whether it is to be administered in solid, liquid or aerosol form, and whether it need to be sterile for such routes of administration as injection. T cell activating bispecific antigen binding molecules of the present invention (and any additional therapeutic agent) can be administered intravenously, intradermally, intraarterially, intraperitoneally, intralesionally, intracranially, intraarticularly, intraprostatically, intrasplenically, intrarenally, intrapleurally, intratracheally, intranasally, intravitreally, intravaginally, intrarectally, intratumorally, intramuscularly, intraperitoneally, subcutaneously, subconjunctivally, intravesicularlly, mucosally, intrapericardially, intraumbilically, intraocularally, orally, topically, locally, by inhalation (e.g. aerosol inhalation), injection, infusion, continuous infusion, localized perfusion bathing target cells directly, via a catheter, via a lavage, in cremes, in lipid compositions (e.g. liposomes), or by other method or any combination of the forgoing as would be known to one of ordinary skill in the art (see, for example, Remington's Pharmaceutical Sciences, 18th Ed. Mack Printing Company, 1990, incorporated herein by reference). Parenteral administration, in particular intravenous injection, is most commonly used for administering polypeptide molecules such as the T cell activating bispecific antigen binding molecules of the invention.

Parenteral compositions include those designed for administration by injection, e.g. subcutaneous, intradermal, intralesional, intravenous, intraarterial intramuscular, intrathecal or intraperitoneal injection. For injection, the T cell activating bispecific antigen binding molecules of the invention may be formulated in aqueous solutions, preferably in physiologically compatible buffers such as Hanks' solution, Ringer's solution, or physiological saline buffer. The solution may contain formulatory agents such as suspending, stabilizing and/or dispersing agents. Alternatively, the T cell activating bispecific antigen binding molecules may be in powder form for constitution with a suitable vehicle, e.g., sterile pyrogen-free water, before use. Sterile injectable solutions are prepared by incorporating the T cell activating bispecific antigen binding molecules of the invention in the required amount in the appropriate solvent with various of the other ingredients enumerated below, as required. Sterility may be readily accomplished, e.g., by filtration through sterile filtration membranes. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein. Suitable pharmaceutically acceptable carriers include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Aqueous injection suspensions may contain compounds which increase the viscosity of the suspension, such as sodium carboxymethyl cellulose, sorbitol, dextran, or the like. Optionally, the suspension may also contain suitable stabilizers or agents which increase the solubility of the compounds to allow for the preparation of highly concentrated solutions. Additionally, suspensions of the active compounds may be prepared as appropriate oily injection suspensions. Suitable lipophilic solvents or vehicles include fatty oils such as sesame oil, or synthetic fatty acid esters, such as ethyl cleats or triglycerides, or liposomes.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences (18th Ed. Mack Printing Company, 1990). Sustained-release preparations may be prepared. Suitable examples of sustained-release preparations include semipermeable matrices of solid hydrophobic polymers containing the polypeptide, which matrices are in the form of shaped articles, e.g. films, or microcapsules. In particular embodiments, prolonged absorption of an injectable composition can be brought about by the use in the compositions of agents delaying absorption, such as, for example, aluminum monostearate, gelatin or combinations thereof.

In addition to the compositions described previously, the T cell activating bispecific antigen binding molecules may also be formulated as a depot preparation. Such long acting formulations may be administered by implantation (for example subcutaneously or intramuscularly) or by intramuscular injection. Thus, for example, the T cell activating bispecific antigen binding molecules may be formulated with suitable polymeric or hydrophobic materials (for example as an emulsion in an acceptable oil) or ion exchange resins, or as sparingly soluble derivatives, for example, as a sparingly soluble salt.

Pharmaceutical compositions comprising the T cell activating bispecific antigen binding molecules of the invention may be manufactured by means of conventional mixing, dissolving, emulsifying, encapsulating, entrapping or lyophilizing processes. Pharmaceutical compositions may be formulated in conventional manner using one or more physiologically acceptable carriers, diluents, excipients or auxiliaries which facilitate processing of the proteins into preparations that can be used pharmaceutically. Proper formulation is dependent upon the route of administration chosen.

The T cell activating bispecific antigen binding molecules may be formulated into a composition in a free acid or base, neutral or salt form. Pharmaceutically acceptable salts are salts that substantially retain the biological activity of the free acid or base. These include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Pharmaceutical salts tend to be more soluble in aqueous and other protic solvents than are the corresponding free base forms.

Therapeutic Methods and Compositions

Any of the T cell activating bispecific antigen binding molecules provided herein may be used in therapeutic methods. T cell activating bispecific antigen binding molecules of the invention can be used as immunotherapeutic agents, for example in the treatment of cancers.

For use in therapeutic methods, T cell activating bispecific antigen binding molecules of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

In one aspect, T cell activating bispecific antigen binding molecules of the invention for use as a medicament are provided. In further aspects, T cell activating bispecific antigen binding molecules of the invention for use in treating a disease are provided. In certain embodiments, T cell activating bispecific antigen binding molecules of the invention for use in a method of treatment are provided.

In one embodiment, the invention provides a T cell activating bispecific antigen binding molecule as described herein for use in the treatment of a disease in an individual in need thereof. In certain embodiments, the invention provides a T cell activating bispecific antigen binding molecule for use in a method of treating an individual having a disease comprising administering to the individual a therapeutically effective amount of the T cell activating bispecific antigen binding molecule. In certain embodiments the disease to be treated is a proliferative disorder. In a particular embodiment the disease is cancer. In certain embodiments the method further comprises administering to the individual a therapeutically effective amount of at least one additional therapeutic agent, e.g., an anti-cancer agent if the disease to be treated is cancer. In further embodiments, the invention provides a T cell activating bispecific antigen binding molecule as described herein for use in inducing lysis of a target cell, particularly a tumor cell. In certain embodiments, the invention provides a T cell activating bispecific antigen binding molecule for use in a method of inducing lysis of a target cell, particularly a tumor cell, in an individual comprising administering to the individual an effective amount of the T cell activating bispecific antigen binding molecule to induce lysis of a target cell. An "individual" according to any of the above embodiments is a mammal, preferably a human.

In a further aspect, the invention provides for the use of a T cell activating bispecific antigen binding molecule of the invention in the manufacture or preparation of a medicament. In one embodiment the medicament is for the treatment of a disease in an individual in need thereof. In a further embodiment, the medicament is for use in a method of treating a disease comprising administering to an individual having the disease a therapeutically effective amount of the medicament. In certain embodiments the disease to be treated is a proliferative disorder. In a particular embodiment the disease is cancer. In one embodiment, the method further comprises administering to the individual a therapeutically effective amount of at least one additional therapeutic agent, e.g., an anti-cancer agent if the disease to be treated is cancer. In a further embodiment, the medicament is for inducing lysis of a target cell, particularly a tumor cell. In still a further embodiment, the medicament is for use in a method of inducing lysis of a target cell, particularly a tumor cell, in an individual comprising administering to the individual an effective amount of the medicament to induce lysis of a target cell. An "individual" according to any of the above embodiments may be a mammal, preferably a human.

In a further aspect, the invention provides a method for treating a disease. In one embodiment, the method comprises administering to an individual having such disease a therapeutically effective amount of a T cell activating bispecific antigen binding molecule of the invention. In one embodiment a composition is administered to said individual, comprising the T cell activating bispecific antigen binding molecule of the invention in a pharmaceutically acceptable form. In certain embodiments the disease to be treated is a proliferative disorder. In a particular embodiment the disease is cancer. In certain embodiments the method further comprises administering to the individual a therapeutically effective amount of at least one additional therapeutic agent, e.g., an anti-cancer agent if the disease to be treated is cancer. An "individual" according to any of the above embodiments may be a mammal, preferably a human.

In a further aspect, the invention provides a method for inducing lysis of a target cell, particularly a tumor cell. In one embodiment the method comprises contacting a target cell with a T cell activating bispecific antigen binding molecule of the invention in the presence of a T cell, particularly a cytotoxic T cell. In a further aspect, a method for inducing lysis of a target cell, particularly a tumor cell, in an individual is provided. In one such embodiment, the method comprises administering to the individual an effective amount of a T cell activating bispecific antigen binding molecule to induce lysis of a target cell. In one embodiment, an "individual" is a human.

In certain embodiments the disease to be treated is a proliferative disorder, particularly cancer. Non-limiting examples of cancers include bladder cancer, brain cancer, head and neck cancer, pancreatic cancer, lung cancer, breast cancer, ovarian cancer, uterine cancer, cervical cancer, endometrial cancer, esophageal cancer, colon cancer, colorectal cancer, rectal cancer, gastric cancer, prostate cancer, blood cancer, skin cancer, squamous cell carcinoma, bone cancer, and kidney cancer. Other cell proliferation disorders that can be treated using a T cell activating bispecific antigen binding molecule of the present invention include, but are not limited to neoplasms located in the: abdomen, bone, breast, digestive system, liver, pancreas, peritoneum, endocrine glands (adrenal, parathyroid, pituitary, testicles, ovary, thymus, thyroid), eye, head and neck, nervous system (central and peripheral), lymphatic system, pelvic, skin, soft tissue, spleen, thoracic region, and urogenital system. Also included are pre-cancerous conditions or lesions and cancer metastases. In certain embodiments the cancer is chosen from the group consisting of renal cell cancer, skin cancer, lung cancer, colorectal cancer, breast cancer, brain cancer, head and neck cancer, gastric cancer, pancreatic cancer, ovarian cancer. In one embodiment, the cancer is a solid tumor. A skilled artisan readily recognizes that in many cases the T cell activating bispecific antigen binding molecule may not provide a cure but may only provide partial benefit. In some embodiments, a physiological change having some benefit is also considered therapeutically beneficial. Thus, in some embodiments, an amount of T cell activating bispecific antigen binding molecule that provides a physiological change is considered an "effective amount" or a "therapeutically effective amount". The subject, patient, or individual in need of treatment is typically a mammal, more specifically a human.

In some embodiments, an effective amount of a T cell activating bispecific antigen binding molecule of the invention is administered to a cell. In other embodiments, a therapeutically effective amount of a T cell activating bispecific antigen binding molecule of the invention is administered to an individual for the treatment of disease.

For the prevention or treatment of disease, the appropriate dosage of a T cell activating bispecific antigen binding molecule of the invention (when used alone or in combination with one or more other additional therapeutic agents) will depend on the type of disease to be treated, the route of administration, the body weight of the patient, the type of T cell activating bispecific antigen binding molecule, the severity and course of the disease, whether the T cell activating bispecific antigen binding molecule is administered for preventive or therapeutic purposes, previous or concurrent therapeutic interventions, the patient's clinical history and response to the T cell activating bispecific antigen binding molecule, and the discretion of the attending physician. The practitioner responsible for administration will, in any event, determine the concentration of active ingredient(s) in a composition and appropriate dose(s) for the individual subject. Various dosing schedules including but not limited to single or multiple administrations over various time-points, bolus administration, and pulse infusion are contemplated herein.

The T cell activating bispecific antigen binding molecule is suitably administered to the patient at one time or over a series of treatments. Depending on the type and severity of the disease, about 1 µg/kg to 15 mg/kg (e.g. 0.1 mg/kg-10 mg/kg) of T cell activating bispecific antigen binding molecule can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the T cell activating bispecific antigen binding molecule would be in the range from about 0.005 mg/kg to about 10 mg/kg. In other non-limiting examples, a dose may also comprise from about 1 microgram/kg body weight, about 5 microgram/kg body weight, about 10 microgram/kg body weight, about 50 microgram/kg body weight, about 100 microgram/kg body weight, about 200 microgram/kg body weight, about 350 microgram/kg body weight, about 500 microgram/kg body weight, about 1 milligram/kg body weight, about 5 milligram/kg body weight, about 10 milligram/kg body weight, about 50 milligram/kg body weight, about 100 milligram/kg body weight, about 200 milligram/kg body weight, about 350 milligram/kg body weight, about 500 milligram/kg body weight, to about 1000 mg/kg body weight or more per administration, and any range derivable therein. In non-limiting examples of a derivable range from the numbers listed herein, a range of about 5 mg/kg body weight to about 100 mg/kg body weight, about 5 microgram/kg body weight to about 500 milligram/kg body weight, etc., can be administered, based on the numbers described above. Thus, one or more doses of about 0.5 mg/kg, 2.0 mg/kg, 5.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the T cell activating bispecific antigen binding molecule). An initial higher loading dose, followed by one or more lower doses may be administered. However, other dosage regimens may be useful. The progress of this therapy is easily monitored by conventional techniques and assays.

The T cell activating bispecific antigen binding molecules of the invention will generally be used in an amount effective to achieve the intended purpose. For use to treat or prevent a disease condition, the T cell activating bispecific antigen binding molecules of the invention, or pharmaceutical compositions thereof, are administered or applied in a therapeutically effective amount. Determination of a therapeutically effective amount is well within the capabilities of those skilled in the art, especially in light of the detailed disclosure provided herein.

For systemic administration, a therapeutically effective dose can be estimated initially from in vitro assays, such as cell culture assays. A dose can then be formulated in animal models to achieve a circulating concentration range that includes the $IC_{50}$ as determined in cell culture. Such information can be used to more accurately determine useful doses in humans.

Initial dosages can also be estimated from in vivo data, e.g., animal models, using techniques that are well known in the art. One having ordinary skill in the art could readily optimize administration to humans based on animal data.

Dosage amount and interval may be adjusted individually to provide plasma levels of the T cell activating bispecific antigen binding molecules which are sufficient to maintain therapeutic effect. Usual patient dosages for administration by injection range from about 0.1 to 50 mg/kg/day, typically from about 0.5 to 1 mg/kg/day. Therapeutically effective plasma levels may be achieved by administering multiple doses each day. Levels in plasma may be measured, for example, by HPLC.

In cases of local administration or selective uptake, the effective local concentration of the T cell activating bispecific antigen binding molecules may not be related to plasma concentration. One having skill in the art will be able to optimize therapeutically effective local dosages without undue experimentation.

A therapeutically effective dose of the T cell activating bispecific antigen binding molecules described herein will generally provide therapeutic benefit without causing substantial toxicity. Toxicity and therapeutic efficacy of a T cell activating bispecific antigen binding molecule can be determined by standard pharmaceutical procedures in cell culture or experimental animals. Cell culture assays and animal studies can be used to determine the $LD_{50}$ (the dose lethal to 50% of a population) and the $ED_{50}$ (the dose therapeutically effective in 50% of a population). The dose ratio between toxic and therapeutic effects is the therapeutic index, which can be expressed as the ratio $LD_{50}/ED_{50}$. T cell activating bispecific antigen binding molecules that exhibit large therapeutic indices are preferred. In one embodiment, the T cell activating bispecific antigen binding molecule according to the present invention exhibits a high therapeutic index. The data obtained from cell culture assays and animal studies can be used in formulating a range of dosages suitable for use in humans. The dosage lies preferably within a range of circulating concentrations that include the $ED_{50}$ with little or no toxicity. The dosage may vary within this range depending upon a variety of factors, e.g., the dosage form employed, the route of administration utilized, the condition of the subject, and the like. The exact formulation, route of administration and dosage can be chosen by the individual physician in view of the patient's condition (see, e.g., Fingl et al., 1975, in: The Pharmacological Basis of Therapeutics, Ch. 1, p. 1, incorporated herein by reference in its entirety).

The attending physician for patients treated with T cell activating bispecific antigen binding molecules of the invention would know how and when to terminate, interrupt, or adjust administration due to toxicity, organ dysfunction, and the like. Conversely, the attending physician would also know to adjust treatment to higher levels if the clinical response were not adequate (precluding toxicity). The magnitude of an administered dose in the management of the disorder of interest will vary with the severity of the condition to be treated, with the route of administration, and the like. The severity of the condition may, for example, be evaluated, in part, by standard prognostic evaluation methods. Further, the dose and perhaps dose frequency will also vary according to the age, body weight, and response of the individual patient.

Other Agents and Treatments

The T cell activating bispecific antigen binding molecules of the invention may be administered in combination with one or more other agents in therapy. For instance, a T cell activating bispecific antigen binding molecule of the invention may be co-administered with at least one additional therapeutic agent. The term "therapeutic agent" encompasses any agent administered to treat a symptom or disease in an individual in need of such treatment. Such additional therapeutic agent may comprise any active ingredients suitable for the particular indication being treated, preferably those with complementary activities that do not adversely affect each other. In certain embodiments, an additional therapeutic agent is an immunomodulatory agent, a cytostatic agent, an inhibitor of cell adhesion, a cytotoxic agent, an activator of cell apoptosis, or an agent that increases the sensitivity of cells to apoptotic inducers. In a particular embodiment, the additional therapeutic agent is an anticancer agent, for example a microtubule disruptor, an antimetabolite, a topoisomerase inhibitor, a DNA intercalator, an alkylating agent, a hormonal therapy, a kinase inhibitor, a receptor antagonist, an activator of tumor cell apoptosis, or an antiangiogenic agent.

Such other agents are suitably present in combination in amounts that are effective for the purpose intended. The effective amount of such other agents depends on the amount of T cell activating bispecific antigen binding molecule used, the type of disorder or treatment, and other factors discussed above. The T cell activating bispecific antigen binding molecules are generally used in the same dosages and with administration routes as described herein, or about from 1 to 99% of the dosages described herein, or in any dosage and by any route that is empirically/clinically determined to be appropriate.

Such combination therapies noted above encompass combined administration (where two or more therapeutic agents are included in the same or separate compositions), and separate administration, in which case, administration of the T cell activating bispecific antigen binding molecule of the invention can occur prior to, simultaneously, and/or following, administration of the additional therapeutic agent and/or adjuvant. T cell activating bispecific antigen binding molecules of the invention can also be used in combination with radiation therapy.

Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is a T cell activating bispecific antigen binding molecule of the invention. The label or package insert indicates that the composition is used for treating the condition of choice. Moreover, the article of manufacture may comprise (a) a first container with a composition contained therein, wherein the composition comprises a T cell activating bispecific antigen binding molecule of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

EXAMPLES

The following are examples of methods and compositions of the invention. It is understood that various other embodiments may be practiced, given the general description provided above.
General Methods
Recombinant DNA Techniques Standard methods were used to manipulate DNA as described in Sambrook et al., Molecular cloning: A laboratory manual; Cold Spring Harbor Laboratory Press, Cold Spring Harbor, N.Y., 1989. The molecular biological reagents were used according to the manufacturers' instructions. General information regarding the nucleotide sequences of human immunoglobulins light and heavy chains is given in: Kabat, E. A. et al., (1991) Sequences of Proteins of Immunological Interest, 5$^{th}$ ed., NIH Publication No. 91-3242.
DNA Sequencing DNA sequences were determined by double strand sequencing.
Gene Synthesis Desired gene segments where required were either generated by PCR using appropriate templates or were synthesized by Geneart AG (Regensburg, Germany) from synthetic oligonucleotides and PCR products by automated gene synthesis. In cases where no exact gene sequence was available, oligonucleotide primers were designed based on sequences from closest homologues and the genes were isolated by RT-PCR from RNA originating from the appropriate tissue. The gene segments flanked by singular restriction endonuclease cleavage sites were cloned into standard cloning/sequencing vectors. The plasmid DNA was purified from transformed bacteria and concentration determined by UV spectroscopy. The DNA sequence of the subcloned gene fragments was confirmed by DNA sequencing. Gene segments were designed with suitable restriction sites to allow sub-cloning into the respective expression vectors. All constructs were designed with a 5'-end DNA sequence coding for a leader peptide which targets proteins for secretion in eukaryotic cells.

Example 1

Binding of Different Humanized Variants of T84.66 IgG to Cells

Novel humanized variants of the murine antibody T84.66 (Wagener et al., J Immunol 130, 2308 (1983), Neumaier et al., J Immunol 135, 3604 (1985)) were developed by grafting of the CDRs onto human germline framework acceptor sequences.

In this example, the binding of different humanized variants of T84.66 IgG was tested on CEA-expressing human gastric adenocarcinoma cells (MKN45, DSMZ ACC 409).

Briefly, cells were harvested, counted, checked for viability and re-suspended at $2\times10^6$ cells/ml in FACS buffer (100 µl PBS 0.1% BSA). 100 µl of cell suspension (containing $0.2\times10^6$ cells) were incubated in round-bottom 96-well plate for 30 min at 4° C. with increasing concentrations of the CEA IgG (4 ng/ml-60 µg/ml), washed twice with cold PBS 0.1% BSA, re-incubated for further 30 min at 4° C. with the PE-conjugated AffiniPure F(ab')2 Fragment goat anti-human IgG Fcg Fragment Specific secondary antibody (Jackson Immuno Research Lab PE #109-116-170), washed twice with cold PBS 0.1% BSA and immediately analyzed by FACS using a FACS Cantoll (Software FACS Diva). Binding curves and EC50 values were obtained and calculated using GraphPadPrism5 (FIG. 2, binding to MKN45 cells).

Figure 2:
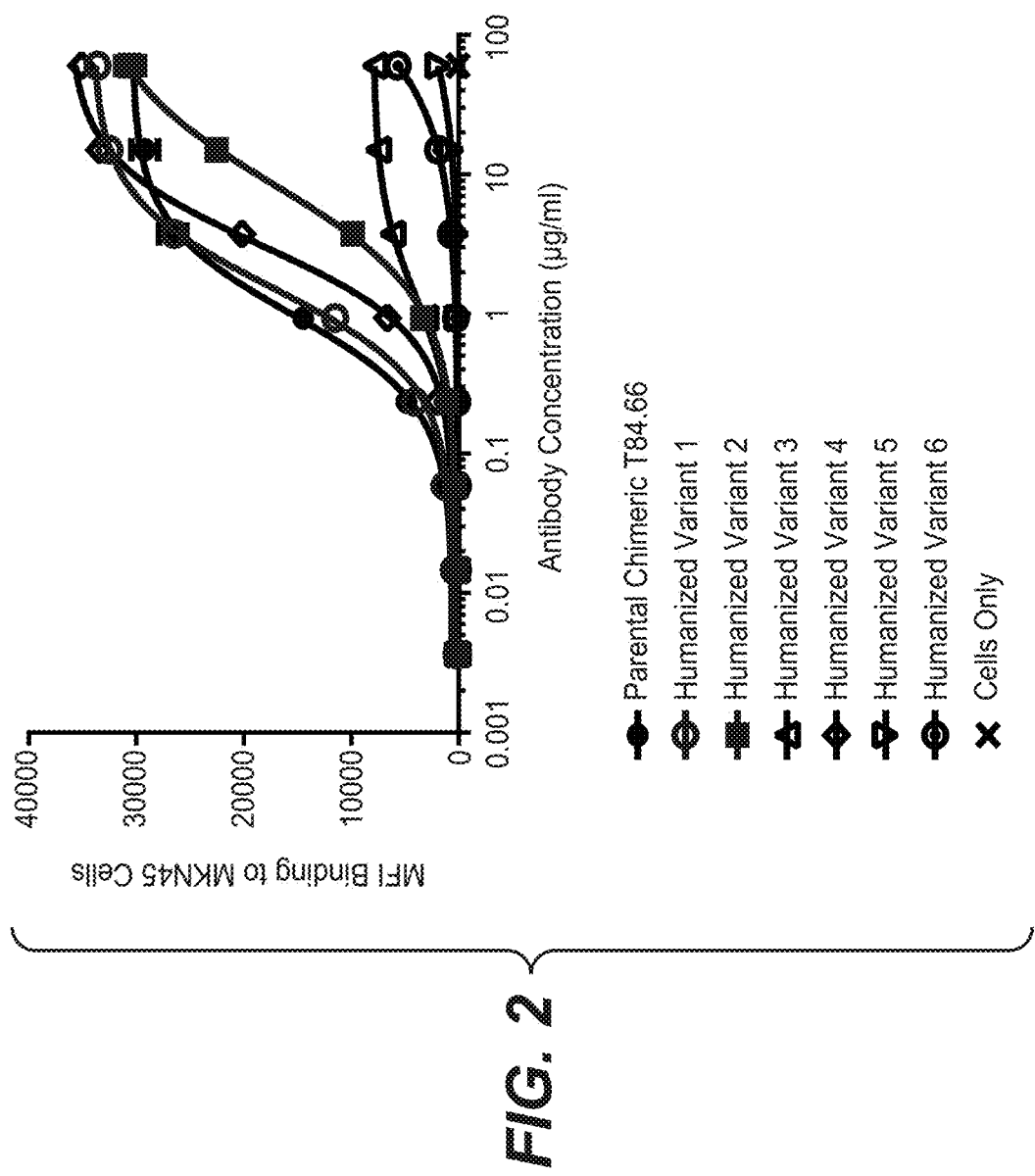
FIG. 2. Binding of different humanized variants of T84.66 IgGs to cells. EC50 values, based on binding curves, were calculated by Graph Pad Prism and are presented in Table 1.

FIG. 2 shows the different binding pattern of selected humanized variants of the T84.66 IgG to human CEA, expressed on MKN45 cells. Based on the binding pattern and the calculated EC50 binding values (Table 1), the humanized variant 1 (SEQ ID NOs 22 and 23) was selected for further evaluation.

TABLE 1

Binding of different humanized variants of T84.66 IgGs to cells (EC50 values, based on binding curves shown in FIG. 2, calculated by Graph Pad Prism).

|  | EC50 (µg/ml) |
| --- | --- |
| Parental chimeric T84.66 | 0.99 |
| Humanized variant 1 | 1.5 |
| Humanized variant 2 | 8.6 |
| Humanized variant 3 | 1.4 |
| Humanized variant 4 | 3.1 |
| Humanized variant 5 | — |
| Humanized variant 6 | — |

Example 2

Preparation of Anti-CEA/Anti-CD3 T Cell Bispecific (TCB) Molecules

The following molecules were prepared in this example; schematic illustrations thereof are shown in FIG. 3:
    A. "2+1 IgG CrossFab, inverted" with charge modifications (VH/VL exchange in CD3 binder, charge modification in CEA binder, parental murine CEA binder (T84.66)) (FIG. 3A, SEQ ID NOs 32-35)
    B. "2+1 IgG CrossFab, inverted" with charge modifications (VH/VL exchange in CD3 binder, charge modification in CEA binder, humanized CEA binder) (FIG. 3B, SEQ ID NOs 34, 36-38)

Figures 3A, 3B:
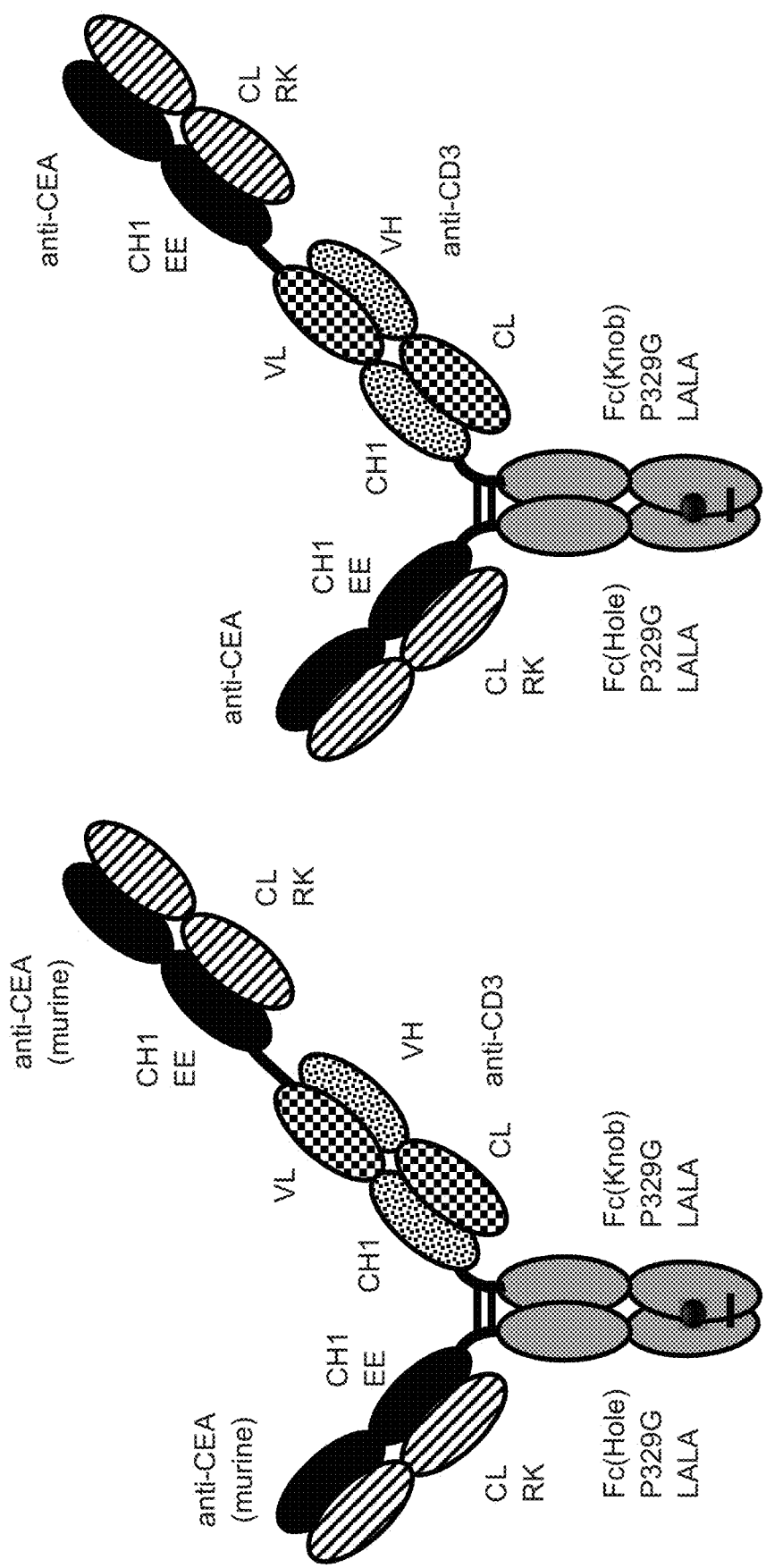
FIGS. 3A-F. Illustration of the TCBs prepared in the Examples. (A, B) Illustration of "2+1 IgG CrossFab, inverted" anti-CEA/anti-CD3 TCB molecules with charge modifications (VH/VL exchange in CD3 binder, charge modification in CEA binder, molecule A and B). (C) Illustration of "1+1 IgG CrossFab, inverted" anti-CEA/anti-CD3 TCB molecule with charge modifications (VH/VL exchange in CD3 binder, charge modification in CEA binder, molecule C). (D) Illustration of "1+1 IgG CrossMab" anti-CEA/anti-CD3 TCB molecule with charge modifications (VH/VL exchange in CD3 binder, charge modification in CEA binder, molecule D). (E) Illustration of "2+1 IgG CrossFab, inverted" anti-CEA/anti-CD3 TCB molecule with charge modifications and longer linker (VH/VL exchange in CD3 binder, charge modification in CEA binder, molecule E). (F) Illustration of "2+1 IgG CrossFab, inverted" anti-CEA/anti-CD3 TCB molecule without charge modifications (VH/VL exchange in CD3 binder, molecule F). EE=147E, 213E; RK=123R, 124K.
Figure 3D:
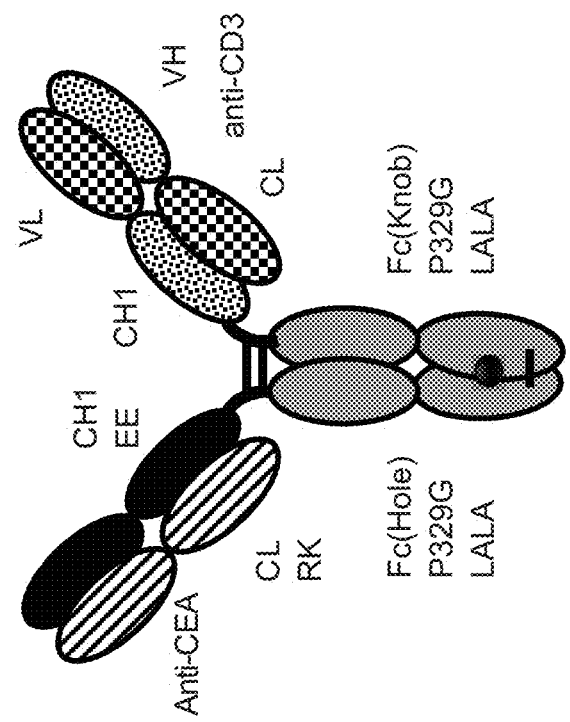
Figure 3C:
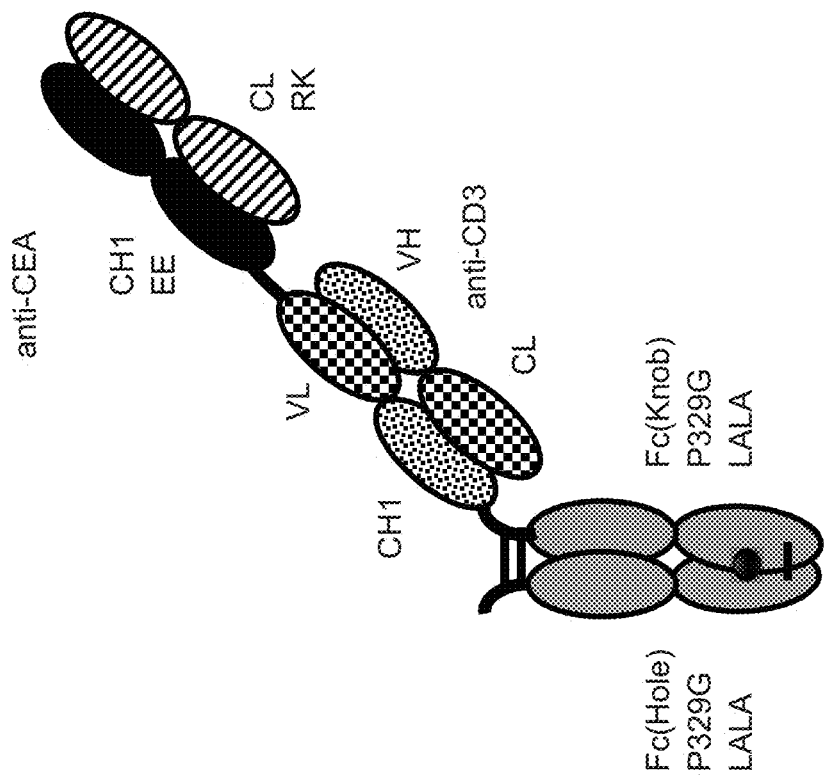

C. "1+1 IgG CrossFab, inverted" with charge modifications (VH/VL exchange in CD3 binder, charge modification in CEA binder, humanized CEA binder) (FIG. 3C, SEQ ID NOs 34, 37-39)

D. "1+1 IgG CrossMab" with charge modifications (VH/VL exchange in CD3 binder, charge modification in CEA binder, humanized CEA binder) (FIG. 3D, SEQ ID NOs 34, 36, 38, 40)

Figure 3F:
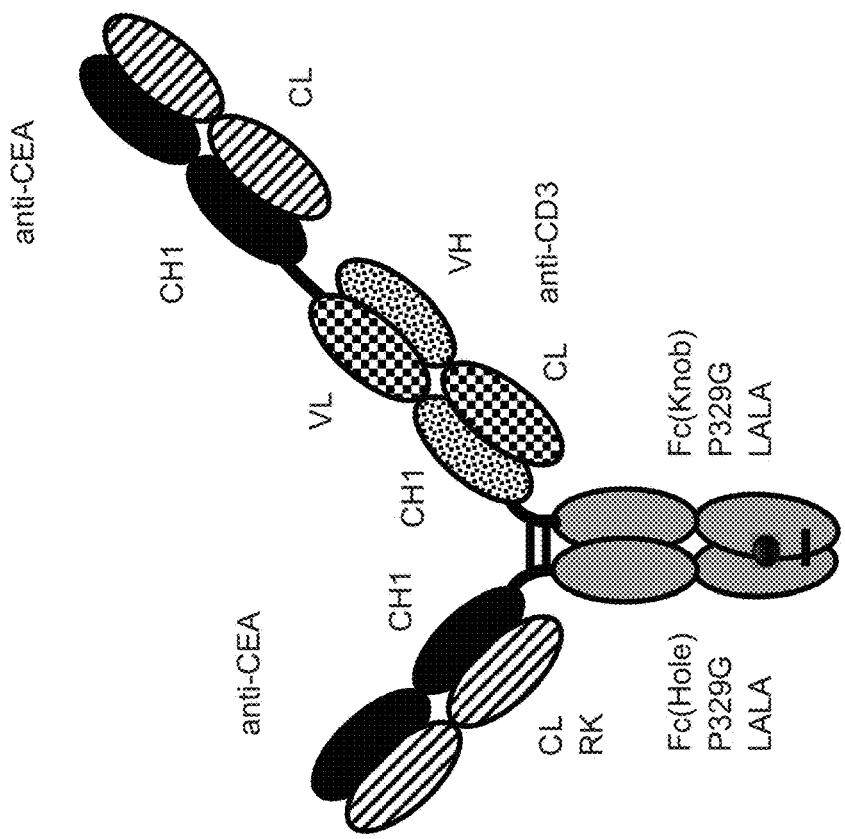
Figure 3E:
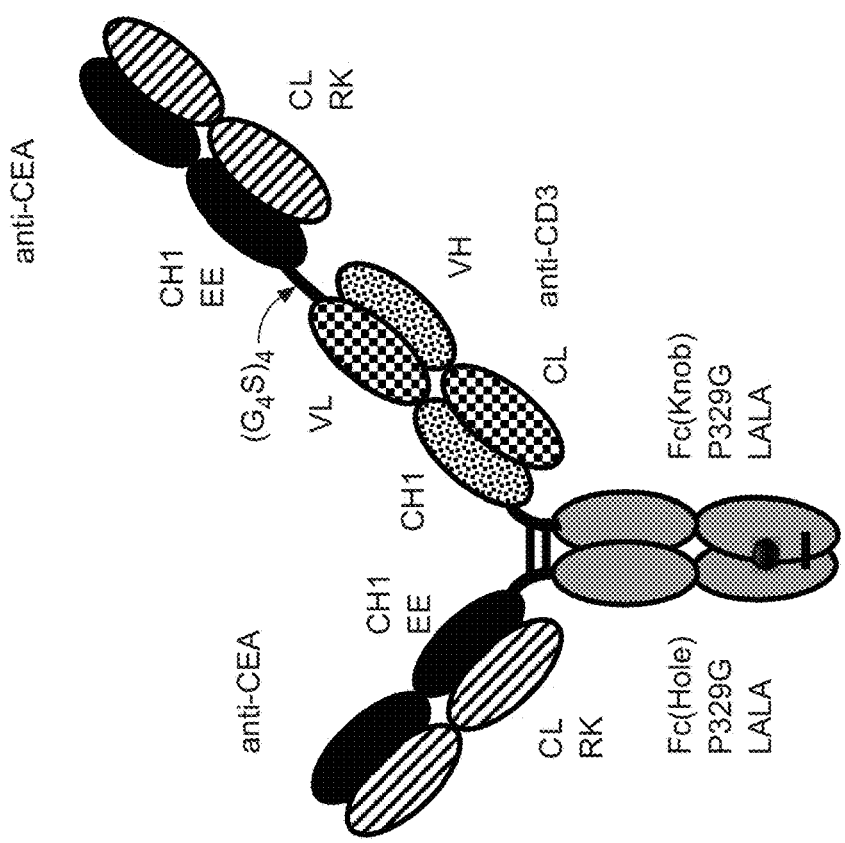
Figure 4B:
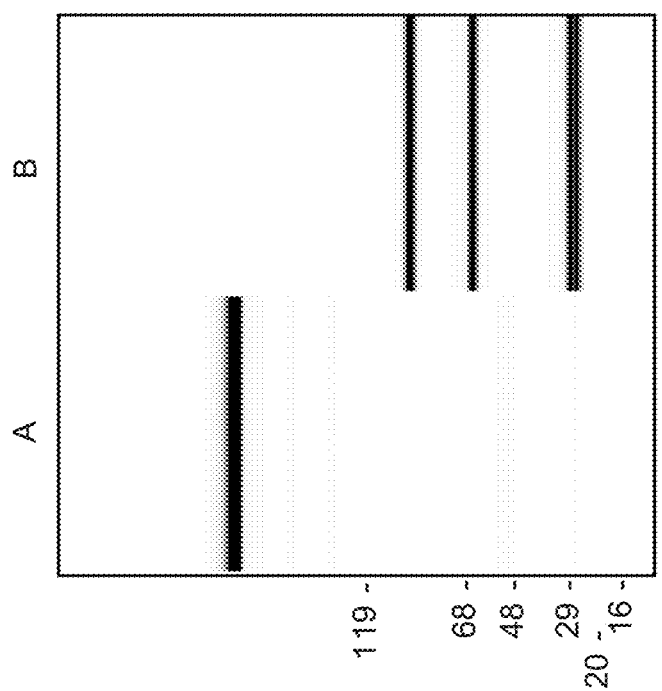
FIGS. 4A-F. CE-SDS analyses of the TCB molecules prepared in the Examples (final purified preparations). (A) Electropherogram of "2+1 IgG CrossFab, inverted" with charge modifications (VH/VL exchange in CD3 binder, charge modification in CEA binder, parental murine CEA binder (T84.66); molecule A). (B) Electropherogram of "2+1 IgG CrossFab, inverted" with charge modifications (VH/VL exchange in CD3 binder, charge modification in CEA binder, humanized CEA binder; molecule B). (C) Electropherogram of "1+1 IgG CrossFab, inverted" with charge modifications (VH/VL exchange in CD3 binder, charge modification in CEA binder, humanized CEA binder; molecule C). (D) Electropherogram of "1+1 IgG CrossMab" with charge modifications (VH/VL exchange in CD3 binder, charge modification in CEA binder, humanized CEA binder; molecule D). (E) Electropherogram of "2+1 IgG CrossFab inverted" with charge modifications and longer linker (VH/VL exchange in CD3 binder, charge modification in CEA binder, humanized CEA binder; molecule E). (F) Electropherogram of "2+1 IgG CrossFab, inverted" without charge modifications (VH/VL exchange in CD3 binder, humanized CEA binder; molecule F). Lane A=non reduced, lane B=reduced.
Figure 4A:
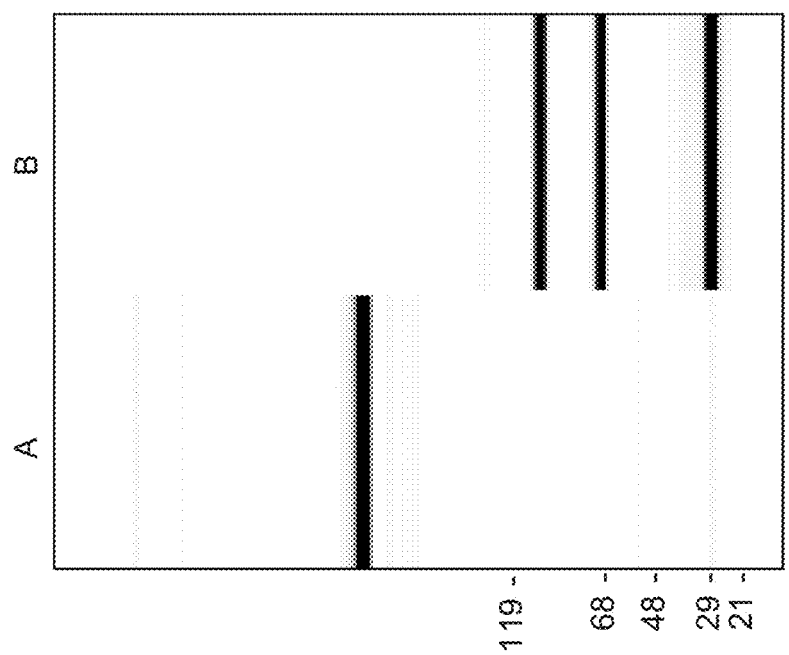
Figure 4D:
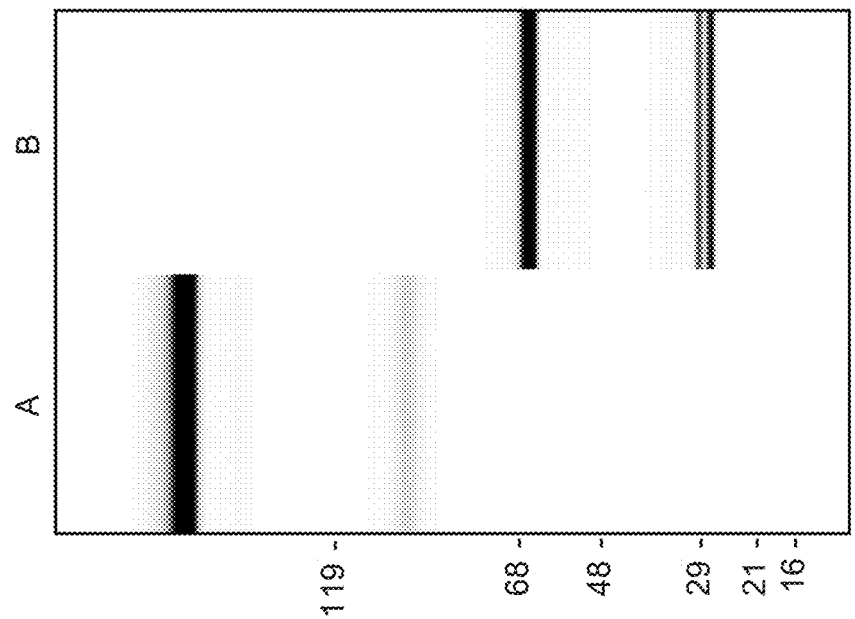
Figure 4C:
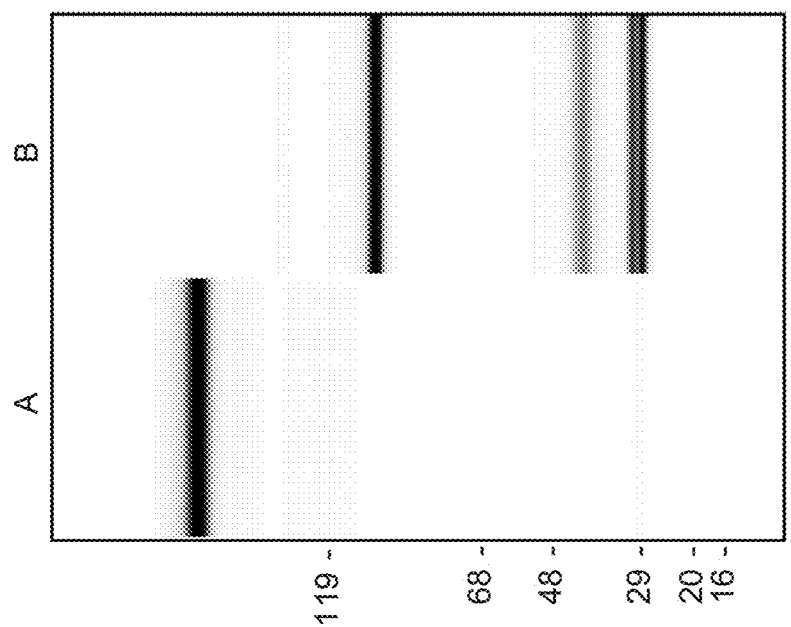
Figure 4F:
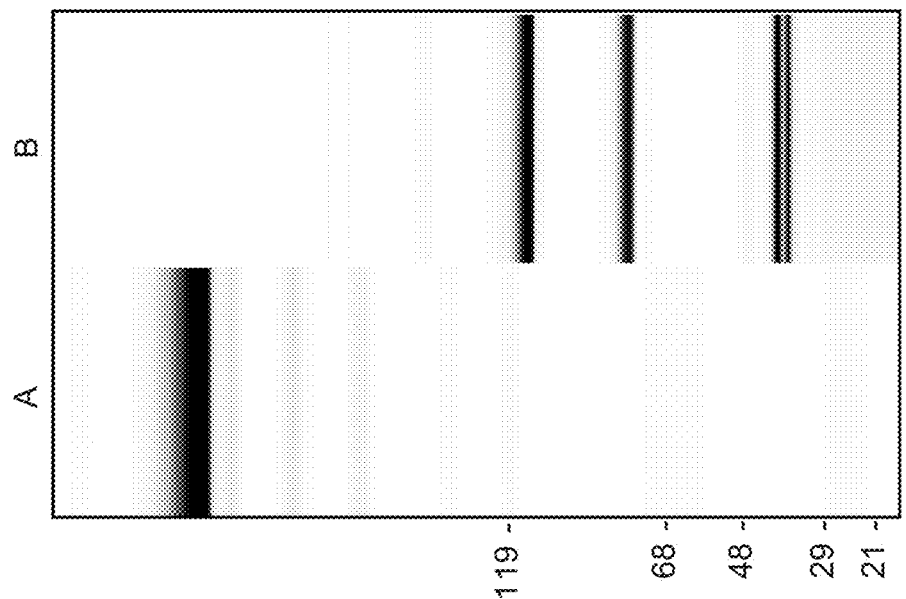
Figure 4E:
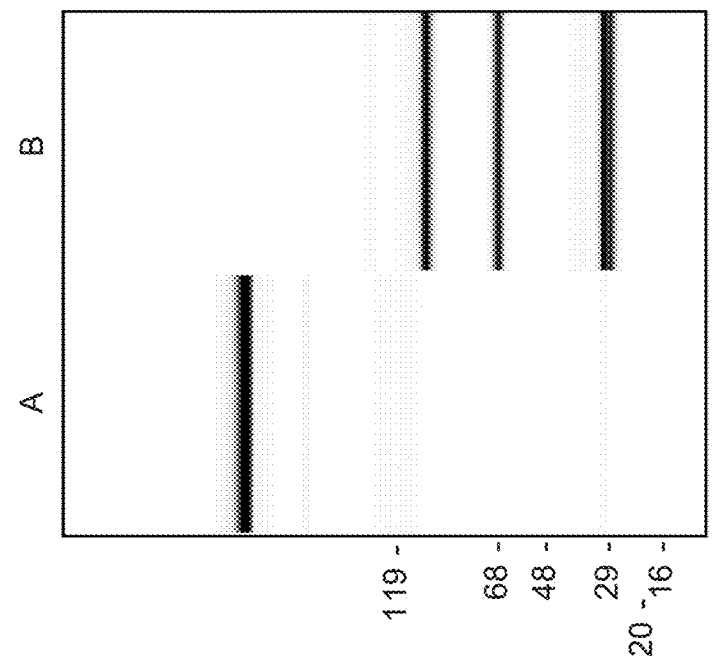
Figure 6A:
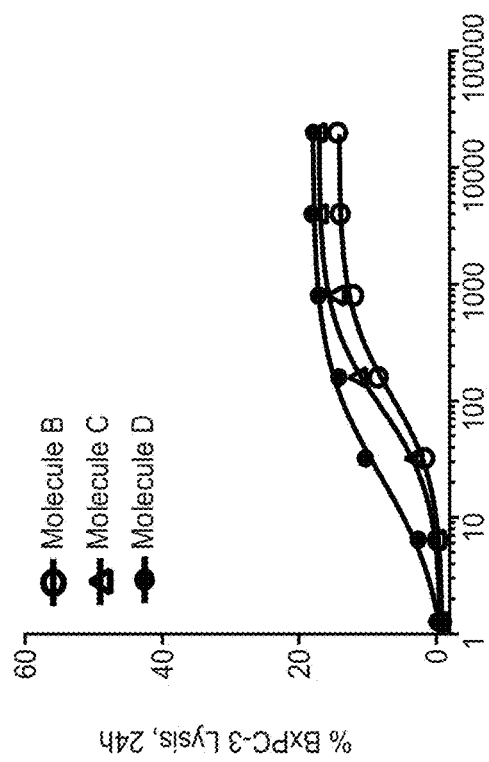
FIGS. 6A-F. T cell mediated lysis of tumor cells induced by different CEA CD3 TCB molecules, as measured by LDH release after 24 h (A-C) or 48 h (D-F). Human PBMCs were used as effector cells and MKN45 (A, D), BxPC-3 (B, E) or HT29 (C, F) cells were used as target cells, at a final effector to target cell ratio of 10:1. Depicted are triplicates with SD. EC50 values were calculated by GraphPadPrism 5 and are given in Table 4 and 5.
Figure 6B:
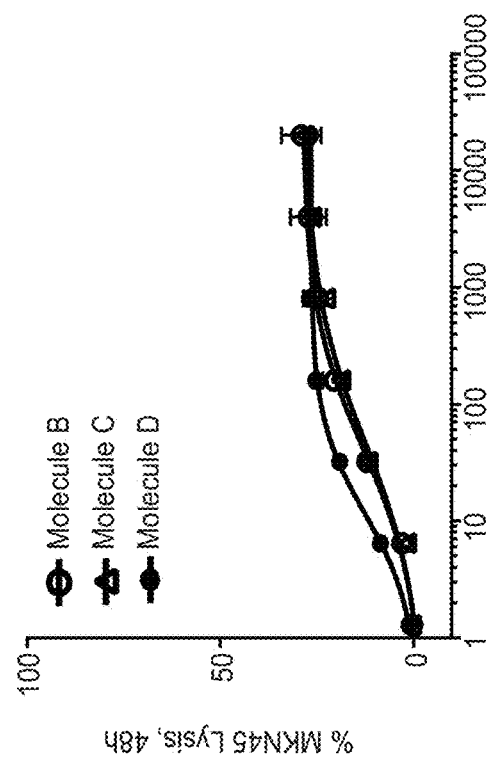
Figure 6C:
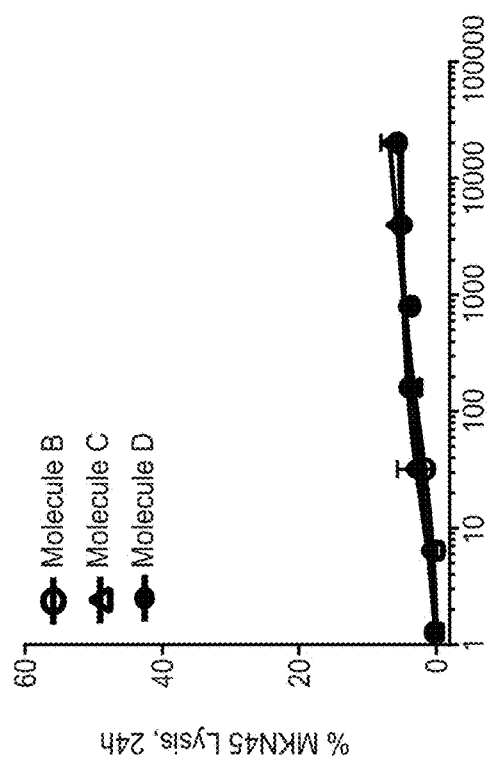
Figure 6D:
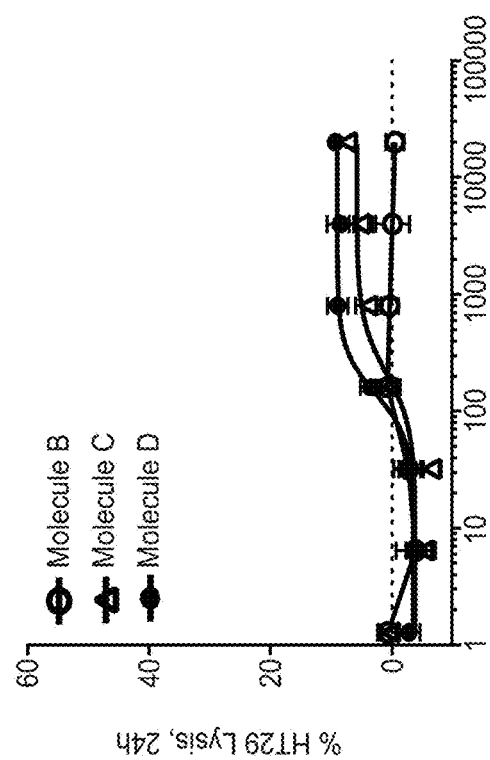
Figure 6E:
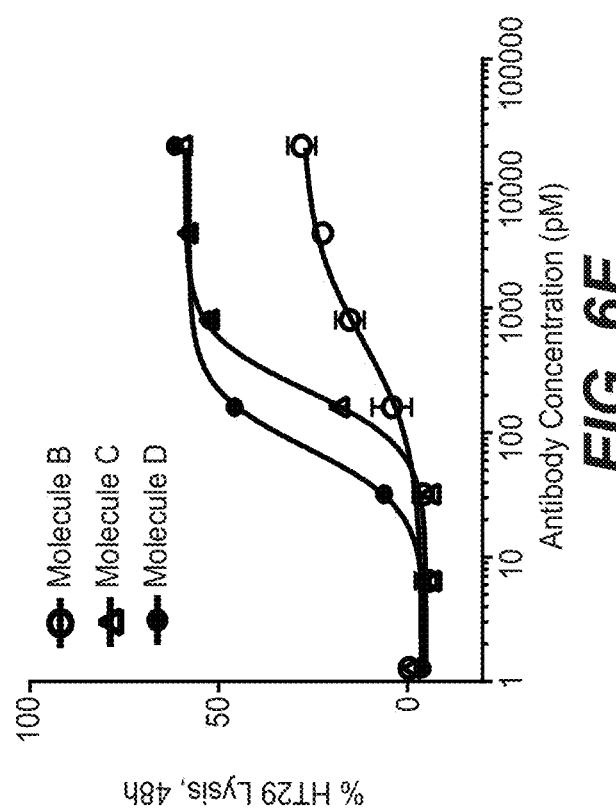
Figure 6F:
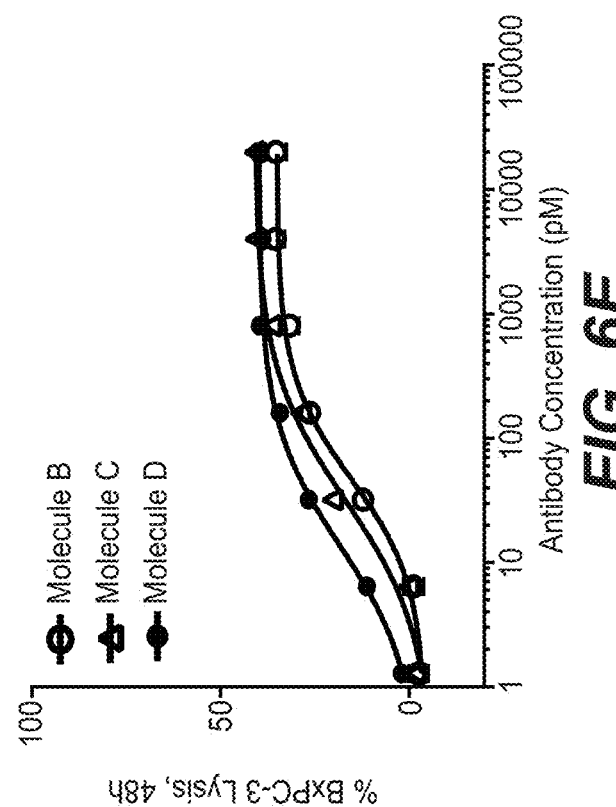
Figure 7A:
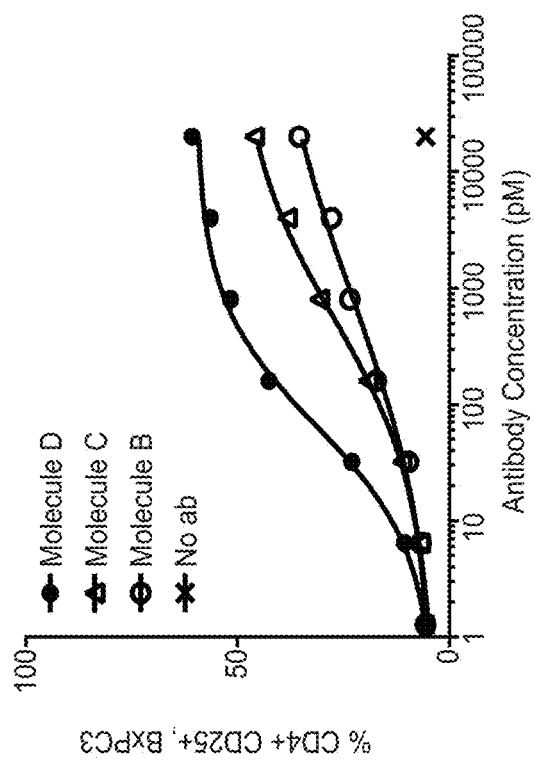
Figure 7B:
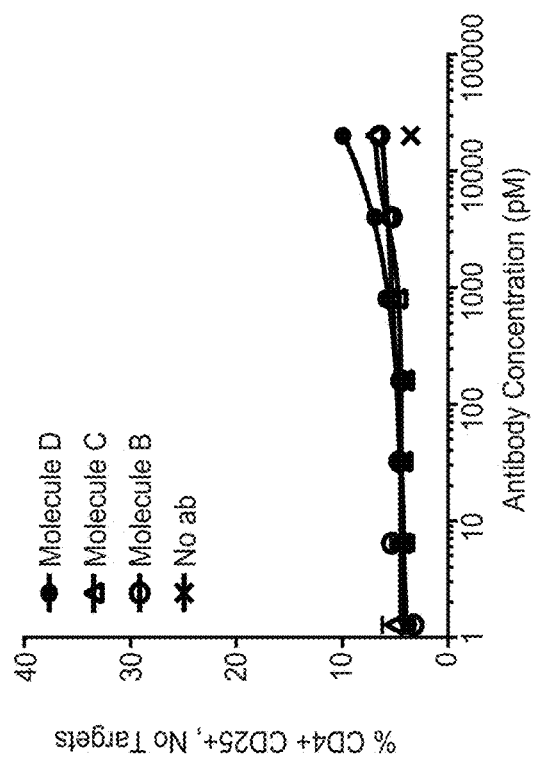
Figure 7C:
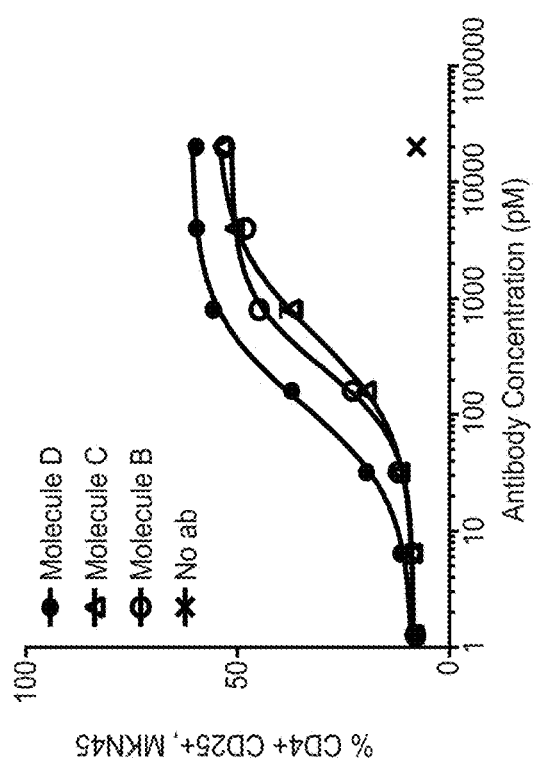
Figure 7D:
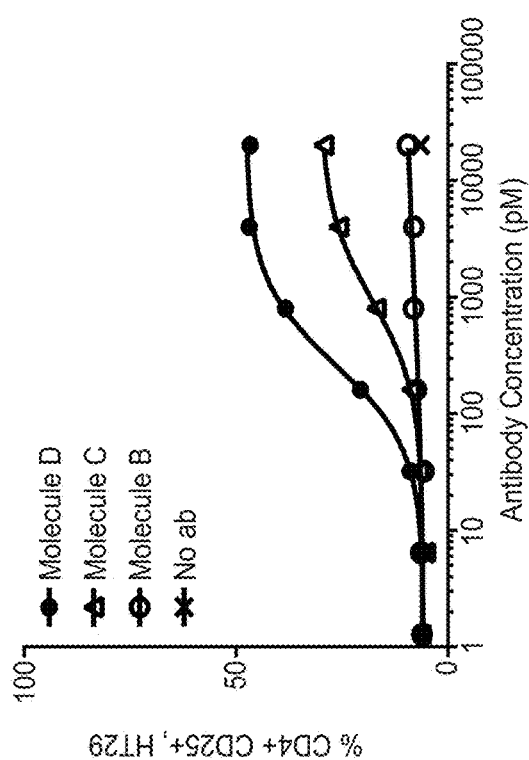

E. "2+1 IgG CrossFab, inverted" with charge modifications (VH/VL exchange in CD3 binder, charge modification in CEA binder, humanized CEA binder, longer linker) (FIG. 3E, SEQ ID NOs 34, 36, 38, 41).

F. "2+1 IgG CrossFab, inverted" without charge modifications (VH/VL exchange in CD3 binder, humanized CEA binder) (FIG. 3F, SEQ ID NOs 34, 50-52).

The DNA sequences encoding the variable heavy and light chain regions of the CD3 and CEA binders were subcloned in frame with the respective constant regions which are pre-inserted into the respective recipient mammalian expression vector. Protein expression is driven by an MPSV or a CMV promoter. Polyadenylation is driven by a synthetic polyA signal sequence located at the 3' end of the CDS. In addition each vector contains an EBV OriP sequence for autosomal replication.

For production of the molecules, HEK293-EBNA cells growing in suspension were co-transfected with the respective expression vectors using polyethylenimine (PEI) as transfection reagent. The cells were transfected with the corresponding expression vectors in a 1:2:1:1 ratio (A, B, E and F: "vector heavy chain (VH-CH1-VL-CH1-CH2-CH3)": "vector light chain (VL-CL)": "vector heavy chain (VH-CH1-CH2-CH3)": "vector light chain (VH-CL)") or in a 1:1:1:1 ratio (C: "vector heavy chain (VH-CH1-VL-CH1-CH2-CH3)": "vector light chain (VL-CL)": "vector heavy chain (CH2-CH3)": "vector light chain (VH-CL)", D: "vector heavy chain (VL-CH1-CH2-CH3)": "vector light chain (VL-CL)": "vector heavy chain (VH-CH1-CH2-CH3)": "vector light chain (VH-CL)"). For transfection, HEK293 EBNA cells were cultivated in suspension serum free in Excell culture medium containing 6 mM L-glutamine and 250 mg/l G418. For the production in 600 ml tubespin flasks (max. working volume 400 ml) 600 million HEK293 EBNA cells were seeded 24 hours before transfection. For transfection, cells were centrifuged for 5 min at 210×g, and supernatant was replaced by 20 ml pre-warmed CD CHO medium. Expression vectors are mixed in 20 ml CD CHO medium to a final amount of 400 μg DNA. After addition of 1080 μl PEI solution (2.7 μg/ml) the mixture was vortexed for 15 s and subsequently incubated for 10 min at room temperature. Afterwards cells were mixed with the DNA/PEI solution, transferred to a 600 ml tubespin flask and incubated for 3 hours at 37° C. in an incubator with a humidified 5% $CO_2$ atmosphere. After incubation, 360 ml Excell medium containing 6 mM L-glutamine, 5 g/L Pepsoy and 1.0 mM VPA was added and cells were cultivated for 24 hours. One day after transfection 7% Feed 1 was added. After 7 days cultivation supernatant was collected for purification by centrifugation for 20-30 min at 3600× g (Sigma 8K centrifuge), the solution was sterile filtered (0.22 μm filter) and sodium azide in a final concentration of 0.01% w/v was added. The solution was kept at 4° C.

The titer of the molecules in the culture medium was determined by Protein A-HPLC (Table 2). Calculation of the titer is based on a two-step process and includes binding of Fc-containing molecules to Protein A at pH 8.0 and release in a step elution at pH 2.5. Both buffers used for the analysis contained Tris (10 mM), glycine (50 mM), and NaCl (100 mM) and were adjusted to the respective pHs (8 and 2.5). The column body was an Upchurch 2×20 mm pre-column with an internal volume of ~63 μl packed with POROS 20A. After initial calibration, 100 μl of each sample was injected with a flow rate of 0.5 ml/min. After 0.67 minutes the sample was eluted with a pH step to pH 2.5. Quantitation was done by determination of 280 nm absorbance and calculation using a standard curve with a concentration range of human $IgG_1$ from 16 to 166 mg/l.

The secreted proteins were purified from cell culture supernatants by affinity chromatography using Protein A affinity chromatography, followed by a size exclusion chromatographic step.

For affinity chromatography supernatant was loaded on a HITRAP® ProteinA HP (molecule A, B and F) or a MabSelectSure (molecule C, D and E) column (CV=5 mL, GE Healthcare) equilibrated with 25 ml 20 mM sodium phosphate, 20 mM sodium citrate, pH 7.5. Unbound protein was removed by washing with at least 10 column volumes 20 mM sodium phosphate, 20 mM sodium citrate, pH 7.5, and target protein was eluted in 6 column volumes 20 mM sodium citrate, 100 mM sodium chloride, 100 mM glycine, pH 3.0. Protein solution was neutralized by adding 1/10 of 0.5 M sodium phosphate, pH 8.0. For in-process analytics after Protein A chromatography, the purity and molecular weight of the molecules in the single fractions were analyzed by SDS-PAGE in the absence of a reducing agent and staining with Coomassie (InstantBlue™, Expedeon). The NuPAGE® Pre-Cast gel system (4-12% Bis-Tris, Invitrogen) was used according to the manufacturer's instruction. Selected fractions of target protein were concentrated and filtrated prior to loading on a HILOAD® SUPERDEX® 200 column (GE Healthcare) equilibrated with 20 mM histidine, 140 mM sodium chloride, 0.01% Tween-20, pH 6.0.

The protein concentration of purified protein samples was determined by measuring the optical density (OD) at 280 nm, using the molar extinction coefficient calculated on the basis of the amino acid sequence.

The aggregate content of the molecules was analyzed using a TSKGEL® G3000 SW XL analytical size-exclusion column (Tosoh) in 25 mM $K_2HPO_4$, 125 mM NaCl, 200 mM L-arginine monohydrocloride, 0.02% (w/v) $NaN_3$, pH 6.7 running buffer at 25° C.

Purity and molecular weight of molecules after the final purification step were analyzed by CE-SDS analyses in the presence and absence of a reducing agent. The Caliper LABCHIP® GXII system (Caliper lifescience) was used according to the manufacturer's instruction (FIG. 5 and Table 3).

Mass spectrometry analysis of the molecules was performed on an Agilent LC-MS system (Agilent Technologies, Santa Clara, Calif., USA). The chromatography system (Agilent 1260 Infinity) was coupled on an Agilent 6224 TOF LC/MS ESI device. About 5 μg of sample were injected on a NUCLEOGEL® RP1000-8, 250 mm×4.6 mm column (MACHEREY-NAGEL GmbH & Co. KG, Duren, Germany) at a flow rate of 1 ml/min at 40° C. The mobile phase was as follows A: 5% acetonitrile, 0.05% formic acid, and B: 95% acetonitrile, 0.05% formic acid. To apply an elution gradient, 15% B was raised to 60% B within 10 min, then to 100% B in 2.5 min.

The mass spectrometer was measuring in high resolution mode 4 GHz positive, and recorded a range from 500 to 3200 m/z. The m/z spectra were deconvoluted manually with the MassAnalyzer 2.4.1 from Roche (Hoffman-La Roche, Ltd).

All molecules were produced and purified essentially following the same method. The final quality was very good for both molecules A and B with almost 100% monomer content and 100% purity on CE-SDS (Table 2 and 3, FIG. 4). LC-MS analysis was performed for molecule B and revealed no mispairing of light chains. In contrast, molecule F (without charge modifications) had a very low recovery because side products had to be removed and LC-MS measurements still showed around 10% mispairing. Molecule C could be purified with a slightly better yield and quality than molecule D. The final quality was also good for both molecules C and D with almost 100% monomer content and >96% purity on CE-SDS (Table 2 and 3, FIG. 4).

TABLE 2

Summary of production and purification of anti-CEA/anti-CD3 TCB molecules with and without charge modifications.

| Molecule | Titer [mg/l] | Recovery [%] | Yield [mg/l] | Analytical SEC (HMW/Monomer/LMW) [%] |
|---|---|---|---|---|
| A | 10 | 40 | 4 | 0/100/0 |
| B | 1.5 | 61 | 0.9 | 0.8/99.2/0 |
| C | 20 | 36 | 7.3 | 0/100/0 |
| D | 10 | 17 | 1.7 | 0/99/1 |
| E | 16 | 27 | 4.3 | 3/97/0 |
| F | 15 | 3 | 0.46 | 0/100/0 |

TABLE 3

CE-SDS analyses (non-reduced) of anti-CEA/anti-CD3 TCB molecules with and without charge modifications.

| Molecule | Peak # | Size [kDa] | Purity [%] |
|---|---|---|---|
| A | 1 | 218.6 | 100 |
| B | 1 | 199.6 | 100 |
| C | 1 | 169 | 100 |
| D | 1 | 98 | 4 |
|   | 2 | 166 | 96 |
| E | 1 | 190 | 2 |
|   | 2 | 200 | 94 |
|   | 3 | 210 | 4 |
| F | 1 | 172 | 2 |
|   | 2 | 197 | 2 |
|   | 3 | 220 | 2 |
|   | 4 | 230 | 94 |

Example 3

Comparison of Different Anti-CEA/Anti-CD3 T Cell Bispecific Molecule Formats

Example 3A

Binding of Different Anti-CEA/Anti-CD3 T Cell Bispecific (CEA CD3 TCB) Molecules to Cells The binding of different formats of anti-CEA/anti-CD3 T cell bispecific (CEA CD3 TCB) molecules was tested on human gastric adenocarcinoma cells (MKN45, DSMZ ACC 409, ~513 000 CEA binding sites), colon adenocarcinoma cells (LS174T, ATCC® CL-188, ~40 700 CEA binding sites), and colon adenocarcinoma cells HT29 (DSMZ ACC 299, ~10 000 CEA binding sites), as well as on CD3-expressing immortalized T lymphocyte cells (Jurkat, DSMZ ACC 282).

Briefly, cells were harvested, counted, checked for viability and resuspended at $2 \times 10^6$ cells/ml in FACS buffer (100 µl PBS 0.1% BSA). 100 µl of cell suspension (containing $0.2 \times 10^6$ cells) were incubated in round-bottom 96-well plate for 30 min at 4° C. with increasing concentrations of the CEA CD3 TCB molecules (310 pM-500 nM), washed twice with cold PBS 0.1% BSA, re-incubated for further 30 min at 4° C. with the Fluorescein (FITC)-AffiniPure F(ab')2 Fragment Goat Anti-Human IgG, Fcγ Fragment Specific antibody (Jackson Immuno Research Lab #109-096-008), washed twice with cold PBS 0.1% BSA.

Staining was fixed by incubation of cells with FACS buffer, containing 2% PFA for 30 min at 4° C. in the dark. For the measurement, cells were re-suspended in 150 µl FACS buffer and fluorescence was measured using Miltenyi MACSQUANT®

Results are shown in FIG. 5. Binding curves were obtained using GraphPadPrism5 (upper row from left to right, MKN45 cells; LS174T cells, binding to HT29 cells, lower row, binding to Jurkat cells).

FIG. 5 shows higher fluorescence intensities for molecule D and molecule C at high concentration on cell lines with medium (LS174T) or low CEA expression level (HT29). This points to the fact, that more of the monovalently binding constructs are able to bind under these conditions compared to molecule B, that binds to human CEA bivalently. The binding to human CD3 on Jurkat cells is comparable for molecule C and molecule B, whereas molecule D shows better binding. This might be due to better accessibility of the CD3-targeting moiety in molecule D.

Example 3B

Tumor Cell Killing Induced by Different Anti-CEA/Anti-CD3 T Cell Bispecific (CEA CD3 TCB) Molecules T-cell mediated killing of different tumor cells by CEA CD3 TCB molecules was assessed using MKN45, BxPC-3 (ECACC 93120816, a human primary pancreatic adenocarcinoma cell line) or HT-29 human tumor cells as targets, and human PBMCs as effector cells. Lysis of tumor cells was detected at 24 h and 48 h of incubation with the indicated CEA CD3 TCB molecules.

Briefly, target cells were harvested with Trypsin/EDTA, washed, and plated at density of 25 000 cells/well using flat-bottom 96-well plates. Cells were left to adhere overnight. Peripheral blood mononuclear cells (PBMCs) were prepared by Histopaque density centrifugation of enriched lymphocyte preparations (buffy coats) obtained from healthy human donors. Fresh blood was diluted with sterile PBS and layered over Histopaque gradient (Sigma, # H8889). After centrifugation (450×g, 30 minutes, room temperature), the plasma above the PBMC-containing interphase was discarded and PBMCs transferred in a new falcon tube subsequently filled with 50 ml of PBS. The mixture was centrifuged (400× g, 10 minutes, room temperature), the supernatant discarded and the PBMC pellet washed twice with sterile PBS (centrifugation steps 350× g, 10 minutes). The resulting PBMC population was counted automatically (ViCell) and stored in RPMI1640 medium containing 10% FCS and 1% L-alanyl-L-glutamine (Biochrom, K0302) at 37° C., 5% $CO_2$ in cell incubator until further use (no longer than 24 h). For the tumor cell lysis assay, the CEA CD3 TCB molecules were added at the indicated concentrations (range of 1 pM-20 nM in triplicates). PBMCs were added to target cells at final E:T ratio of 10:1. Target cell killing was assessed after 24 h and 48 h of incubation at 37° C., 5% $CO_2$ by quantification of LDH released into cell supernatants by apoptotic/necrotic cells (LDH detection kit, Roche Applied Science, #11 644 793 001). Maximal lysis of the target cells (=100%) was achieved by incubation of target cells with 1% Triton X-100. Minimal lysis (=0%) refers to target cells co-incubated with effector cells without bispecific construct.

FIG. 6 shows that molecule D induced the strongest killing of target cell lines, followed by molecule C and finally molecule B. The best differentiation between the three different formats may be seen on tumor cells lines with low CEA expression levels (FIGS. 6C and 6F). EC50 values of tumor cell lysis were calculated using Graph Pad Prism5 and are given in Table 4 (24 h) and Table 5 (48 h).

TABLE 4

EC50 values (pM) for T-cell mediated killing of CEA-expressing tumor cells induced by different CEA CD3 TCB molecules after 24 h.

| Cell line | CEA binding sites | Molecule B | Molecule C | Molecule D |
| --- | --- | --- | --- | --- |
| MKN45 | 513 000 | 78.46 | 72.96 | 13.58 |
| BxPC-3 | 44 400 | 113.5 | 91.33 | 22.19 |
| HT-29 | 10 000 |  | 214.5 | 142.0 |

TABLE 5

EC50 values (pM) for T-cell mediated killing of CEA-expressing tumor cells induced by different CEA CD3 TCB molecules after 48 h.

| Cell line | CEA binding sites | Molecule B | Molecule C | Molecule D |
| --- | --- | --- | --- | --- |
| MKN45 | 513 000 | 41.24 | 47.64 | 11.60 |
| BxPC-3 | 44 400 | 46.98 | 32.42 | 13.67 |
| HT-29 | 10 000 | 31.72 | 63.80 | 62.44 |

Example 3C

CD25 Up-Regulation on CD4+ and CD8+ Effector Cells after Killing of CEA-Expressing Tumor Cells Induced by Different CEA CD3 TCB Molecules Activation of CD4+(FIG. 7 A-D) and CD8+ T cells (FIG. 7 E-H) after killing of CEA-expressing MKN45, BxPC3 or HT29 tumor cells mediated by different CEA CD3 TCB molecules was assessed by FACS analysis using antibodies recognizing the T cell activation marker CD25 (late activation marker). In addition, CD25 was analyzed on CD4 and CD8 T effector cells upon co-incubation of effector cells with the different CEA CD3 TCB molecules in the absence of target cells to check for antigen-unspecific T cell activation.

The antibody and the killing assay conditions were essentially as described above (Example 3B), using the same antibody concentration range (1 pM-20 nM in triplicates), E:T ratio 10:1 and an incubation time of 48 h.

After the incubation, PBMCs were transferred to a round-bottom 96-well plate, centrifuged at 350× g for 5 min and washed twice with PBS containing 0.1% BSA. Surface staining for CD8 (FITC anti-human CD8, BioLegend #344704), CD4 (PECy7 anti-human CD4, BioLegend #344612) and CD25 (APC anti-human CD25 BioLegend #302610) was performed according to the suppliers' indications. Cells were washed twice with 150 µl/well PBS containing 0.1% BSA and fixed for 30 min at 4° C. using 150 µl/well of FACS buffer, containing 2% PFA. After centrifugation, the samples were re-suspended in 200 µl/well PBS 0.1% BSA and analyzed using a BD FACS Fortessa.

FIG. 7 shows that molecule D induced the strongest T cell activation, as measured by percentage of CD25-positive T cells. However, this molecule also induced activation of T cells in the absence of target cells at the highest 2-3 concentrations and was therefore not selected as preferred format. Molecule C is the second most potent molecule to induce T cell activation in the presence of CEA-expressing target cells, which is especially apparent in settings with target cells that express rather low levels of CEA (FIG. 7C). Also molecule B is able to induce strong and concentration-dependent T cell activation in the presence of CEA-expressing target cells. In this example, both molecules B and C do not induce significant T cell activation in the absence of target cells.

To further elaborate this important safety point, additional assays were performed.

Example 3D

CD69 Up-Regulation on CD4+ and CD8+ Effector Cells Upon Co-Incubation with Different CEA CD3 TCB Molecules and CEA-Expressing Tumor or Primary Epithelial Cells Activation of CD4+(FIG. 8 A-E) and CD8+ T cells (FIG. 8 F-J) was assessed after co-incubation of CEA-expressing MKN45, LS174T (ECACC 87060401, a human colon adenocarcinoma cell line with approximately 40 700 CEA binding sites), HT29 or CCD 841 CoN (ATCC® CRL-1790™, a primary epithelial cell line from human colon, expressing <2000 CEA binding sites) with human PBMCs and different CEA CD3 TCB molecules for 48 h. To check for antigen-unspecific T cell activation, CD69 was analyzed on CD4 and CD8 T effector cells upon co-incubation of effector cells with the different CEA CD3 TCB molecules in the absence of target cells as well.

Figure 8A:
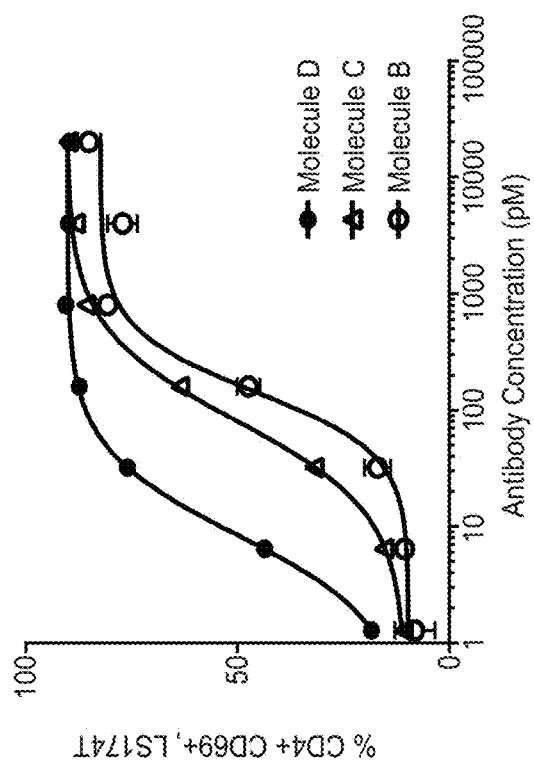
FIGS. 8A-J. Up-regulation of CD69 on human CD4+(A-E) and CD8+(F-J) T cells upon co-incubation with CEA-expressing tumor or primary epithelial cells and different CEA CD3 TCB molecules. Human PBMCs were used as effector cells and MKN45 (A, F), LS174T (B, G), HT29 (C, H), CCD841 (D, I) cells were used as target cells, at a final effector to target cell ratio of 10:1. Results without target cells are shown in (E) and (J). Percentage of CD69-positive T cells was determined by FACS after 48 h. Depicted are triplicates with SD.
Figure 8B:
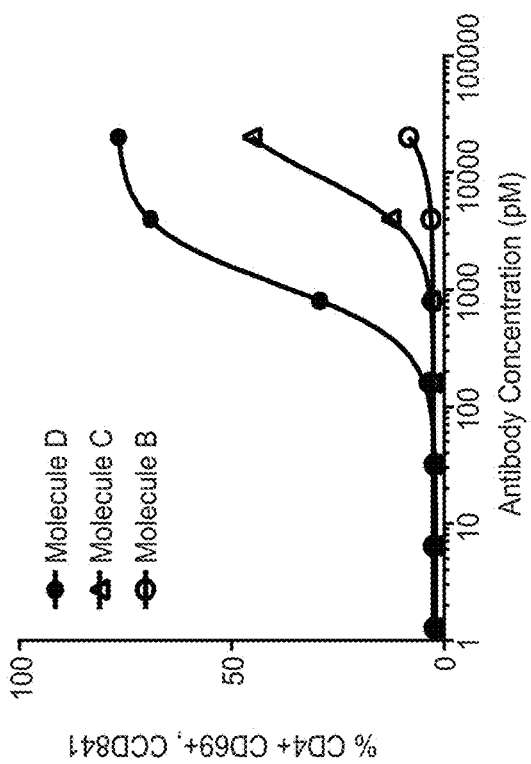
Figure 8C:
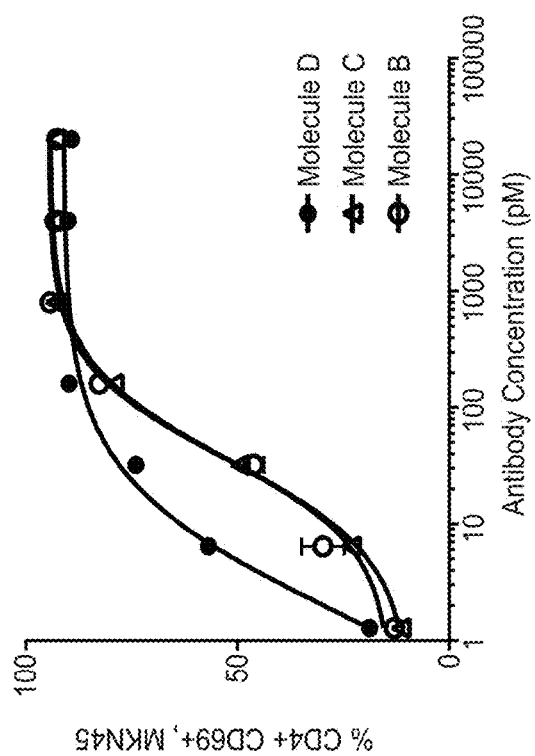
Figure 8D:
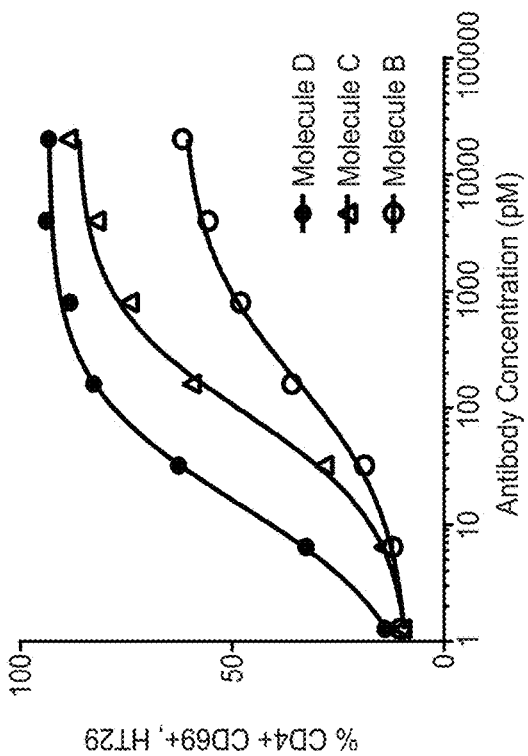
Figure 8E:
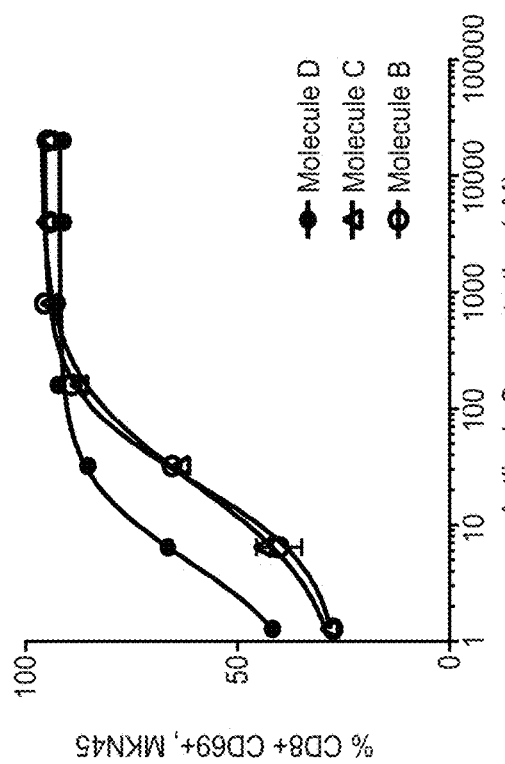
Figure 8F:
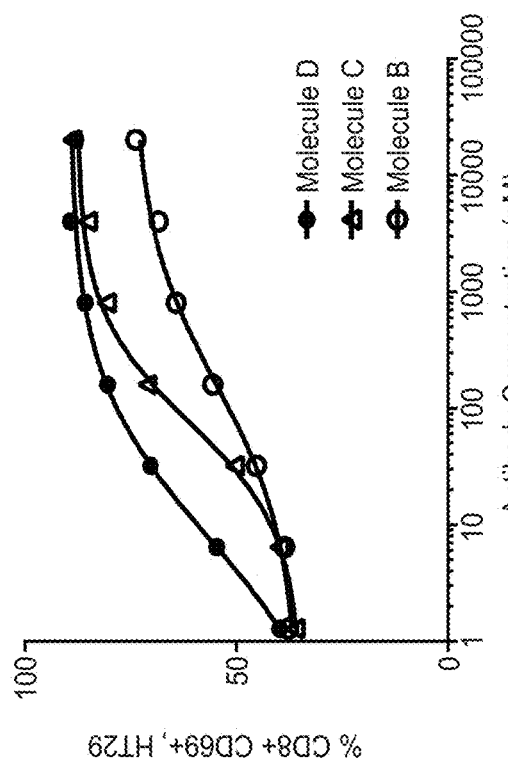
Figure 8G:
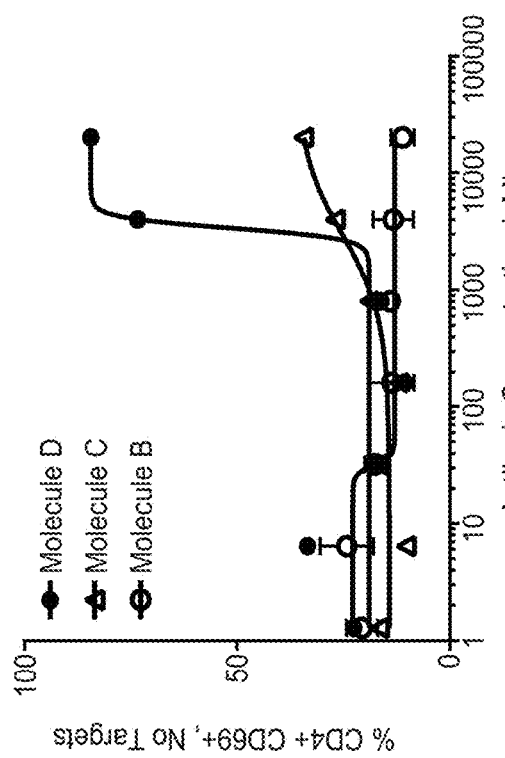
Figure 8H:
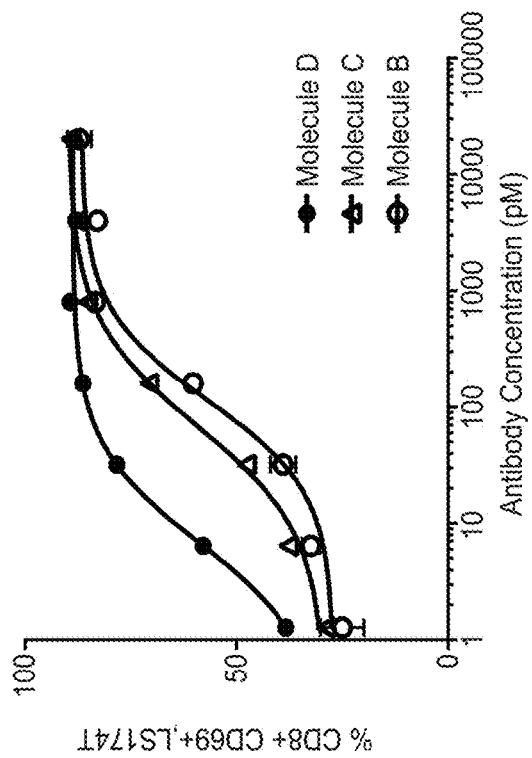
Figure 8J:
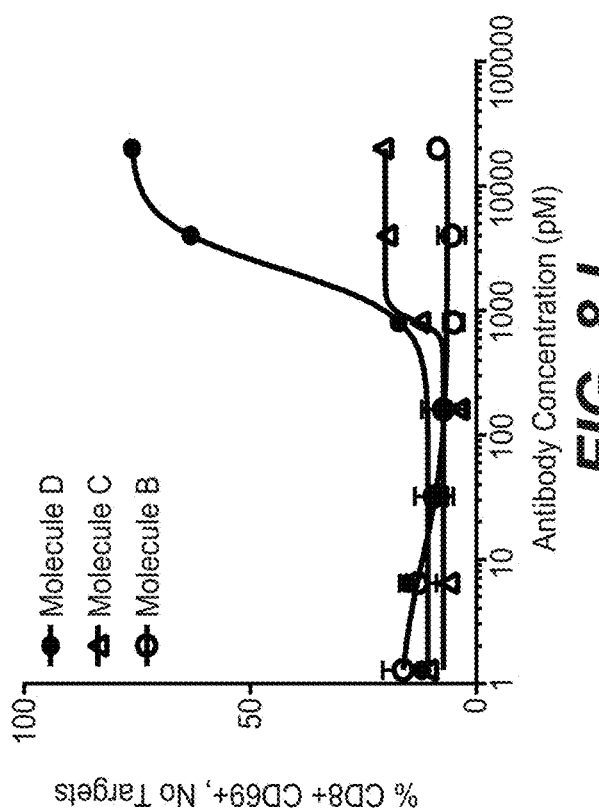
Figure 8I:
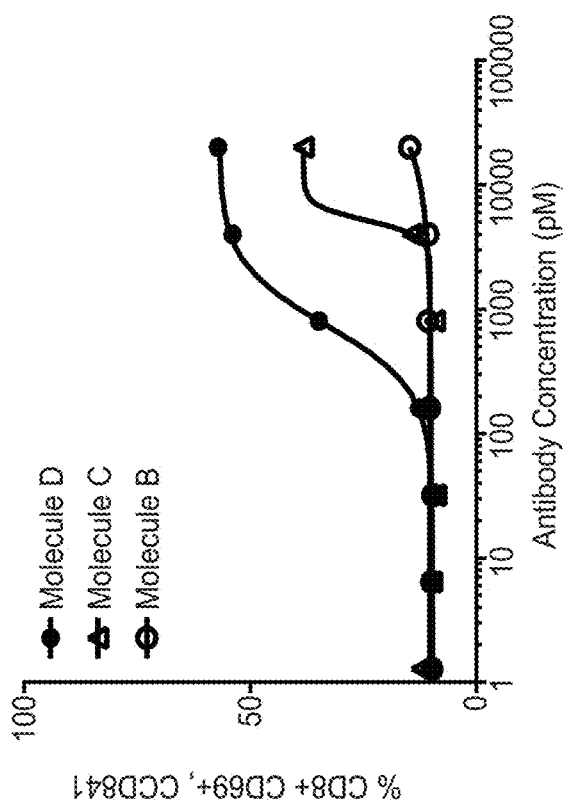
Figure 11A:
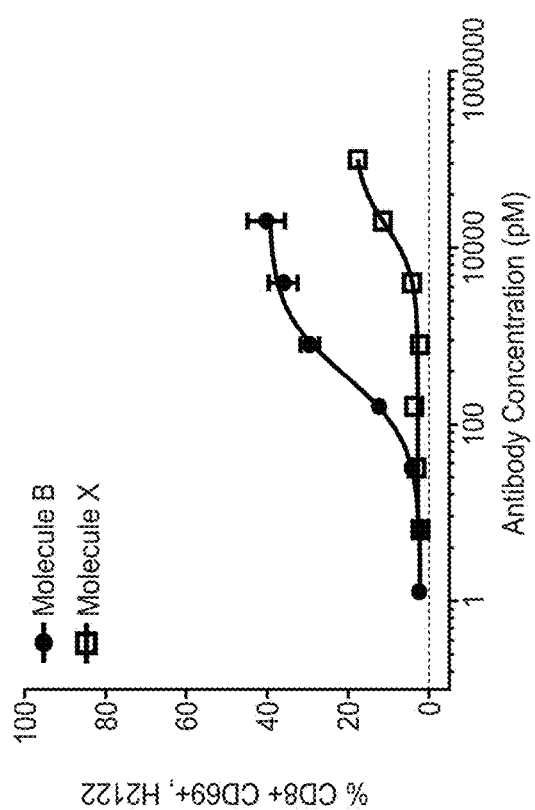
FIGS. 11A-H. T cell activation (A-D) and tumor cell lysis (E-H) induced by different CEA CD3 TCB molecules, as measured by FACS (A-D, percent of CD69-positive CD8+ T cells), or LDH (E-H) after 48 h. Human PBMCs were used as effector cells at a final effector to target cell ratio of 10:1. Target cells were either medium CEA expressing BxPC-3 (A, E), low CEA-expressing NCI-H2122 (B, F) cells or very low CEA expressing COR-L105 (C, G) or primary epithelial cells HBEpiC (D, H). Depicted are triplicates with SD.
Figure 11B:
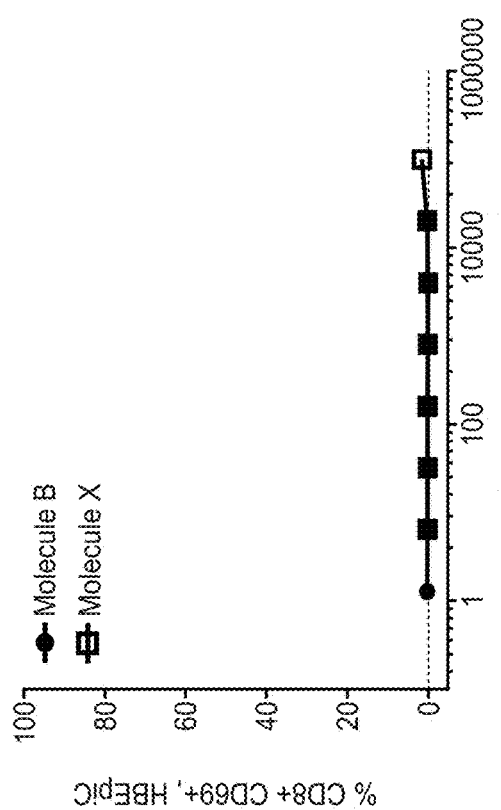
Figure 11C:
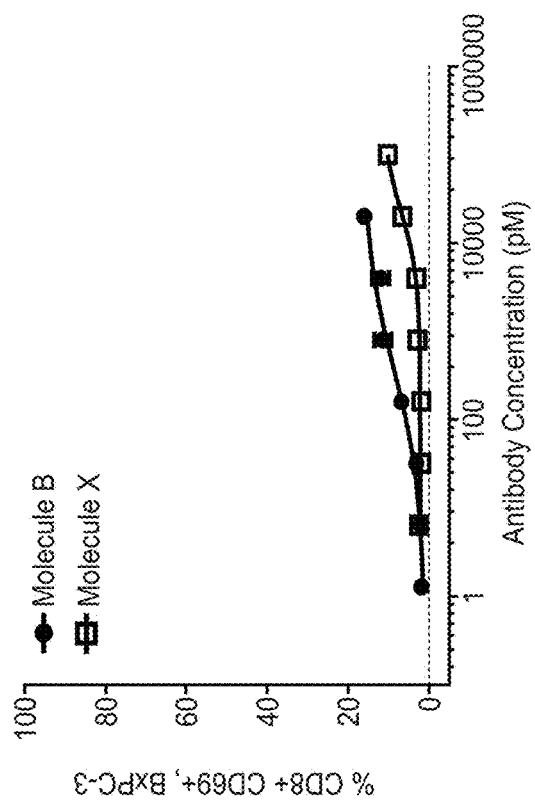
Figure 11D:
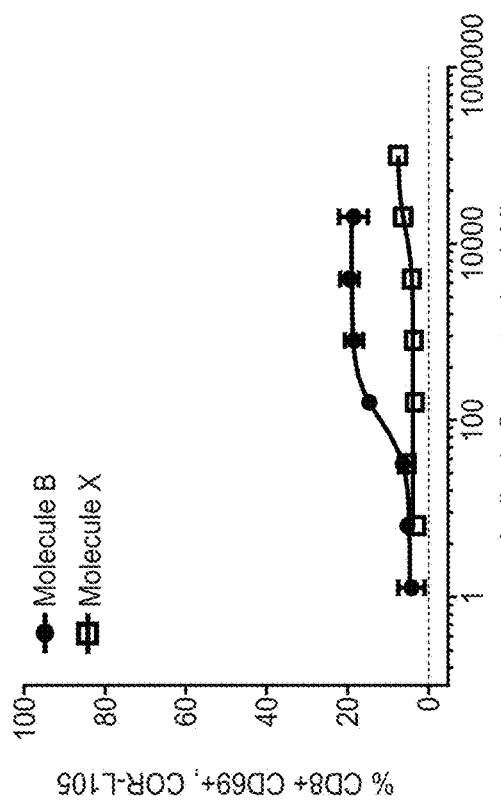
Figure 11E:
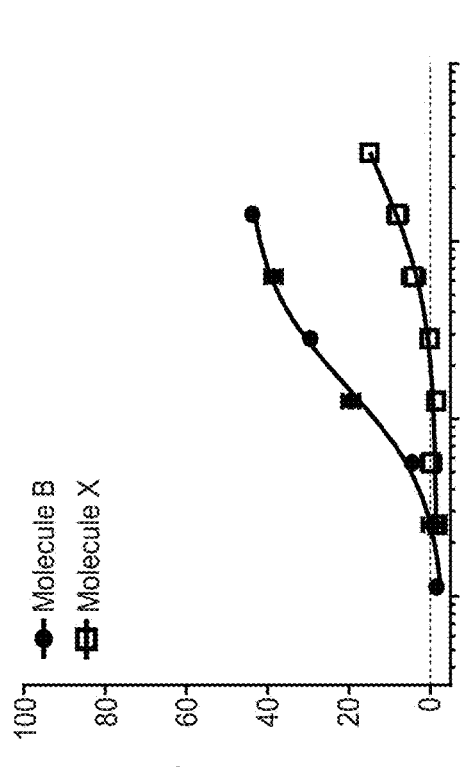
Figure 11F:
Figure 11G:
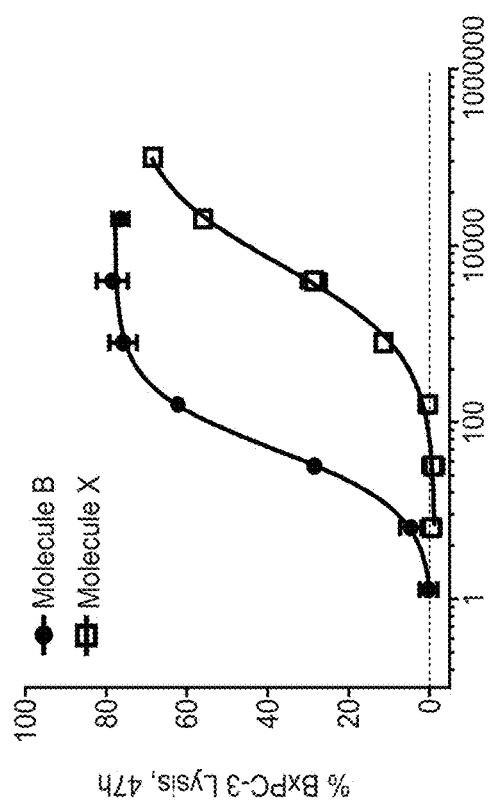
Figure 11H:
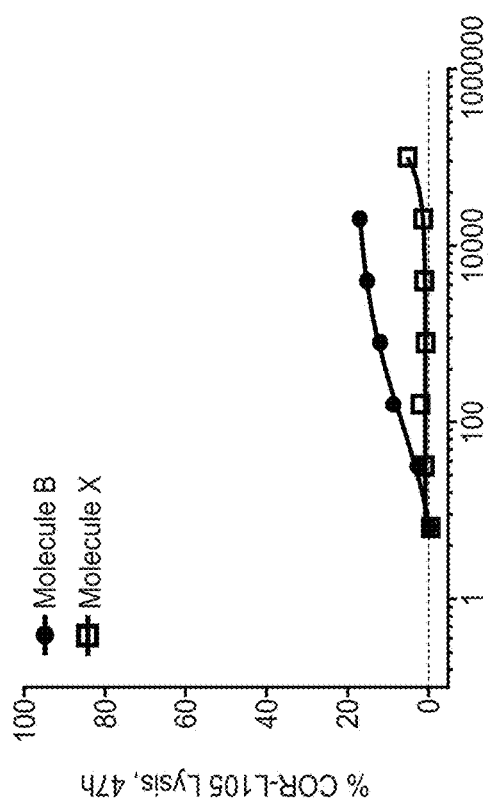
Figure 12E:
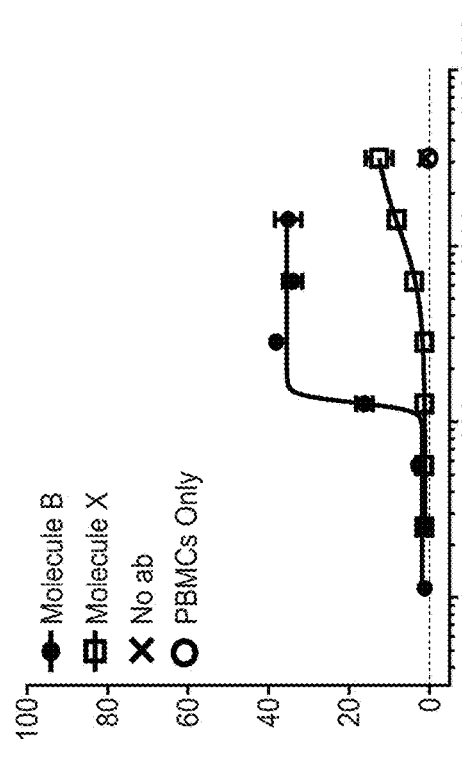
Figure 12F:
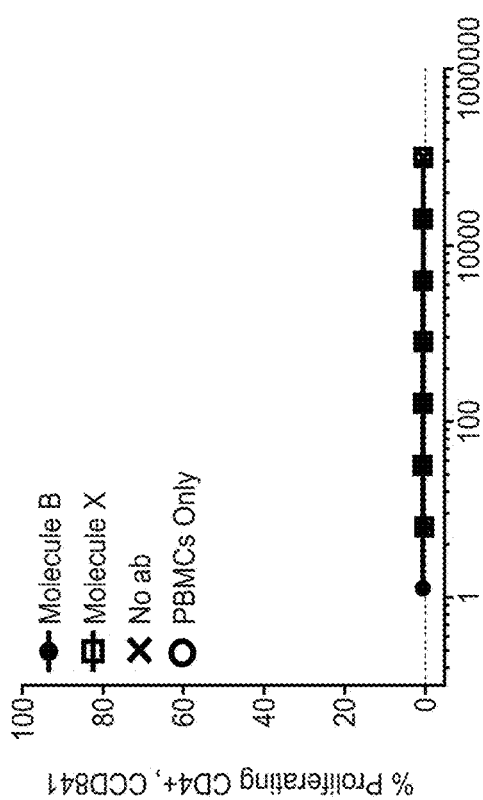
Figure 12G:
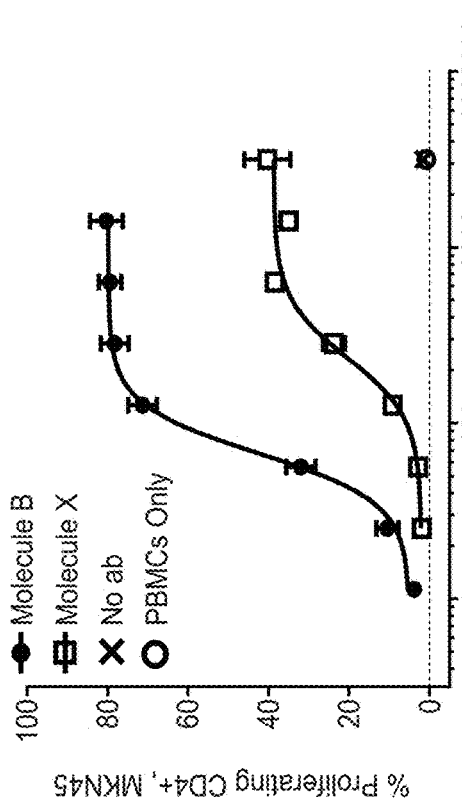
Figure 12H:
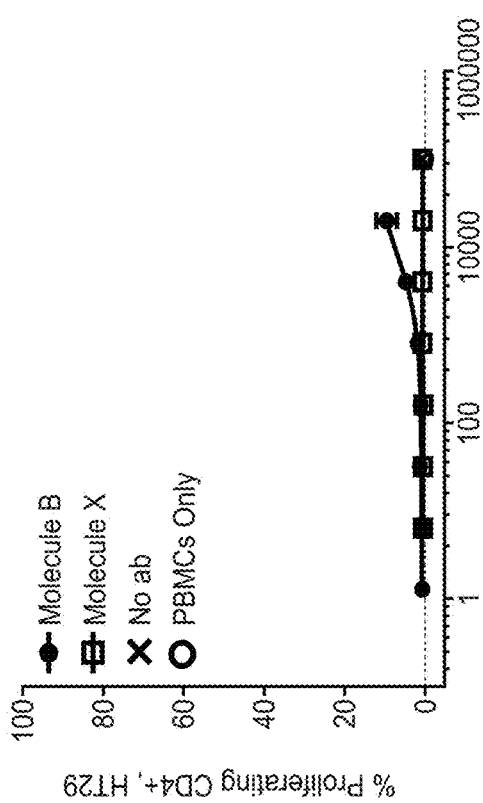
Figure 14A:
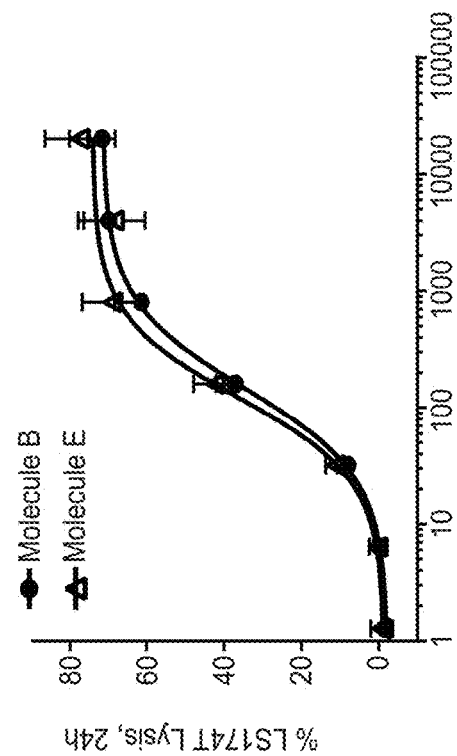
FIGS. 14A-H. T cell mediated lysis of tumor cells induced by different CEA CD3 TCB molecules (molecule B and molecule E), as measured by LDH release after 24 h (A-D) or 48 h (E-H). Human PBMCs were used as effector cells and MKN45 (A, E), LS174T (B, F), HT29 (C, G), HBEpiC (D, H) cells were used as target cells, at a final effector to target cell ratio of 10:1. Depicted are triplicates with SD. EC50 values were calculated by GraphPadPrism 5 and are given in Table 6.
Figure 14B:
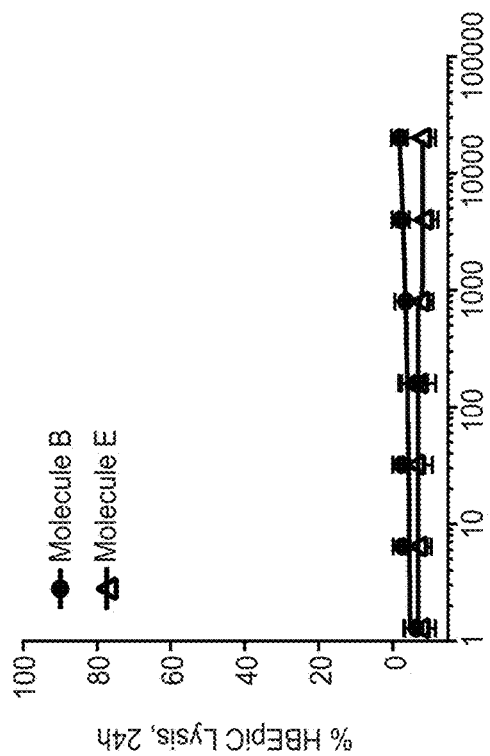
Figure 14C:
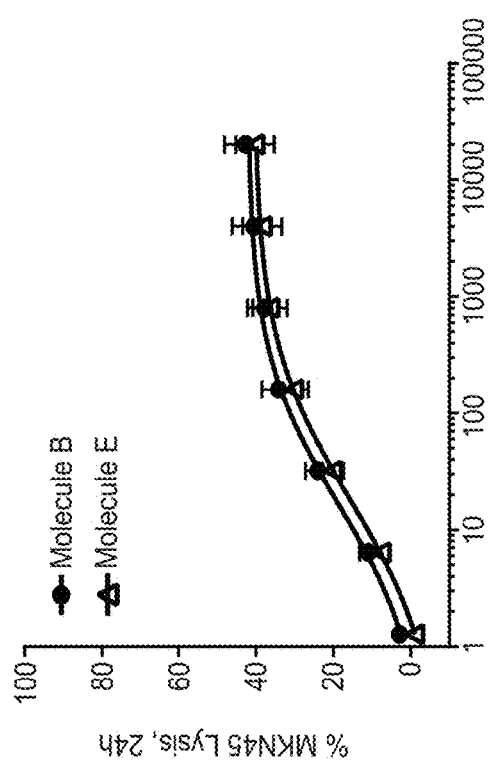
Figure 14D:
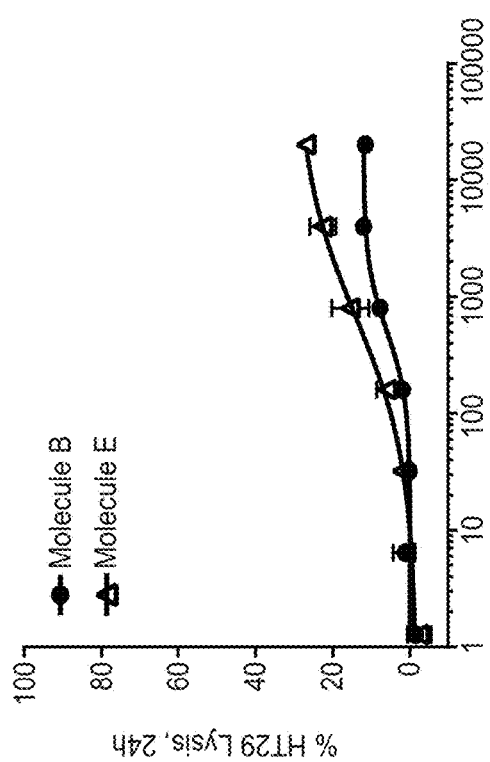
Figure 14F:
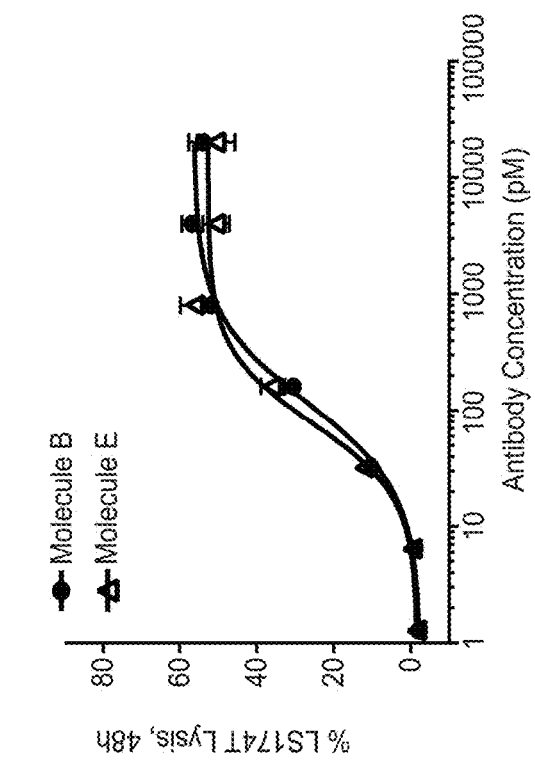
Figure 14H:
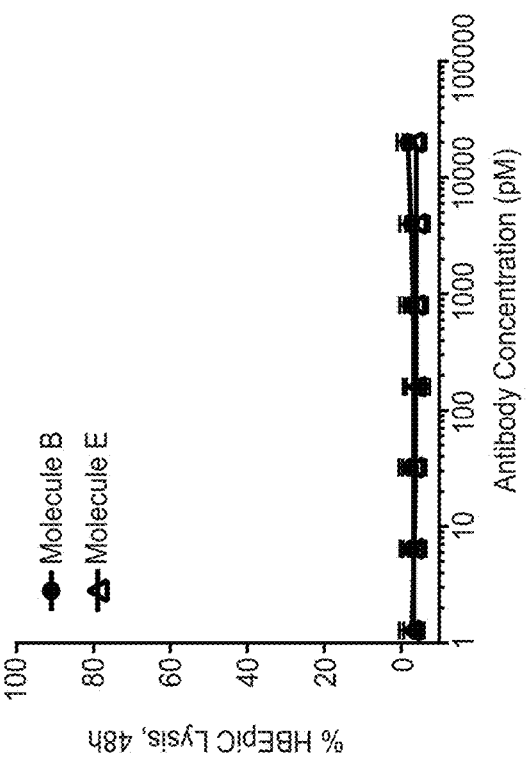
Figure 14E:
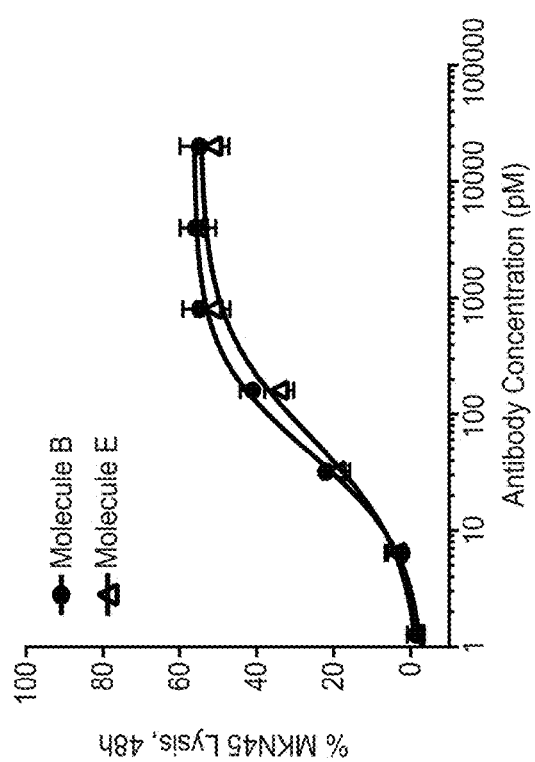
Figure 14G:
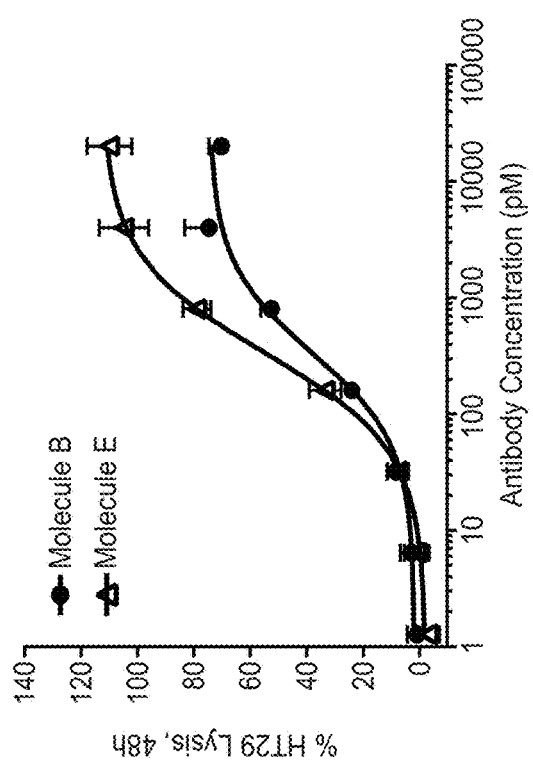

The antibody and assay conditions were essentially as described above (Example 3B and 3C), using the same antibody concentration range (1 pM-20 nM in triplicates) and an E:T ratio of 10:1, as well as the FACS staining protocol as described above (PE anti-human CD69, BioLegend #310906). FIG. 8 shows that again molecule D induced the strongest T cell activation, as measured by percentage of CD69-positive T cells in the presence of different CEA-expressing tumor cells. However, this molecule also induced activation of T cells in the presence of primary epithelial cells (CCD841, see FIGS. 8D and 8I), as well as in the absence of target cells (FIGS. 8E and 8J). These findings confirm the antigen-independent activation of T cells and in addition point to a potential safety issue in the presence of primary epithelial cells with very low CEA expression levels. However, with these reactive PBMC effector cells, antigen-independent T cell activation was observed with the second most potent molecule as well, molecule C. Consequently, the only format that showed strong and concentration-dependent killing of various CEA-expressing tumor cells, but no significant killing of primary epithelial cells, nor antigen-independent T cell activation in the presence of primary epithelial cells or in the absence of target cells is molecule B. Therefore, the "2+1 IgG CrossFab, inverted" format was selected as the preferred format.

Example 4

Comparison of Anti-CEA/Anti-CD3 T Cell Bispecific Molecules Comprising Parental or Humanized CEA Binders

Example 4A

T Cell Activation and Tumor Cell Killing Induced by Different CEA CD3 TCB Molecules (Chimeric T84.66 Versus Humanized Variant 1)

The impact of the CEA binder (parental chimeric T84.66 versus humanized variant 1) on the final potency of the CEA CD3 TCB to induce T cell activation or tumor cell lysis was assessed with a classical tumor cell lysis assay with subsequent staining of T cell activation markers as described above (Example 3B and Example 3C). To further evaluate the safety window, both molecules were co-incubated with effector cells only as well.

Briefly, target cells included in this assay were MKN45 and CCD841 CoN cells. The CEA CD3 TCB molecules A and B were added at the indicated concentration range of 1 pM-20 nM (in triplicates). PBMCs were added to target cells at a final E:T ratio of 10:1. Lysis of tumor or primary epithelial cells was detected at 48 h of incubation with the indicated CEA CD3 TCB molecules. PBMCs of this assay were harvested and stained for CD8+ and the early activation marker CD69 as described above (Example 3C).

FIG. 9 shows that the CEA CD3 TCB molecule containing the parental chimeric T84.66 CEA binder (molecule A) induced both T cell activation (FIG. 9 A, B) and cell lysis (FIG. 9 C, D) not only in the presence of CEA high expressing tumor cells (MKN45), but also in the presence of primary epithelial cells CCD841 with very low CEA expression levels or in the absence of target cells.

In contrast, the CEA CD3 TCB molecule containing the humanized binder (molecule B) induced T cell activation only in the presence of the tumor cell line MKN45, but not in the presence of the primary epithelial cell line. The same is true for cell lysis. In addition, there was no sign of significant T cell activation in the absence of target cells.

Example 4B

To further evaluate the safety window of the CEA CD3 TCB molecules, containing either the parental, chimeric T84.66 CEA binder (molecule A) or the humanized variant 1 (molecule B), a sensitive Jurkat-NFAT reporter assay was conducted. In principle, the simultaneous binding of the TCB molecule to human CEA on antigen-expressing cells and to human CD3 on Jurkat-NFAT reporter cells (a human acute lymphatic leukemia reporter cell line with a NFAT promoter-regulated luciferase expression, GloResponse Jurkat NFAT-RE-luc2P, Promega # CS176501) the NFAT promoter is activated and leads to expression of active firefly luciferase. The intensity of the luminescence signal (obtained upon addition of luciferase substrate) is proportional to the intensity of CD3 activation and signaling.

For the assay, target cells were harvested with trypsin/EDTA and viability was determined using ViCell. 20 000 cells/well were plated in a flat-bottom, white-walled 96-well-plate (#655098, greiner bio-one) and diluted antibodies or medium (for controls) was added at the indicated concentration range (0.4 pM-100 nM). Subsequently, Jurkat-NFAT reporter cells were harvested and viability assessed using ViCell. Cells were resuspended in cell culture medium and added to tumor cells to obtain a final E:T of 2.5:1 and a final volume of 100 µl per well. Cells were incubated for 4 h at 37° C. in a humidified incubator. At the end of the incubation time, 100 µl/well of ONE-Glo solution (1:1 ONE-Glo and assay medium volume per well) were added to wells and incubated for 10 min at room temperature in the dark. Luminescence was detected using WALLAC Victor3 ELISA reader (PerkinElmer2030), 1 sec/well as detection time.

FIG. 10 shows that the CEA CD3 TCB molecule containing the parental chimeric T84.66 CEA binder (molecule A) induced Jurkat T cell activation not only in the presence of CEA high and medium expressing tumor cells (MKN45 and LS174T respectively), but also in the presence of primary epithelial cells CCD841 with very low CEA expression levels or in the absence of target cells (FIG. 10A).

In contrast, the CEA CD3 TCB molecule containing the humanized binder (molecule B) induced Jurkat T cell activation only in the presence of the tumor cell lines MKN45 and LS174T, but not in the presence of the primary epithelial cell line or in the absence of targets (FIG. 10B). These results surprisingly show that the molecule comprising the humanized CEA binder is better in terms of safety.

Example 5

Comparison of Anti-CEA/Anti-CD3 T Cell Bispecific Molecules Comprising Different Humanized CEA Binders

Example 5A

T Cell Activation and Tumor Cell Killing Induced by CEA CD3 TCB Molecules Comprising Different Humanized CEA Binders The impact of the CEA binder (humanized variant 1 (SEQ ID NOs 22 and 23) versus a different humanized CEA binder (SEQ ID NOs 30 and 31, not based on T84.66)) on the final potency of the CEA TCB to induce tumor cell lysis was assessed with a classical tumor cell lysis assay as described above (Example 3B).

Briefly, target cells included in this assay were BxPC-3, NCI-H2122 (ATCC® CRL-5985, a human non-small cell lung cancer cell line, ~13 300 CEA binding sites), COR-L105 (Sigma-Aldrich #92031918, a human lung adenocarcinoma cell line, ~1200 CEA binding sites) and HBEpiC (Chemie Brunschwig AG #3210, human bronchial epithelial cells, <500 CEA binding sites). The CEA CD3 TCB molecule comprising the humanized variant 1 CEA binder (molecule B) was added at the indicated concentration range of 1 pM-20 nM (in triplicates), the CEA CD3 TCB molecule comprising the different humanized CEA binder (i.e. a CEA CD3 TCB molecule of similar structure as molecule B, but comprising a different CEA binder, see SEQ ID NOs 42-45) was added at the indicated concentration range of 6 pM-100 nM. PBMCs were added to target cells at a final E:T ratio of 10:1. Lysis of tumor or primary epithelial cells was detected at 47 h of incubation with the indicated CEA CD3 TCB molecules.

Subsequently, PBMCs of this assay were harvested and stained for the early activation marker CD69 on human CD8+ T cells as described above.

FIG. 11 A-D shows that the CEA CD3 TCB based on humanized variant 1 (molecule B of Example 2) induced stronger T cell activation upon simultaneous binding to T effector and CEA-positive target cells compared to the TCB molecule based on the different humanized CEA binder (referred to in the following as "molecule X", SEQ ID NOs 42-45).

This is in line with the tumor cell lysis data depicted in FIG. 11 E-H, where stronger killing of CEA-expressing tumor cells was observed with the molecule based on humanized variant 1. Remarkably, none of the CEA CD3 TCB molecules induced lysis of CEA-low primary epithelial HBEpiC cells.

Taken together, the CEA CD3 TCB molecule based on humanized variant 1 (molecule B) is able to kill tumor cells with much lower CEA levels as compared to the CEA CD3 TCB based on a different humanized CEA binder (molecule X), while maintaining the safety window.

Example 5B

T Cell Proliferation Induced by CEA CD3 TCB Molecules Comprising Different Humanized CEA Binders As an alternative read-out, the TCB molecules used in Example 5A were analyzed for their capability to induce T cell proliferation upon cross-linkage in the presence of the respective tumor target cells (MKN45, LS174T, HT29). As a control, primary epithelial cells CCD841 CoN with very low CEA expression levels were included as alternative target cells as well.

Briefly, freshly isolated human PBMCs were adjusted to 1 million cells per ml in warm PBS and stained with 0.1 µM CFSE in a humidified incubator at 37° C. for 15 minutes. The staining was stopped by addition of 1/10 volume of FCS, that was incubated for 1 min at room temperature. Subsequently, the cells were centrifuged, re-suspended in pre-warmed medium and incubated for another 30 min in a humidified incubator at 37° C. to remove remaining CFSE. After the incubation the cells were washed once with warm medium, counted and re-suspended in medium at 2 mio cells per ml.

0.02 million target cells were plated per well of a flat-bottom 96-well plate and the different TCB molecules were added at the indicated concentrations. CFSE-labeled PBMCs were added to obtain a final E:T ratio of 10:1 and the assay plates were incubated for five days in a humidified incubator at 37° C.

On day five, the effector cells were harvested, washed twice with FACS buffer (PBS, 0.1% BSA) and stained for surface expression of CD4 and CD8. Proliferation of the different T cell subpopulations was analyzed using a BD FACS Fortessa, equipped with PD FACS Diva Software. Proliferation curves were analyzed by GraphPadPrism5.

FIG. 12 shows that the CEA CD3 TCB based on humanized variant 1 (molecule B) induced stronger T cell activation and subsequent T cell proliferation in the presence of CEA-positive tumor target cells compared to the CEA CD3 TCB based on the different humanized CEA binder (molecule X). Proliferation of CD8+ T cells is shown in FIG. 12 A-D, proliferation of CD4+ T cells in FIG. 12 E-H.

Notably, even after 5 days of incubation no sign of significant T cell activation and subsequent T cell proliferation could be observed with either one of the molecules in the presence of primary epithelial cells (FIG. 12, CCD841 CoN cells).

This further confirms the favorable potency and safety window of the CEA CD3 TCB based on humanized variant 1 (molecule B), even as compared to the CEA CD3 TCB based on a different humanized CEA binder (molecule X).

Example 5C

Binding of Different Anti-CEA/Anti-CD3 T Cell Bispecific (CEA CD3 TCB) Molecules to Cells The binding of the TCB molecules used in Example 5A and B was tested on different CEA-expressing tumor and CD3-expressing Jurkat (DSMZ ACC 282) cells.

Briefly, cells were harvested, counted, checked for viability and re-suspended at $2 \times 10^6$ cells/ml in FACS buffer (100 µl PBS 0.1% BSA). 100 µl of cell suspension (containing $0.2 \times 10^6$ cells) were incubated in round-bottom 96-well plate for 30 min at 4° C. with increasing concentrations of the CEA IgG (31 pM-500 nM), washed twice with cold PBS 0.1% BSA, re-incubated for further 30 min at 4° C. with the FITC-conjugated AffiniPure F(ab')2 Fragment goat anti-human IgG Fcg Fragment Specific secondary antibody (Jackson Immuno Research Lab FITC #109-096-008, 1:40 pre-diluted in PBS 0.1% BSA), washed twice with cold PBS 0.1% BSA and fixed using 150 µl PBS 0.1% BSA, containing 2% PFA and incubation at 4° C. for 20 min. Thereafter, cells were washed once for 8 min at 400 xg, 4° C. and finally re-suspended in 150 µl FACS buffer for the FACS measurement. Fluorescence was measured using Miltenyi MAC-SQuant.

Binding curves and EC50 values were obtained and calculated using GraphPadPrism6 (FIG. 16 A, binding to MKN45 cells, FIG. 16 B, binding to LS-174T cells, FIG. 16 C, binding to HT-29 cells, FIG. 16 D, Table 6).

FIG. 16 shows, that the CEA CD3 molecule based on humanized variant 1 (molecule B) displays better binding to CEA-expressing tumor cells than the CEA CD3 TCB based on a different humanized CEA binder (molecule X) (better EC50 values and maximal binding, particularly on medium and low CEA-expressing target cells). Both TCB molecules show concentration-dependent binding to human CD3 on Jurkat cells.

TABLE 6

Binding of CEA CD3 TCB molecule B and CEA CD3 TCB molecule X to cells (EC50 values, based on binding curves shown in FIG. 16, calculated by Graph Pad Prism).

| Cell Line | Vendor | CEA binding sites | Molecule B EC50 binding (nM) | Molecule X EC50 binding (nM) |
|---|---|---|---|---|
| MKN45 | DSMZ #ACC409 | ~513 300 | 26.61 | 27.85 |
| LS-174T | ATCC ® #CL-188 | ~40 700 | 4.256 | 11.69 |
| HT-29 | DSMZ #ACC299 | ~10 000 | 18.66 | n.c. |

CEA binding sites were determined by a FACS-based Qifikit analysis, according to the manufacturers' instructions, using 10 µg/ml anti-human CEA antibody (Santa Cruz Biotechnology, sc-23928).

Example 5D

Tumor Cell Lysis Induced by CEA CD3 TCB Molecules Comprising Different Humanized CEA Binders T-cell mediated lysis of different tumor cells by the CEA CD3 TCB molecules used in Examples 5A-C was assessed using human tumor cells as target cells, and human PBMCs as effector cells. Lysis of tumor cells was detected at 48 h of incubation with the indicated CEA CD3 TCB molecules. Briefly, target cells were harvested with Trypsin/EDTA, washed, and plated at density of 25 000-30 000 cells/well using flat-bottom 96-well plates. Cells were left to adhere overnight. Peripheral blood mononuclear cells (PBMCs) were prepared by Histopaque density centrifugation of enriched lymphocyte preparations (buffy coats) obtained from healthy human donors. Fresh blood was diluted with sterile PBS and layered over Histopaque gradient (Sigma, # H8889). After centrifugation (450×g, 30 minutes, room temperature), the plasma above the PBMC-containing interphase was discarded and PBMCs transferred in a new falcon tube subsequently filled with 50 ml of PBS. The mixture was centrifuged (400× g, 10 minutes, room temperature), the supernatant discarded and the PBMC pellet washed twice with sterile PBS (centrifugation steps 350×g, 10 minutes). The resulting PBMC population was counted automatically (ViCell) and stored in RPMI1640 medium containing 10% FCS and 1% L-alanyl-L-glutamine (Biochrom, K0302) at 37° C., 5% $CO_2$ in a cell incubator until further use (no longer than 24 h). For the tumor cell lysis assay, the CEA CD3 TCB molecules were added at the indicated concentrations (range of 0.26 pM-20 nM for CEA CD3 TCB based on humanized variant 1 (molecule B), respective 1.28 pM-100 nM for CEA CD3 TCB based on different humanized CEA binder (molecule X), in triplicates). PBMCs were added to target cells at final E:T ratio of 10:1. Target cell killing was assessed after 48 h of incubation at 37° C., 5% $CO_2$ by quantification of LDH released into cell supernatants by apoptotic/necrotic cells (LDH detection kit, Roche Applied Science, #11 644 793 001). Maximal lysis of the target cells (=100%) was achieved by incubation of target cells with 1% Triton X-100. Minimal lysis (=0%) refers to target cells co-incubated with effector cells without bispecific construct.

Figure 17E:
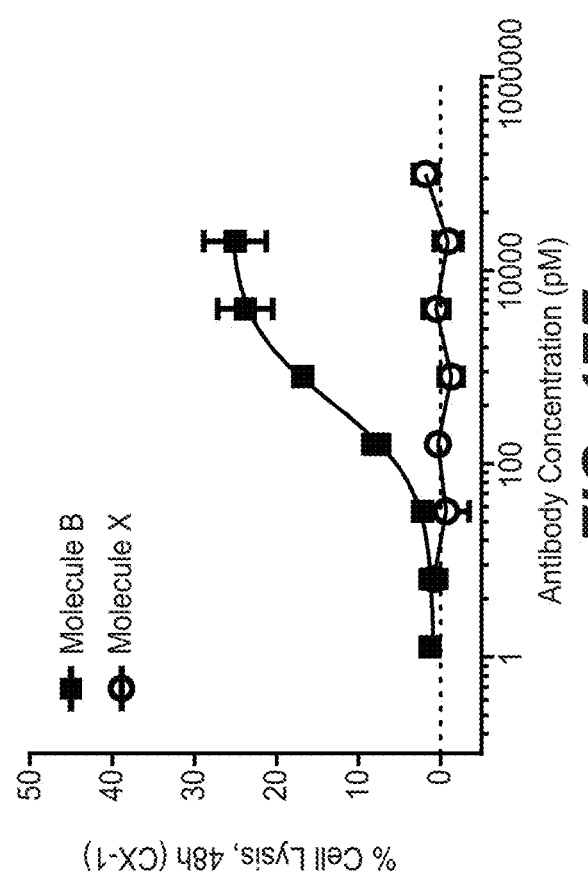

FIG. 17 shows that the CEA CD3 TCB molecule based on humanized variant 1 (molecule B) induced significant and concentration-dependent lysis of all shown tumor cell lines, whereas the CEA CD3 TCB based on the different humanized CEA binder (molecule X) induced tumor lysis of KatoIII and to a lesser extent of NCI-H2122 only. This clearly demonstrates the higher potency of molecule B as compared to molecule X, especially for tumor cell lines with rather low CEA expression levels.

EC50 values of tumor cell lysis were calculated using Graph Pad Prism6 and are given in Table 7 (48 h).

CEA binding sites were determined by a FACS-based Qifikit analysis, according to the manufacturers' instructions, using 10 µg/ml anti-human CEA antibody (Santa Cruz Biotechnology, sc-23928).

Example 6

Comparison of Anti-CEA/Anti-CD3 T Cell Bispecific Molecules Comprising Different Linkers Between CEA and CD3 Binders Example 6A Binding of CEA CD3 TCB Molecules Comprising Different Linkers Between CEA and CD3 Binders to Cells The binding of a variant of molecule B with a longer linker between the CD3 Fab and the CEA Fab (molecule E) was compared to molecule B for its binding to cells.

The binding to human CEA was tested on MKN45, LS174T or HT29, the binding to human CD3 was tested on Jurkat cells. The assay set-up and conditions were as described above (Example 3A). Results are shown in FIG. 13. Binding curves were obtained using GraphPadPrism5 (A, binding to MKN45 cells; B, binding to LS174T cells, C, binding to HT29 cells, D, binding to Jurkat cells). FIG. 13 shows comparable binding of both molecules to human CEA, as well as to human CD3 on cells.

Example 6B

Lysis of Various Tumor Cells by CEA CD3 TCB Molecules Comprising Different Linkers Between CEA and CD3 Binders To further evaluate the impact of the linker length on the potency of the molecule to induce T cell-mediated lysis of CEA-expressing tumor cells, a classical tumor cell lysis assay was performed, as described above (e.g. in Example 3B). The CEA CD3 TCB molecules of Example 6A (molecule B and a corresponding molecule with a longer linker between the CEA and CD3 binders, molecule E) were added at the indicated concentrations (range of 1 pM-20 nM in triplicates) and tumor cell lysis was assessed after 24 h (FIG. 14 A-D) and 48 h (FIG. 14 E-H). EC50 values were calculated by GraphPadPrism5 and are given in Table 8.

TABLE 7

EC50 values (pM) for T-cell mediated lysis of low CEA-expressing tumor cells induced by different CEA CD3 TCB molecules after 48 h.

| Cell Line | Tumor Indication | Reference | CEA binding sites | Molecule B EC50 lysis | Molecule X EC50 lysis |
|---|---|---|---|---|---|
| Kato III | Gastric Cancer | ECACC #86093004 | ~22 700 | 55.4 | 8233 |
| HCC1954 | Breast Cancer | ATCC #CRL-2338 | ~15 750 | 421.7 | — |
| NCI-H2122 | Lung Cancer | ATCC #CRL-598 | ~13 300 | 27.9 | — |
| CX-1 | Colon Cancer | DSMZ #ACC129 | ~4750 | 430.4 | — |
| NCI-H596 | Lung Cancer | ATCC #HTB-178 | ~1 900 | 18.5 | — |

FIG. 14 shows comparable lysis of tumor cells expressing high (MKN45) or medium levels of CEA (LS174T) and no killing of primary epithelial cells CCD841.

However, target cells with low CEA expression levels (HT29) showed higher overall killing with the molecule comprising the longer linker.

TABLE 8

EC50 values (pM) for T-cell mediated killing of low CEA-expressing HT29 tumor cells induced by different CEA CD3 TCB molecules after 24 h and 48 h.

| EC50 (pM) | Molecule B | Molecule E |
|---|---|---|
| 24 h | 512 | 679 |
| 48 h | 338 | 342 |

Example 7

Tumor Cell Lysis and T Cell Activation Induced by CEA CD3 TCB Molecule

Example 7A

Lysis of Cell Lines with Different CEA Expression Levels by CEA CD3 TCB Molecule B In another experiment (FIG. 18A), the CEA CD3 TCB molecule B was characterized in the presence of the low CEA-expressing primary epithelial cell line HBEpiC versus different tumor cell lines to assess its safety. The assay set-up and antibody range was as described in Example 5D for molecule B. EC50 values of tumor cell lysis were calculated using Graph Pad Prism6 and are given in Table 9 (48 h).

As depicted in FIG. 18A and Table 9, primary epithelial cells were not killed by the CEA CD3 TCB molecule, whereas tumor cell lines with varying CEA expression levels could be lysed by the CEA CD3 TCB molecule in a concentration-dependent manner.

TABLE 9

EC50 values (pM) for T-cell mediated lysis of CEA-expressing tumor cells induced by CEA CD3 TCB molecule B after 48 h.

| Cell Line | Reference | CEA binding sites | Molecule B |
|---|---|---|---|
| BxPC-3 | ECACC #93120816 | ~44 000 | 49.63 |
| NCI-H2122 | ATCC #CRL-598 | ~13 300 | 237.5 |
| COR-L105 | Sigma-Aldrich #92031918 | ~1 200 | n.c.* |
| HBEpiC | ScienCell #3210 | <600 | — |

*he EC50 for COR-L105 could not be calculated properly because the curve did not reach saturation at high concentrations.

CEA binding sites were determined by a FACS-based Qifikit analysis, according to the manufacturers' instructions, using 10 µg/ml anti-human CEA antibody (Santa Cruz Biotechnology, sc-23928).

In another experiment (FIG. 19A), the CEA CD3 TCB molecule B was characterized in the presence of another low CEA-expressing primary epithelial cell line (CCD841CoN) versus different tumor cell lines to assess its safety, using another PBMC donor. The assay set-up and antibody range was as described in Example 5D for the CEA CD3 TCB molecule B. EC50 values of tumor cell lysis were calculated using Graph Pad Prism6 and are given in Table 10 (48 h).

TABLE 10

EC50 values (pM) for T-cell mediated lysis of CEA-expressing tumor cells induced by CEA CD3 TCB molecule B after 48 h.

| Cell Line | Reference | CEA binding sites | Molecule B |
|---|---|---|---|
| MKN45 | DSMZ #ACC409 | ~513 300 | 41.24 |
| BxPC-3 | ECACC #93120816 | ~44 000 | 46.98 |
| HT-29 | DSMZ #ACC299 | ~10 000 | 562.7 |
| CCD-841CoN | ATCC #CRL-1790 | <600 | — |

CEA binding sites were determined by a FACS-based Qifikit analysis, according to the manufacturers' instructions, using 10 µg/ml anti-human CEA antibody (Santa Cruz Biotechnology, sc-23928).

Figure 19B:
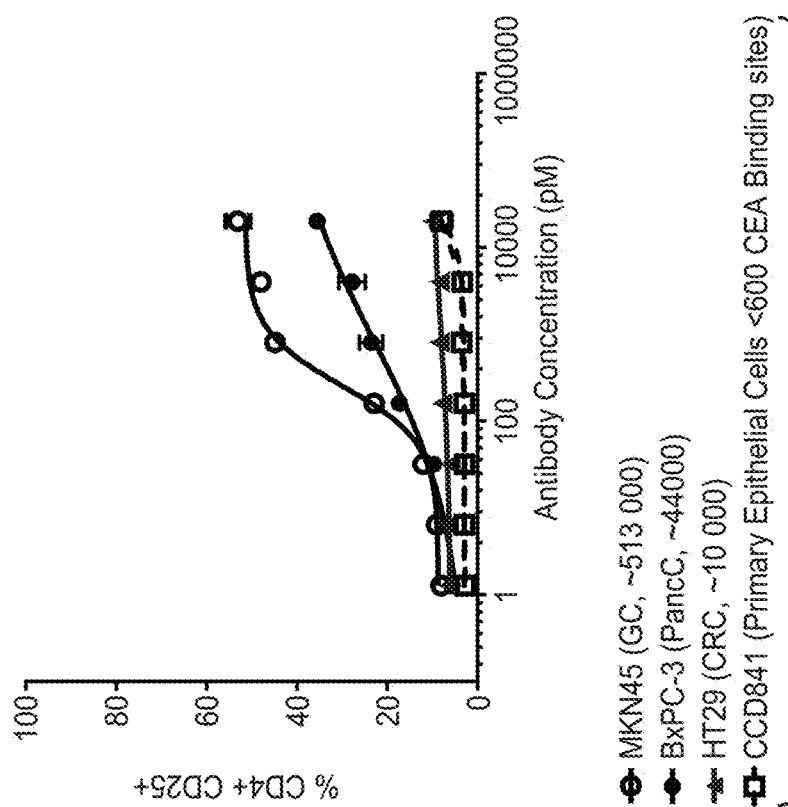
FIGS. 19A-B. Antigen-dependent T cell activation and tumor lysis induced by CEA CD3 TCB molecule B in the presence of CEA-positive tumor cells, but not in the presence of low CEA-expres sing primary epithelial cells. Tumor cell lysis was determined by quantification of LDH released from apoptotic/necrotic tumor cells (A). T cell activation was determined by FACS measurement of up-regulation of the late activation marker CD25 on CD4+ effector cells (B). Depicted are triplicates with SD. EC50 values of tumor cell lysis were calculated by Graph Pad Prism and are presented in Table 10.
Figure 19A:
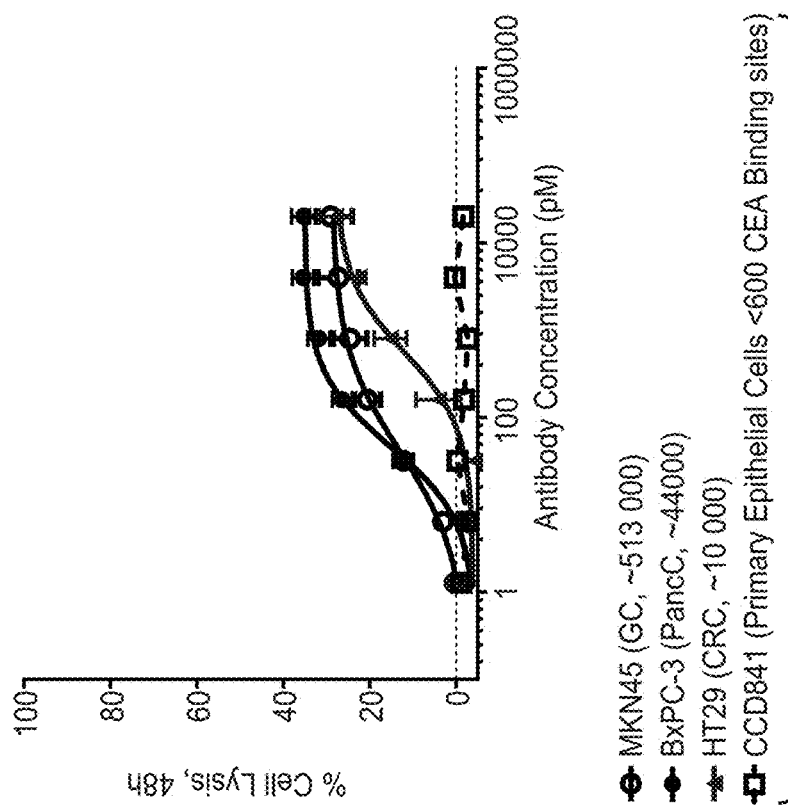

As depicted in FIG. 19A and Table 10, primary epithelial cells were not killed by CEA CD3 TCB molecule B, whereas tumor cell lines with varying CEA expression levels could be lysed by the CEA CD3 TCB molecule in a concentration-dependent manner.

Example 7B

CD69 Up-Regulation on CD4+ Effector Cells after Killing of CEA-Expressing Tumor Cells Induced by CEA CD3 TCB Molecule B Activation of CD4+ and CD8+ effector cells after lysis of CEA-expressing tumor cells mediated by the CEA CD3 TCB molecule B was assessed by FACS analysis using antibodies recognizing the T cell activation marker CD69 (early activation marker).

The antibody and the killing assay conditions were essentially as described above (Example 5D), using the same antibody concentration range (0.26 pM-20 nM in triplicates), E:T ratio 10:1 and an incubation time of 48 h.

After the incubation, PBMCs were transferred to a round-bottom 96-well plate, centrifuged at 350× g for 5 min and washed twice with PBS containing 0.1% BSA. Surface staining for CD8 (FITC anti-human CD8, BD Biosciences #555634), CD4 (PECy7 anti-human CD4, BD Biosciences #557852) and CD69 (PE anti-human CD69 BioLegend #310906) was performed according to the suppliers' indications. Cells were washed twice with 150 µl/well PBS containing 0.1% BSA and fixed for 30 min at 4° C. using 150 µl/well of FACS buffer, containing 2% PFA. After centrifugation, the samples were re-suspended in 200 µl/well PBS 0.1% BSA and analyzed using a BD FACS Fortessa.

FIG. 18B shows that the CEA CD3 TCB molecule B induced concentration-dependent T cell activation in the presence of different CEA-expressing tumor cell lines, as measured by percentage of CD69-positive CD4+ T cells. In contrast, no T cell activation occurred in the presence of low CEA-expressing primary epithelial cells. Similar results were obtained for CD8+ cells (data not shown). The data suggests that therapeutic administration of CEA CD3 TCB molecule B should not lead to adverse effects on primary epithelial cells with low CEA expression levels.

EC50 values of T-cell activation were calculated using Graph Pad Prism6 and are given in Table 11.

TABLE 11

EC50 values (pM) for T-cell activation upon simultaneous binding of CEA CD3 TCB molecule B to CEA-expressing cells and CD3-expressing T cells after 48 h

| Cell Line | Reference | CEA binding sites | Molecule B |
|---|---|---|---|
| BxPC-3 | ECACC #93120816 | ~44 000 | 84.74 |
| NCI-H2122 | ATCC #CRL-598 | ~13 300 | 149.1 |
| COR-L105 | Sigma-Aldrich #92031918 | ~1 200 | n.c.* |
| HBEpiC | ScienCell #3210 | <600 | — |

*The EC50 for COR-L105 could not be calculated properly because the curve did not reach saturation at high concentrations.

CEA binding sites were determined by a FACS-based Qifikit analysis, according to the manufacturers' instructions, using 10 µg/ml anti-human CEA antibody (Santa Cruz Biotechnology, sc-23928).

Example 7C

CD25 Up-Regulation on CD4+ Effector Cells after Killing of CEA-Expressing Tumor Cells Induced by CEA CD3 TCB Molecule B Activation of CD4+ and CD8+ after lysis of CEA-expressing tumor cells mediated by the CEA CD3 TCB molecule B was assessed by FACS analysis using antibodies recognizing the T cell activation marker CD25 (late activation marker).

The antibody and the killing assay conditions were essentially as described above (Example 5D), using the same antibody concentration range (0.26 pM-20 nM in triplicates), E:T ratio 10:1 and an incubation time of 48 h.

After the incubation, PBMCs were transferred to a round-bottom 96-well plate, centrifuged at 350× g for 5 min and washed twice with PBS containing 0.1% BSA. Surface staining for CD8 (FITC anti-human CD8, BioLegend #344704), CD4 (PECy7 anti-human CD4, BioLegend #344612) and CD25 (APC anti-human CD25 BioLegend #302610) was performed according to the suppliers' indications. Cells were washed twice with 150 µl/well PBS containing 0.1% BSA and fixed for 30 min at 4° C. using 150 µl/well of FACS buffer, containing 2% PFA. After centrifugation, the samples were re-suspended in 200 µl/well PBS 0.1% BSA and analyzed using a BD FACS Fortessa.

FIG. 19B shows that the CEA CD3 TCB molecule B induced concentration-dependent T cell activation in the presence of CEA-expressing tumor cells, as measured by percentage of CD25-positive T cells. In contrast, no T cell activation occurred in the presence of low CEA-expressing primary epithelial cells. Similar results were obtained for CD8+ cells (data not shown). The data suggests that therapeutic administration of CEA CD3 TCB molecule B should not lead to adverse effects on primary epithelial cells with low CEA expression levels.

Example 8

Specific Binding of CEA CD3 Molecule B to Human CEACAM5

To show the specific binding of the CEA CD3 TCB molecule B to human CEACAM5, but not to the other closest family members CEACAM1 and CEACAM6, binding of CEA CD3 TCB molecule B to transient HEK293T transfected cells, expressing either human CEACAM5, CEACAM1 or CEACAM6, was evaluated.

Figure 20A:
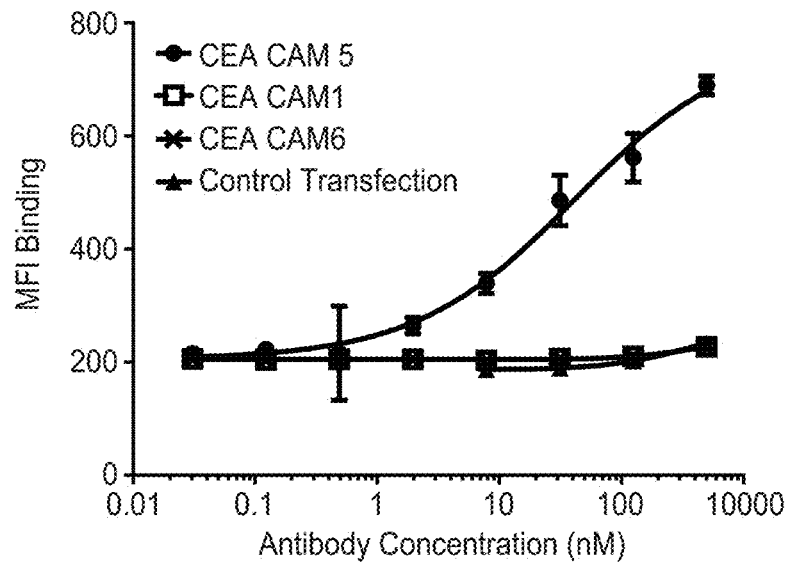
FIGS. 20A-B. (A) Binding of CEA CD3 TCB molecule B to transient HEK293T transfectants, expressing either human CEACAM5, CEACAM1 or CEACAM6. Depicted are triplicates with SD. (B) Binding of an anti-CD66 antibody to transient HEK293T transfectants shows the transfection efficacy, respectively expression levels of the three CEACAM family members. Depicted are MFI (median fluorescence signals), based on triplicates and SD.

Briefly, cells were harvested, counted, checked for viability and re-suspended at $1\times10^6$ cells/ml in FACS buffer (100 µl PBS 0.1% BSA). 100 µl of the cell suspension (containing $0.1\times10^6$ cells) were plated iton round-bottom 96-well plates and washed twice with 150 µl of cold PBS. Cells were stained for 30 min at 4° C., using a 1:5000 pre-diluted suspension of the fixable viability dye eFluor660 (eBioscience, #65-0864-14) in PBS. Thereafter, the cells were washed twice with PBS, once with FACS buffer and stained for 30 min at 4° C. with increasing concentrations of the CEA CD3 TCB molecule B. The antibody concentration range was 30.5 pM-500 nM. Cells were washed twice with cold PBS 0.1% BSA, re-incubated for further 30 min at 4° C. with the FITC-conjugated AffiniPure F(ab')2 Fragment goat anti-human IgG Fcg Fragment Specific secondary antibody (Jackson Immuno Research Lab FITC #109-096-098, 1:50 pre-diluted in PBS 0.1% BSA), washed twice with cold PBS 0.1% BSA and fixed using 150 µl PBS 0.1% BSA, containing 2% PFA and incubation at 4° C. for 20 min. Thereafter, cells were washed once for 8 min at 400× g, 4° C. and finally re-suspended in 150 µl FACS buffer for the FACS measurement. Fluorescence was measured using BD FACS Cantoll. Binding curves were obtained using GraphPadPrism6 (FIG. 20A).

Figure 20B:
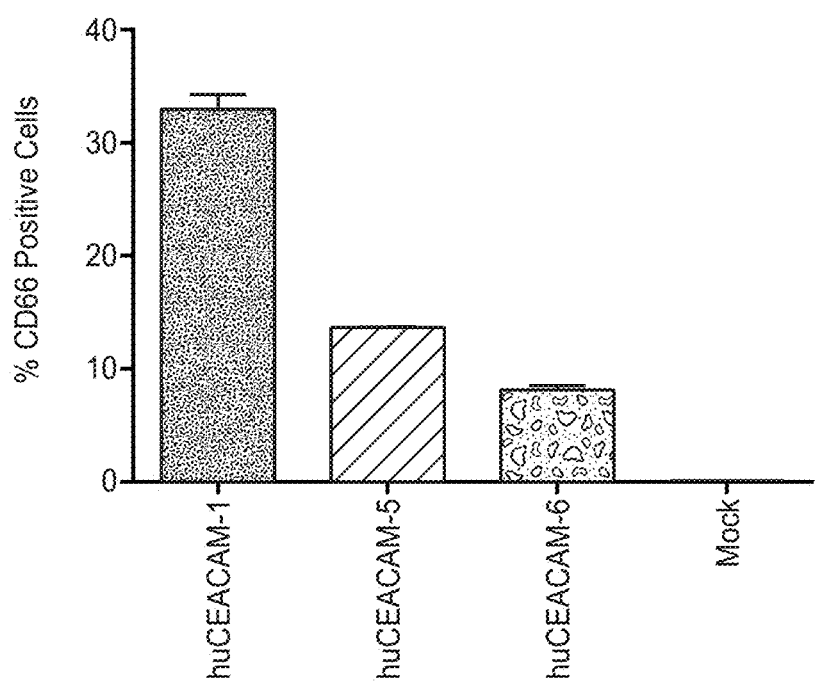

To determine the transfection efficacy, all transfectants were stained for 30 min at 4° C., using a commercially available anti-human CD66 antibody (FITC mouse anti-human CD66, BD Biosciences #551479, 20 µl per sample) (FIG. 20B). As shown in FIG. 20B, the highest expression level was detected for human CEACAM1, followed by CEACAM5 and CEACAM6. FIG. 20A clearly shows that the CEA CD3 TCB molecule B shows concentration-dependent binding to transient transfectants expressing human CEACAM5, but not to any of the other transfectants, expressing human CEACAM1 or CEACAM6, demonstrating the specificity of the binding to CEA.

Example 9

Figure 15:
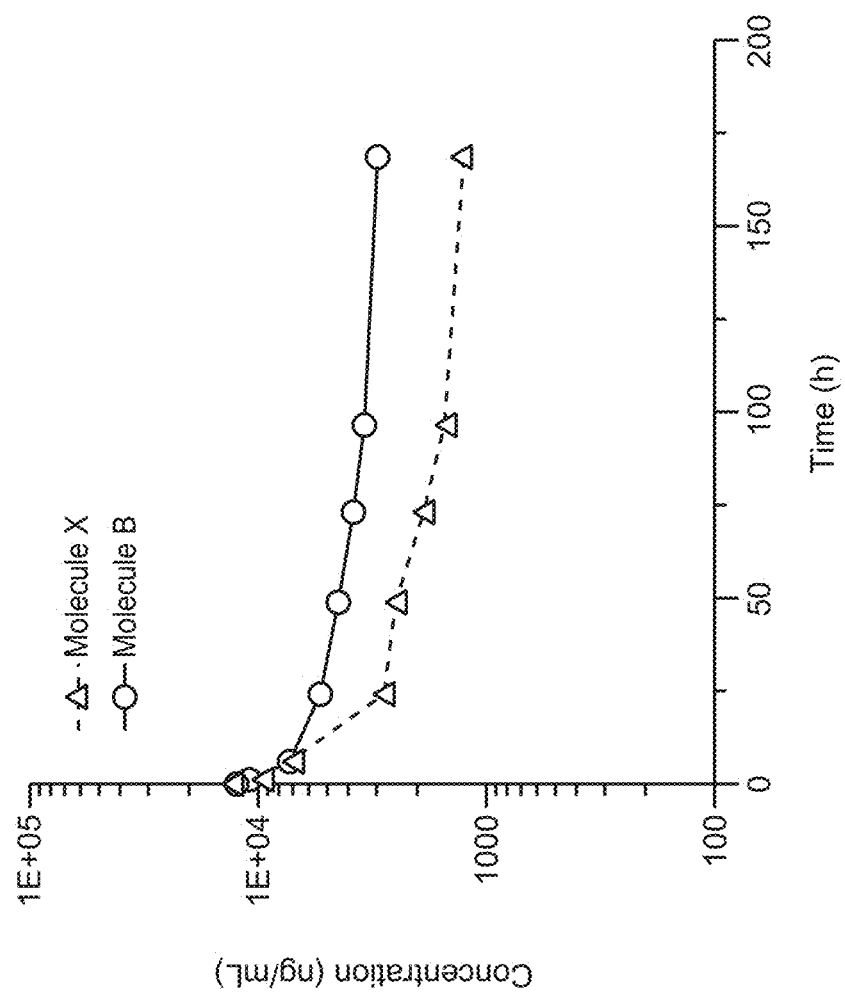
FIG. 15. Comparison of pharmacokinetics of CEA CD3 TCB molecule B and CEA CD3 TCB molecule X after a single i.v. bolus administration in NOG mice.
Figure 16A:
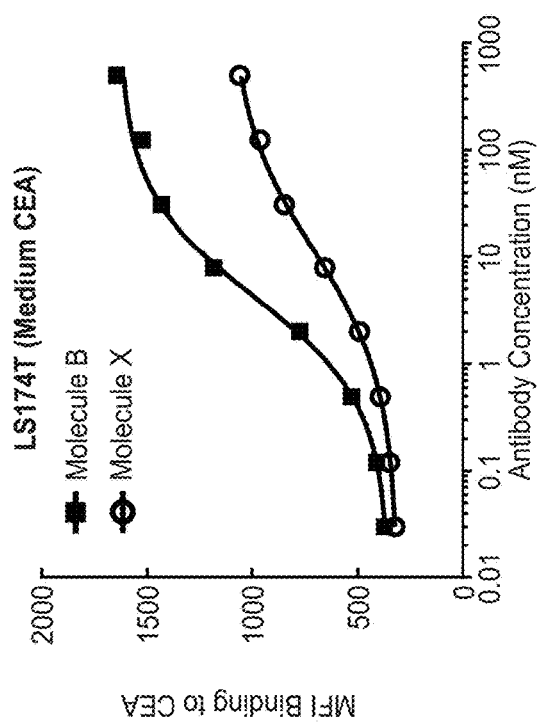
FIGS. 16A-D. Binding of different CEA CD3 TCB molecules to human CEA, expressed on MKN45 (A), LS174T (B) and HT29 (C) cells, or to human CD3, expressed on Jurkat cells (D). Depicted are triplicates and SD. EC50 values, based on binding curves, were calculated by Graph Pad Prism and are presented in Table 6.
Figure 16B:
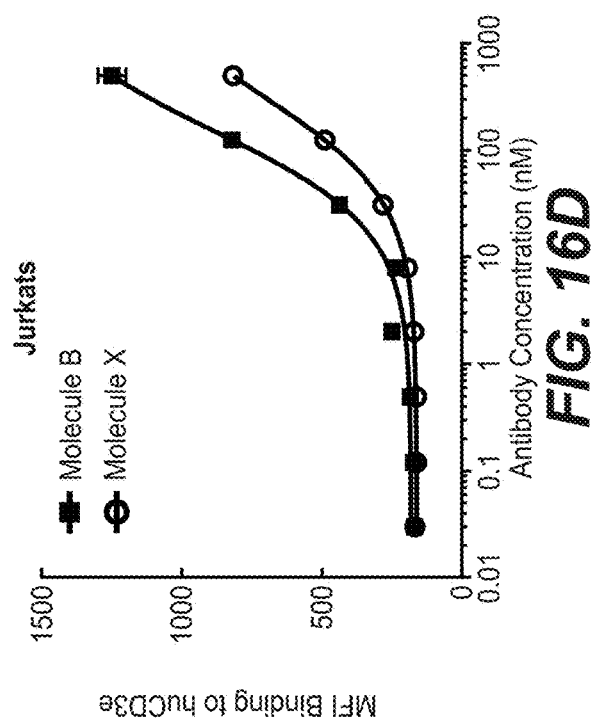
Figure 16C:
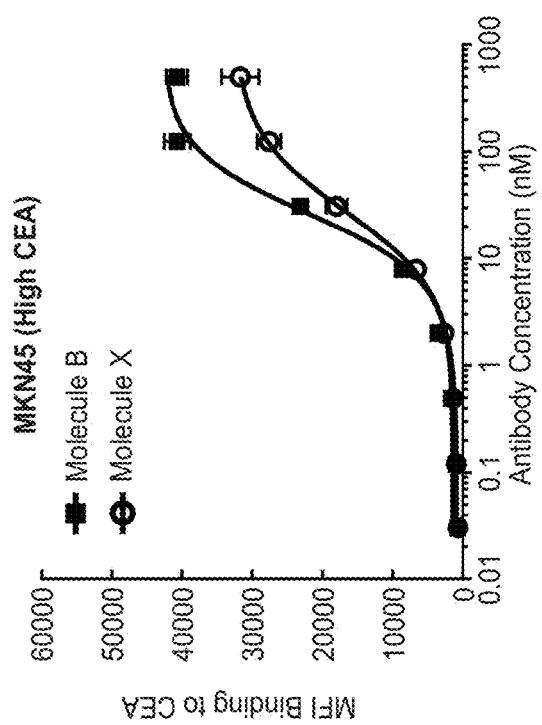
Figure 16D:
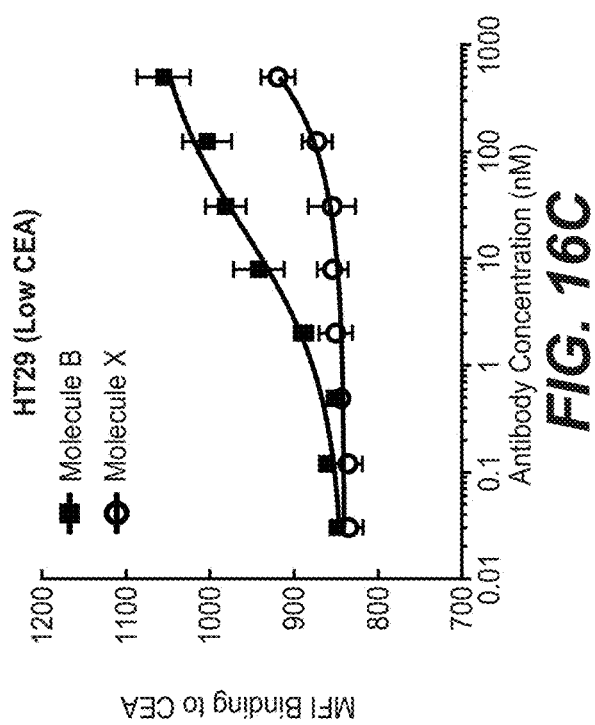

Single Dose PK of CEA CD3 TCB Molecules Comprising Different Humanized CEA Binders in Healthy NOG Mice Single dose pharmacokinetic studies (SDPK) were performed in healthy NOG mice to evaluate exposure of CEA CD3 TCB molecule B and CEA CD3 TCB molecule X (FIG. 15). An intravenous (i.v.) bolus injection of 0.5 mg/kg was administered to NOG mice and blood samples were taken at selected time points for pharmacokinetic evaluation. A generic immunoassay was used for measuring total concentrations of CEA CD3 TCB molecules. The calibration range of the standard curve for both TCB molecules was 0.078 to 5 ng/ml, where 1.5 ng/ml is the lower limit of quantification (LLOQ).

A biphasic decline was observed with a half-life of 10 days (non-compartmental analysis) for CEA CD3 TCB molecule B and 6.5 days for CEA CD3 TCB molecule X. A clearance (CL) of 8.1 ml/d/kg was detected for CEA CD3 TCB molecule B and 19 ml/d/kg for CEA CD3 TCB molecule X, respectively (Table 12). Overall, CEA CD3 TCB molecule B showed longer half-life and lower CL in NOG mice compared to CEA CD3 TCB molecule X.

The Phoenix v6.4 from Pharsight Ltd was used for PK analysis, modelling and simulation.

TABLE 12

Pharmacokinetic parameters of a 0.5 mg/kg iv bolus administration of CEA CD3 TCB molecules in NOG mice.

| Construct | Half-life (d) | CL (mL/d/kg) |
|---|---|---|
| Molecule B | 10 | 8.1 |
| Molecule X | 6.5 | 19 |

Example 10

Anti-Tumor Activity of CEA CD3 TCB Molecules Comprising Different Humanized CEA Binders in the MKN45 Model Anti-tumor activity of CEA CD3 TCB molecule B and CEA CD3 TCB molecule X was tested in fully humanized NOD/Shi-scid/IL-2Rγ$^{null}$ (NOG) mice bearing the gastric carcinoma cell line MKN45.

Figure 21A:
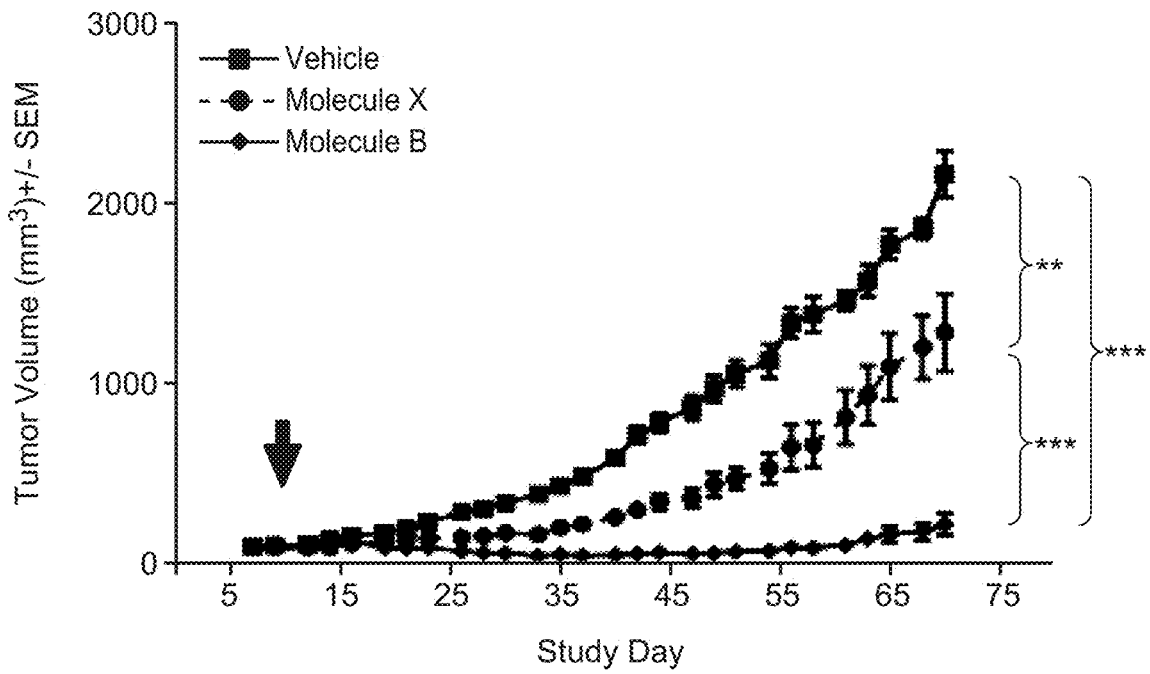
FIGS. 21A-C. Anti-tumor activity of CEA CD3 TCB molecule B versus CEA CD3 TCB molecule X in the MKN45 model in fully humanized NOG mice. Different doses and schedules of administration were tested: (A) 2.5 mg/kg twice/week, (B) 2.5 mg/kg once/week, (C) 0.5 mg/kg once/week. Black arrow indicates start of therapy. Treatment was administered for 9 weeks. *p<0.05 p<0.01; *p<0.001 Two-tailed unpaired t-test at study termination (day 70) (8<n<9).
Figure 21B:
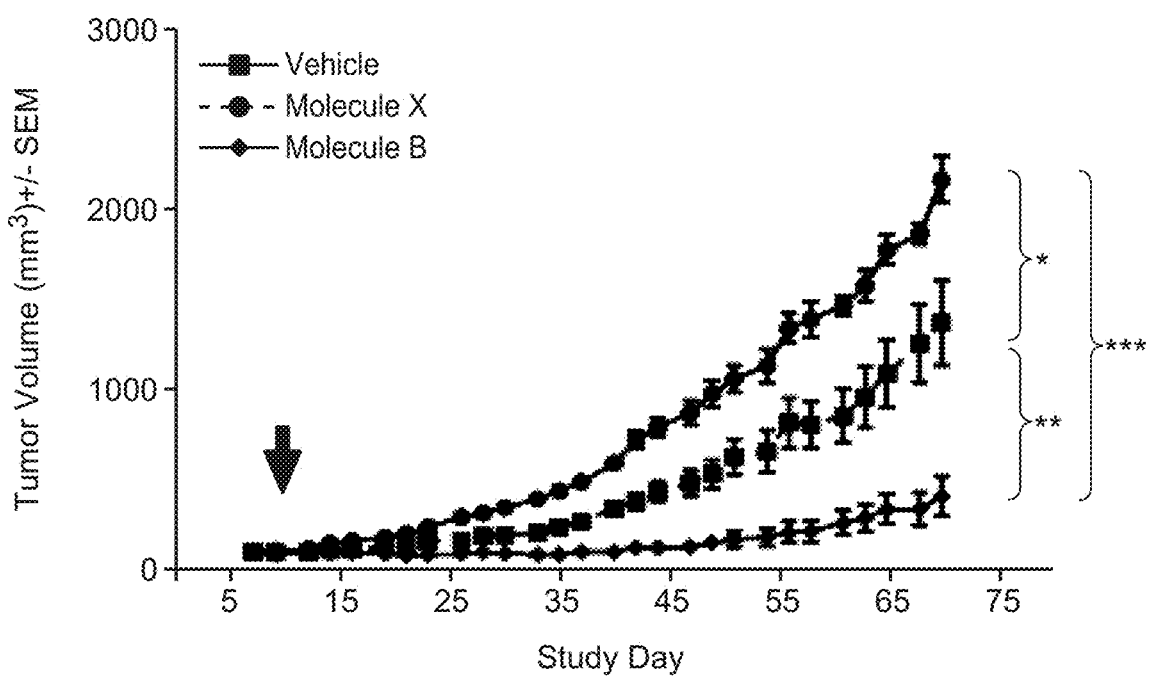
Figure 21C:
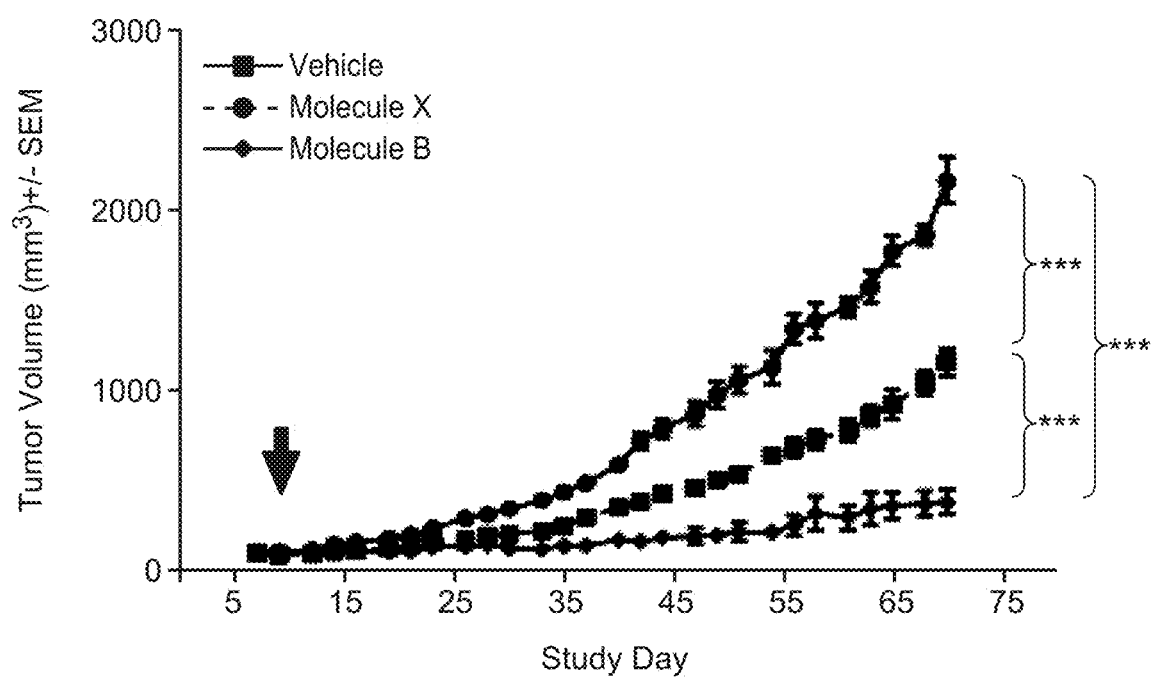

Fully humanized NOG mice at 14 weeks of age, bearing physiological levels of circulating human B- and T-cells (Hayakawa et al., Stem Cells 27 (2009) 175-182), were injected sub-cutaneous (s.c.) with 1×10$^6$ MKN45 cells (originally obtained from the DSMZ-Deutsche Sammlung von Mikroorganismen and Zellkulturen GmbH). When average tumor volume reached 100 mm$^3$, mice received CEA CD3 TCB molecule X or CEA CD3 TCB molecule B i.v. at the dose of 2.5 mg/kg administered either twice or once a week, and at the dose of 0.5 mg/kg administered once a week (FIG. 21). CEA CD3 TCB molecule B showed significantly stronger anti-tumor activity at all tested doses and schedules. Importantly, only CEA CD3 TCB molecule B could mediate tumor regression with tumor-free mice detected in the 2.5 mg/kg and 0.5 mg/kg treated groups (FIG. 21, Table 13).

TABLE 13

Number of tumor-free mice per group at study termination (day 70).

| Treatment | Tumor-free mice at termination (study day 70) |
|---|---|
| Vehicle | 0/9 |
| Molecule X 2.5 mg/kg twice/week | 0/9 |
| Molecule B 2.5 mg/kg twice/week | 3/9 |
| Molecule X 2.5 mg/kg once/week | 0/9 |
| Molecule B 2.5 mg/kg once/week | 1/9 |
| Molecule X 0.5 mg/kg once/week | 0/9 |
| Molecule B 0.5 mg/kg once/week | 1/8 |

Example 11

Figure 22:
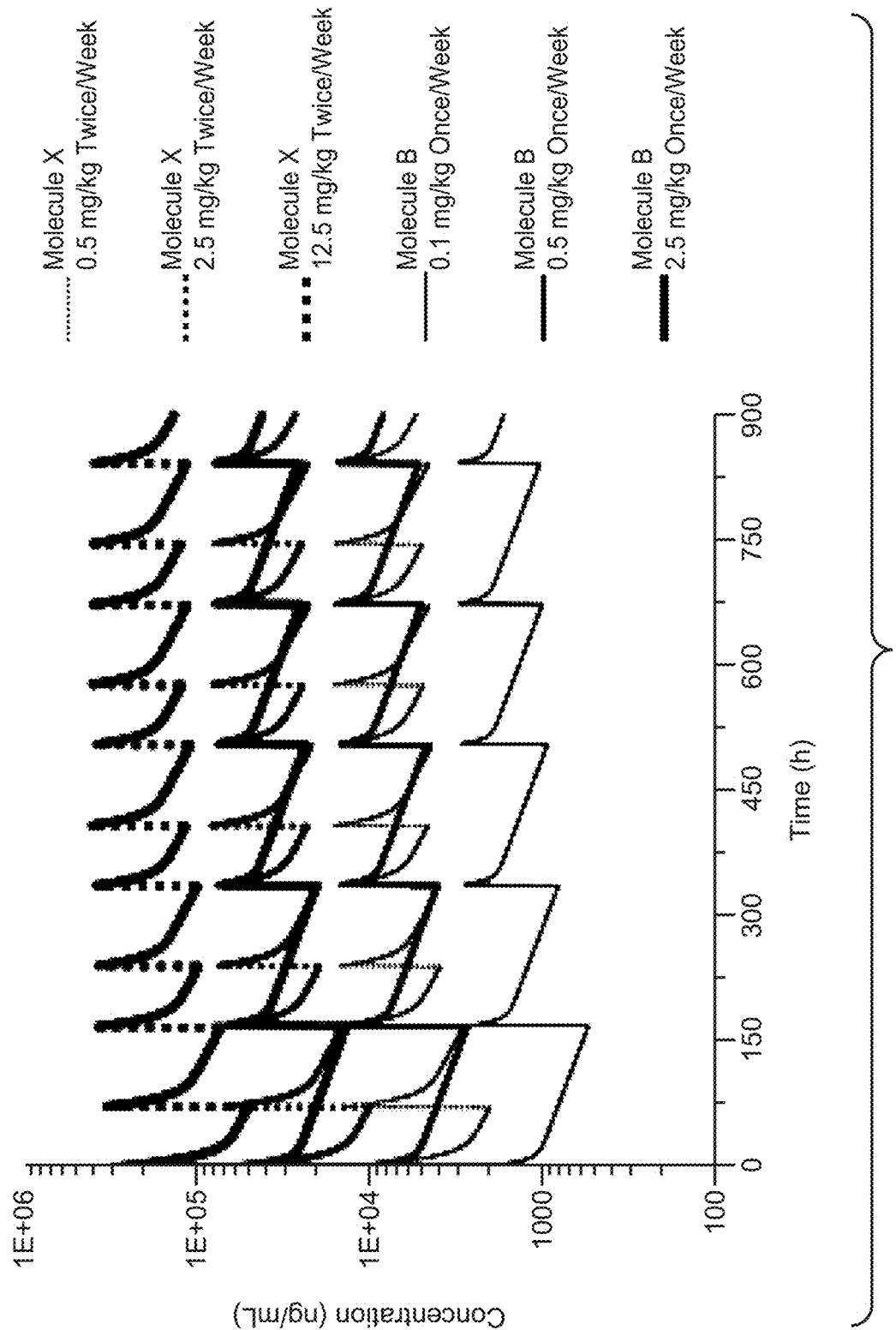
FIG. 22. Simulated PK of different dose levels and schedules used in the dose-range efficacy study (Example 12). A 2-compartment model was used and the simulation was based on the SDPK data.

Based on the SDPK data shown in Example 9, a 2-compartmental model was compiled to describe the PK of CEA CD3 TCB molecule B and CEA CD3 TCB molecule X in NOG mice (FIG. 22). The different dose levels and schedules selected for the dose-range efficacy study described in the next example were simulated. As shown in FIG. 22, to compensate for the lower clearance of CEAS CD3 TCB molecule B the design of the study was adapted. The frequency of administration for CEA CD3 TCB molecule X was increased to a twice weekly schedule and also higher dose levels up to 12.5 mg/kg were used. The simulated profiles show that at a bi-weekly dose of 12.5 mg of CEA CD3 TCB molecule X the exposure is substantially higher as compared to 0.5 mg/kg CEA CD3 TCB molecule B.

Example 12

Figure 23A:
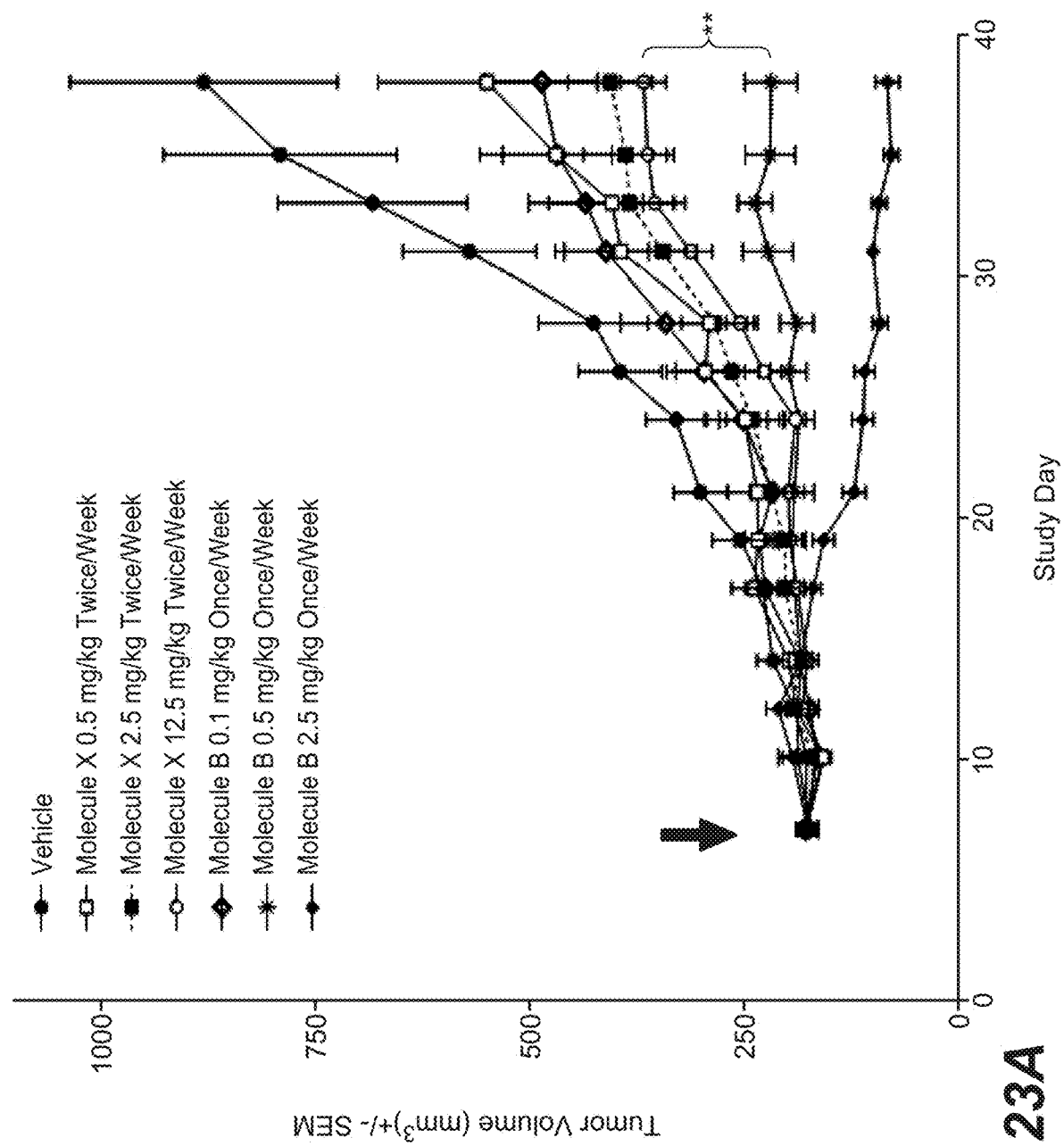

Dose-Range Efficacy Study with CEA CD3 TCB Molecules Comprising Different Humanized CEA Binders in the MKN45 Model To more specifically assess the in vivo fold difference in anti-tumor activity between the two molecules, CEA CD3 TCB molecule B and CEA CD3 TCB molecule X were tested at a larger range of doses in fully humanized NSG mice bearing the gastric carcinoma cell line MKN45 (FIG. 23).

Fully humanized NSG mice were injected s.c. with 1×10$^6$ MKN45 cells. When average tumor volume reached 180 mm$^3$, mice received CEA CD3 TCB molecule B or CEA CD3 TCB molecule X i.v. at the different doses and schedules depicted in FIG. 23. The doses and schedules were selected based on the analysis described in Example 11. The efficacy data obtained clearly show that CEA CD3 TCB molecule B could mediate stronger anti-tumor activity when compared to CEA CD3 TCB molecule X with a significant fold difference of at least 25 times (as highlighted by the star in the graph on FIG. 23).

Example 13

Figure 24:
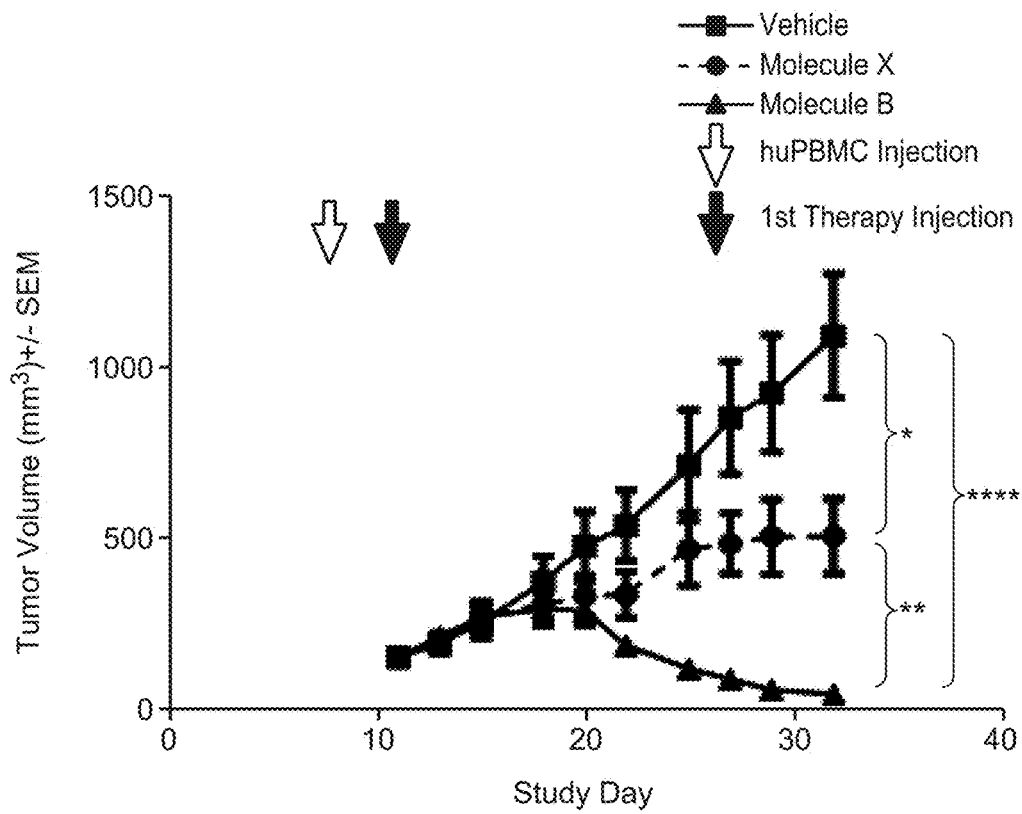
FIG. 24. Anti-tumor activity of CEA CD3 TCB molecule B versus CEA CD3 TCB molecule X (2.5 mg/kg, once a week) in the HPAF-II model in NOG mice with huPBMC transfer. Grey arrow indicates human PBMC (huPBMC) injection and black arrow indicates start of therapy. Treatment was administered for 3 weeks. *p<0.05; p<0.01; **p<0.0001 Two-tailed unpaired t-test at study termination (day 32) (n=10).

Anti-Tumor Activity of CEA CD3 TCB Molecules Comprising Different Humanized CEA Binders in the HPAF-II Model Anti-tumor activity of CEA CD3 TCB molecule B and CEA CD3 TCB molecule X was tested in NOD.Cg-Prkdc$^{scid}$ Il2rg$^{tm1Wjl}$/SzJ (NSG) mice bearing the human pancreatic carcinoma cell line HPAF-II and transferred with human peripheral mononuclear cells (PBMC). Briefly, female NOG mice were injected sub-cutaneously (s.c.) with 1×10$^6$ HPAF-II cells (originally obtained from the American Type Culture Collection (ATCC)). When average tumor volume reached 150 mm$^3$, mice received i.v. injection of human PBMC (10×10$^6$ cells per mouse) as source of human T-cells. Three days later, mice received CEA CD3 TCB molecule B or CEA CD3 TCB molecule X i.v. at a dose of 2.5 mg/kg, administered once a week. As depicted in FIG. 24, after 3 weeks treatment, both TCB molecules s show potent anti-tumor activity, with only molecule B able to mediate tumor regression (at day 32, study day termination) (FIG. 24).

Example 14

Figure 25:
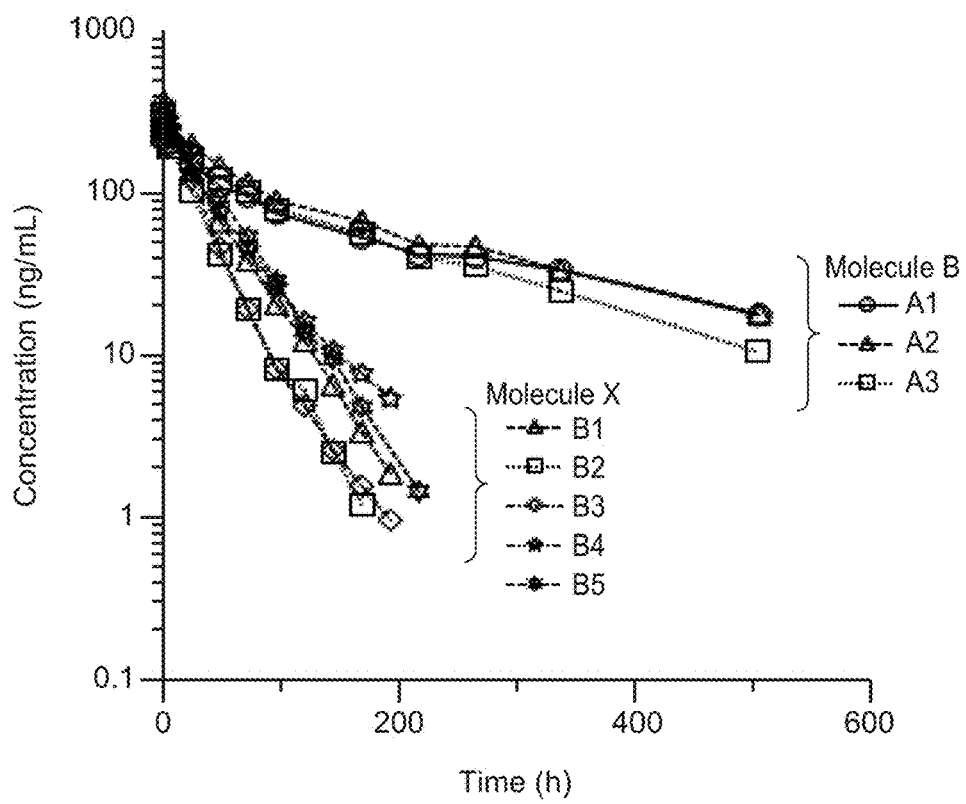
FIG. 25. Comparison of pharmacokinetics of CEA CD3 TCB molecule B and CEA CD3 TCB molecule X after iv bolus administration in cynomolgus monkeys. The pharmacokinetics of individual representative animals is depicted.

Single Dose PK of CEA CD3 TCB Molecules Comprising Different Humanized CEA Binders in Cynomolgus Monkeys Single dose pharmacokinetic studies (SDPK) were performed in cynomolgus monkeys to assess the exposure of CEA CD3 TCB molecule B and CEA CD3 TCB molecule B, respectively (FIG. 25). An IV bolus administration of 0.01 mg/kg was administered and blood samples were taken at selected time points for pharmacokinetic evaluation. Specific immunoassays were used measuring binding competent concentrations of CEA CD3 TCB molecule B and CEA CD3 TCB molecule X. For CEA CD3 TCB molecule X the lower limit of quantification (LLOQ) was 0.1 ng/ml and for CEA CD3 TCB molecule B 0.44 ng/ml.

A biphasic decline was observed with a half-life of 184±40 hours (non-compartmental analysis) for CEA CD3 TCB molecule B versus 32±11 hours for CEA CD3 TCB molecule X. A clearance (CL) of 7±0.9 ml/d/kg was detected for CEA CD3 TCB molecule B and 25±6 ml/d/kg for CEA CD3 TCB molecule X. Overall, CEA CD3 TCB molecule B showed IgG-like properties and displayed a longer half-life and a slower clearance in cynomolgus monkeys as compared to CEA CD3 TCB molecule X.

TABLE 14

Summary of pharmacokinetic parameters of CEA CD3 TCB molecule B in serum after a single intravenous (bolus) administration of 0.01 mg/kg to cynomolgus monkeys (N = 3).

| ID | Half Life (h) | CL (ml/day/kg) | Cmax (ng/ml) | $AUC_{INF}$ (h * ng/ml) | Vc (ml/kg) |
|---|---|---|---|---|---|
| Mean | 184 | 7 | 257 | 33351 | 39 |
| SD | 40 | 0.9 | 18 | 4259 | 2 |
| CV % | 22 | 13 | 7 | 13 | 6 |

TABLE 15

Summary of pharmacokinetic parameters of CEA CD3 TCB molecule X in serum after a single intravenous (bolus) administration of 0.01 mg/kg to cynomolgus monkeys (N = 5).

| ID | Half Life (h) | CL (ml/day/kg) | Cmax (ng/ml) | $AUC_{INF}$ (h * ng/ml) | Vc (ml/kg) |
|---|---|---|---|---|---|
| Mean | 32 | 25 | 321 | 9991 | 31 |
| SD | 11 | 6 | 24 | 2133 | 2 |
| CV % | 34 | 23 | 7 | 21 | 7 |

The Phoenix v6.4 from Pharsight Ltd was used for PK assessment.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

What is claimed is:

1. A T cell activating bispecific antigen-binding molecule comprising:
   (a) a first Fab molecule which specifically binds to a first antigen;
   (b) a second Fab molecule which specifically binds to a second antigen, and wherein the variable domains VL and VH of the Fab light chain and the Fab heavy chain are replaced by each other;
   wherein the first antigen is CD3 and the second antigen is CEA, or the first antigen is CEA and the second antigen is CD3;
   wherein the Fab molecule which specifically binds to CD3 comprises a heavy chain variable region comprising the heavy chain complementarity determining region (HCDR) 1 of SEQ ID NO: 4, the HCDR 2 of SEQ ID NO: 5, and the HCDR 3 of SEQ ID NO: 6, and a light chain variable region comprising the light chain complementarity determining region (LCDR) 1 of SEQ ID NO: 8, the LCDR 2 of SEQ ID NO: 9, and the LCDR 3 of SEQ ID NO: 10; and
   wherein the Fab molecule which specifically binds to CEA comprises a heavy chain variable region comprising the amino acid sequence of SEQ ID NO: 22 and a light chain variable region comprising the amino acid sequence of SEQ ID NO: 23.

2. The T cell activating bispecific antigen-binding molecule of claim 1, wherein the CD3 is CD3 epsilon.

3. The T cell activating bispecific antigen-binding molecule of claim 1, wherein the Fab molecule which specifically binds to CD3 comprises a heavy chain variable region comprising an amino acid sequence that is at least 95% identical to the amino acid sequence of SEQ ID NO: 3 and a light chain variable region comprising an amino acid sequence that is at least 95% identical to the amino acid sequence of SEQ ID NO: 7.

4. The T cell activating bispecific antigen-binding molecule of claim 1, further comprising a third Fab molecule which specifically binds to the first antigen.

5. The T cell activating bispecific antigen-binding molecule of claim 4, wherein the third Fab molecule is identical to the first Fab molecule.

6. The T cell activating bispecific antigen-binding molecule of claim 4, wherein the first Fab molecule and the third Fab molecule specifically bind to CEA, and the second Fab molecule specifically binds to CD3.

7. The T cell activating bispecific antigen-binding molecule of claim 1, additionally comprising an Fc domain comprising a first subunit and a second subunit capable of stable association.

8. The T cell activating bispecific antigen-binding molecule of claim 1, wherein the first Fab molecule is fused at the C-terminus of the Fab heavy chain to the N-terminus of the Fab heavy chain of the second Fab molecule.

9. The T cell activating bispecific antigen-binding molecule of claim 7, wherein the second Fab molecule is fused at the C-terminus of the Fab heavy chain to the N-terminus of the first subunit or the second subunit of the Fc domain.

10. The T cell activating bispecific antigen-binding molecule of claim 7, further comprising a third Fab molecule which specifically binds to the first antigen, wherein the third Fab molecule is fused at the C-terminus of the Fab heavy chain to the N-terminus of the first subunit or the second subunit of the Fc domain.

11. The T cell activating bispecific antigen-binding molecule of claim 7, further comprising a third Fab molecule which specifically binds to the first antigen, wherein the second Fab molecule and the third Fab molecule are each fused at the C-terminus of the Fab heavy chain to the N-terminus of one of the subunits of the Fc domain, and the first Fab molecule is fused at the C-terminus of the Fab heavy chain to the N-terminus of the Fab heavy chain of the second Fab molecule.

12. The T cell activating bispecific antigen-binding molecule of claim 7, wherein the Fc domain is an IgG Fc domain.

13. The T cell activating bispecific antigen-binding molecule of claim 7, wherein the Fc domain is a human Fc domain.

14. The T cell activating bispecific antigen-binding molecule of claim 7, wherein the Fc domain comprises a modification promoting the association of the first subunit and the second subunit of the Fc domain.

15. The T cell activating bispecific antigen-binding molecule of claim 14, wherein in the CH3 domain of the first subunit of the Fc domain an amino acid residue is replaced with an amino acid residue having a larger side chain volume, thereby generating a protuberance within the CH3 domain of the first subunit which is positionable in a cavity within the CH3 domain of the second subunit, and in the CH3 domain of the second subunit of the Fc domain an amino acid residue is replaced with an amino acid residue having a smaller side chain volume, thereby generating a cavity within the CH3 domain of the second subunit within which the protuberance within the CH3 domain of the first subunit is positionable.

16. The T cell activating bispecific antigen-binding molecule of claim 15, wherein in the CH3 domain of the first subunit of the Fc domain the threonine residue at position 366 is replaced with a tryptophan residue (T366W), and in the CH3 domain of the second subunit of the Fc domain the tyrosine residue at position 407 is replaced with a valine residue (Y407V) (numberings according to Kabat EU index).

17. The T cell activating bispecific antigen-binding molecule of claim 16, wherein in the first subunit of the Fc domain additionally the serine residue at position 354 is replaced with a cysteine residue (S354C) or the glutamic acid residue at position 356 is replaced with a cysteine residue (E356C), and in the second subunit of the Fc domain additionally the tyrosine residue at position 349 is replaced by a cysteine residue (Y349C) (numberings according to Kabat EU index).

18. The T cell activating bispecific antigen-binding molecule of claim 7, wherein the Fc domain comprises one or more amino acid substitution that reduces binding to an Fc receptor and/or effector function.

19. The T cell activating bispecific antigen-binding molecule of claim 18, wherein said one or more amino acid substitution is at one or more position selected from the group consisting of L234, L235, and P329 (numberings according to Kabat EU index).

20. The T cell activating bispecific antigen-binding molecule of claim 7, wherein each subunit of the Fc domain comprises the amino acid substitutions L234A, L235A, and P329G (numberings according to Kabat EU index).

21. One or more isolated polynucleotide encoding the T cell activating bispecific antigen-binding molecule of claim 1.

22. A host cell comprising the polynucleotide(s) of claim 21.

23. A method of producing a T cell activating bispecific antigen-binding molecule, the method comprising culturing the host cell of claim 22 under conditions suitable for the expression of the T cell activating bispecific antigen-binding molecule, wherein the T cell activating bispecific antigen-binding molecule comprises:
  (a) a first Fab molecule which specifically binds to a first antigen;
  (b) a second Fab molecule which specifically binds to a second antigen, and wherein the variable domains VL and VH of the Fab light chain and the Fab heavy chain are replaced by each other;
  wherein the first antigen is CD3 and the second antigen is CEA, or the first antigen is CEA and the second antigen is CD3;
  wherein the Fab molecule which specifically binds to CD3 comprises a heavy chain variable region comprising the HCDR 1 of SEQ ID NO: 4, the HCDR 2 of SEQ ID NO: 5, and the HCDR 3 of SEQ ID NO: 6, and a light chain variable region comprising the LCDR 1 of SEQ ID NO: 8, the LCDR 2 of SEQ ID NO: 9, and the LCDR 3 of SEQ ID NO: 10; and
  wherein the Fab molecule which specifically binds to CEA comprises a heavy chain variable region comprising the amino acid sequence of SEQ ID NO: 22 and a light chain variable region comprising the amino acid sequence of SEQ ID NO: 23.

24. The T cell activating bispecific antigen-binding molecule produced by the method of claim 23.

25. A pharmaceutical composition comprising the T cell activating bispecific antigen-binding molecule of claim 1 and a pharmaceutically acceptable carrier.

26. The T cell activating bispecific antigen-binding molecule of claim 6, wherein the CD3 is CD3 epsilon.

27. The T cell activating bispecific antigen-binding molecule of claim 12, wherein the IgG Fc domain is an $IgG_1$ Fc domain or an $IgG_4$ Fc domain.

28. The T cell activating bispecific antigen-binding molecule of claim 16, wherein in the second subunit of the Fc domain the threonine residue at position 366 is replaced with a serine residue (T366S) and the leucine residue at position 368 is replaced with an alanine residue (L368A) (numberings according to Kabat EU index).

29. The T cell activating bispecific antigen-binding molecule of claim 1, wherein the Fab molecule which specifically binds to CD3 comprises a heavy chain variable region comprising the amino acid sequence of SEQ ID NO: 3 and a light chain variable region comprising the amino acid sequence of SEQ ID NO: 7.

30. The T cell activating bispecific antigen-binding molecule of claim 1, wherein the first Fab molecule is a conventional Fab molecule.

31. The T cell activating bispecific antigen-binding molecule of claim 4, wherein the third Fab molecule is a conventional Fab molecule.

32. The T cell activating bispecific antigen-binding molecule of claim 1, wherein (i) in the constant domain CL of the first Fab molecule the amino acid at position 124 is substituted independently by lysine (K), arginine (R), or histidine (H) (numbering according to Kabat), and in the constant domain CH1 of the first Fab molecule the amino acid at position 147 or the amino acid at position 213 is substituted independently by glutamic acid (E) or aspartic acid (D) (numbering according to Kabat EU index); or (ii) in the constant domain CL of the second Fab molecule the amino acid at position 124 is substituted independently by lysine (K), arginine (R), or histidine (H) (numbering according to Kabat), and in the constant domain CH1 of the second Fab molecule the amino acid at position 147 or the amino acid at position 213 is substituted independently by glutamic acid (E) or aspartic acid (D) (numbering according to Kabat EU index).

33. The T cell activating bispecific antigen-binding molecule of claim 32, wherein in the constant domain CL of the first Fab molecule the amino acid at position 124 is substituted independently by lysine (K), arginine (R), or histidine (H) (numbering according to Kabat) and the amino acid at position 123 is substituted independently by lysine (K), arginine (R), or histidine (H) (numbering according to Kabat), and wherein in the constant domain CH1 of the first Fab molecule the amino acid at position 147 is substituted independently by glutamic acid (E) or aspartic acid (D) (numbering according to Kabat EU index) and the amino acid at position 213 is substituted independently by glutamic acid (E) or aspartic acid (D) (numbering according to Kabat EU index).

34. The T cell activating bispecific antigen-binding molecule of claim 33, wherein in the constant domain CL of the first Fab molecule the amino acid at position 124 is substituted by lysine (K) (numbering according to Kabat) and the amino acid at position 123 is substituted by arginine (R) (numbering according to Kabat), and wherein in the constant domain CH1 of the first Fab molecule the amino acid at position 147 is substituted by glutamic acid (E) (numbering according to Kabat EU index) and the amino acid at position 213 is substituted by glutamic acid (E) (numbering according to Kabat EU index).

35. A T cell activating bispecific antigen-binding molecule, comprising:
(a) a first Fab molecule which specifically binds to a first antigen;
(b) a second Fab molecule which specifically binds to a second antigen, and wherein the variable domains VL and VH of the Fab light chain and the Fab heavy chain are replaced by each other;
(c) a third Fab molecule which specifically binds to the first antigen; and
(d) an Fc domain composed of a first and a second subunit capable of stable association;
wherein the first antigen is CEA and the second antigen is CD3;
wherein the third Fab molecule is identical to the first Fab molecule;
wherein the first Fab molecule is fused at the C-terminus of the Fab heavy chain to the N-terminus of the Fab heavy chain of the second Fab molecule, and the second Fab molecule and the third Fab molecule are each fused at the C-terminus of the Fab heavy chain to the N-terminus of one of the subunits of the Fc domain;
wherein the first Fab molecule and the third Fab molecule comprise a heavy chain variable region comprising the amino acid sequence of SEQ ID NO: 22 and a light chain variable region comprising the amino acid sequence of SEQ ID NO: 23; and
wherein the second Fab molecule comprises a heavy chain variable region comprising the HCDR 1 of SEQ ID NO: 4, the HCDR 2 of SEQ ID NO: 5, the HCDR 3 of SEQ ID NO: 6, and a light chain variable region comprising the LCDR 1 of SEQ ID NO: 8, the LCDR 2 of SEQ ID NO: 9, and the LCDR 3 of SEQ ID NO: 10.

36. The T cell activating bispecific antigen-binding molecule of claim 35, wherein the second Fab molecule comprises a heavy chain variable region comprising an amino acid sequence that is at least 95% identical to the amino acid sequence of SEQ ID NO: 3 and a light chain variable region comprising an amino acid sequence that is at least 95% identical to the amino acid sequence of SEQ ID NO: 7.

37. The T cell activating bispecific antigen-binding molecule of claim 35, wherein:
(a) the Fc domain is a human IgG$_1$ Fc domain;
(b) the first subunit of the Fc domain comprises amino acid substitutions S354C and T366W, and the second subunit of the Fc domain comprises amino acid substitutions Y3490, T366S, L368A, and Y407V; and
(c) each subunit of the Fc domain comprises the amino acid substitutions L234A, L235A, and P329G (numberings according to Kabat EU index).

38. A pharmaceutical composition comprising the T cell activating bispecific antigen-binding molecule of claim 35.

39. The T cell activating bispecific antigen-binding molecule of claim 35, wherein the second Fab molecule comprises a heavy chain variable region comprising the amino acid sequence of SEQ ID NO: 3 and a light chain variable region comprising the amino acid sequence of SEQ ID NO: 7.

40. The T cell activating bispecific antigen-binding molecule of claim 35, wherein in the constant domain CL of the first Fab molecule and the third Fab molecule the amino acid at position 124 is substituted by lysine (K) (numbering according to Kabat) and the amino acid at position 123 is substituted by arginine (R) (numbering according to Kabat), and wherein in the constant domain CH1 of the first Fab molecule and the third Fab molecule the amino acid at position 147 is substituted by glutamic acid (E) (numbering according to Kabat EU index) and the amino acid at position 213 is substituted by glutamic acid (E) (numbering according to Kabat EU index).

41. A T cell activating bispecific antigen-binding molecule, comprising:
(a) a first Fab molecule which specifically binds to a first antigen;
(b) a second Fab molecule which specifically binds to a second antigen, and wherein the variable domains VL and VH of the Fab light chain and the Fab heavy chain are replaced by each other;
(c) a third Fab molecule which specifically binds to the first antigen; and
(d) an Fc domain composed of a first and a second subunit capable of stable association;
wherein the first antigen is CEA and the second antigen is CD3;
wherein the third Fab molecule is identical to the first Fab molecule;
wherein the first Fab molecule is fused at the C-terminus of the Fab heavy chain to the N-terminus of the Fab heavy chain of the second Fab molecule, and the second Fab molecule and the third Fab molecule are each fused at the C-terminus of the Fab heavy chain to the N-terminus of one of the subunits of the Fc domain;
wherein the first Fab molecule and the third Fab molecule comprise a heavy chain variable region comprising the amino acid sequence of SEQ ID NO: 22 and a light chain variable region comprising the amino acid sequence of SEQ ID NO: 23;
wherein the second Fab molecule comprises a heavy chain variable region comprising the amino acid sequence of SEQ ID NO: 3 and a light chain variable region comprising the amino acid sequence of SEQ ID NO: 7; and wherein:
(a) the Fc domain is a human IgG$_1$ Fc domain;
(b) the first subunit of the Fc domain comprises amino acid substitutions S354C and T366W, and the second subunit of the Fc domain comprises amino acid substitutions Y3490, T366S, L368A, and Y407V; and
(c) each subunit of the Fc domain comprises the amino acid substitutions L234A, L235A, and P329G (numberings according to Kabat EU index).

42. The T cell activating bispecific antigen-binding molecule of claim 41, comprising a polypeptide that is at least 95% identical to the amino acid sequence of SEQ ID NO: 34, a polypeptide that is at least 95% identical to the amino acid sequence of SEQ ID NO: 36, a polypeptide that is at least 95% identical to the amino acid sequence of SEQ ID NO: 37, and a polypeptide that is at least 95% identical to the amino acid sequence of SEQ ID NO: 38.

43. A pharmaceutical composition comprising the T cell activating bispecific antigen-binding molecule of claim 41.

44. The T cell activating bispecific antigen-binding molecule of claim 41, comprising a polypeptide comprising the amino acid sequence of SEQ ID NO: 34, a polypeptide comprising the amino acid sequence of SEQ ID NO: 36, a polypeptide comprising the amino acid sequence of SEQ ID NO: 37, and a polypeptide comprising the amino acid sequence of SEQ ID NO: 38.

45. The T cell activating bispecific antigen-binding molecule of claim 41, wherein in the constant domain CL of the first Fab molecule and the third Fab molecule the amino acid at position 124 is substituted by lysine (K) (numbering according to Kabat) and the amino acid at position 123 is substituted by arginine (R) (numbering according to Kabat), and wherein in the constant domain CH1 of the first Fab molecule and the third Fab molecule the amino acid at position 147 is substituted by glutamic acid (E) (numbering according to Kabat EU index) and the amino acid at position 213 is substituted by glutamic acid (E) (numbering according to Kabat EU index).

46. A T cell activating bispecific antigen-binding molecule comprising:
(a) a first antigen-binding moiety and a third antigen-binding moiety, each of which specifically binds to CEA; wherein each of the first antigen-binding moiety and the third antigen-binding moiety is a conventional Fab molecule comprising:
  (i) a heavy chain variable region comprising the amino acid sequence of SEQ ID NO: 22; and
  (ii) a light chain variable region comprising the amino acid sequence of SEQ ID NO: 23, and wherein in the constant domain CL the amino acid at position 124 is substituted by lysine (K) (numbering according to Kabat) and the amino acid at position 123 is substituted by arginine (R) (numbering according to Kabat), and wherein in the constant domain CH1 the amino acid at position 147 is substituted by glutamic acid (E) (numbering according to Kabat EU index) and the amino acid at position 213 is substituted by glutamic acid (E) (numbering according to Kabat EU index);

(b) a second antigen-binding moiety which specifically binds to CD3; wherein the second antigen-binding moiety is a crossover Fab molecule wherein the variable domains VL and VH of the Fab light chain and the Fab heavy chain are replaced by each other, wherein the second antigen-binding moiety comprises:
  (i) a heavy chain variable region comprising an amino acid sequence that is at least 95% identical to the amino acid sequence of SEQ ID NO: 3, wherein the amino acid sequence that is at least 95% identical to the amino acid sequence of SEQ ID NO: 3 comprises the HCDR1 of SEQ ID NO: 4, the HCDR2 of SEQ ID NO: 5, and the HCDR3 of SEQ ID NO: 6; and
  (ii) a light chain variable region comprising an amino acid sequence that is at least 95% identical to the amino acid sequence of SEQ ID NO: 7, wherein the amino acid sequence that is at least 95% identical to the amino acid sequence of SEQ ID NO: 7 comprises the LCDR1 of SEQ ID NO: 8, the LCDR2 of SEQ ID NO: 9, and the LCDR3 of SEQ ID NO: 10; and
(c) an Fc domain composed of a first and a second subunit capable of stable association, wherein the Fc domain is a human IgG$_1$ Fc domain, wherein the first subunit of the Fc domain comprises the amino acid substitutions S354C and T366W, the second subunit of the Fc domain comprises the amino acid substitutions Y3490, T366S, L368A, and Y407V, and wherein each subunit of the Fc domain comprises the amino acid substitutions L234A, L235A, and P329G (numberings according to Kabat EU index),
wherein the second and the third antigen-binding moiety are each fused at the C-terminus of the Fab heavy chain to the N-terminus of one of the subunits of the Fc domain, and the first antigen-binding moiety is fused at the C-terminus of the Fab heavy chain to the N-terminus of the Fab heavy chain of the second antigen-binding moiety.

47. The T cell activating bispecific antigen-binding molecule of claim 46, wherein the second antigen-binding moiety comprises a heavy chain variable region comprising the amino acid sequence of SEQ ID NO: 3 and a light chain variable region comprising the amino acid sequence of SEQ ID NO: 7.

48. The T cell activating bispecific antigen-binding molecule of claim 46, comprising a polypeptide that is at least 95% identical to the sequence of SEQ ID NO: 34, a polypeptide that is at least 95% identical to the sequence of SEQ ID NO: 36, a polypeptide that is at least 95% identical to the sequence of SEQ ID NO: 37, and a polypeptide that is at least 95% identical to the sequence of SEQ ID NO: 38.

49. The T cell activating bispecific antigen-binding molecule of claim 46, comprising a polypeptide comprising the amino acid sequence of SEQ ID NO: 34, a polypeptide comprising the amino acid sequence of SEQ ID NO: 36, a polypeptide comprising the amino acid sequence of SEQ ID NO: 37, and a polypeptide comprising the amino acid sequence of SEQ ID NO: 38.

50. A pharmaceutical composition comprising the T cell activating bispecific antigen-binding molecule of claim 49.

* * * * *

UNITED STATES PATENT AND TRADEMARK OFFICE
CERTIFICATE OF CORRECTION

PATENT NO. : 10,766,967 B2  
APPLICATION NO. : 15/281484  
DATED : September 8, 2020  
INVENTOR(S) : Marina Bacac et al.

Page 1 of 1

It is certified that error appears in the above-identified patent and that said Letters Patent is hereby corrected as shown below:

In the Claims

Column 160, Line 9, Claim 37, replace "Y3490" with --Y349C--.  
Column 161, Line 6, Claim 41, replace "Y3490" with --Y349C--.  
Column 162, Line 25, Claim 46, replace "Y3490" with --Y349C--.

Signed and Sealed this  
Third Day of August, 2021

Drew Hirshfeld  
*Performing the Functions and Duties of the*  
*Under Secretary of Commerce for Intellectual Property and*  
*Director of the United States Patent and Trademark Office*